United States Patent
Caracciolo et al.

(10) Patent No.: US 7,828,147 B2
(45) Date of Patent: Nov. 9, 2010

(54) MULTI-LAYER MEDICATION CARRIER

(75) Inventors: Cathy L. Caracciolo, Fallentimber, PA (US); William S. Arnold, Plumesteadville, PA (US); Christopher E. Bossi, Altoona, PA (US)

(73) Assignee: InRange Systems, Inc., Altoona, PA (US)

(*) Notice: Subject to any disclaimer, the term of this patent is extended or adjusted under 35 U.S.C. 154(b) by 436 days.

(21) Appl. No.: 11/779,831

(22) Filed: Jul. 18, 2007

(65) Prior Publication Data

US 2008/0035520 A1    Feb. 14, 2008

Related U.S. Application Data

(63) Continuation-in-part of application No. 11/685,191, filed on Mar. 12, 2007, which is a continuation-in-part of application No. 11/013,285, filed on Dec. 15, 2004.

(60) Provisional application No. 60/565,221, filed on Apr. 24, 2004.

(51) Int. Cl.
    *B65D 83/04*    (2006.01)
(52) U.S. Cl. .......................... 206/530; 206/531
(58) Field of Classification Search .............. 206/528, 206/530, 531, 532, 534, 538, 539, 534.1, 206/534.2, 469
    See application file for complete search history.

(56) References Cited

U.S. PATENT DOCUMENTS

| | | | |
|---|---|---|---|
| 2,771,214 A | 9/1953 | LeFebvre |
| 3,143,207 A | 8/1964 | Wagner |
| 3,329,080 A | 7/1967 | Reach |
| 3,351,192 A | 11/1967 | LaPlante |
| 3,390,766 A | 7/1968 | Stockdale |

(Continued)

FOREIGN PATENT DOCUMENTS

EP    0129785 B1    1/1985

(Continued)

OTHER PUBLICATIONS

Communication Relating to the Results of the Partial International Search for PCT/US2008/070305 dated Dec. 3, 2008.

(Continued)

*Primary Examiner*—Luan K Bui
(74) *Attorney, Agent, or Firm*—Vedder Price PC

(57) ABSTRACT

A multi-layer medication carrier or blister card may comprise a plurality of layers. A support layer is provided with one or more openings to receive corresponding blisters formed in a blister layer. A backing layer is provided over the blister layer to form one or more enclosures capable of holding unit doses of a medication. Perforations provided in at least the blister layer define unit dose packages. Dimples may be provided in the blister layer within a boundary defined by the perforations, which dimples may be used to ensure subsequent ejection of each unit dose package. An adhesive-free region in the backing layer may be provided in alignment with the perforations defining each unit dose package to further ensure proper ejection. Additionally, a partial-depth cut in the backing layer may be provided in substantial alignment with each blister, thereby facilitating removal of the unit dose of medication.

23 Claims, 66 Drawing Sheets

U.S. PATENT DOCUMENTS

| | | |
|---|---|---|
| 3,393,795 A | 7/1968 | Covert, Jr. |
| 3,410,450 A | 11/1968 | Fortenberry |
| 3,450,306 A | 6/1969 | Gill |
| 3,482,733 A | 12/1969 | Groves |
| 3,503,493 A | 3/1970 | Nagy |
| 3,563,405 A | 2/1971 | Zaremski |
| 3,654,890 A | 4/1972 | Rigney et al. |
| 3,673,885 A | 7/1972 | Guglielmo |
| 3,773,250 A | 11/1973 | Phillips |
| 3,831,006 A | 8/1974 | Chaffin, III et al. |
| 3,848,112 A | 11/1974 | Weischselbaum et al. |
| 3,876,268 A | 4/1975 | Colver |
| 3,921,196 A | 11/1975 | Patterson |
| 4,019,793 A | 4/1977 | Gerding |
| 4,148,273 A | 4/1979 | Hollingsworth et al. |
| 4,164,320 A | 8/1979 | Irazoque et al. |
| 4,165,709 A | 8/1979 | Studer |
| 4,176,762 A | 12/1979 | Scalera |
| 4,223,801 A | 9/1980 | Carlson |
| 4,415,802 A | 11/1983 | Long |
| 4,482,896 A | 7/1984 | Yung et al. |
| 4,476,381 A | 10/1984 | Rubin |
| 4,504,153 A | 3/1985 | Schollmeyer |
| 4,572,403 A | 2/1986 | Benaroya |
| 4,573,580 A | 3/1986 | Messer |
| 4,614,366 A | 9/1986 | North et al. |
| 4,616,316 A | 10/1986 | Hanpeter et al. |
| 4,628,193 A | 12/1986 | Blum |
| 4,655,026 A | 4/1987 | Wigoda |
| 4,660,991 A | 4/1987 | Simon |
| 4,695,954 A | 9/1987 | Rose et al. |
| 4,704,517 A | 11/1987 | Campisi et al. |
| 4,725,997 A | 2/1988 | Urquhart et al. |
| 4,733,797 A | 3/1988 | Haber |
| 4,748,600 A | 5/1988 | Urquhart |
| 4,763,810 A | 8/1988 | Christiansen |
| 4,768,177 A | 8/1988 | Kehr et al. |
| 4,785,969 A | 11/1988 | McLaughlin |
| 4,790,118 A | 12/1988 | Chilcoate |
| 4,818,850 A | 4/1989 | Gombrich et al. |
| 4,823,982 A | 4/1989 | Aten et al. |
| 4,835,372 A | 5/1989 | Gombrich et al. |
| 4,847,764 A | 7/1989 | Halvorson |
| 4,853,521 A | 8/1989 | Claeys et al. |
| 4,857,716 A | 8/1989 | Gambrich |
| 4,869,392 A | 9/1989 | Moulding, Jr. et al. |
| 4,872,591 A | 10/1989 | Konopka |
| 4,911,327 A | 3/1990 | Shepherd et al. |
| 4,933,873 A | 6/1990 | Kaufman et al. |
| 4,953,745 A | 9/1990 | Rowlett, Jr. |
| 4,970,669 A | 11/1990 | McIntosh et al. |
| 4,978,335 A | 12/1990 | Arthur |
| 4,998,623 A | 3/1991 | Doull |
| 5,006,699 A | 4/1991 | Felkner et al. |
| 5,014,851 A | 5/1991 | Wick |
| 5,014,875 A | 5/1991 | McLaughlin et al. |
| 5,016,172 A | 5/1991 | Dessertine |
| 5,020,037 A | 5/1991 | Raven |
| 5,036,462 A | 7/1991 | Kaufman et al. |
| 5,047,948 A | 9/1991 | Turner |
| 5,065,655 A | 11/1991 | Haber |
| 5,071,168 A | 12/1991 | Shamos |
| 5,072,430 A | 12/1991 | Eckernas et al. |
| 5,082,113 A | 1/1992 | Romick |
| 5,084,828 A | 1/1992 | Kaufman et al. |
| 5,102,008 A | 4/1992 | Kaufman et al. |
| 5,109,984 A | 5/1992 | Romick |
| 5,110,007 A | 5/1992 | Law et al. |
| 5,119,969 A | 6/1992 | Haber |
| 5,126,957 A | 6/1992 | Kaufman et al. |
| 5,142,484 A | 8/1992 | Kaufman et al. |
| 5,148,944 A | 9/1992 | Kaufman et al. |
| 5,159,581 A | 10/1992 | Agans |
| 5,163,559 A | 11/1992 | Bunin |
| 5,176,285 A | 1/1993 | Shaw |
| 5,180,518 A | 1/1993 | Sugihara et al. |
| 5,181,189 A | 1/1993 | Hafner |
| 5,197,632 A | 3/1993 | Kaufman et al. |
| 5,230,441 A | 7/1993 | Kaufman et al. |
| 5,244,091 A | 9/1993 | Tannenbaum |
| 5,251,757 A | 10/1993 | Relyea et al. |
| 5,263,596 A | 11/1993 | Williams |
| 5,267,174 A | 11/1993 | Kaufman et al. |
| 5,291,191 A | 3/1994 | Moore |
| 5,299,122 A | 3/1994 | Wang et al. |
| 5,314,243 A | 5/1994 | McDonald |
| 5,323,920 A | 6/1994 | Harris et al. |
| 5,329,459 A | 7/1994 | Kaufman et al. |
| 5,335,816 A | 8/1994 | Kaufman et al. |
| 5,337,919 A | 8/1994 | Spaulding et al. |
| 5,347,453 A | 9/1994 | Maestre |
| 5,368,187 A | 11/1994 | Poncetta et al. |
| 5,377,839 A | 1/1995 | Relyea et al. |
| 5,390,238 A | 2/1995 | Kirk et al. |
| 5,392,952 A | 2/1995 | Bowden |
| 5,405,011 A | 4/1995 | Haber et al. |
| 5,408,443 A | 4/1995 | Weinberger |
| 5,412,372 A | 5/1995 | Parkhurst et al. |
| 5,429,761 A | 7/1995 | Havelka et al. |
| 5,431,299 A | 7/1995 | Brewer et al. |
| 5,439,648 A | 8/1995 | Balderson et al. |
| 5,441,165 A | 8/1995 | Kemp et al. |
| 5,454,900 A | 10/1995 | Han et al. |
| 5,460,294 A | 10/1995 | Williams |
| 5,468,110 A | 11/1995 | McDonald et al. |
| 5,472,113 A | 12/1995 | Shaw |
| 5,489,025 A | 2/1996 | Romick |
| 5,508,499 A | 4/1996 | Ferrario |
| 5,508,912 A | 4/1996 | Schneiderman |
| 5,511,594 A | 4/1996 | Brennan et al. |
| 5,529,188 A | 6/1996 | Coggswell |
| 5,542,236 A | 8/1996 | Miller |
| 5,564,593 A | 10/1996 | East, Sr. |
| 5,566,829 A | 10/1996 | Cotilletta |
| 5,570,810 A | 11/1996 | Lambelet, Jr. et al. |
| 5,582,323 A | 12/1996 | Kurtenbach |
| 5,582,593 A | 12/1996 | Hultman |
| 5,583,831 A | 12/1996 | Churchill et al. |
| 5,593,390 A | 1/1997 | Castellano et al. |
| 5,597,495 A | 1/1997 | Keil et al. |
| 5,597,995 A | 1/1997 | Williams et al. |
| 5,609,268 A | 3/1997 | Shaw |
| 5,623,242 A | 4/1997 | Dawson, Jr. et al. |
| 5,630,347 A | 5/1997 | Elvio |
| 5,642,731 A | 7/1997 | Kehr |
| 5,646,912 A | 7/1997 | Cousin |
| 5,651,775 A | 7/1997 | Walker et al. |
| 5,657,236 A | 8/1997 | Conkright |
| 5,703,786 A | 12/1997 | Conkright |
| 5,710,551 A | 1/1998 | Ridgeway |
| 5,713,856 A | 2/1998 | Eggers et al. |
| 5,737,539 A | 4/1998 | Edelson et al. |
| 5,752,235 A | 5/1998 | Kehr |
| 5,752,621 A | 5/1998 | Passamante |
| 5,755,357 A | 5/1998 | Orkin et al. |
| 5,771,657 A | 6/1998 | Lasher et al. |
| 5,775,505 A * | 7/1998 | Vasquez et al. ............ 206/538 |
| 5,781,442 A | 7/1998 | Engleson et al. |
| 5,791,478 A | 8/1998 | Kalvelage et al. |
| 5,797,515 A | 8/1998 | Liff |
| 5,833,071 A * | 11/1998 | Ray ........................ 206/532 |
| 5,836,474 A | 11/1998 | Wessberg |
| 5,850,344 A | 12/1998 | Conkright |
| 5,852,408 A | 12/1998 | Christiansen et al. |

| | | | | | | | |
|---|---|---|---|---|---|---|---|
| 5,852,590 | A | 12/1998 | De la Huerga | 6,471,087 | B1 | 10/2002 | Shusterman |
| 5,860,419 | A | 1/1999 | Davies et al. | 6,471,089 | B1 | 10/2002 | Liff et al. |
| 5,868,135 | A | 2/1999 | Kaufman et al. | 6,507,275 | B2 | 1/2003 | Romano et al. |
| 5,878,885 | A | 3/1999 | Wangu et al. | 6,527,138 | B2 | 3/2003 | Palow et al. |
| 5,878,887 | A | 3/1999 | Parker et al. | 6,529,446 | B1 | 3/2003 | de la Huerga |
| 5,885,245 | A | 3/1999 | Lynch et al. | 6,529,801 | B1 | 3/2003 | Rosenblum |
| 5,898,586 | A | 4/1999 | Jeatran et al. | 6,532,399 | B2 | 3/2003 | Mase |
| 5,904,249 | A | 5/1999 | Roulin et al. | 6,539,281 | B2 | 3/2003 | Wan et al. |
| 5,909,822 | A | 6/1999 | George et al. | 6,540,081 | B2 | 4/2003 | Balz et al. |
| 5,913,197 | A | 6/1999 | Kameda | 6,564,121 | B1 | 5/2003 | Wallace et al. |
| 5,927,500 | A * | 7/1999 | Godfrey et al. ............ 206/531 | 6,574,166 | B2 | 6/2003 | Niemiec |
| 5,945,651 | A | 8/1999 | Chorosinski et al. | 6,578,734 | B1 | 6/2003 | Coughlin |
| 5,954,641 | A | 9/1999 | Kehr et al. | RE38,189 | E | 7/2003 | Walker et al. |
| 5,963,136 | A | 10/1999 | O'Brien | 6,588,670 | B2 | 7/2003 | Bukowski |
| 5,971,594 | A | 10/1999 | Sahai et al. | 6,589,787 | B2 | 7/2003 | Dietrich et al. |
| 5,990,782 | A | 11/1999 | Lee | 6,594,549 | B2 | 7/2003 | Siegel |
| 6,000,828 | A | 12/1999 | Leet | 6,601,729 | B1 | 8/2003 | Papp |
| 6,003,722 | A | 12/1999 | Thurner | 6,615,107 | B2 | 9/2003 | Hubicki |
| 6,004,020 | A | 12/1999 | Bartur | 6,625,518 | B2 | 9/2003 | Depeursinge |
| 6,006,946 | A | 12/1999 | Williams et al. | 6,636,780 | B1 | 10/2003 | Haitin et al. |
| 6,011,999 | A | 1/2000 | Holmes | 6,640,212 | B1 | 10/2003 | Rosse |
| 6,018,289 | A | 1/2000 | Sekura | 6,650,964 | B2 | 11/2003 | Spano, Jr. et al. |
| 6,021,392 | A | 2/2000 | Lester et al. | 6,655,545 | B1 | 12/2003 | Sonneborn |
| 6,021,918 | A | 2/2000 | Dumont et al. | 6,681,935 | B1 | 1/2004 | Lewis |
| 6,024,699 | A | 2/2000 | Surwit et al. | 6,689,091 | B2 | 2/2004 | Bui et al. |
| 6,032,155 | A | 2/2000 | de la Huerga | 6,697,704 | B2 | 2/2004 | Rosenblum |
| 6,036,016 | A * | 3/2000 | Arnold ....................... 206/532 | 6,697,783 | B1 | 2/2004 | Brinkman et al. |
| 6,036,018 | A | 3/2000 | Harrold | 6,702,146 | B2 | 3/2004 | Varis |
| 6,062,420 | A | 5/2000 | Krouwel et al. | 6,732,884 | B2 | 5/2004 | Topliffe et al. |
| 6,068,156 | A | 5/2000 | Liff et al. | 6,735,497 | B2 | 5/2004 | Wallace et al. |
| 6,082,544 | A | 7/2000 | Romick | 6,735,551 | B2 | 5/2004 | Voegeli et al. |
| 6,085,752 | A | 7/2000 | Kehr et al. | 6,766,218 | B2 | 7/2004 | Rosenblum |
| 6,102,855 | A | 8/2000 | Kehr et al. | 6,766,219 | B1 | 7/2004 | Hasey |
| 6,112,502 | A | 9/2000 | Frederick et al. | 6,783,492 | B2 | 8/2004 | Dominguez et al. |
| 6,116,461 | A | 9/2000 | Broadfield et al. | 6,785,589 | B2 | 8/2004 | Eggenberger et al. |
| 6,138,865 | A | 10/2000 | Gilmore | 6,799,149 | B2 | 9/2004 | Hartlaub |
| 6,150,942 | A | 11/2000 | O'Brien | 6,802,422 | B2 | 10/2004 | Kalvelage et al. |
| 6,152,364 | A | 11/2000 | Schoonen et al. | 6,822,554 | B2 | 11/2004 | Vrijens et al. |
| 6,155,454 | A | 12/2000 | George et al. | 6,832,200 | B2 | 12/2004 | Greeven et al. |
| 6,155,485 | A | 12/2000 | Coughlin et al. | 6,839,304 | B2 | 1/2005 | Niemiec et al. |
| 6,161,095 | A | 12/2000 | Brown | 6,842,736 | B1 | 1/2005 | Brzozowski |
| 6,161,699 | A | 12/2000 | Gartland | 6,848,593 | B2 | 2/2005 | Papp |
| 6,168,563 | B1 | 1/2001 | Brown | 6,854,618 | B2 | 2/2005 | Harrold |
| 6,175,779 | B1 | 1/2001 | Barrett | 6,871,783 | B2 | 3/2005 | Kaafarani et al. |
| 6,193,103 | B1 | 2/2001 | Clarijis | 6,892,512 | B2 | 5/2005 | Rice et al. |
| 6,198,383 | B1 | 3/2001 | Sekura et al. | 6,892,941 | B2 | 5/2005 | Rosenblum |
| 6,202,642 | B1 | 3/2001 | McKinnon et al. | 6,909,359 | B1 | 6/2005 | McGovern |
| 6,206,233 | B1 | 3/2001 | Schulze | 6,910,601 | B2 | 6/2005 | Thomas et al. |
| 6,219,587 | B1 | 4/2001 | Ahlin et al. | 6,913,149 | B2 | 7/2005 | Gelardi et al. |
| 6,234,343 | B1 | 5/2001 | Papp | 6,928,338 | B1 | 8/2005 | Buchser et al. |
| 6,263,259 | B1 | 7/2001 | Bartur | 6,935,560 | B2 | 8/2005 | Andreasson et al. |
| 6,270,455 | B1 | 8/2001 | Brown | 6,951,282 | B2 * | 10/2005 | Jones ........................ 206/469 |
| 6,273,260 | B1 * | 8/2001 | ColDepietro et al. ........ 206/532 | 6,951,353 | B2 | 10/2005 | Kozlowski et al. |
| 6,294,999 | B1 | 9/2001 | Yarin et al. | 6,973,371 | B1 | 12/2005 | Benouali |
| 6,304,797 | B1 | 10/2001 | Shusterman | 6,978,286 | B2 | 12/2005 | Francis et al. |
| 6,314,384 | B1 | 11/2001 | Goetz | 6,981,609 | B2 | 1/2006 | Yuyama et al. |
| 6,330,957 | B1 | 12/2001 | Bell-Greenstreet | 6,985,846 | B1 | 1/2006 | Dunlavey |
| 6,332,100 | B1 | 12/2001 | Sahai et al. | 6,985,869 | B1 | 1/2006 | Stoll et al. |
| 6,338,007 | B1 | 1/2002 | Broadfield et al. | 6,994,249 | B2 | 2/2006 | Peterka et al. |
| 6,338,408 | B1 | 1/2002 | Anderson | 7,000,769 | B2 | 2/2006 | Killinger |
| 6,357,593 | B1 | 3/2002 | Bolnick et al. | 7,002,476 | B2 | 2/2006 | Rapchak |
| 6,370,841 | B1 | 4/2002 | Chudy et al. | 7,006,893 | B2 | 2/2006 | Hart et al. |
| 6,373,787 | B1 | 4/2002 | Breimesser et al. | 7,010,431 | B2 | 3/2006 | Boucher |
| 6,375,225 | B1 | 4/2002 | Lapsker | 7,055,294 | B1 | 6/2006 | Lewis |
| 6,375,956 | B1 | 4/2002 | Hemelin et al. | 7,093,716 | B2 | 8/2006 | Intini |
| 6,382,420 | B1 | 5/2002 | Bouthiette | 7,113,101 | B2 | 9/2006 | Petersen |
| 6,401,991 | B1 | 6/2002 | Eannone | 7,126,879 | B2 | 10/2006 | Snyder |
| 6,411,567 | B1 | 6/2002 | Niemiec et al. | 7,328,802 | B2 | 2/2008 | Killinger |
| 6,415,202 | B1 | 7/2002 | Halfacre | 7,336,564 | B2 | 2/2008 | Feodoroff |
| 6,415,916 | B1 | 7/2002 | Rini | 7,419,056 | B2 | 9/2008 | Gattefosse |
| 6,421,584 | B1 | 7/2002 | Norberg et al. | 7,422,110 | B2 | 9/2008 | Zanden |
| 6,439,422 | B1 | 8/2002 | Papp et al. | 7,451,876 | B2 | 11/2008 | Bossi et al. |
| 6,464,142 | B1 | 10/2002 | Denenberg et al. | 2002/0104773 | A1 | 8/2002 | Kalvelage et al. |

| | | | | | | |
|---|---|---|---|---|---|---|
| 2002/0147526 | A1 | 10/2002 | Siegel | WO | 03073977 A2 | 9/2003 |
| 2002/0173875 | A1 | 11/2002 | Wallace et al. | WO | 03079959 A1 | 10/2003 |
| 2003/0042167 | A1 | 3/2003 | Balz et al. | WO | 2004002396 A1 | 1/2004 |
| 2003/0057230 | A1 | 3/2003 | Stevens et al. | WO | 2005009326 A1 | 2/2005 |
| 2003/0102247 | A1 | 6/2003 | Inoue et al. | WO | 2005065628 A1 | 7/2005 |
| 2003/0209558 | A1 | 11/2003 | Cross | WO | 2005109119 A2 | 11/2005 |
| 2004/0133305 | A1 | 7/2004 | Jean-Pierre | | | |
| 2004/0149135 | A1 | 8/2004 | Cai | | | |
| 2005/0087473 | A1 | 4/2005 | Fabricus et al. | | | |
| 2005/0150897 | A1 | 7/2005 | Fabricus et al. | | | |
| 2005/0237222 | A1 | 10/2005 | Bogash | | | |
| 2005/0240305 | A1 | 10/2005 | Bogash et al. | | | |
| 2005/0256830 | A1 | 11/2005 | Siegel et al. | | | |
| 2005/0274643 | A1 | 12/2005 | Arnold | | | |
| 2006/0058917 | A1 | 3/2006 | Vonk et al. | | | |
| 2006/0249421 | A1 * | 11/2006 | Pham ........................ 206/531 | | | |

FOREIGN PATENT DOCUMENTS

| | | | |
|---|---|---|---|
| EP | 0852208 | A1 | 6/1996 |
| EP | 1119501 | B1 | 6/1998 |
| EP | 1363579 | | 11/2003 |
| EP | 1401729 | B1 | 3/2004 |
| FR | 2611671 | | 9/1988 |
| GB | 2343440 | | 10/2000 |
| JP | 2002279068 | | 9/2002 |
| JP | 2003002361 | | 1/2003 |
| WO | 9917218 | A1 | 4/1999 |
| WO | 9943283 | A1 | 9/1999 |
| WO | 99/60982 | A2 | 12/1999 |
| WO | 0007538 | A2 | 2/2000 |
| WO | 0025720 | A3 | 5/2000 |
| WO | 0108106 | A2 | 2/2001 |
| WO | 0147466 | A1 | 7/2001 |
| WO | 0224141 | | 3/2002 |
| WO | 03003970 | | 1/2003 |

OTHER PUBLICATIONS

Adds, Inc.: VA and DOD Clinic Dispensing System Software (1998).
Telepharmacy: VA Pharmacy Finds Convenience in Vending Machines, Veterans Health System Journal, Sep. 1998, pp. 74-75.
Written Opinion for PCT/US04/42187, dated Nov. 9, 2006.
Modified Abstract, Search Report and Modified Search Report to Application No. 01301108.5-2308 (European Patent Office) dated Nov. 7, 2001.
European Search Report for European Patent Application EP 0030 2342.
Annex to European Search Report for EP 00 20 2342, including Abstract.
Carrier Tape by Advantek Inc. (Mar. 2000) pp. 1-2.
Cover Tapes by Advantek, Inc. (Mar. 2000) pp. 1-2.
LOKREEL packaging reels by Advantek Inc. (Mar. 2000) pp. 1-2.
ATR-1000 content, Advantek Inc. (Mar. 2000), p. 1.
3M production information: component handling and materials (Feb. 2000), pp. 1-4.
International Search Report for PCT/US04/42187, dated Nov. 9, 2006.
International Preliminary Report on Patentability for PCT/US04/42187, dated Aug. 20, 2007.
"Examiner's First Report on Patent Application No. 2004319508 by INRange Systems, Inc." issued by the Australian Patent Office on Mar. 4, 2010.
Office Action on Mar. 3, 2010 in U.S. Appl. No. 12/244,504.

* cited by examiner

MULTI-LAYER MEDICATION CARRIER

CROSS-REFERENCE TO RELATED APPLICATIONS

The instant application is a continuation-in-part of U.S. patent application Ser. No. 11/685,191 entitled "Remote Medication Management System" and filed Mar. 12, 2007, pending, which prior application is a continuation-in-part of prior U.S. patent application Ser. No. 11/013,285 entitled "Integrated, Non-Sequential, Remote Medication Management and Compliance System" and filed Dec. 15, 2004, pending, which prior application claims the benefit of Provisional U.S. Patent Application Ser. No. 60/565,221 entitled "Non-Sequential Medication Delivery System" and filed Apr. 24, 2004. The entirety of each of these prior applications is incorporated herein by this reference. The instant application is also related to U.S. patent application Ser. No. 11/366,295 entitled "Medicament Carriers and Method of Using Same" and filed Mar. 2, 2006, now abandoned, and U.S. patent application Ser. No. 12/244,504 entitled "Medicament Carriers Comprising A Ribbing and Method of Using Same".

FIELD OF THE INVENTION

The disclosure relates generally to systems for facilitating patient medication compliance, and more particularly to a multi-layer medication carrier capable of use within an apparatus for remotely delivering individual doses of therapeutic products to a patient.

BACKGROUND OF THE INVENTION

Patient non-adherence to prescribed medication regimens is a significant problem which undermines efforts to manage chronic illnesses. Factors such as an overall increase in outpatient medical procedures have contributed to an increased level of responsibility being placed upon patients and caregivers in the administration of prescription drugs. While estimates of medication non-adherence in remote, residential settings typically range from 30-60%, depending on the disease state, elderly patients average a rate of more than 45% due in part to visual, auditory, and cognitive impairments. Drugs not taken, or taken incorrectly, incur the same health care costs as fully adherent regimens, but without the expected medical outcome. The consequences of non-adherence can be significant, resulting in emergency room visits, extended hospitalizations, long-term care facility admissions, and death.

The ability to comply with a medication regimen is complicated in situations where dosing amounts change over time. For instance, prescribed dosing amounts are frequently a function of ongoing laboratory tests that determine the patient's status. Likewise, appropriate dosage amounts are determined in accordance with a patient's health condition and must reflect unexpected changes in such condition. In these situations, healthcare practitioners such as physicians, pharmacists, and nurses need to be able to adjust a patient's dosage as quickly as possible. Medication compliance is particularly important when narrow therapeutic index drugs are prescribed, as over-medicating or under-medicating a patient can cause serious side effects, illness and even death.

A fairly large number of devices have been developed for prompting a patient to take a prescribed dose of medication at the correct times. Existing devices function primarily to remind patients when to take a particular medication and to sequentially deliver that medication in accordance with a predetermined schedule. Many of these devices are designed to expel medication automatically, in accordance with a predetermined schedule. In this regard, the devices do not provide adequate protection against both under-dosage and over-dosage. If the patient fails to take the medication according to schedule, the devices continue to expel medication at set intervals based on the premise that the patient took all previous medications appropriately. Such a situation greatly enhances the risk of non-compliance, wherein a patient takes less medication than is prescribed. Conversely, if the patient does not take the medication according to schedule, but too close to the time for taking subsequent medication, the patient faces the risk of over-dosage.

Certain devices incorporate means for retrieving pills which are discharged but not removed from the device. Some of these devices provide notification to caregivers of a patient's failure to take medication according to schedule. Other devices have been integrated into comprehensive medication management and delivery systems in which a healthcare practitioner remotely monitors information regarding patient compliance and non-compliance with a medication regimen. While these systems enhance patient compliance with a prescribed treatment regimen, they are deficient in one notable respect, that is, they do not provide a mechanism by which a patient's failure to take a scheduled dose of medication can be rectified in minutes. As such, the systems do not overcome the problem of patient under-dosage and over-dosage. This drawback is particularly significant with respect to high risk patient populations, where patients frequently suffer from cognitive, visual and/or auditory impairments which contribute to non-adherence.

An additional shortcoming of the existing systems is that they fail to provide a mechanism by which a prescribed dosage can be remotely adjusted in minutes, in response to an unexpected change in a patient's health condition. Although the systems allow a healthcare practitioner to communicate a change in dosing amount to the patient, they do not enable the practitioner to immediately and remotely change, adjust or discontinue a prescribed dosage. There is often a delay of several hours, and in some cases, several days, before a patient is able to procure the new dosage. During this period, the patient may be confused as to the correct regimen and continue to take the discontinued dosage. In addition, because a new prescription is required every time a dose is adjusted, the patient is must travel to a physician's office and/or a pharmacy. Although this may pose an inconvenience to some patients, this is particularly disadvantageous to mobility-impaired patients and is a major contributor to drug non-compliance. Frequently the patient's condition deteriorates, as the patient is unable to continue the correct course of treatment.

A further drawback of the conventional systems is that prescriptions are filled in either standard thirty day or sixty day allotments. With such means, there is no accurate way to inventory pharmaceuticals and/or to audit patient compliance or consumption of the product. This is due in part to the fact that the pharmaceuticals are dispensed in a lot, and not every pill or dose is separately bar coded and traceable.

The above-described medication management and delivery systems suffer from a still further limitation, namely, they fail to establish a secure data communication process to deploy communications to and from a remote medication delivery device based in a patient's home while protecting patient privacy. Maintaining patient privacy in the data communication process has to date been a formidable challenge. Moreover, an increasing number of regulations regarding the maintenance and storage of patient data have been enacted in response to the Health Insurance Portability Accountability Act. Accordingly, there is a need and a desire for a cost-effective system that quickly addresses a patient's non-compliance with a prescribed drug regimen in real time and minimizes disruptions to a patient's course of treatment while protecting patient information.

SUMMARY OF THE INVENTION

The present disclosure describes a medication management and compliance system for enabling a healthcare practitioner to remotely manage and deliver sealed unit dose packages of prescription and non-prescription therapeutic products to a patient, on a dose by dose basis, and in a manner that provides immediate confirmation that a dose has been delivered. Clinical software is used for storing patient prescription and dosing regimen information, enabling authorized healthcare personnel to remotely deliver a unit dose therapy to a patient and monitor patient compliance with a dosing regimen, without violating patient privacy. The system includes delivery apparatus located in proximity to the patient, wherein the delivery apparatus is remotely coupled to the clinical software and to a control center by means of a data communications network.

Within such a medication management and compliance system, medication carriers (or blister packs) may be employed for the delivery the medications to patients, particularly using an automated delivery device. Thus, in one embodiment, a medication carrier may include a ribbing comprising a plurality of blisters, whereby when sufficient force is applied to a blister, the blister is displaced from the ribbing and the ribbing provides substantially equivalent support to any remaining blisters as the ribbing provided prior to such displacement.

In another embodiment, a medication carrier may include a backing layer comprising at least one partial-thickness cut though a thickness of the backing layer and substantially aligned with a corresponding one of at least one blister, each partial-thickness cut facilitating ready removal of the medicament from a unit dose package, whether or not the unit dose package has been removed from the medication carrier.

In another embodiment, a blister layer comprising the blisters and interstitial ribbing also includes first perforations corresponding to the blisters, each one of the first perforations defining a boundary between the ribbing and an individually-ejectable, unit dose package comprising a corresponding blister. A backing layer, coupled to the blister layer, may include second perforations substantially aligned with the first perforations and further comprising an adhesive applied to a side of the backing layer facing the blister layer, except that a plurality of adhesive-free regions is provided corresponding to the plurality of second perforations.

In yet another embodiment, each blister comprises one or more dimples disposed within the boundary defined by its corresponding first perforation.

BRIEF DESCRIPTION OF THE DRAWINGS

Figure 28:
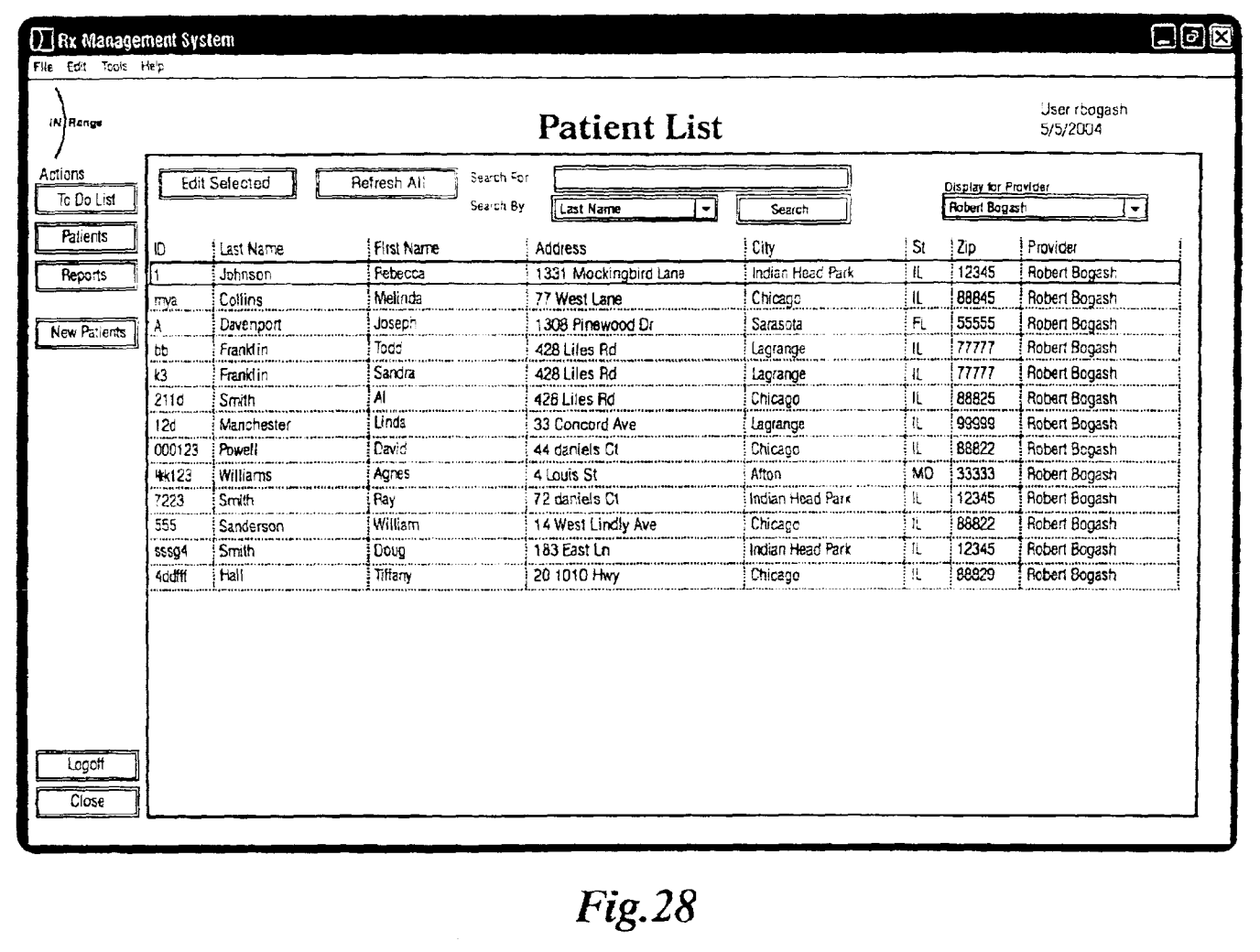

FIGS. 27-31 are examples of worksheets that appear on the computer monitor of healthcare personnel.

DETAILED DESCRIPTION OF THE PRESENT EMBODIMENTS

The present invention provides a fully integrated, real-time, non-sequential medication management and compliance system for prompting a patient remote from a clinical environment to take medication in accordance with a prescribed schedule. A principal advantage of the delivery module of the present invention is that it implements a prescribed medication regimen by delivering a selected unit dose package of medication to a patient upon receipt of an encrypted command signal and patient confirmation. These multiple safeguards ensure that the patient receives the prescribed medication at the correct dosing times. In this manner, the invention enhances patient compliance and allows for chronotherapeutic applications that maximize medication benefits and minimize medication side effects. Also significant is the fact that command signals are securely transmitted to and from the delivery module without compromising patient privacy in any way.

A further advantage of the present invention is that it enables a healthcare practitioner to remotely monitor patient compliance with a prescribed medication regimen and receive rapid notification of non-compliance. Most notably, the healthcare practitioner can promptly adjust the patient's treatment plan to accommodate a missed dosage or to reflect other fluid medical conditions, such as an unexpected change in the health status of the patient. Where necessary, dosage adjustments can be made immediately, without the need for a new prescription. As such, the invention minimizes any loss of time which may complicate non-compliance and reduces medication waste by eliminating the need for a patient to discard remaining doses in the event of a dose adjustment.

A still further advantage of the invention is that it protects the patient from adverse drug reactions and related consequences of over- and under-medicating by ensuring that the patient remains within recommended therapeutic levels. The patient receives a required dosage at the proper time, thereby reducing the incidence of emergency room visits and hospital admissions occasioned by non-adherence to a prescribed drug regimen or other delays in the administration of prescribed medication. In addition, unanticipated visits to health care providers are reduced, thereby reducing overall health care costs. This cost-effective system can be used by healthcare practitioners operating in a variety of settings.

Figure 2:
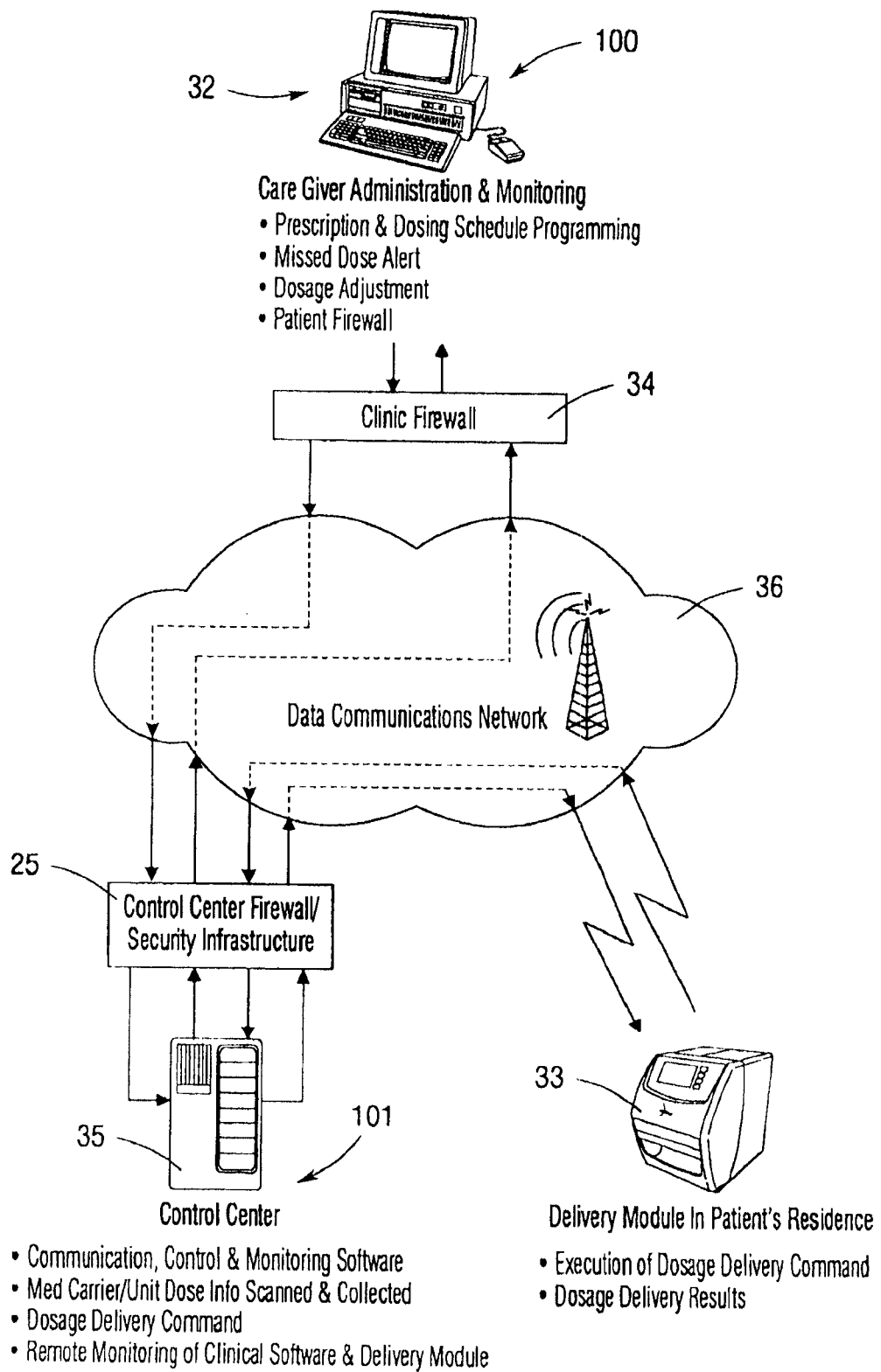
FIG. 2 is a block diagram showing a non-sequential medication delivery module with remote monitoring and access control in accordance with an embodiment of the invention.

Referring now to the Figures, there is shown in FIG. 2 an overview of the system of the present invention. A control center 101, such as a facility operated by INRange Systems, Inc., stocks custom packaged and prepackaged, unit dose prescription and non-prescription medical products, pharmaceuticals and nutraceuticals from various drug manufacturers and suppliers. Such therapeutic products include, but are not limited to, solid orally consumed doses, liquid orally consumed dosages, and injection devices that contain doses that are delivered or administered at the point of care. It will be understood that the term "medication" as used herein is intended to include individual, unit-of-issue doses of prescription and non-prescription medications, medical supplies, pharmaceuticals and nutraceuticals, in a variety of dosage forms and strengths, including single and multiple compound medications. Specific examples include pills, tablets, capsules, suppositories, inhalers, lotions, pre-filled syringes, powders, suspensions, and diagnostic materials such as blood testing strips. At the control center 101, the typically foil-wrapped or blister-packed unit dose packages 27 are inserted into individual stalls 28 of one of several different medication carriers 26, each carrier being designed and sized to accommodate almost any commercially available unit dose package 27.

Exterior dimensions of the medication carrier 26 can be slightly varied, but must be configured to allow the carrier 26 to easily fit within the delivery module 33. An electronic code 29, such as a bar code or radio frequency identification tag, is affixed to each medication carrier 26. The electronic code 29 identifies the carrier type and configuration and provides medication related information, based on a unique identifier such as a serial number. The encoded data is programmed into the control center 101 computer database 35, enabling the control center 101 to accurately track and account for each unit dose package 27 at all times, in conjunction with the delivery module 33, as described below.

Figure 15:
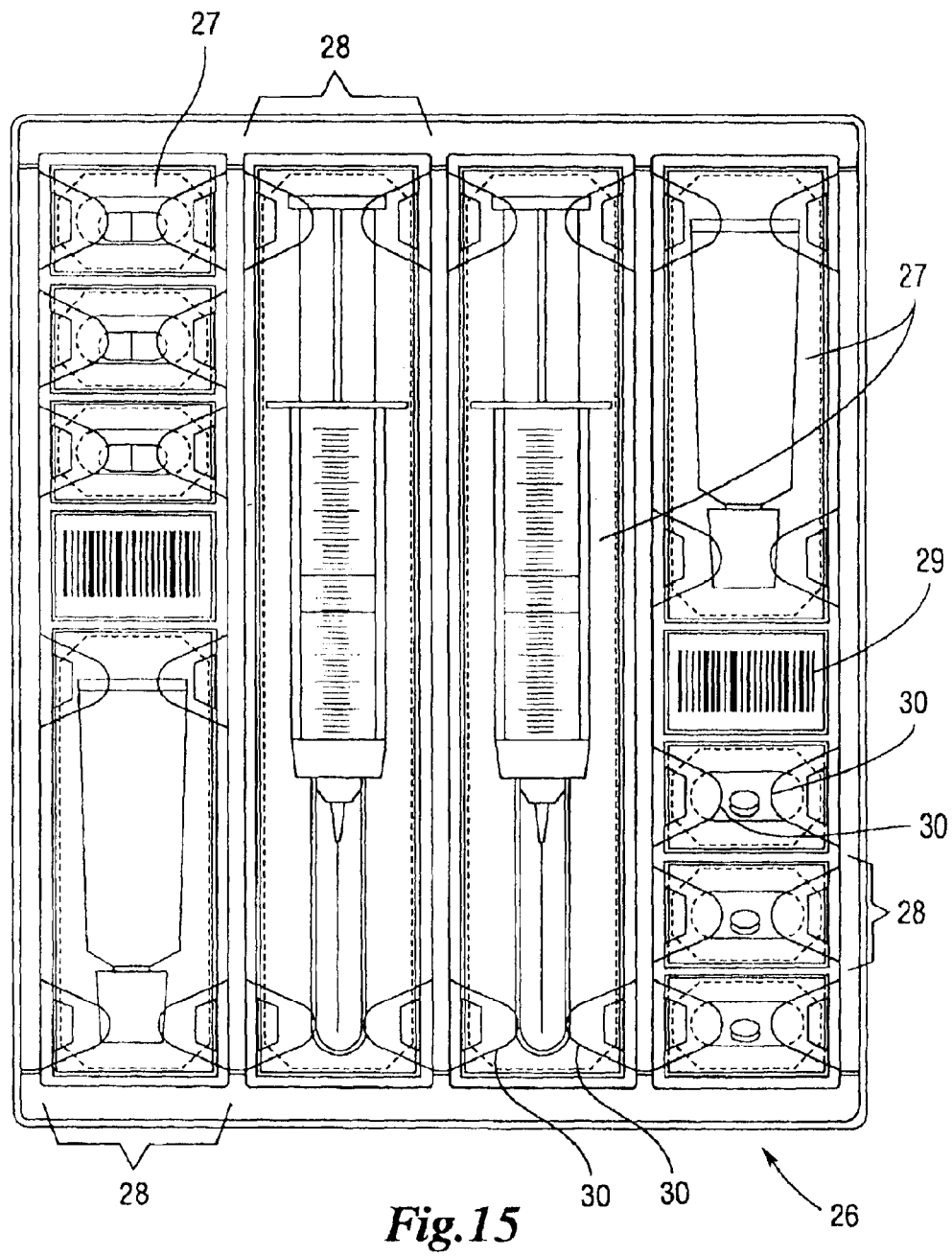
Figure 16:
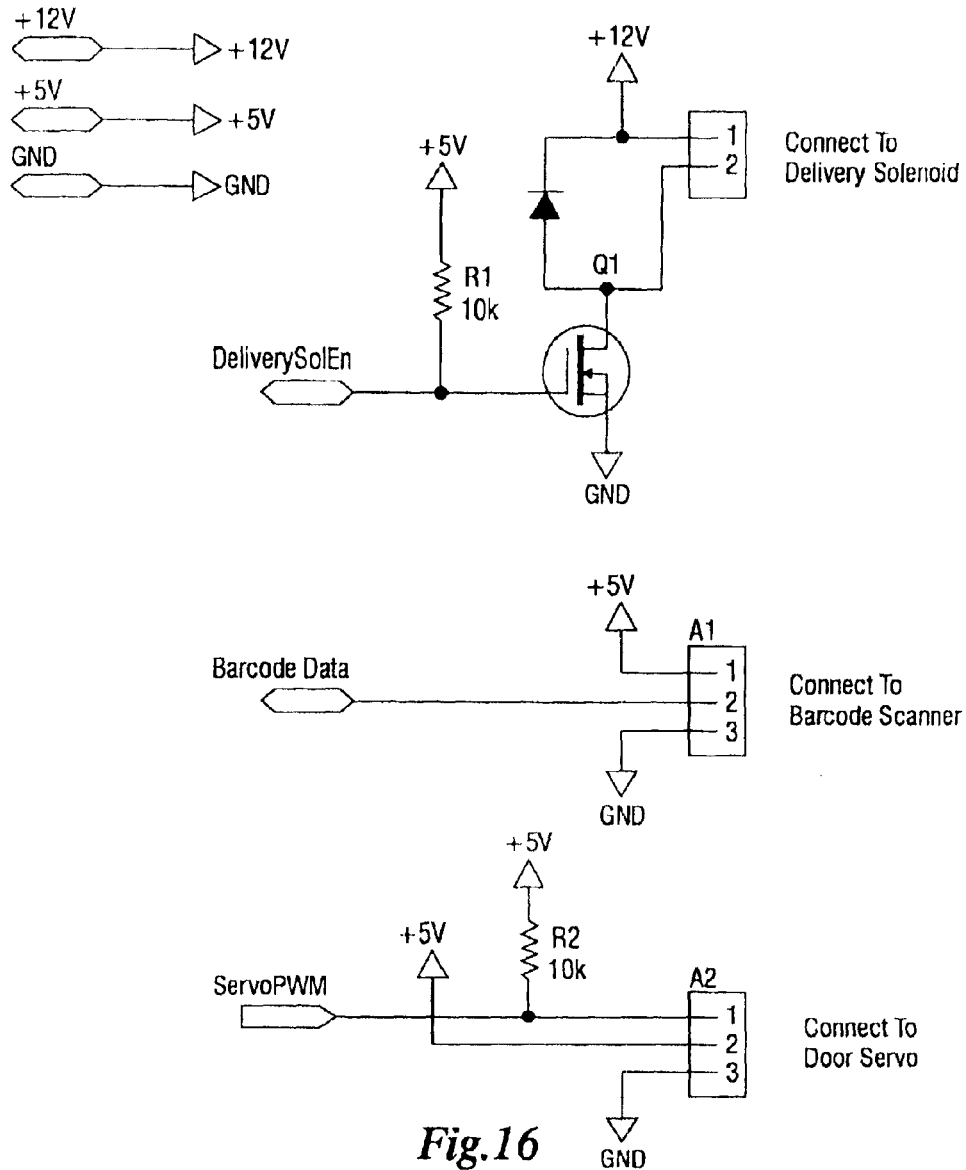
FIGS. 16-20 are electrical schematics illustrating various operations of the non-sequential medication delivery module in accordance with the present invention.
Figure 17:
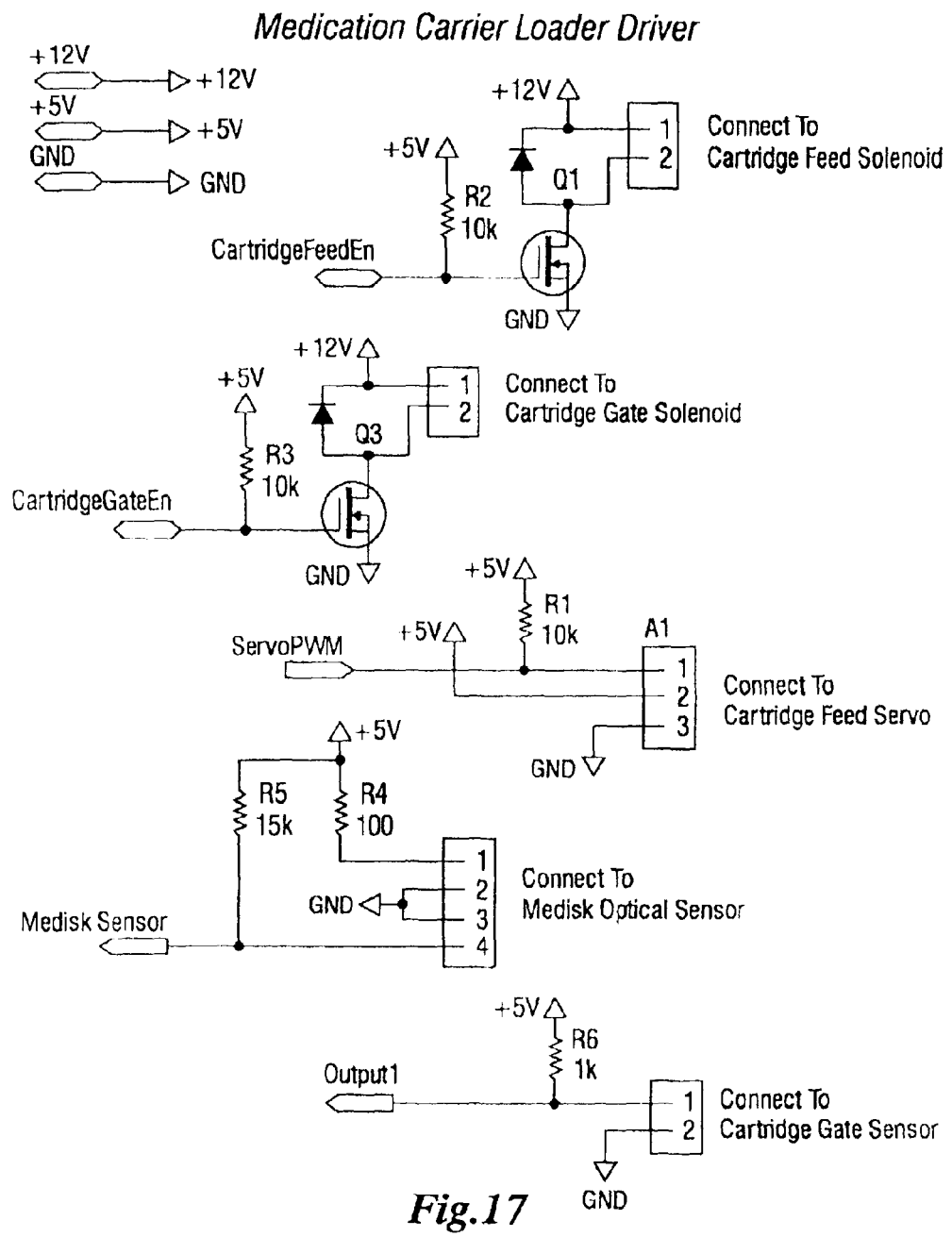

Referring to FIG. 15, the medication carrier 26 includes a receptacle for holding individual, unit dose packages 27 in a non-sequential fashion. Standard unit dose packages 28 normally include a plastic bubble for holding the unit dose therapy and a seal fabricated from paper or foil laminate for retaining the unit dose within the plastic bubble. "Identifying indicia" 31 such as, for example, an electronic code and human readable information, is imprinted on the seal of the unit dose package 27 to denote the medication contained in such package. The medication carrier 26 is designed to permit the identifying indicia 31 to be electronically read by a bar code scanner 98, optical recognition scanner, radio frequency scanner or other such device, without removing the unit dose packages 27 from the medication carrier 26. The medication carrier 26 allows an individual, unit dose package 27 to be remotely and non-consecutively accessed and discharged from the carrier 26 without disrupting the other unit dose packages 27 contained therein. In an embodiment, the unit dose may be discharged from its unit dose package 27 without disrupting other unit dose packages 27 in a medication carrier 26.

Figures 21A, 21B, 21C:
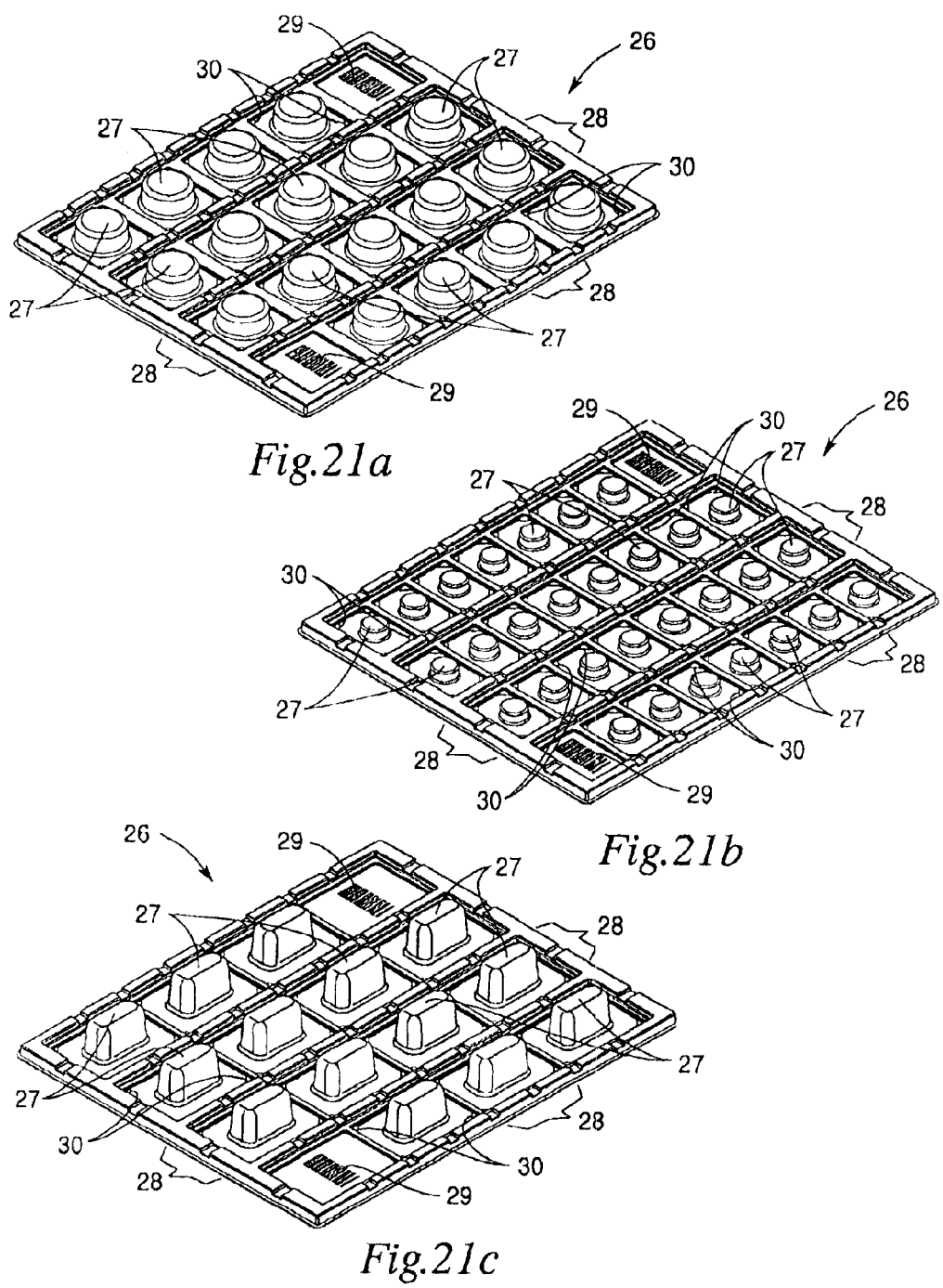
FIGS. 21a, b and c are perspective views of medication carriers containing 32, 20 and 16 stalls, respectively, for accommodating different sized unit dose packages.

As shown in FIG. 21b, the medication carrier 26 may include 32 stalls arranged in four rows of eight stalls 28. In this arrangement, the carrier 26 stores medication for up to 30 calendar days and provides additional surfaces for affixing a label containing a unique electronic identifier 29. FIGS. 21a and 21c illustrate medication carriers 26 having 20 and 16 stalls, respectively, sized and shaped to accommodate larger unit dose packages 27. Each stall 28 of the medication carrier 26 includes retaining means 30 for holding the sealed, unit dose package 27 within the stall 28 until a scheduled dosing time. At such time, the unit dose package 27 is expelled through an aperture in said stall 28. In an embodiment, a unit dose may be expelled through the aperture in the stall 28 and the unit dose package 27 may remain.

A printable surface containing identifying indicia is provided on the upper surface of the medication carrier 26, along its peripheral edges. The printable surface features location markers such as, for example, infrared absorbent ink dots which indicate certain points of interest on the carrier 26.

Normally, the delivery module 33 is remotely located from a clinical facility where healthcare personnel are based such as, for example, a physician's office, pharmacy, pharmacy benefit manager (PBM), hospital, outpatient clinic, nursing station, assisted living facility or long-term care facility. Each clinical facility is equipped with a computer that includes, for example, a standard microprocessor, input-output circuits, a memory for storing patient records including prescription and dosing schedules, a ROM for storing the operating program and other system information, and a monitor for receiving visual feedback. Software 32 such as the Fulfillment, Adjustment and Compliance Tracking System (FACT™), commercially available from INRange Systems, Inc., operates on computer servers at the clinical facility. Patient information is accessed by way of the software's 32 user interface 100, which features a complement of menu-driven worksheets that appear on the monitor of a designated healthcare practitioner (FIGS. 27-31).

The user interface 100 enables the healthcare practitioner to remotely and actively treat a patient by entering appropriate instructions into his/her computer terminal using a keyboard, mouse or other input device. The healthcare practitioner may, for example, input or retrieve prescription information, configure formularies or therapeutic regimens, remotely schedule a new regimen, monitor patient compliance with a dosing regimen, or modify the dosage amounts of an existing regimen. The entered instructions are transmitted to the control center 101, where the instructions are interpreted and routed to the appropriate delivery module 33 based on a unique identifier assigned thereto. The user interface 100 also displays real-time notification of dosage delivery results communicated to the clinical software 32, enabling the healthcare practitioner to take immediate action, if necessary.

The clinical software 32 is securely installed within the confines of each clinical facility and utilizes the facility's network security 34 policies and procedures to authenticate users and network access to patient data. As described below, the control center 101 has no access to patient identifiable information and cannot in any way determine the identity or location of any patient utilizing the delivery module 33. This secure technical and physical information infrastructure is in accord with the Health Insurance Portability and Accountability Act (HIPAA).

Control software 35 programmed to constantly monitor for signals from both the clinical software 32 and delivery module 33 is installed on computer servers based at the control center 101. The control software 35 administers the various treatment instructions entered by the healthcare practitioner, but does not implicate patient information stored within the software database 32 of the clinical facility. In general, the control software 32 records and stores information related to the operation and contents of the delivery module 33, such as the types and locations of medication carriers 26 stored within the module 33, a complete inventory of the unit dose packages 27 contained within each medication carrier 26, and a history of all dose administration operations over a set time period. This record keeping and inventorying function may be achieved, in part, through the use of electronic coding and other identifiers which are assigned to the delivery module 33, medication carriers 26 and unit dose packages 27, respectively. The identifiers enable the control center 101 to correlate a particular medication carrier 26 to the inventory of unit dose packages 27 contained therein, with the assistance of electronic code scanners 92, 98 located within the delivery module 33 for imaging and transmitting encoded information to the controller.

A unique identifier such as a serial number (Unit Identification Number) is typically programmed into the delivery module 33 at the time of manufacture. Similarly, identifying indicia 31 (FIG. 14), including an electronic code and human readable information, is imprinted on the seal of each unit dose package 27 by the drug manufacturers or repackagers. The electronic code 31 identifies the package 27 contents, including, for example, the medication name, dosage strength, lot number, expiration date, national drug code number (NDC), a unique package serial number, a quantity within a unit dose package, a quantity within a medication carrier and whether a unit dose package comprises a fractional portion of a unit dose (e.g., a half, quarter, etc. portion of a pill). A plurality of unit dose packages 27 representing a prescribed course of medication are placed into the stalls 28 of a medication carrier 26, in any order. The unit dose packages 27 need not be organized chronologically, as is required in the existing dosage delivery systems, since each package 27 is randomly accessed and retrieved. The identifying indicia 31 on the seal of each unit dose package is scanned into the control center computer so that an audit trail of each package 27 is maintained.

The control software 35 assigns a unique identifier 29, such as a serial number, to the medication carrier 26. The identifier 29 correlates the medication carrier 26 to the inventory of unit dose packages 27 contained therein and denotes the contents and location of each unit dose package 27. The carrier identifier 29 is reflected within one or more electronic codes which are printed onto a label and affixed to separate locations on the medication carrier 26. This redundancy ensures that at least one electronic identifier 29 is accessible to a code reader 92, 98. This information is stored within the control software database 35.

As discussed above, the unit dose packages 27 are placed into one of several different medication carriers 26, according to the size and configuration of the package 27. For instance, packages containing syringes are typically placed in a medication carrier 26 having longer and wider cells, while packages of oral solid doses are normally placed in a carrier 26 containing smaller cells. Position coordinates, based on the internal geometry of the medication carrier 26, are stored in the control software database 35 to pinpoint the location of each unit dose package 27 within the carrier 26. These coordinates are also reflected in the electronic identifier label 29 that is affixed to the medication carrier 26. The carrier 26 can be inserted into the delivery module 33 in more than one way. Therefore the control software 35 also generates a set of location markers such as, for example, infrared absorbent ink dots or lines which indicate certain points of interest on the carrier 26, which are included on a printable surface (e.g. cardboard) preferably disposed on the upper surface of the medication carrier 26. This redundancy ensures that at least one location marker can be imaged by an optical recognition reader or other electronic scanner 98.

Communication between the delivery module 33 and a healthcare practitioner is accomplished through the control software layer 35. Contained within this layer are the communication protocols for each delivery module 33, which correspond to the type of communication link that is selected for a particular module. Suitable communications media 36 include radio frequency, internet, modem, telephone line, land line, wireless network, pager network or other transmission means that enables control and data signals to be exchanged with the delivery module 33. Preferred communications media include dedicated Local Area Network and/or existing Local Area Networks (e.g. copper, fiber or wireless). The control software 35 communication protocols enable alert signals to be conveyed from the delivery module 33 to the clinical facility 32 to notify appropriate medical personnel of patient non-compliance actions or other urgent conditions. The control software 35 protocols also enable the control center 101 to accurately monitor each unit dose package 27 contained within a particular delivery module 33 and update the database inventory records as each unit dose package 27 is delivered to a patient.

In order to ensure the security of patient information transmitted through the control software layer 35, a preferred embodiment of the present invention utilizes a secure, encrypted connection 25 which maintains the confidentiality and integrity of patient information. The data communication process ensures that the only record correlating a delivery module 33 to a particular patient is contained within the clinical software database 32. This process is described in detail below.

As previously discussed, the clinical software 32 enables a healthcare practitioner to remotely manage and monitor a patient's drug therapy and compliance. All patient information is stored in the clinical software database 32 and utilizes the clinical facility's network security 34 policies and procedures to authenticate users and network access to patient data (FIG. 2). Contained within the clinical software 32 are three key data elements that correlate the delivery module 33 to a particular patient. These include: 1) the delivery module serial number; 2) a randomly generated registration number (used in the initial setup of the module), and 3) a randomly generated Unit Identification Number (UIN).

To communicate with a delivery module 33, the clinical software 32 sends an encrypted signal using a Secure Socket Layer ("SSL") to the URL of the control center 101 computer servers. This signal is the same protocol used in processing credit card payments via the internet and operates on Port 443 of the clinical facility's firewall 34. The signal is an XML instruction set that contains the UIN, identifiers required for authentication by the control center 101 servers, and a command instruction set. Neither the patient's name nor any information identifying the patient is transmitted beyond the clinical facility's firewall 34.

This encrypted signal is sent to the control software layer 35, which is designed to authenticate signals from only the clinical software 32 and delivery module 33. Once a command set is authenticated by the control center 101 servers, utilizing the UIN, the command set references the control software database 35 to determine the data communications method 36 to the particular delivery module 33 (e.g. pager network, wireless network, IP address) and obtains its address information. The signal is reformatted into a proprietary protocol, assigned a randomly generated communication's token and transmitted to the delivery module 33 to be activated.

Once the signal is received by the delivery module 33, the signal is decoded and verified. If authentic, the delivery module 33 transmits a signal back to the control center 101 servers confirming receipt of the command instruction. This confirmation contains the communications token for verification by the control center 101 servers. Certain commands, such as the dosage delivery command, require a reconfirmation from the control center 101 servers to engage the command. This verification process prevents the delivery module 33 from processing any unauthorized commands.

The data communication process 36, as described above, ensures that only the clinical software 32 can correlate data contained on the control center 101 servers to a particular patient, or correlate the delivery module's serial number to a particular patient. In this manner, patient identifiable health information is retained securely within the confines of the clinical facility 34. A principal advantage of the present invention, therefore, is that it enables bidirectional communication between the delivery module 33 and a healthcare practitioner to be conducted using a secure, encrypted connection 25 that maintains the integrity of HIPAA protected patient information.

It will be understood that the present invention may be employed in connection with "non-HIPAA compliant" applications. Stated otherwise, the secure, encrypted data transmission protocol 25 provided herein is not necessary for remote actuation of the delivery module 33. For example, the invention may be used independently of the secure data transmission feature 25 to document various drug consumption events that occur during the course of a clinical research trial or drug detoxification program. In this way, the invention provides a means of capturing longitudinal healthcare outcomes associated with drug and nutritional interventions. Similarly, the delivery module 33 may be equipped with suitable measuring devices and/or employed in connection with a home telemetry unit for remote monitoring of a patient's position, blood pressure, pulse, oxygen level, temperature, respiration, serum glucose etc., or for remote monitoring of environmental conditions such as, for example, temperature, humidity, pressure, smoke and carbon dioxide. For example, the delivery module 33 may include a wireless transceiver used to communicate with one or more sensors on a patient's body. The sensor information may be stored within the delivery module and/or transmitted to one or more remote controller. The sensor information may be used to assist a healthcare provider, for example, in adjusting a medication regimen for a patient.

The non-sequential delivery module 33 features a microprocessor-based controller having standard digital data storage features both for data and for the microprocessor programs. The controller receives command signals related to the patient's prescribed medication regimen. These signals, initiated at the clinical software layer 32, are authenticated and transmitted through the control layer 35 by way of a suitable data communications link 36. The controller then executes the entered dosage delivery command by alerting the patient through visual, audible or other means, at each of the programmed dosing times. The controller concurrently establishes a window of time, relative to the alerting signal, during which the patient can input a delivery signal via, for example, a verbal command or an appropriate confirmation key 43. The duration of the time window is set by the entered program or by a default value.

If the patient input signal is received before expiration of the time window, a fully sealed unit dose or unit-of-issue package 27 is ejected from the medication carrier 26 and discharged from the delivery module 33 as described in further detail below. Alternately, a unit dose may be ejected from the medication carrier 26 and discharged from the delivery module 33. If the patient has not responded, e.g., pressed the "drop" key 43 of the delivery module 33 at the end of the time window, the module automatically transmits an alert, via a suitable data communications link 36, to designated medical personnel. In this manner, the instant invention ensures that medication is not administered until confirmation is received from the patient. This overcomes a significant deficiency of existing medication delivery systems, in which medication is expelled automatically in accordance with a predetermined schedule, increasing the risk of patient under-dosage and over-dosage.

The present invention includes a unique delivery scheme through which a healthcare practitioner, by entering appropriate commands into the user interface, can instantaneously select, modify, queue, change or discontinue any of 300 unit dose packages 27 of prescription or non-prescription medications, pharmaceuticals or nutraceuticals stored within the delivery module 33 of a particular patient. The commands also specify the specific dosage form and strength of the unit dose package 27 to be delivered. The commands are received and interpreted by the control center computer servers, which correlate the instruction to a particular delivery module 33 and medication carrier 26. In this manner, the invention provides the flexible and convenient dosage administration that is required for situations where a patient's regimen is the subject of frequent dosage adjustments or where the patient is prescribed more than one therapy to be administered at varying times over the course of a day, a week or several months.

The present invention enables the healthcare practitioner to remotely and non-consecutively access and deliver any of the unit dose packages 27 (or a therapeutic product from any unit dose package) contained within the delivery module 33 to a patient, in any order, without being limited by a predetermined sequence or serial delivery restriction. Unlike existing systems, the system of the present invention is capable of delivering diverse types of unit dose and unit-of-issue therapeutic products out of sequence, and in minutes, enabling the patient's medication regimen to be appropriately tailored to adapt to fluid medical conditions. An example circumstance requiring modification of the patient's regimen is where there is an unexpected change in the patient's health condition. Notably, the invention ensures that any change in patient medication ordered by a doctor is effective immediately. This is a tremendous advantage over existing systems, which take at least several hours, and in some cases, several days for new medication orders to be filled.

Figure 26:
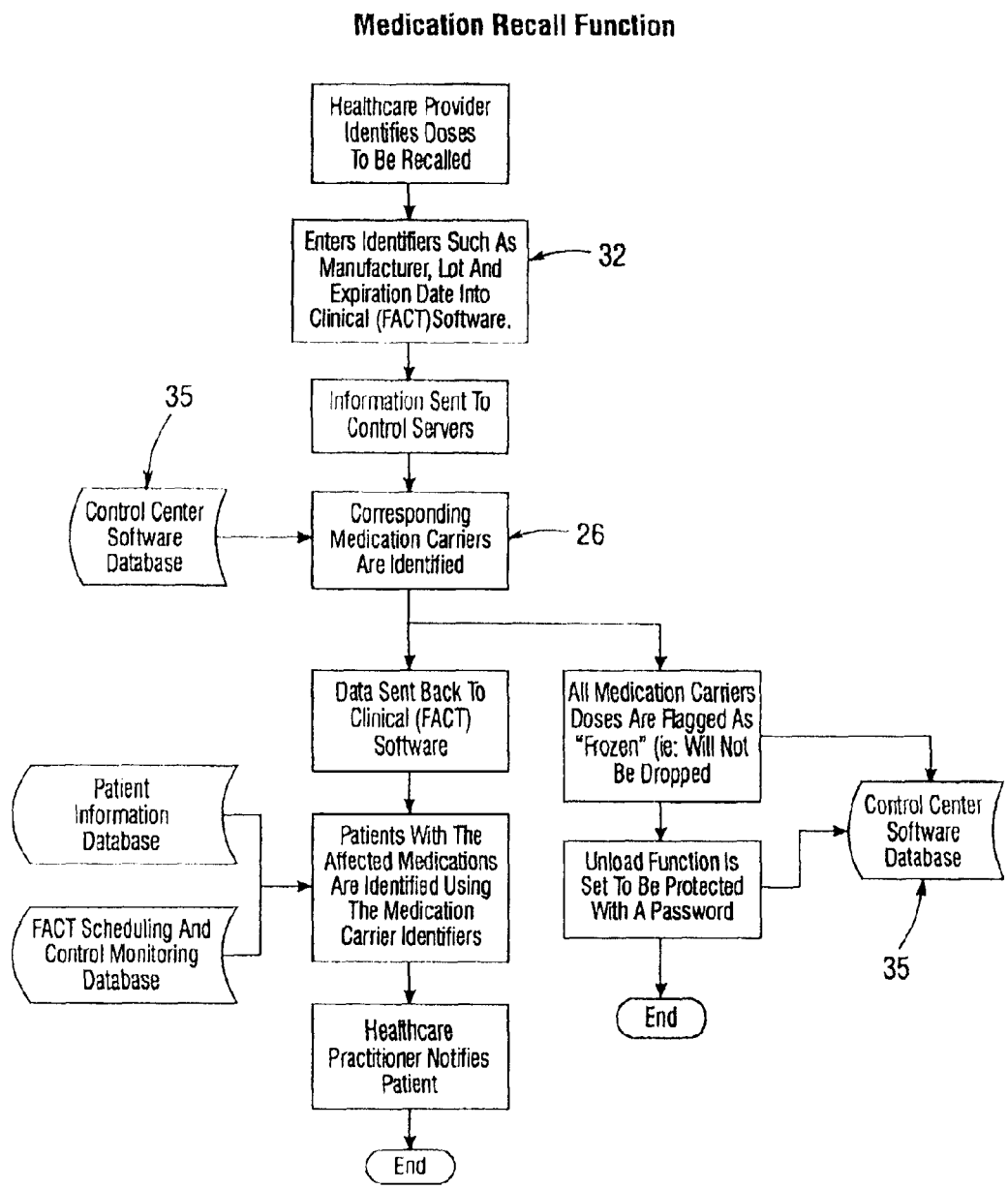
Figure 27:
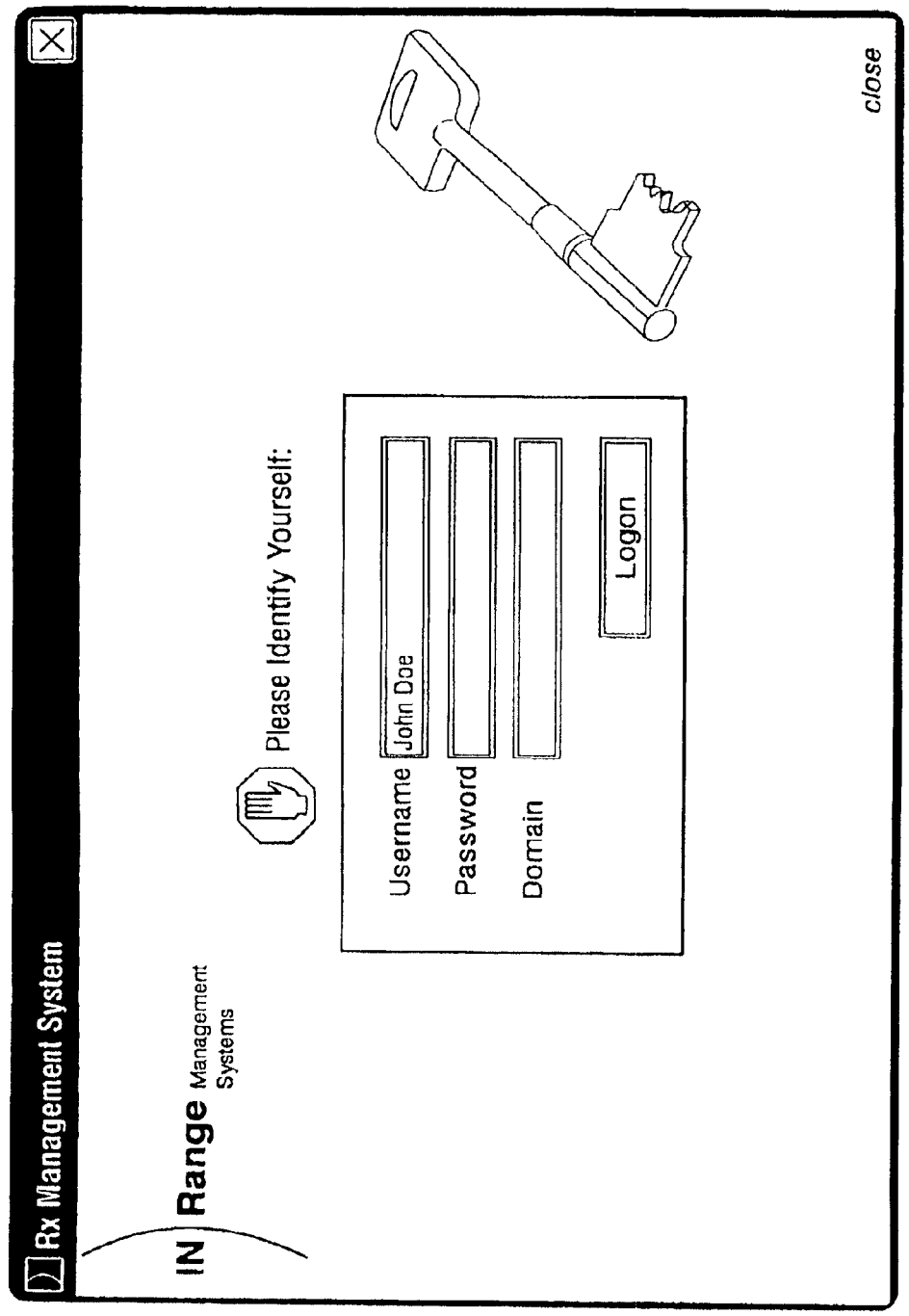

The subject invention is particularly useful in situations where it is necessary to immediately discontinue or recall a therapy prescribed as part of a clinical research trial, a frequent occurrence (FIG. 26). In such instances, the clinical software initiates a lock-out procedure to prevent delivery of any of the unit dose packages that have been recalled. To the inventors' knowledge, the present system is the only technology platform that enables real-time quarantine of remotely located products/lots. In this way, the invention provides a unique safeguard that protects patients in the event of a drug recall. This feature is particularly important with respect to narrow therapeutic index drugs that are mislabeled, subpotent or superpotent.

The delivery module 33 is designed so that each unit dose and unit-of-issue package 27 ejected from the medication carrier 26 remains fully sealed until the point of delivery to a patient. Therefore, the present invention avoids the medication contamination and degradation problems common to medication delivery systems known in the art. Alternately, if medication contamination and degradation is not of concern, a therapeutic product may be ejected from a unit dose package 27 for delivery to a patient.

A further embodiment of the invention combines an early dosing capability with the programmed regimen delivery described above. In this embodiment, the delivery module 33 has an added programmability feature by which a designated healthcare practitioner, by entering appropriate commands into the user interface 100, can obtain an early delivery of one or more unit dose packages 27 of the patient's medication or one or more therapeutic products. An example circumstance requiring this would be where the patient intends to temporarily leave his/her residence, during which time medication would still be needed, regardless of the patient being remote from the delivery module 33. In emergency situations, the medication carrier 26 may be removed from the delivery module 33 for out-of-system use. In such situations, access to the delivery module 33 may be granted to the patient or other authorized personnel by means of a security code, video/smart card or other appropriate safe guard.

As described above, the control center 101 server is connected to the non-sequential delivery module 33 via, for example, a radio frequency connection 36, wherein the control center 101 is provided with a record keeping and inventorying function. In addition to one or more clinical facilities receiving alerts from the delivery module 33, information regarding the module's 33 operation, status and unit dose/unit-of-issue package 27 inventory is automatically transmitted to the control center 101 server. This information includes, for example, a history of all delivery operations over a set time period. Reporting to the control center 101 is achieved, in part, through the use of electronic codes 29, 31 imprinted on each medication carrier 26 and on each unit dose package 27 contained therein. The electronic code 29 contains identifying information, such as, for example, the serial number, lot number, and expiration date of an individual unit dose package 27. In this way, the invention permits a continuously updated, complete inventory of each medication carrier 26 and unit dose package 27 stored within the module 33 to be maintained, and simultaneously provides a complete audit trail of each unit dose package 27 from its manufacture to delivery of the unit dose package 27 or a therapeutic product container therein to a patient.

Although the control center 101 maintains a record of the encoded information 29, 31 in its computer server, patient identifiable information is inaccessible to the control center 101 and is securely maintained within data servers physically located within the confines of each clinical facility 34. The electronic identifiers 29, 31 imprinted on the medication carrier 26 and unit dose/unit-of-issue packages 27 do not include patient identification information. Instead, the medication carrier 26 is identified according to its uniquely assigned serial number 29, while each unit dose package 27 is identified according to serial number and/or national drug code number (NDC) 31. As such, the present system is compliant with the Health Insurance Portability and Accountability Act (HIPAA).

In a further embodiment, which may be combined with the above-described reporting function, the control center 101 sends queries to the delivery module 33, e.g. via radio frequency transmission 36, requesting inventory status information. The specific apparatus and details of operation of the delivery module 33 are described further below.

Figure 1:
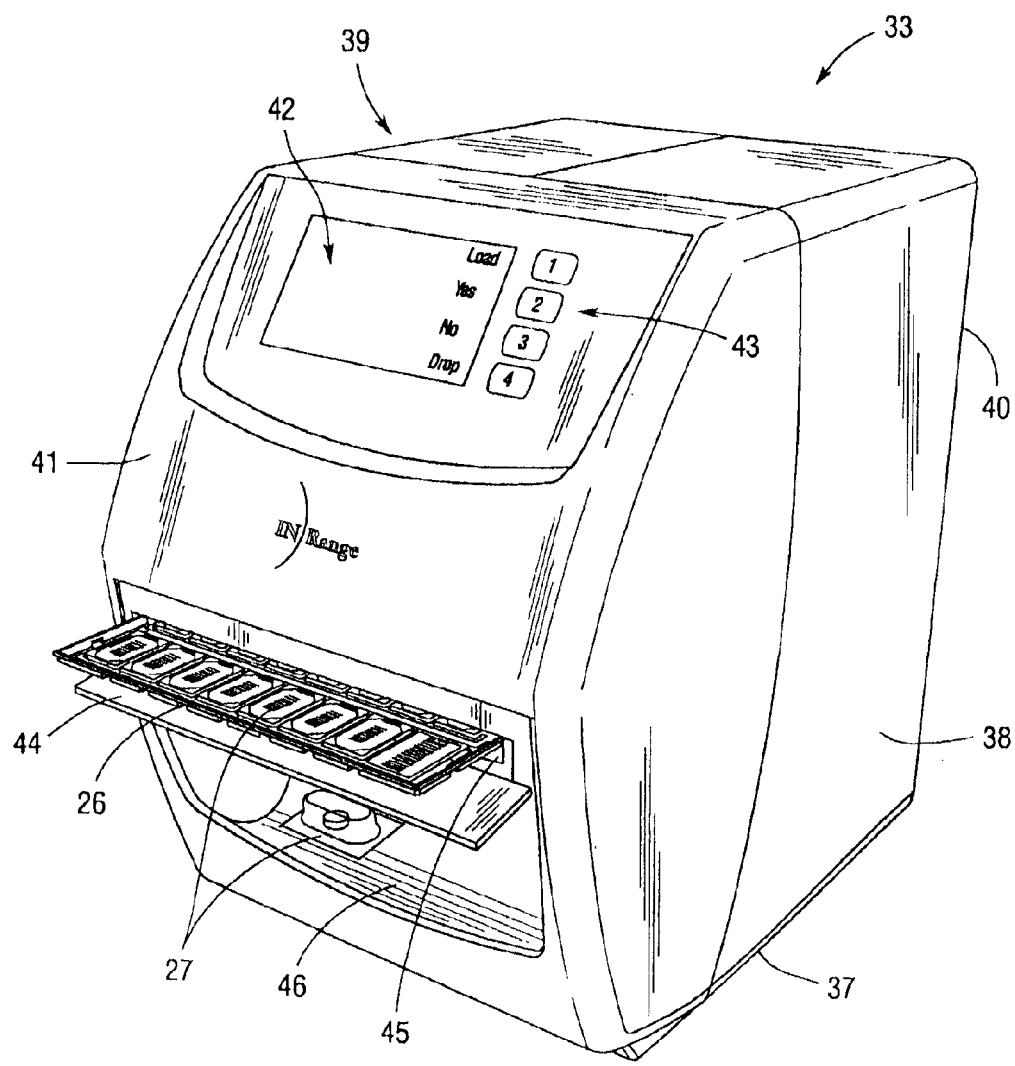
FIG. 1 is a perspective view of a non-sequential medication delivery module in accordance with one embodiment of the invention.

There is shown in FIG. 1, a delivery module 33 including a preferably plastic, box-like housing adapted to rest upon a surface and having a base 37 which supports top, side 38, 39, front 41 and rear 40 panels. The front panel 41 features an electronic display 42 on which alphanumeric information and instructions related to a particular unit dose are communicated to the patient. In an embodiment, the electronic display 42 may also display a picture of a therapeutic product prior to, during and/or after dispensing such product. The electronic display 42 may comprise, for example, a liquid crystal display, digital display or other suitable communication means. Portions of the front panel 41 are also configured with an audible alarm to alert the patient of the need to take a prescribed unit dose package 27. To allow for patient input, the front panel 41 of the housing includes control keys 43 that function as confirmation keys in accordance with the audible alarm and electronic display 42 to enable the patient to take delivery of a prescribed dosage. An audio speaker and remote communication interface may optionally be incorporated within the housing for providing additional instructions to or receiving feedback information from the patient. An alternative embodiment of the invention includes temperature control means (e.g. refrigeration means) for regulating the temperature of the module 33 as may be required for certain medications. A power outlet allows the delivery module 33 to be connected to an external AC power source.

In an embodiment, the delivery module 33 may include a battery backup that powers the unit when external power is lost. Such battery backup may be charged using external power during normal operation, as known in the art. The delivery module 33 may automatically eject one or more medication carriers 26 stored within the delivery module when external power is not present and the battery level falls below a pre-defined threshold, as described in further detail below.

In a further embodiment, the invention includes a wireless communication device worn by the patient which is communicatively linked with the delivery module 33 to provide an additional alert to some patients. The wireless communication device may be, for example, a wrist watch, pager or pendant. Alternatively, a patient may be alerted via telephone or email.

Access to the medication carriers 26 and internal hardware of the delivery module 33 is provided when the side panels 38, 39 are unlocked and open. In order to prevent unwanted access to the medication carriers 26, the side panels 38, 39 may remain locked at all times unless actuated by the controller in response to a command originating from the control center or clinical facility. Alternatively, access to the interior of the module 33 can be granted to a patient, designated caregiver or other authorized personnel by way of a smart card or security access password. The smart card or restrictive password must typically be entered prior to interacting with the delivery module in instances where one or more unit dose packages have been quarantined or recalled. In a further embodiment, the delivery module 33 includes speech recognition means for receiving and interpreting prescribed verbal commands made by the patient or other authorized personnel.

In a manner well known in the art, each constituent of the delivery module 33 is operatively coupled to and controlled by the controller, through control signals, in response to a command instruction set received from a computer server based at the control center 101. The controller transmits verification to the control center 101 that information has been received and instructions have been carried out. The controller is programmed to activate the dosage "drop" function at appropriate times based on information remotely communicated from the control center 101. In particular, the controller activates the alarm, key pad 43, wireless communication circuitry, electronic display 42, sensors, scanners 92, 98, actuators 60, 72, 91, motors 54, 73, 80, 87 and other electronic devices.

The controller can be one of several standard microprocessor-based controllers having standard type actuator or servo drive interfaces and detector inputs, or other suitable circuitry capable of employing software control, hardware control or a combination thereof. Internal memory is used to store, for example, dosage delivery instructions and logic programs. In an embodiment, and as described in further detail below, the internal memory may store medication administration information for one or more medications, such as medications to be administered to a patient on an "as needed" basis or some other basis. The management and administration of such medications may be controlled by one or more of the logic programs stored in the internal memory. The controller may be used to perform the programs stored in internal memory. Control signals travel by way of a distribution panel to and from the various components configured within the delivery module 33. FIGS. 16-20 further illustrate the controller's mode of communicating with electronic architecture of the delivery module 33.

In an embodiment, the memory may store a user-defined description for each medication stored in the delivery module 33. The user-defined description may include a commonly used or slang name for the product that enables the user to more easily identify the dose that is being administered. For example, the user may refer to particular medications as "water pill," "sleeping pill," etc. and not by the product name. Accordingly, by using the user-defined description, the user may have more complete knowledge of the medications that are being taken.

Figure 6:
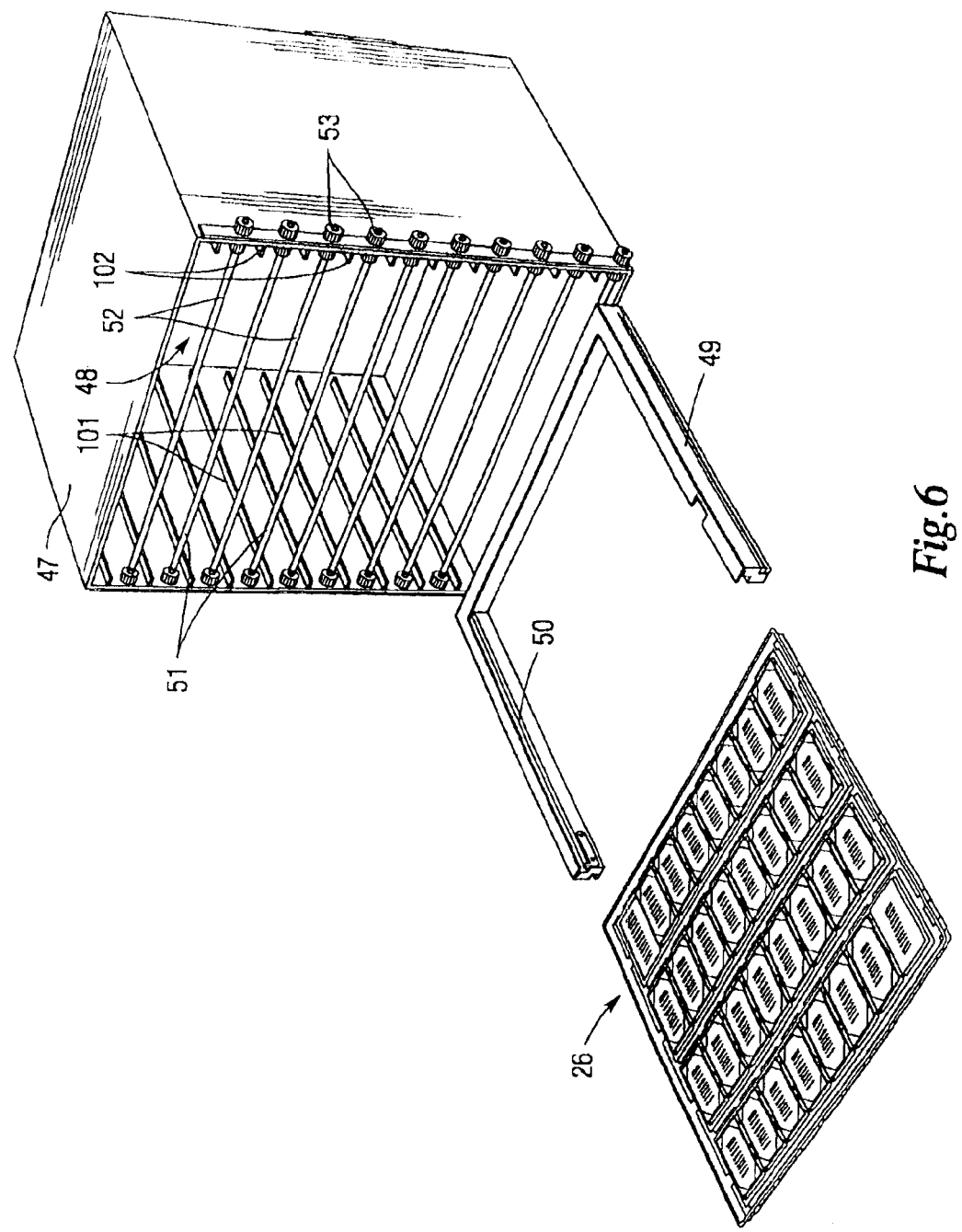
FIG. 6 is a perspective view depicting the storage apparatus in accordance with the present invention.
Figure 7:
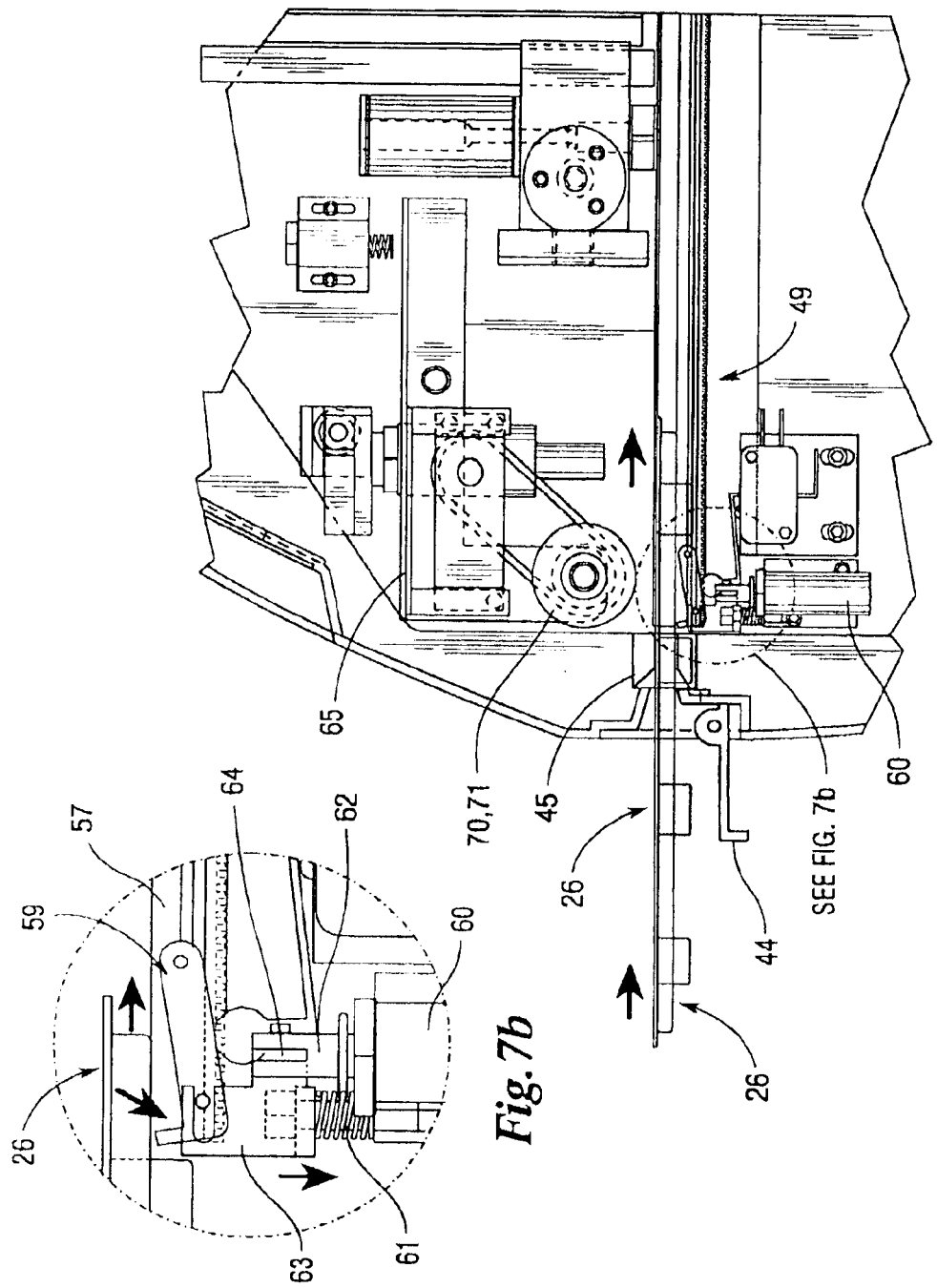
FIG. 7a is a cross-sectional view illustrating the mechanism of operation of the latch apparatus.
FIG. 7b is an exploded view of the latch apparatus in an unlocked position.
Figure 8:
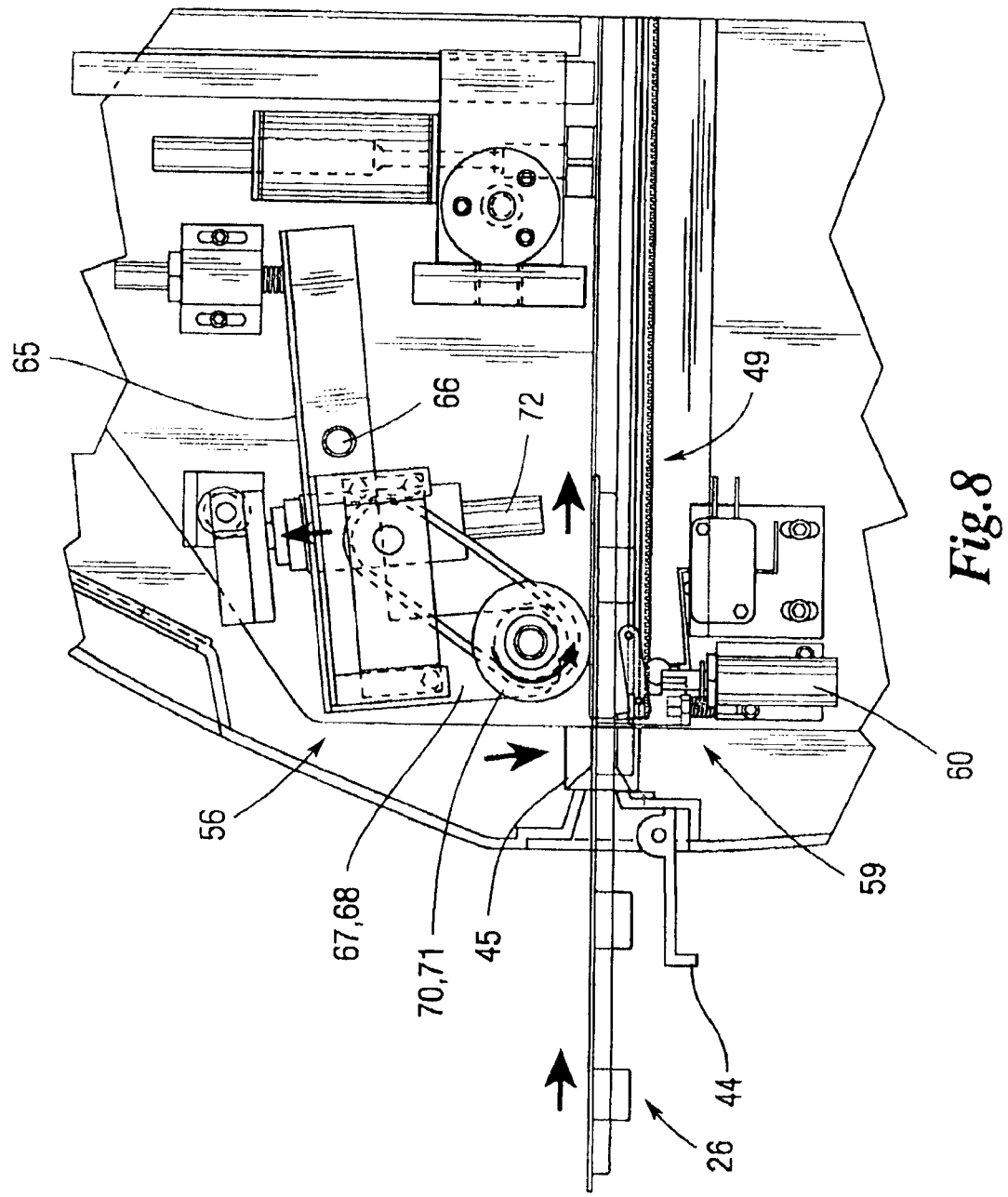
FIG. 8 is a cross-sectional view illustrating the mechanism of operation of the friction drive assembly with respect to an incoming medication carrier in accordance with an embodiment of the invention.
Figure 14:
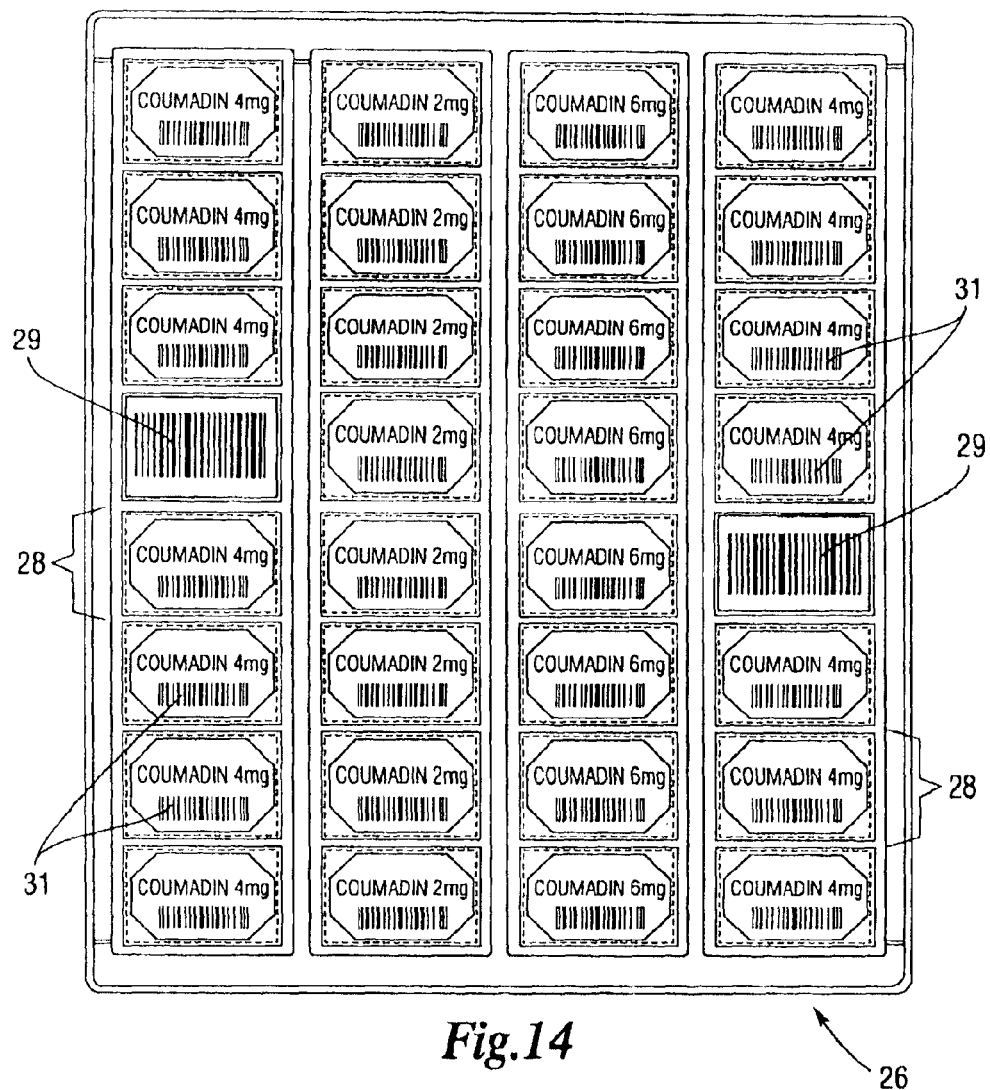
FIGS. 14 and 15 depict medication carriers containing unit dose packages of varying strengths in accordance with the present invention.

In the exemplary embodiment shown in FIG. 6, a storage elevator 47 is designed to accommodate up to ten medication carriers 26, each containing a thirty day supply of different therapeutic agents in a variety of dosage forms and strengths. The delivery module 33 is therefore capable of storing approximately three hundred unit dose and unit-of-issue packages 27 of medication. As shown in FIG. 14, each carrier 26 may include different dosage strengths for a single medication. This allows different dosage strengths to be combined to obtain a desired dosage amount. While the instant design is appropriate for use in a home, assisted living facility, long-term care facility or other residential setting, a delivery module 33 having a storage elevator 47 that can accommodate, for example, up to three hundred medication carriers 26 is preferable for use in an institutional environment (e.g. a correctional institution). The storage elevator 47 may store medication carriers 26 in any orientation, such as horizontally and/or vertically, within the scope of the present disclosure.

The location of each unit dose package 27 and medication carrier 26 within the delivery module 33 is determined, in part, through the use of electronic identifier codes 29, 31 or other inventory code systems. The electronic codes 29, 31 imprinted on the medication carriers 26 and individual unit dose packages 27 are scanned by an electronic code reader 98 as each medication carrier 26 is loaded into the delivery module 33. The encoded information is transmitted to the control center 101 computer server, where it is associated with a stored database record by the control software 35. This information allows a healthcare practitioner to actively treat a patient remotely located from a clinical facility.

The healthcare practitioner, by way of the menu-driven user interface 100, simply retrieves and reviews the inventory of unit dose and unit-of-issue packages 27 stored within the patient's delivery module 33 and selects an appropriate dosage within the parameters prescribed for the patient. Upon receipt of a command signal from the control center 101 computer server, the patient's delivery module 33 expels the selected dosage based on the electronic identifiers 29, 31 and position coordinates of such dosage within the delivery module 33.

As shown in FIG. 6, the storage elevator 47 includes a cavity which is partitioned into multiple storage bays 48 disposed on separate levels of the elevator 47. Each storage bay 48 has a horizontal opening of a sufficient size to provide the range of motion necessary to allow a transport carriage 49 stored within the bay 48 to be moved in both forward and rearward directions. The transport carriage 49 includes an open-ended frame that defines a fluting 50 disposed along the length of said frame, such that peripheral edges of the medication carrier 26 can be readily fitted within said fluting 50. The carriage 49 is supported by a horizontal railing 51 which extends along the interior surfaces of the storage bay 48. Ends of the railing 51 terminate about a concentric shaft 52 that is generally flush with the opening of the bay 48.

Rotatable spur gears or sprocket drives 53 are mounted at both ends of the shaft 52 so as to come into contact with and suitably engage corresponding stationary gears that protrude from peripheral edges of the carriage 49 for effecting forward and rearward movement of the transport carriage 49. The spur gears 53 are rotated by a drive motor (e.g. a servo motor) 54 in a controlled fashion, in response to signals from the controller. While a gear assembly is described herein for moving the transport carriage 49 in both forward and rearward directions, it should be understood that any suitable drive assembly may be employed. Location markers are provided along an outer edge of the transport carriage, which indicate the exact horizontal position ("y-axis") of the carriage 49 and integral medication carrier 26. This information is monitored by the controller through a feedback loop arrangement. Once the controller determines that an appropriate number of markers have been scanned by an electronic code reader 98 mounted within the storage elevator, the drive motor 54 is disengaged. The transport carriage 49 normally resides within the storage bay 48 (the "home position" 99) until a prescribed dosage is to be taken or a medication carrier 26 is to be replenished.

Figure 9:
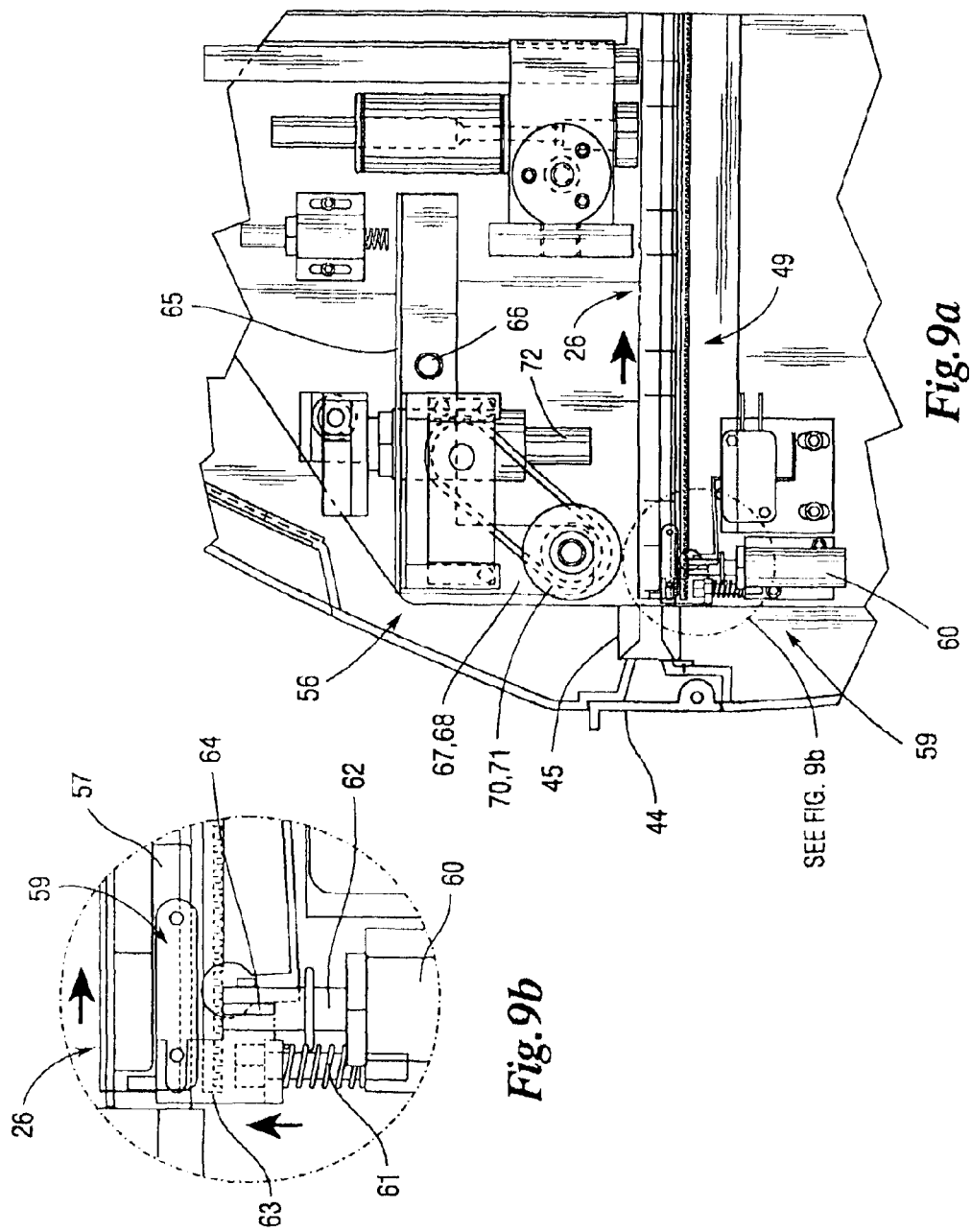
FIG. 9a is a cross-sectional view of a medication carrier fully inserted into the delivery module.
FIG. 9b is an exploded view of the latch apparatus in a locked position.
Figure 10:
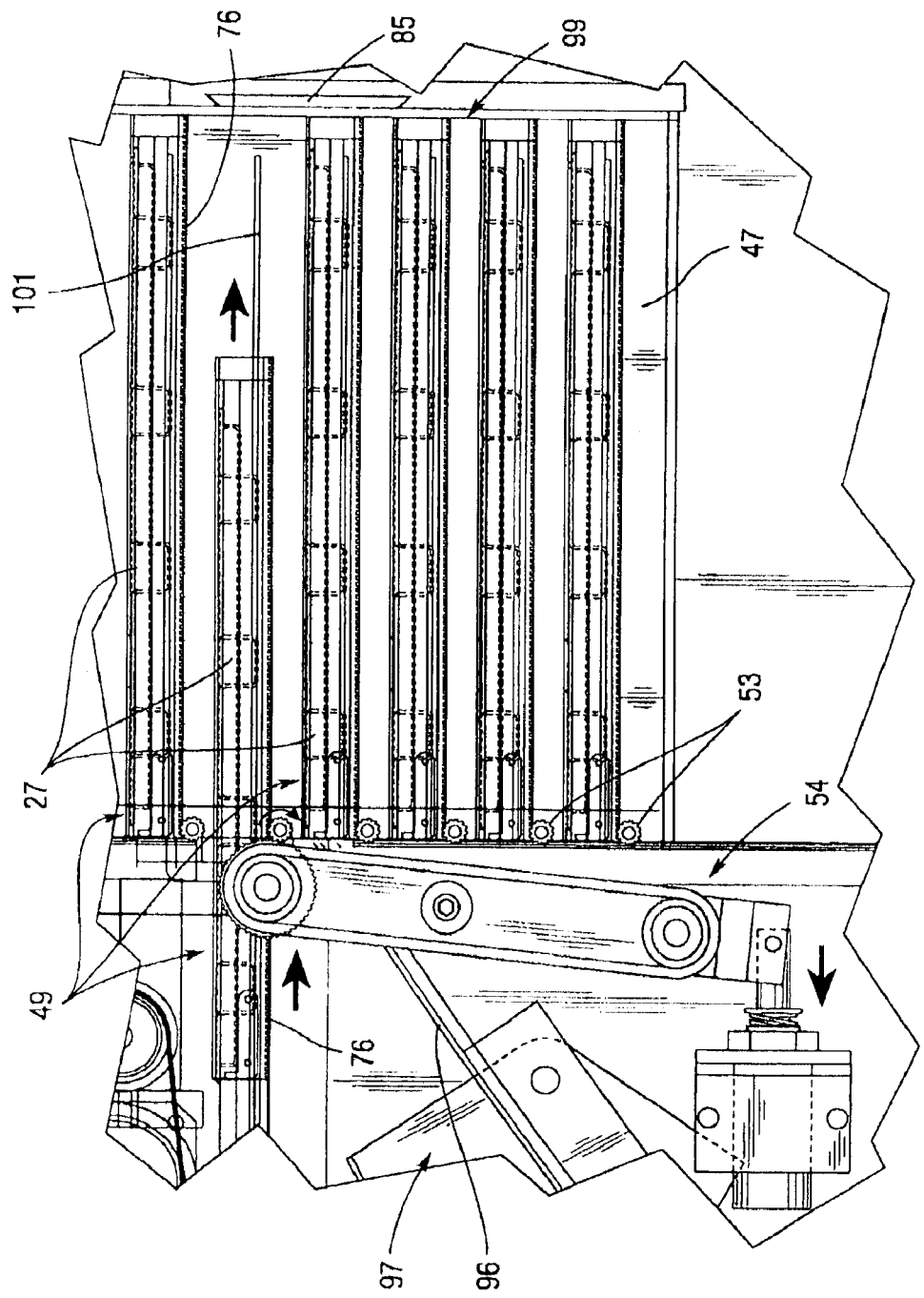
FIG. 10 is a cross-sectional view illustrating the mechanism of operation of the carriage drive assembly in accordance with one embodiment of the invention.

As discussed above, the transport carriage 49 is adapted for horizontal (x-axis) movement between rear and forward positions (FIGS. 9 and 10). Upon receiving a "dose delivery" signal from the controller, the drive motor 54 rotates spur gears 53 of the desired storage bay 48, such that the carriage 49 and integral medication carrier 26 are moved in a forward direction, sufficiently to clear the opening of the storage bay 48, and achieve a "delivery ready" position in proximity to a vertically disposed plunger 93. Likewise, during a carrier 26 unloading operation, the drive motor 54 advances the transport carriage 49 to a forward position in which a portion of the carriage extends beyond the opening of the storage bay 48. At such point, additional forward movement of the carriage 49 is accomplished through the action of a friction drive assembly 56. Sensors are located to monitor the movement and alignment of the transport carriage 49 as it is moved in both forward and rearward directions.

Referring now to FIG. 1, a handle equipped loading door 44 and insertion/retrieval slot 45 are provided in the front panel 41 of the housing. When the door 44 is open, the slot 45 is accessible for inserting a medication carrier 26 filled with unit dose packages 27 of prescription or non-prescription medications and supplies. Adjoining the interior surface of the front panel 41 is a loading area with components for receiving the medication carrier 26 into the delivery module 33. Each of these components will be described in detail below in reference to FIGS. 7-10 and 17.

A sensor is located in the loading area to detect the presence of an incoming medication carrier 26. The sensor is, for example, a micro-switch, optical eye or other electrical contact suitable for monitoring the orientation of the medication carrier 26 relative to a limit switch embedded within the loading area. When the sensor detects that the medication carrier 26 has been fully inserted, through activation of the limit switch, a friction drive assembly 56 is immediately actuated.

A pair of parallel guide rails 57, 58 are horizontally mounted to the side panels 38, 39 to enable the transport carriage 49 and an incoming medication carrier 26 to be properly aligned and dispatched through the loading area of the housing to the storage elevator 47. One end of each of the guide rails 57, 58 abuts the interior surface of the front panel 41 such that the guide rails 57, 58 at that point intersect the insertion/retrieval slot 45 configured in the front panel. The guide rails 57, 58 extend through the midsection of the housing and terminate in front of the storage elevator 47.

Latch apparatus 59 is configured to allow the incoming medication carrier 26 to be secured onto the transport carriage 49 and dispatched through the loading area. The latch apparatus is 59 operatively coupled to a solenoid 60, or other electromechanical actuator, which is mounted to a side panel 38 of the housing by a bracket and screws, or similar hardware. A retractable spring 61 and plunger 62 are provided at the upper end of the solenoid 60, the plunger 62 including a groove 64 in a top portion thereof which supports one end of the latch apparatus 59. An opposite end of the latch apparatus 59 features an angle 63 that abuts peripheral edges of the guide rail 57 and vertically protrudes above the guide rail 57 so as to obstruct the loading pathway.

Upon actuation by the controller, the solenoid 60 biases the spring 61 and plunger 62 downward. This, in turn, lowers the latch apparatus 59 to a position below the guide rail 57 so that the transport carriage 49 can be positioned on the exposed, upper surface of the guide rails 57, 58 for movement beyond the storage bay 48 to a "prime" position, planate with the front panel 41 of the housing. The solenoid 60 retains the latch apparatus 59 in this suppressed orientation while the medication carrier 26 is loaded into the delivery module 33, through the insertion/retrieval slot 45. As the incoming medication carrier 26 enters the loading area, the carrier's 26 peripheral edges automatically slot into the carriage fluting 50 so as to form an integral unit therewith for transport to a storage bay 48. At such time, the latch apparatus 59 is returned to its initial, indexed position against the peripheral edges of the guide rail 57 under the force of the solenoid 60.

A short distance above the guide rails 57, 58 is a swivel bracket 65 which is mounted to and pivots about a horizontal rod 66 attached to the side panels 38, 39 of the housing. The bracket 65 is configured for mounting a friction drive assembly 56 that controls movement of the transport carriage 49 and medication carrier 26 through the loading area. The bracket 65 forms an arch about its anterior, peripheral edges which features opposing vertical flanges 67, 68. The flanges permit a drive shaft 69 and a pair of drive wheels 70, 71, spaced substantially equally apart, to be conveniently attached to the bracket 65. It should be noted that the drive wheels 70, 71 are preferably made of rubber, soft, compressible polyurethane foam or other material that is capable of gripping a medication carrier 26 containing individual unit dose packages 27 without breaking or damaging the medication contained therein. Vertically suspended from an opening in a top surface of the bracket 65, directly above a guide rail 57, is an electromechanical actuator 72 which distends to mate with and exert pressure on an upper surface of the medication carrier 26, in response to a control signal. This action causes the bracket 65 to pivot downwardly, so as to assume an angled position and lower the drive wheels 70, 71 onto the upper surface of the transport carriage 49.

A drive motor 73 such as, for example, a servo motor, is secured to the swivel bracket 65 and operatively coupled to a pulley system 74. The pulley 74 is mounted in perpendicular relation to the drive shaft 69 and is moveable relative thereto by means of the motor 73. Upon actuation, the motor 73 rotates the pulley 74, which in turn, rotates the drive wheels 70, 71. The rotary motion of the drive wheels 70, 71 directs the medication carrier 26 and transport carriage 49 inwardly, toward the storage elevator 47. Once the transport carriage 49 and carrier 26 reach the opening of the vacant storage bay 48, the carriage's 49 protruding gear elements engage rotatable spur gears or sprocket drives 53 mounted about the opening of the storage bay 48, moving the carriage 49 and medication carrier 26 toward the rear of the storage bay 48. When the sensor detects that the medication carrier 26 and transport carriage 49 have arrived at their home position 99, the controller disengages the motor 73 and drive wheels 70, 71.

Figure 3:
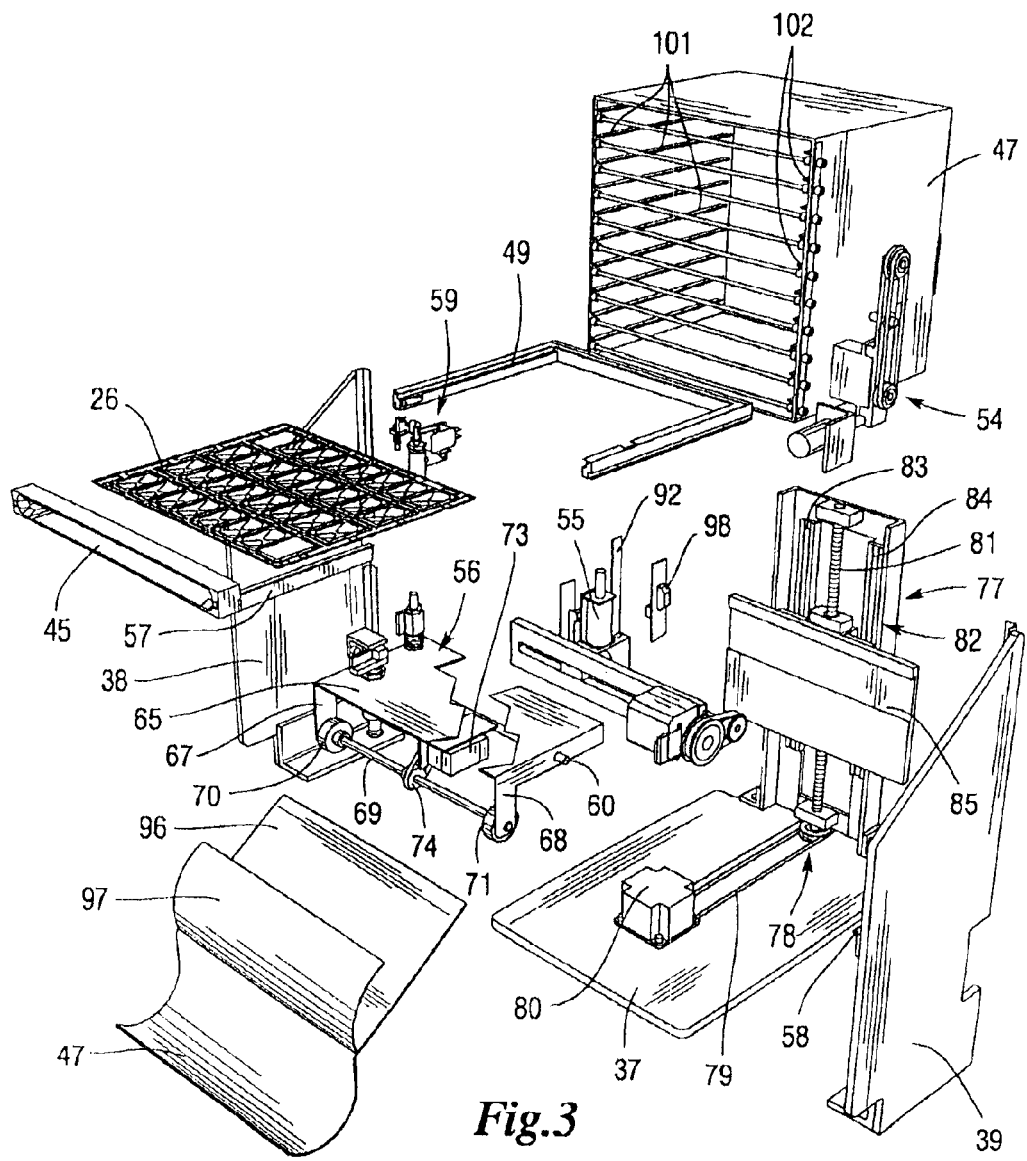
FIG. 3 is an assembly view of one example of a non-sequential medication delivery module in accordance with an embodiment of the invention.
Figure 4:
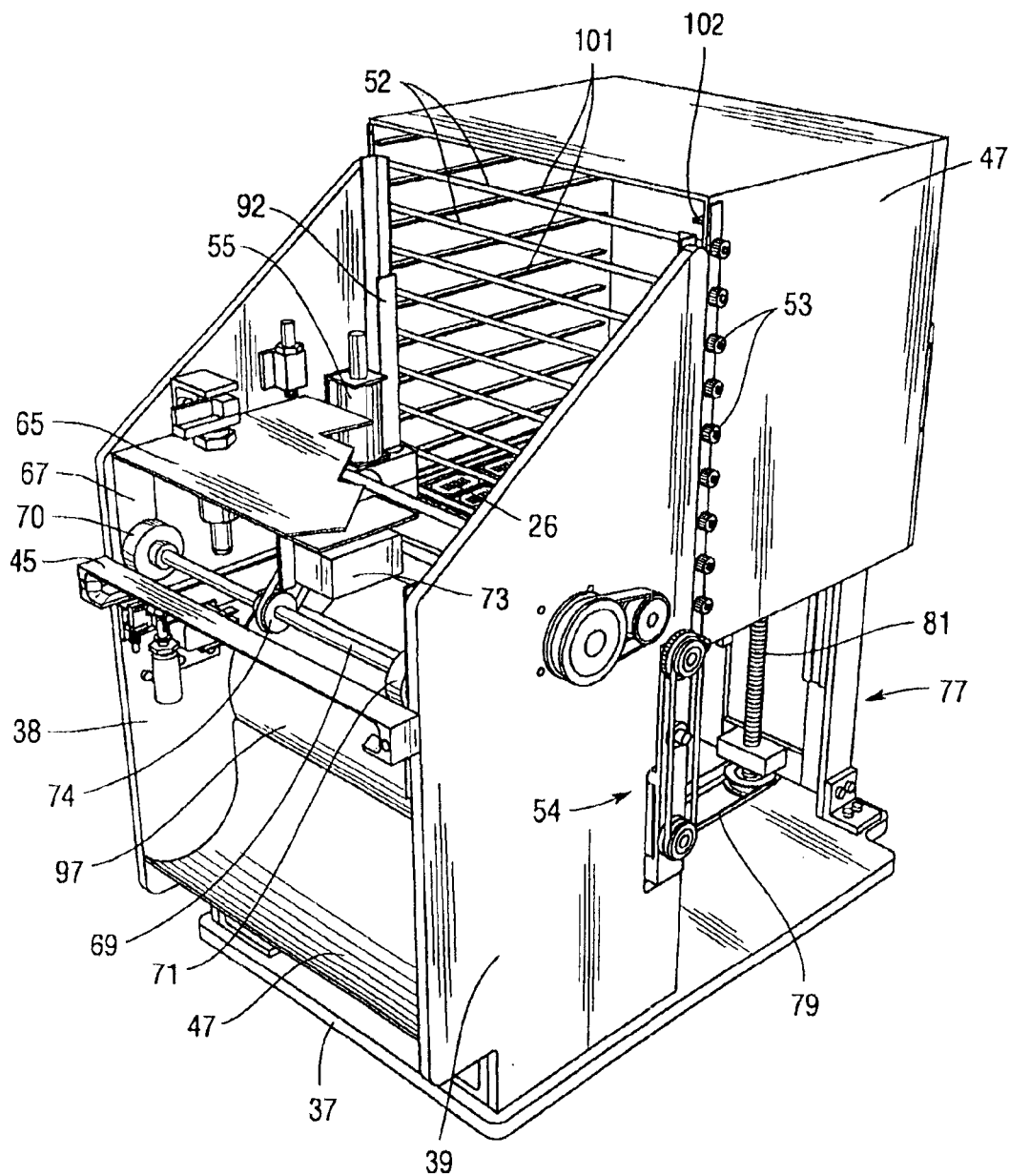
FIGS. 4 and 5 are cutaway views showing the friction drive assembly and storage elevator in accordance with one embodiment of the invention.
Figure 5:
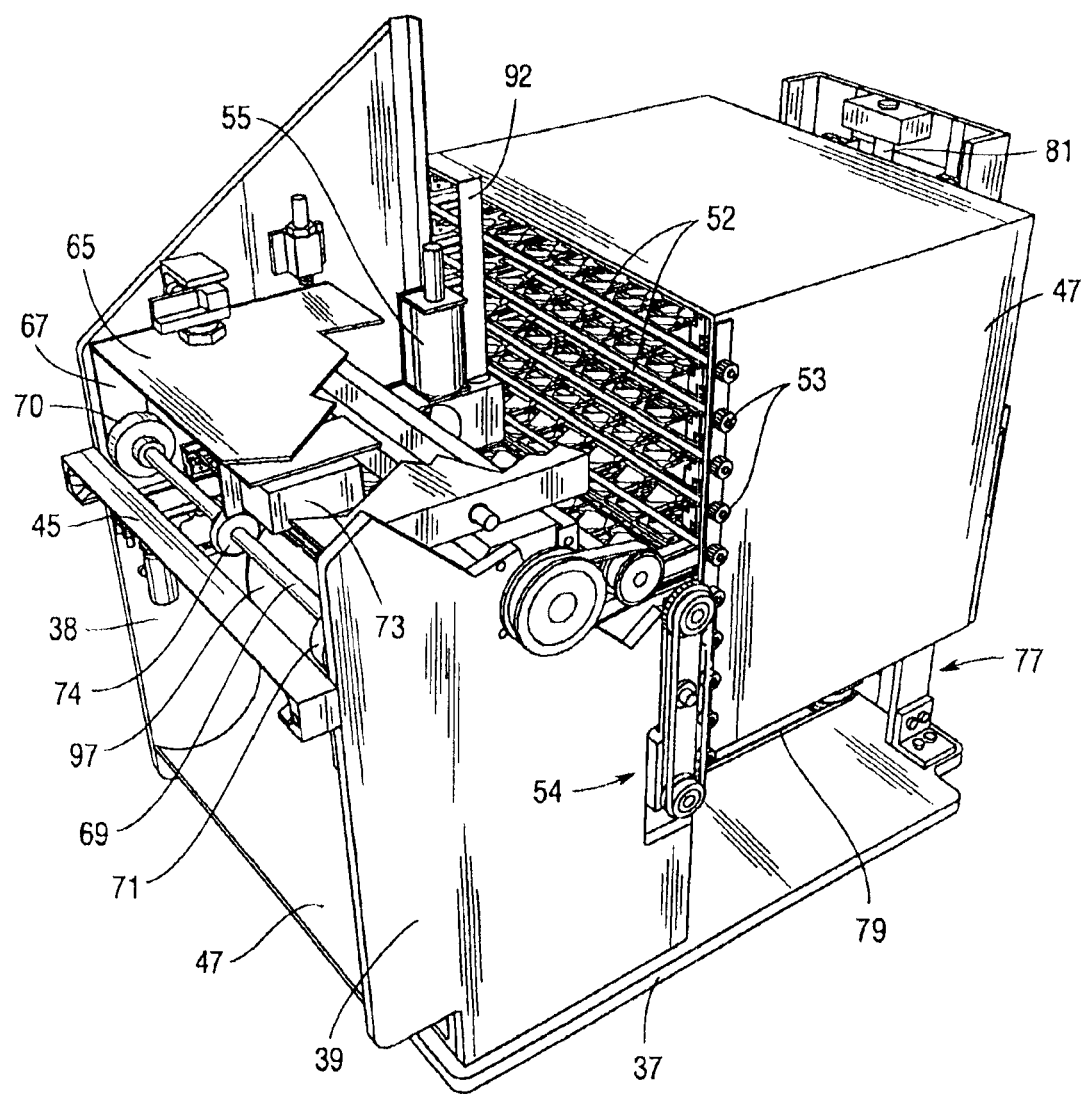
Figure 11:
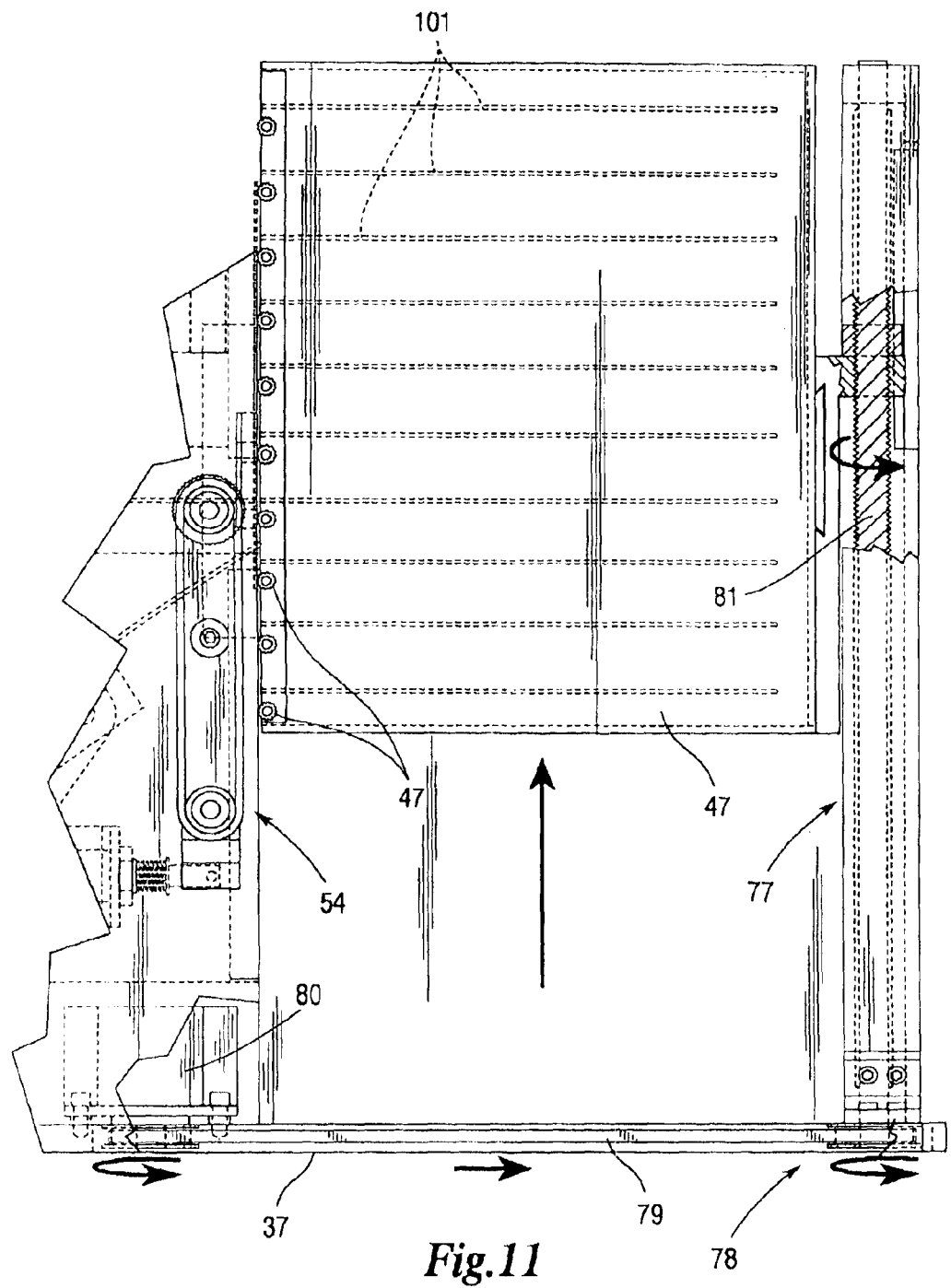
FIG. 11 is a cross-sectional view illustrating the operation of the storage elevator and associated linear motion assembly in accordance with an embodiment of the invention.
Figure 18:
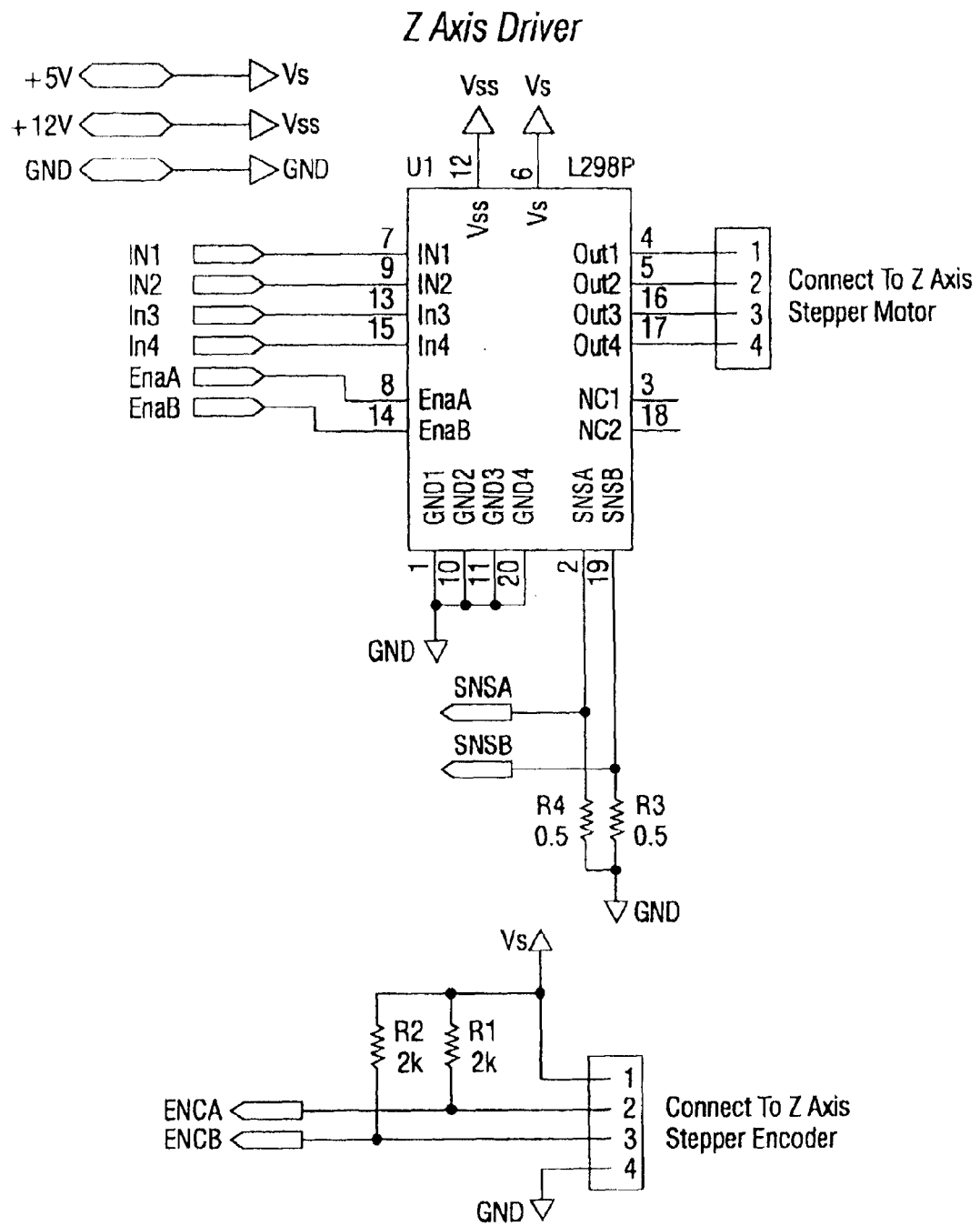
Figure 19:
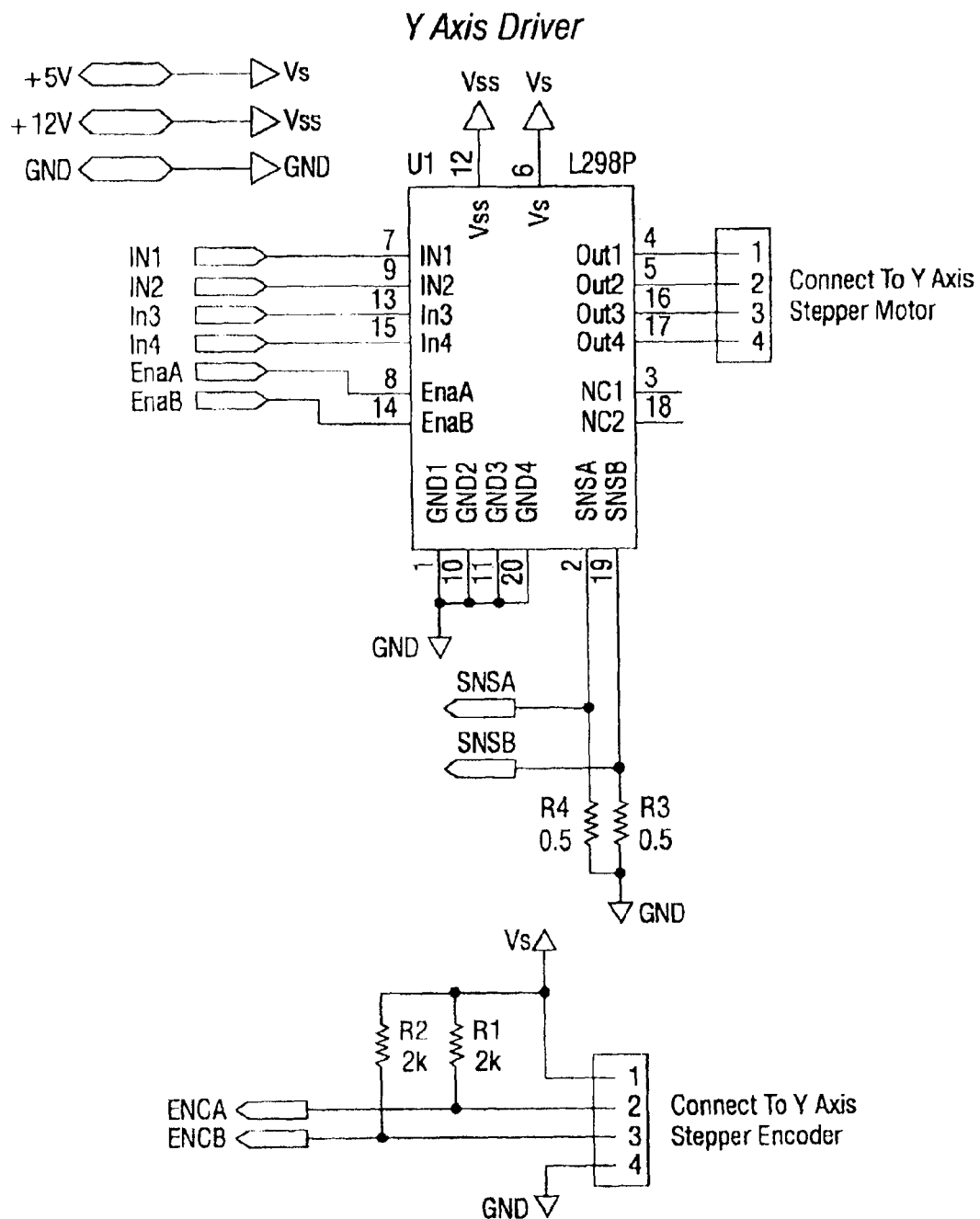
Figure 20:
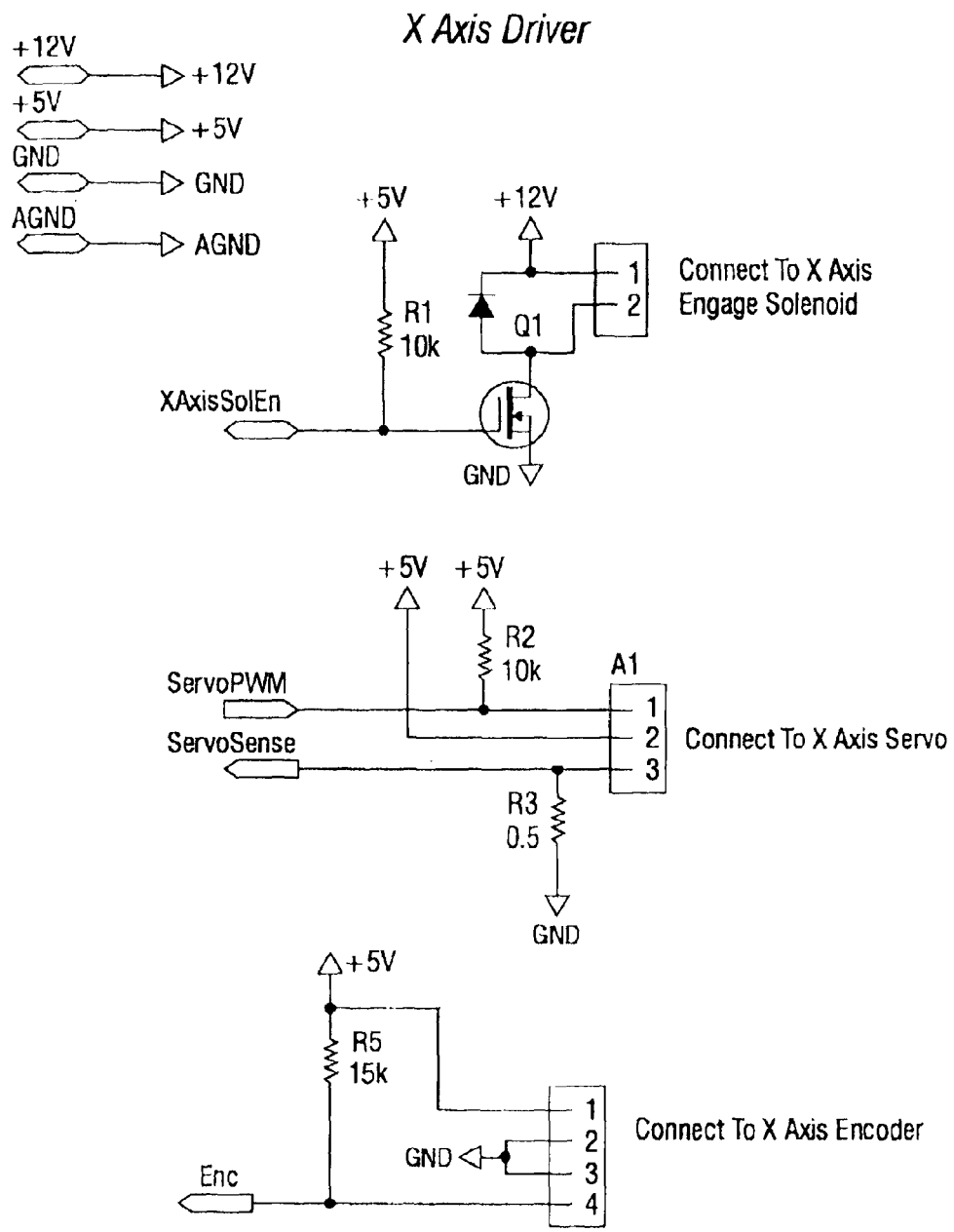

Referring now to FIGS. 3 and 11, the storage elevator 47 is operably connected to an elevator bracket 77 which moves the elevator 47 from a rest position, in the lower section of the housing, to an operative position, adjacent the delivery area, along a vertical ("z") axis. Vertical movement is achieved by means of a linear motion assembly 78 such as a gear belt and lead screw 81, pulley, or other standard drive component capable of converting rotary motion from a drive motor to linear motion. In the exemplary embodiment, a timing belt and lead screw 81 are rotated by a stepper motor 80 mounted to the base 37 of the housing. The motor 80 is actuated in accordance with electrical signals received from the controller (FIG. 18). The base 37 also accommodates the controller and a battery pack (not shown).

The elevator bracket 77 generally spans the length of the delivery module 33 so as to allow the storage elevator 47 to be raised and lowered to a desired level for accessing a medication carrier 26 stored within a particular storage bay 48. The elevator bracket 77 includes a channel housing 82 having a hollow portion in the center thereof and corresponding openings in upper and lower surfaces through which the lead screw 81 and one or more guide rods 83, 84 vertically extend. In general, the channel housing 82 serves as a frame for supporting the various components of the elevator bracket 77 and imparting stability to the guide rods 83, 84, or other suitable vertical shaft, such as, for example, an adjustable slide and block assembly. The channel housing 82 is vertically mounted to the base 37 of the delivery module 33, adjacent the rear panel 40, and is secured in place by bolts, casters or other suitable hardware.

Also featured in the hollow portion of the channel housing 82 are upper and lower cross members 102, 26, mounted in horizontal relation to the guide rods 83, 84 and lead screw 81, and interpolated by through holes in which the guide rods 83, 84 and lead screw 81, respectively, are slidably disposed. The cross members 102, 26 move along the perpendicular guide rods 83, 84 by operation of the motor 80 and lead screw assembly 81. This configuration permits a carrier plate 85 attached to the anterior surface of the cross members 102, 26 to be raised and lowered, in accordance with the direction of motion of the lead screw 81. The carrier plate 85 generally extends across the width of the housing and serves as a platform for attachment and support of the storage elevator 47. The storage elevator 47 includes a metal protrusion that projects outwardly from the rear wall of the elevator. The protrusion is suitably shaped to conform to a corresponding depression in the carrier plate 85 so that the carrier plate and storage elevator 47 can be conveniently and securely attached thereby.

The position of the storage elevator 47 within the housing is determined by means of an encoder located in the drive motor 80 which relays positional information to the controller in the form of electrical pulses as the motor 80 rotates (FIG. 11). Once the appropriate number of pulses is emitted by the encoder, signaling that the storage elevator 47 has attained the correct position for accessing a desired medication carrier 26, the controller disengages the motor 80. In this manner, the storage elevator 47 can be raised or lowered to an appropriate level within the housing.

Figure 12A:
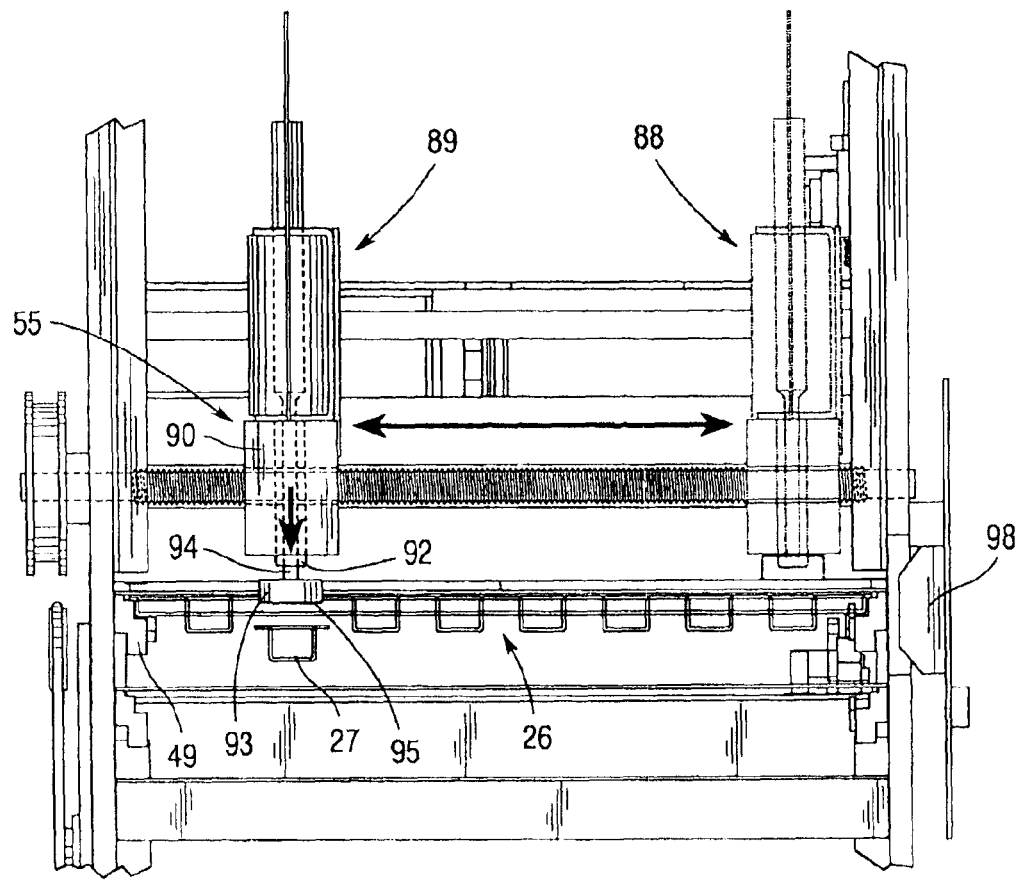
FIG. 12a is a cross-sectional view showing the ejector assembly in a rest position and operative position for ejecting a unit dose package from a medication carrier in accordance with one embodiment of the invention.
Figure 12B:
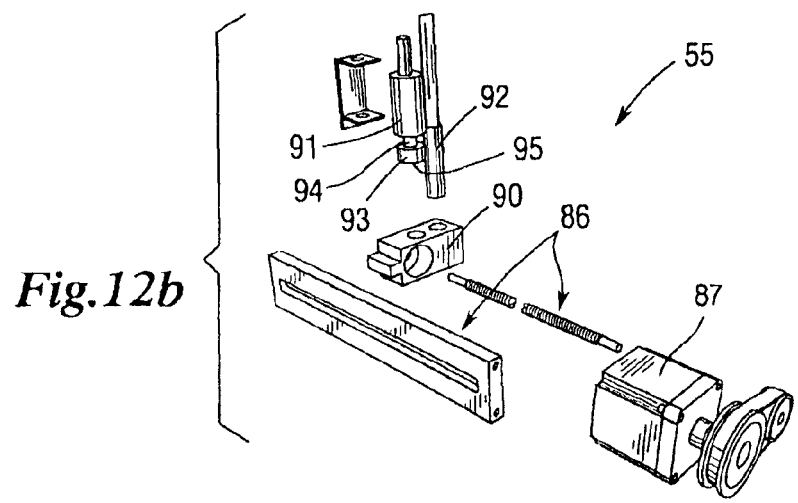
FIG. 12b is an assembly view of the ejector assembly shown in FIG. 12a in accordance with an embodiment of the invention.
Figure 13:
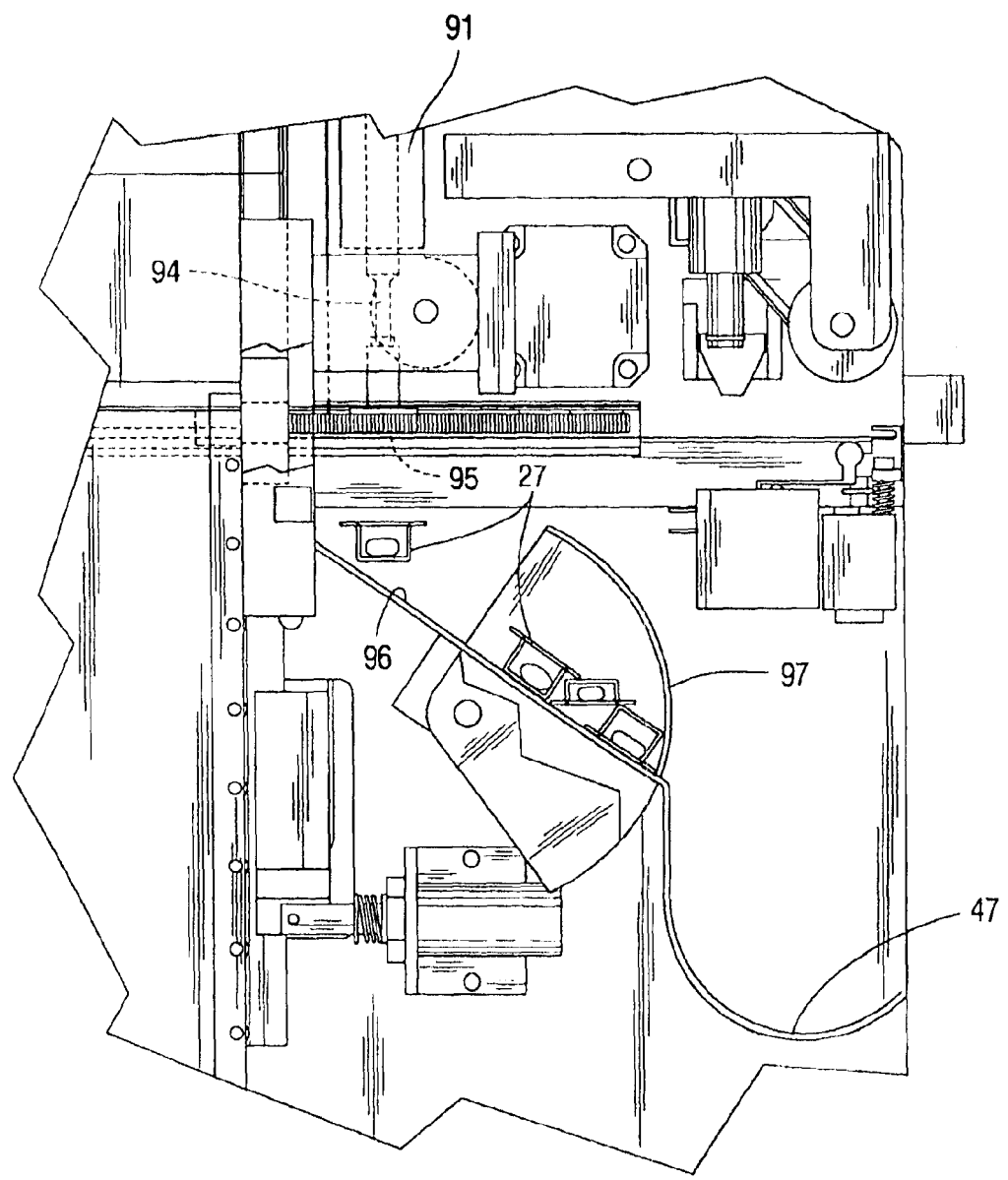
FIG. 13 is a cross-sectional view showing the ejected unit dose package of FIG. 12a along with previously ejected unit dose packages.

Referring now to FIG. 12, an ejector assembly 55 is provided for releasing a prescribed unit dose/unit-of-issue therapy 27 to a patient at a predetermined time, in accordance with a drop command originating from the clinical software 32. The ejector assembly 55 is mounted on and moves along a horizontal slide ("x-axis") 86 which extends across the width of the delivery module 33, between the storage elevator 47 and loading area. During dose delivery, the ejector assembly 55 is moved from a rest position 88 into an operative position 89 suitable for achieving contact with a desired unit dose package 27. Identification of the correct unit dose package 27 is determined by the control software 35, which correlates each instruction from a healthcare practitioner with a specific unit dose package 27. The ejector assembly 55 includes a sensor, electronic code scanner 92, electromechanical actuator 91, and a plunger 93, wherein each component is vertically positioned within and supported by a receptacle 90 that is slidably attached to the horizontal slide 86. The ejector assembly 55 is moved in the x-direction by means of a motor 87 operatively coupled to and under the control of the controller. The electromechanical drives on the ejector/reader (y-axis), elevator (z-axis), and carriage (x-axis) are specifically designed for non-slip reliability.

A sensor (not shown), such as an optical sensor, is located to sense the movement and alignment of the ejector assembly 55 as it is moved into an operative position 89 in proximity to the desired unit dose package 27. The sensor ensures that such operative position 89 corresponds to the designated position coordinates of the selected therapy. This is accomplished by means of a feedback loop arrangement with the controller.

An electronic code scanner 92, such as a bar code reader, optical recognition reader, radio frequency identification tag reader or other similar device, is operatively coupled to and suspended from a lower end of the actuator 91 so that the head of the scanner is positioned in proximity to upwardly facing electronic identifier codes 29, 31 imprinted on the medication carrier 26 and seal of the desired unit dose package 27. The scanner 92 detects removal of a unit dose package 27 from a stall 28 of the medication carrier 26, through interruption of a light beam emitted therefrom, and thereafter, transmits a signal to the controller confirming such removal. An electronic imaging device (e.g. a camera) may also be incorporated to provide visual feedback that the desired medication is suitably discharged from the medication carrier 26.

A plunger 93, having an elongated shaft 94, is mounted for vertical movement between raised and lowered positions by means of a linear actuator 91 attached to the shaft 94 thereof. The lowermost end of the shaft 94 terminates in a flat, compacting edge 95 which is suspended directly above the stall 28 of the medication carrier 26 containing the desired unit dose package 27. Upon receipt of a control signal, the actuator 91 forces the plunger 93 downward such that the plunger 93 achieves contact with the encoded surface of the unit dose package 27, pushing the package 27 through the opening of the stall 28. Alternately, the actuator 91 forces the plunger 93 downward such that the plunger 93 achieves contact with the non-encoded surface of the unit dose package 27, pushing a therapeutic product contained therein out of the unit dose package 27.

A ramp 96 or chute is mounted to the side panels 38, 39 of the housing beneath the ejector assembly 55. The ramp 96 is generally a flat surface which extends across the width of the delivery module 33 and slopes downwardly so as to channel the ejected unit dose package 27 or therapeutic product to a rotatable guard 97 located at the end of the ramp 96. The guard 97 is used for temporarily retaining an ejected unit dose package 27 until each of the medications within the patient's regimen is expelled. Once each of the prescribed medications is expelled, the guard 97 is rotated away from its initial position by a servo motor, releasing the ejected unit dose packages 27 or therapeutic products into a receiving area 46 for collection by the patient.

The receiving area 46 is an open section configured in the front panel 41 of the housing where the medication is retrieved by a patient for consumption. Medication related information, such as the type, quantity and dosage of the discharged unit dose packages 27 or therapeutic products, appears on the electronic display 42. Alternatively, or in addition, a healthcare practitioner may communicate directly with the patient by providing instructions, additional information, or receiving feedback from the patient through the remote communication interface and display 42, keypad 43 or speaker.

Figure 23:
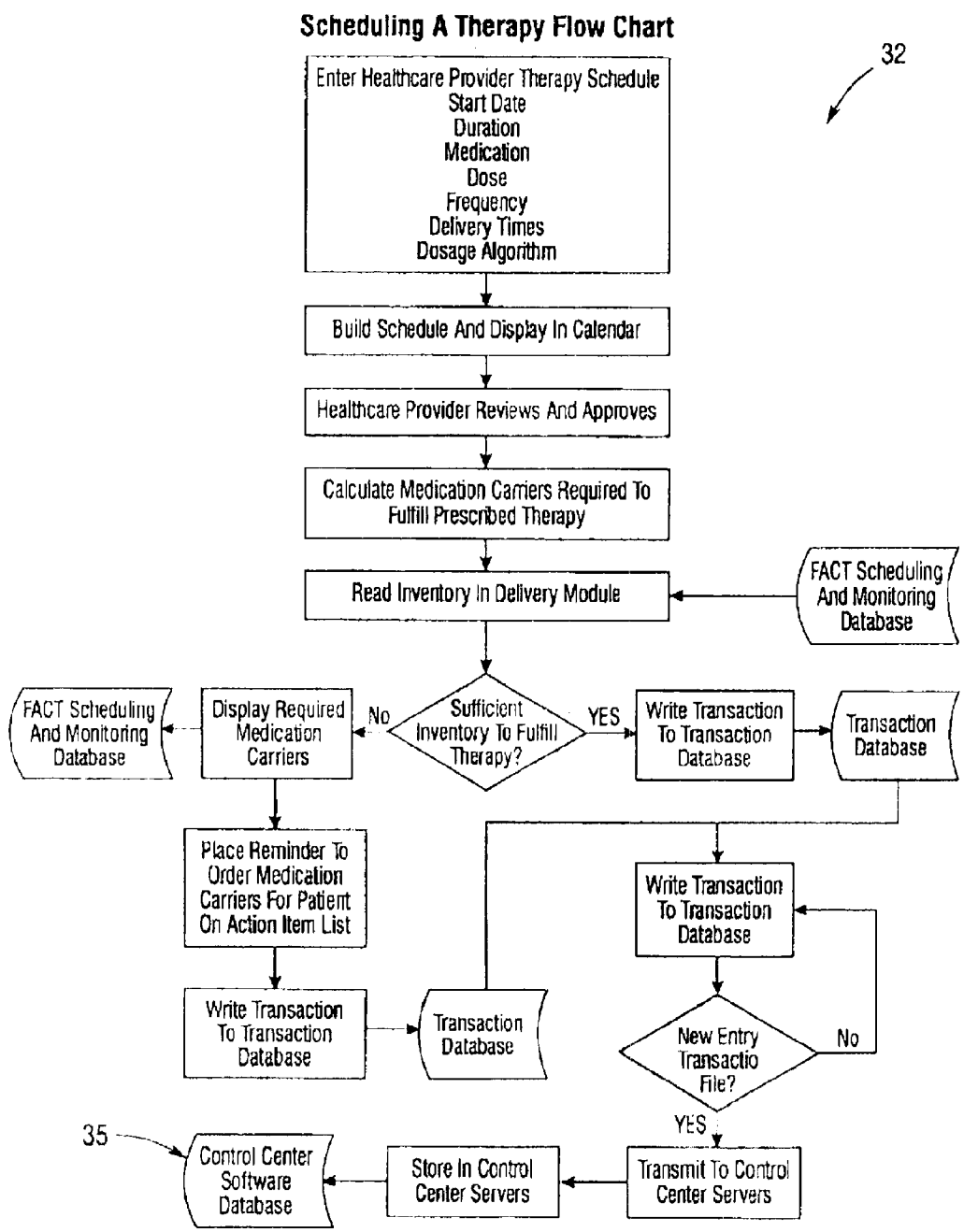
Figure 24A:
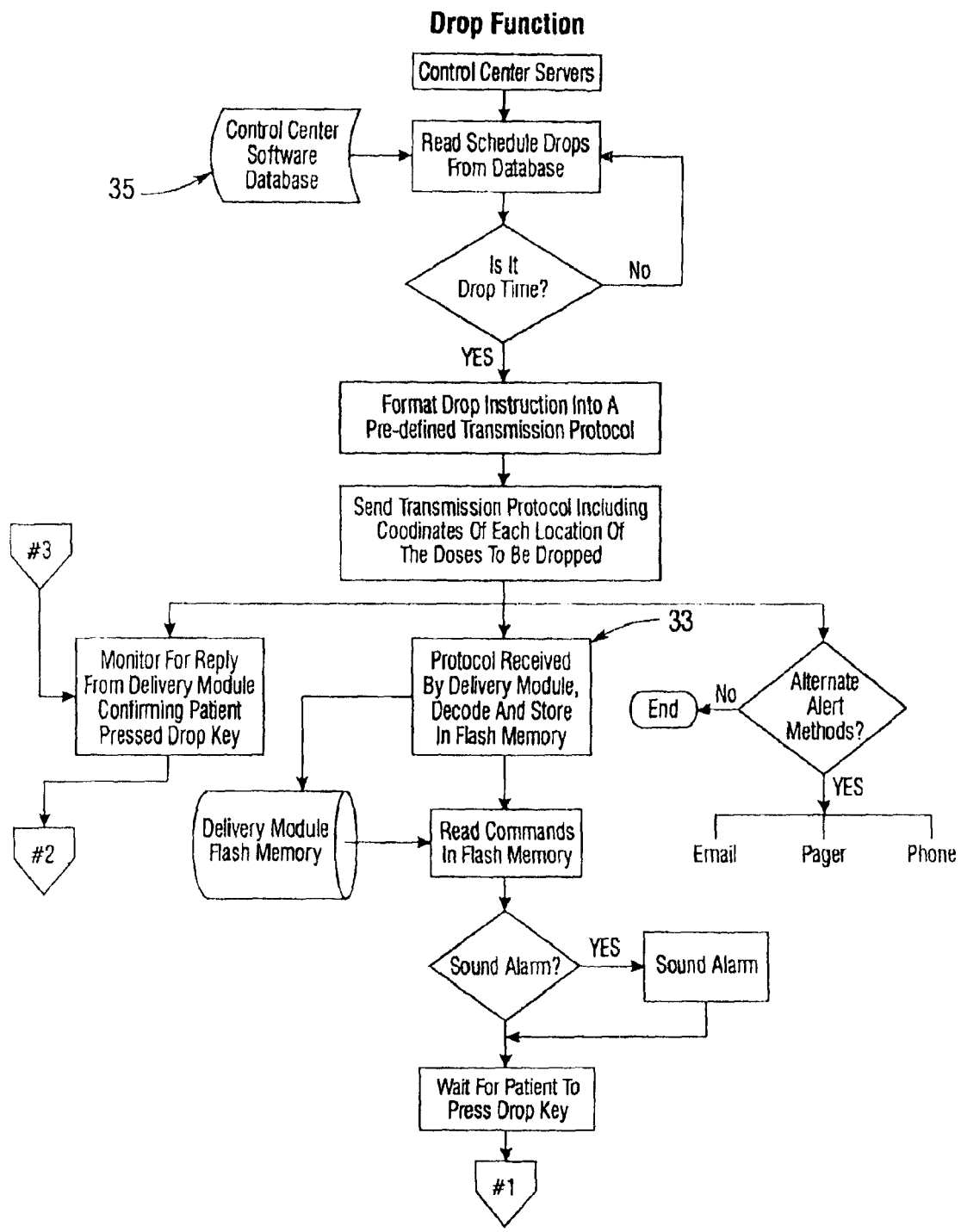
FIG. 24 is a flow chart illustrating the process that may take place to suitably deliver a prescribed dosage to a patient in accordance with an embodiment of the invention.
Figure 24B:
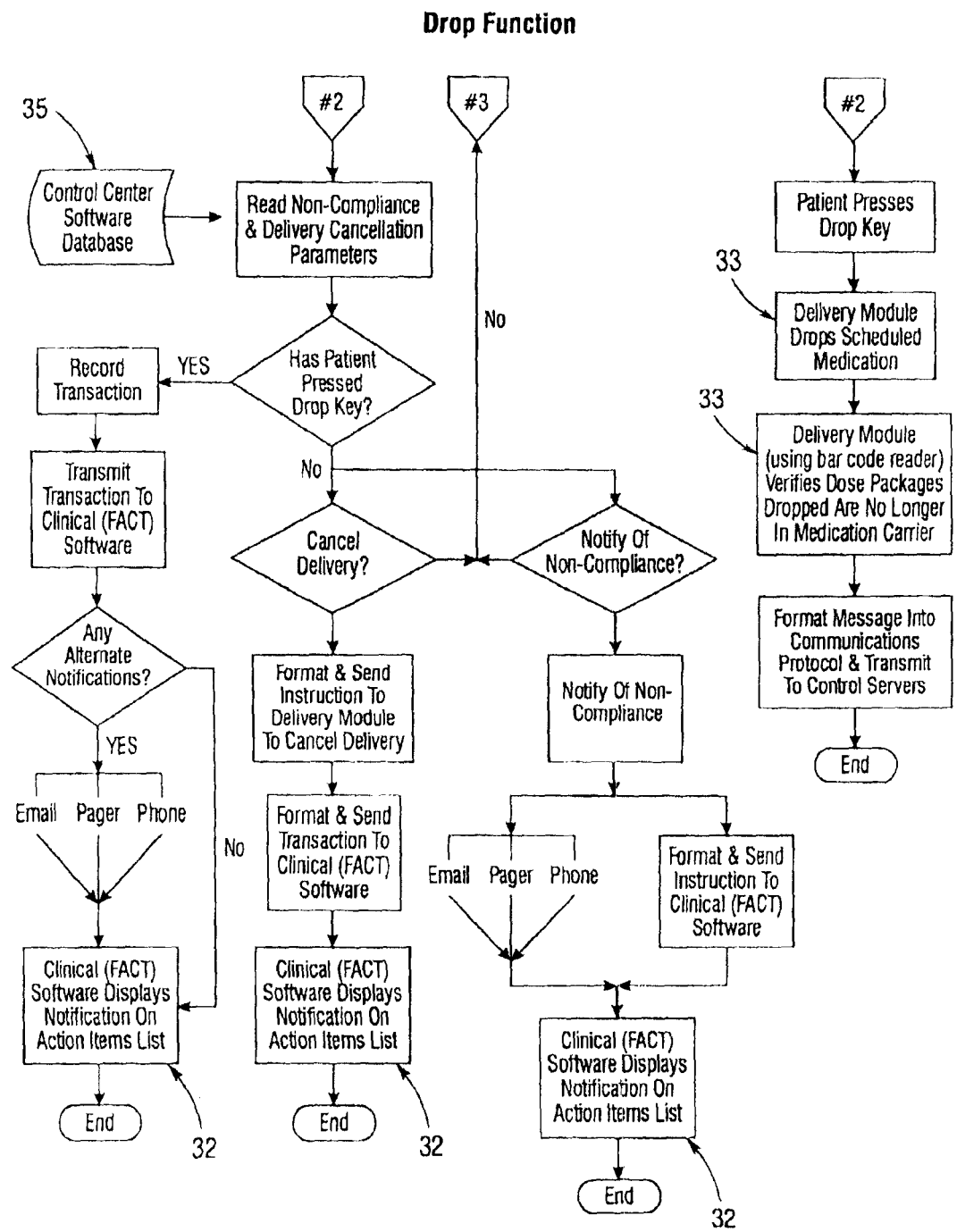

FIGS. 23 and 24 are flowcharts of the functional steps employed in the non-sequential delivery sequence of the present invention to deliver a desired therapeutic dosage to a patient as part of the same prescription period.

As mentioned above, a significant aspect of the instant invention is that it enables a physician, pharmacist, nurse or other healthcare practitioner remotely located from a patient to deliver any of the unit dose and unit-of-issue packages 27 (or therapeutic products contained therein) stored within the delivery module 33 to the patient, in non-consecutive order, without being limited by a predetermined sequence. This unique delivery scheme allows the healthcare practitioner to instantaneously modify, queue, change, or discontinue a prescribed dosage in response to fluid medical conditions. Therefore, the precise location and contents of each unit dose package 27 contained within the delivery module 33 must be known at all times, both prior to and during the dose delivery process. The present system uses a feedback loop arrangement to manage this flow of data.

Figure 22:
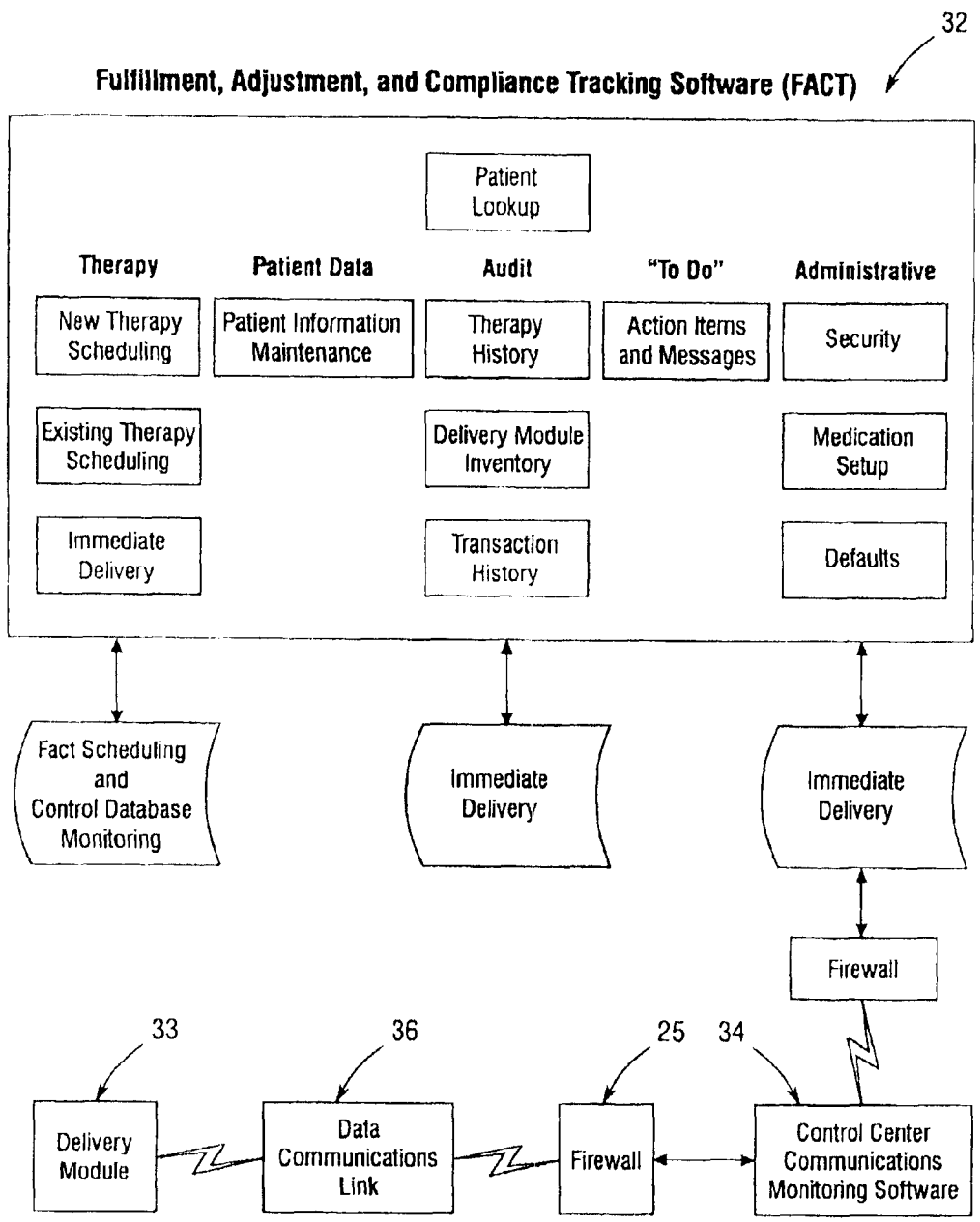
FIGS. 22-23 and 25-26 are flow charts illustrating the operations of the non-sequential medication delivery module and compliance system of the present invention.
Figure 29:
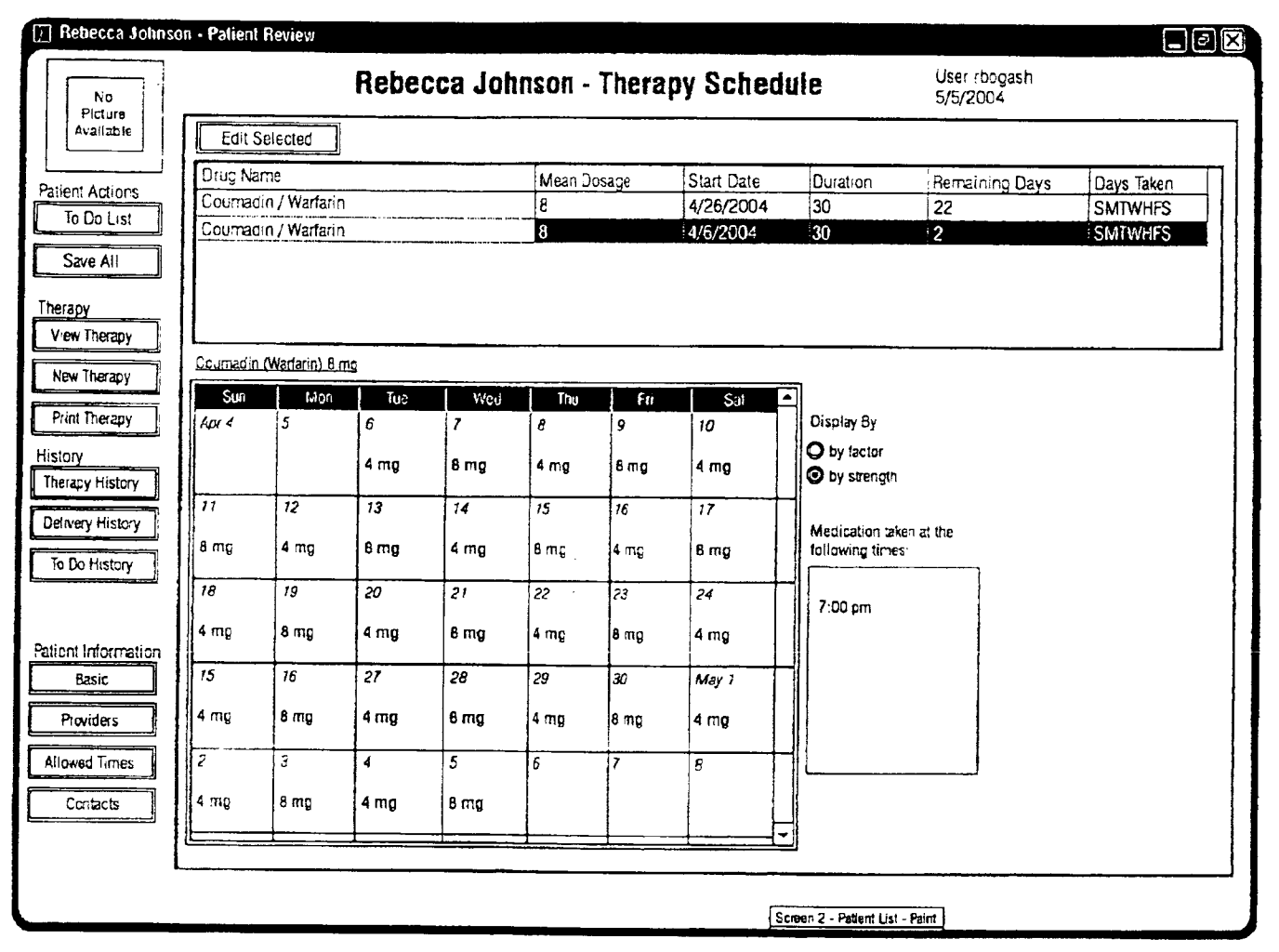
Figure 30:
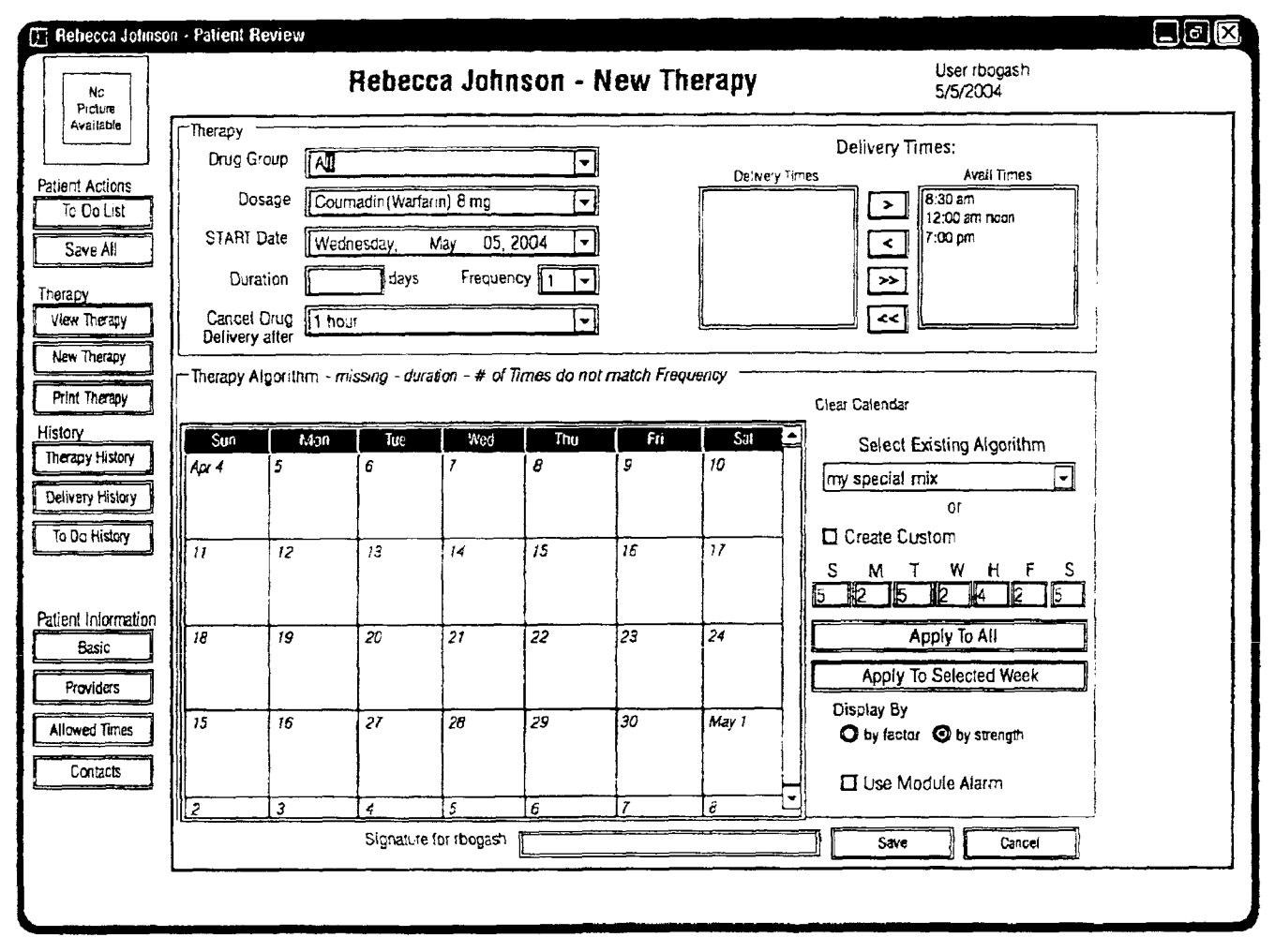
Figure 31:
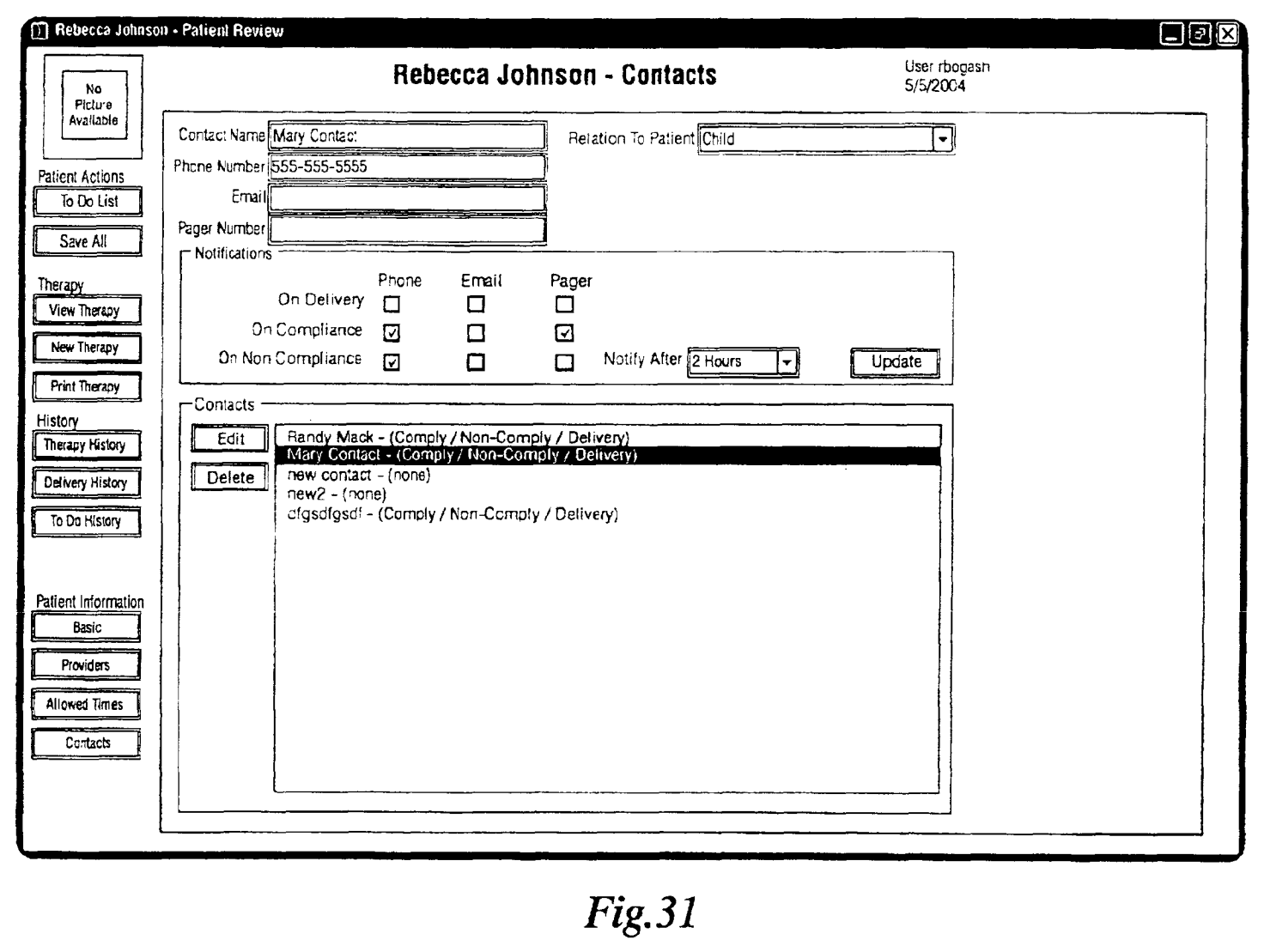

In operation, a healthcare practitioner enters patient prescription information and dosage schedules using the Fulfillment, Adjustment and Compliance Tracking System (FACT™), or other clinical software application 32 (FIG. 22). Patient information is accessed by way of the software's user interface 100, which features a complement of menu-driven worksheets that appear on the practitioner's computer monitor. FIG. 29 is a worksheet showing a monthly therapy schedule for a patient, which is stored in memory. Other examples of worksheets which the health care provider uses to interact with the clinical software 32 are provided in FIGS. 27-28 and 30-31. All patient information, which includes, for example, prescription information, medication dosing schedules, dosage delivery criteria such as drug-drug interactions and food-drug interactions, and a history of dosage delivery results, is stored within the clinical software database 32. The clinical software database 32 utilizes the clinical facility's network security 34 policies and procedures to authenticate users and network access to patient information, in conformity with the Health Insurance Portability Accountability Act.

Just before a scheduled dosing time, the clinical software 32 transmits an encrypted signal to the control software 32 operating on a server located at the control center 101 to initiate delivery of a particular medication for a particular patient. The signal contains a command instruction set representing a prescribed medication regimen and dosing schedule for the patient, as well as a randomly generated Unit Identification Number (UIN) assigned to that patient's delivery module 33. Neither the patient's name nor any information identifying the patient is transmitted beyond the medical facility's firewall 34. Accordingly, only the clinical software 32 can correlate the prescribed regimen and dosing schedule, or delivery module 33, to the patient.

Following transmission, the signal is interpreted and authenticated by a control center 101 computer server. Utilizing the UIN, the server's control software 35 links each command instruction embedded within the signal to a specific delivery module 33. Next, the control software 35 utilizes a look up routine to correlate the instruction to a specific medication carrier 26 containing the desired unit dose package 27. This information, based on the encoded identifiers 29, 31 assigned to the medication carrier 26 and unit dose packages 27, is stored in the control software 35 database. The control software 35 ascertains the specific location within the delivery module 33 of the unit dose package 27 or therapeutic product that is to be delivered to the patient in accordance with the programmed dosing schedule.

The control software 35 database specifies the vertical location (z-coordinate) of the medication carrier 26 as well as the row and column positions of the stall 28 containing such dose (y- and x-coordinates, respectively). In addition, the control software 35 database provides specific dose ejection parameters based on the internal configuration of the medication carrier 26 and the type of medication contained therein. This is accomplished using the stored electronic data which is communicated to the control center 101 computer server as the medication carriers 26 are loaded into the delivery module 33.

In the next step, the control software 35 reformats the signal into a proprietary protocol which includes a randomly generated communication's token and instructions for the delivery module 33 to drop the desired medication based on the x-, y- and z-coordinates of such medication. The instructions ensure that the correct medication, in an appropriate dosage form and amount, is delivered to the patient. The server transmits the reformatted signal to the controller located within the patient's delivery module 33 via radio frequency, or other suitable link. The controller interprets the command sent from the control center 101 server and sends confirmation thereto. This confirmation contains the communications token required for verification by the control server 101. In response, the control server 101 transmits a reconfirmation signal to the delivery module 33, authorizing the controller to drop the prescribed medication.

The module's 33 dose delivery sequence is activated upon receipt of the reconfirmation signal. The controller alerts the patient of the need to take the prescribed unit dose therapy 27 by way of the alarm, display 42 or other suitable visual, audible or other means. In an embodiment, a speaker may be used to provide an alert in a language known to the user. The controller concurrently establishes a window of time, relative to the alerting signal, during which the patient can input a delivery signal by, for example, depressing the drop key on the control panel 43. If the aural and visual signaling is ignored by the patient, the signaling will repeat every minute or more up to a programmed interval. The duration of the time window is set by the entered program or by a default value.

If the patient depresses the drop key 43 during the programmed time window, the controller, in cooperation with the drive motor 80, raises the storage elevator 47 to the correct vertical position (FIGS. 11 and 18) for accessing the storage bay 48 containing the unit dose package 27 or unit dose to be delivered, in accordance with z-coordinate specified in the command instruction set. The position of the storage elevator 47 within the housing is determined by means of the motor-based encoder which relays positional information to the controller, in the form of electrical pulses, as the motor 80 rotates. Once the appropriate number of pulses is emitted, signaling that the storage elevator 47 has attained the correct position, the controller disengages the drive motor 80.

When the storage elevator 47 reaches the correct level for accessing the designated storage bay 48, the controller actuates the servo motor and pulley assembly 54 which controls horizontal movement in the y-direction (FIG. 19) so as to move a transport carriage 49 and integral medication carrier 26 housed within the storage bay 48 forward, away from the home position 99. An electronic code scanner 98 located within the storage elevator 47 reads location markers disposed along the outer edge of the carriage 49, which indicate the position of the carriage 49 and medication carrier 26 as they are advanced. This positional information is monitored by the controller through a feedback loop arrangement. Once the controller determines that an appropriate number of markers have been scanned, in accordance with the y-coordinate instruction received from the control server, the motor and pulley assembly 54 are disengaged. As the transport carriage 49 and carrier 26 are moved into proper position, the scanner 98 also reads an encoded identifier label 29 affixed to the upwardly oriented surface of the medication carrier 26, which contains the x-coordinate operational parameters.

At this point, the transport carriage 49 and medication carrier 26 have sufficiently cleared the opening of the storage elevator 47 such that the desired unit dose package 27 or unit dose is positioned beneath the horizontal slide 86 of the ejector assembly 55. A control signal (FIGS. 16 and 20) is sent to the motor 87 responsible for movement about the x-axis so as to advance the slide-mounted receptacle 90 from a rest position 88 into an operative position 89 above the medication that is to be delivered. In this delivery ready position, the compacting edge 95 of the plunger 93 is suspended directly above the upwardly oriented, encoded 31 surface of the unit dose package 27. In an alternate embodiment, the compacting edge 95 of the ejector assembly or plunger 93 is suspended above the non-encoded surface of the unit dose package 27 when a unit dose is to be removed from the unit dose package. Other embodiments are possible within the scope of this disclosure.

In this orientation, the code scanner 92 suspended from the lower end of the actuator 91 is also positioned in proximity to the electronic identifier code 31 on the seal of the unit dose package 27. In instances where supplementary confirmation of delivery is desired, the scanner 92 reads the identifier code 31 and transmits verification to the controller that the selected dosage is the correct one, as a redundant check. The control software 35 layer links each command to a specific medication carrier 26 and unit dose package 27, the identification of which is scanned and verified at the time of loading the delivery module 33.

In the next step, a control signal is sent to the actuator 91 connected to the shaft 94 of the plunger 93. As this occurs, the shaft 94 is biased downward, whereby the compacting edge 95 contacts the encoded 31 surface of the unit dose package 27. This action causes the retaining means 30 of the affected stall 28 to release the unit dose package 27 contained therein. The ejected package 27 drops onto the ramp 96 situated beneath the ejector assembly 55, and thereafter slides into the rotatable guard 97 located at the bottom of the ramp 96. The guard 97 temporarily retains the ejected medication until each of the medications within the patient's regimen is expelled. In an alternate embodiment, the compacting edge 95 may contact the non-encoded surface of the unit dose package 27 causing the surface to compress and push the therapeutic product (or unit dose) through the encoded surface 31 of the unit dose package. In an embodiment, the unit dose package 27 may be retained within the retaining means 30 of the affected stall 28 when the therapeutic product is released. The therapeutic product may then drop onto the ramp 96 situated beneath the ejector assembly 95, and slide into the rotatable guard 97, which temporarily retains the ejected medication until each medication in the patient's regimen is expelled.

When the electronic code scanner 92 detects removal of the unit dose package 27 out of the medication carrier 26 or the removal of the therapeutic product from the unit dose package 27, a signal is sent to the controller, verifying that the prescribed dose is suitably removed from the carrier 26. In instances where visual identification is desirable, an electronic imaging device may be used to independently verify that the desired medication is suitably discharged from the carrier 26.

If additional unit dose packages 27 or therapeutic products are scheduled to be expelled from the same medication carrier 26, e.g. in instances where multiple dosage strengths of the same medication are combined to obtain a correct dosage amount, the carrier 26 is again advanced in the y-direction, while the ejector assembly 55 is moved into the appropriate x-position. Once all of the prescribed medications have been ejected from the medication carrier 26, the transport carriage 49 and carrier 26 return to their home position 99 within the storage bay 48.

If a prescribed unit dose package 27 or therapeutic product is contained in a different medication carrier 26, the storage elevator 47 is raised or lowered to the appropriate level, in accordance with the z-coordinate specified in the command instruction set. Thereafter, the transport carriage 49 and medication carrier 26 are moved forwardly, into the correct y-position, while the receptacle 90 of the ejector assembly 55 is moved in the x-direction. When the medication carrier 26 is in proper position, the plunger 93 pushes the dose 27 out of the carrier 26, causing the ejected dose 27 to fall onto the ramp 96. Alternately, the plunger 93 may release the therapeutic product from the unit dose package 27 to fall onto the ramp 96. This sequence is repeated for each of the medications within the patient's regimen, in accordance with the instructions received from the control center 101 computer server. It should be understood that all of the medications for a particular dosage period are ejected in rapid succession, typically requiring less than ten seconds to eject each medication.

Once all the medications for the scheduled dosage time are expelled from their respective medication carriers 26, the controller activates the audible alarm, electronic display 42 or other suitable alert mechanism to notify the patient that medication is ready to be taken. Simultaneously, a control signal actuates the servo motor that is operatively coupled to the rotatable guard 97 at the base of the ramp 96. As the guard 97 rotates, the ejected, fully sealed unit dose packages 27 or therapeutic products fall into the receiving area 46 for collection by the patient. At the same time, the electronic display 42 presents a description of the medical products placed into the receiving area 46, which may include, for example, the type, quantity and dosage of the delivered medical products.

In order to monitor compliance as well as maintain a complete audit trail of the patient's interaction with the delivery module 33, the module automatically transmits a signal to the control center 101 computer server, via radio frequency, or other communication link 36, once the dosage is discharged. The signal confirms that the prescribed dosage has been delivered to the patient within the scheduled dosing period. The transmission is date and time stamped in order to provide an accurate record of the transaction. The control software 35, which operates on the control center 101 server, receives and decodes the signal. Once the signal is authenticated, the control software 35 systematically updates the status of each unit dose package 27 or therapeutic product delivered during the scheduled dosing period. The updated usage information is stored in the control software 35 database so as to provide precise inventory control and flawless delivery of the diverse medical products contained within the delivery module 33. The dosage administration transaction record is also stored in the control software 35 database, then formatted into an XML message stream and sent to the clinical software layer 32 in the succeeding polling cycle, using an encrypted Secure Socket Layer 25.

As described in further detail below, a user may enter one or more dates and/or times corresponding to a period of time in which the user will not have access to the delivery module 33, such as if the user is going on vacation, to work, to school, shopping or the like. The delivery module 33 may determine the doses to be administered based on the entered dates and/or times and may eject such doses to the user. The user may enter the one or more dates and/or times via an input device, such as a key pad 43, and may display information pertaining to when to take each dose to the user via a display device, such as 42.

Every few minutes, the clinical software 32 checks for status updates sent to the clinical facility's data server. When the clinical software 32 receives the transaction record, the software 32 stores the information in the database which houses the patient's therapeutic regimen and dose delivery instructions entered by the healthcare practitioner. The transaction record provides, for example, an updated, complete inventory of the unit dose packages 27 contained within the patient's delivery module 33 as well as the date and time that the prescribed dosage was received by the patient. This information is directly provided to one or more computer stations 100 within the clinical facility, enabling an authorized healthcare practitioner to review the patient's dosage delivery results in real time. Once the dosage confirmation message is received from the control center server, signifying that the prescribed dosage has been delivered to a patient, the clinical software 32 initializes a routine to remove that particular dosage delivery event from the pending list.

If the patient fails to respond to the alarm generated by the delivery module 33 at a scheduled dosing time, e.g., by pressing the drop key 43 of the delivery module 33 at the end of the programmed time window, a routine is initialized which may include a call to the patient or a call to the patient's care provider, doctor, pharmacist or other designated individual. The delivery module 33 automatically transmits an alert to the control center 101 server, via radio frequency or other suitable communications link 36. Immediately thereafter, notification of the missed dosage is transmitted to the clinical facility's data server using the secure encryption method 25 as described above.

A further embodiment uses, for example, two time windows during which the patient may input the delivery signal, e.g., depress the drop key 43. In the first time window, the delivery module 33 generates an audible, visual or other alarm at a first intensity. If that first time window ends and the patient has not yet entered the delivery signal the module 33 increases the alarm level. The increased alarm level is continuous or, alternatively, steadily increases until the end of the second time window. Notification of the non-compliance action is transmitted to the control center 101 servers if the patient, at the end of the second time window, has still not responded to the alarm.

Delivery of the scheduled dosage does not occur unless the patient actuates the drop key 43 within the designated time interval. In this way, the present invention ensures that the patient receives the exact dose prescribed at the correct dosing time. This feature improves adherence and protects the patient from adverse drug interactions which may result from taking multiple doses of medication at unscheduled dosing times.

Patient dosage administration results are routed to and received by the clinical facility in real time. The clinical software 32 automatically alerts the healthcare practitioner of the non-compliance action by generating an alert message which is displayed on the practitioner's computer monitor (user interface 100). The practitioner can then take timely action by directly contacting the patient and/or directing an appropriate command back to the delivery module 33, or as otherwise described below.

After reviewing the notification of non-compliance, the patient's physician, pharmacist or other licensed healthcare practitioner retrieves and evaluates the patient's treatment regimen, which is stored within the clinical software 32 database and is accessed by way of the user interface 100. This information includes, but is not limited to, prescription information such as the name, type (brand or generic), potency strength and dosage form of a prescribed medical product, dosing schedules, dosage administration criteria such as drug-drug interactions and drug-food interactions, and the next pending dosage delivery event. The healthcare practitioner then determines whether the patient's medication regimen, dosing schedule, or both, should be modified to accommodate the missed dosage by, for example, entering an instruction that cancels, queues or modifies a prescribed dosage amount, using the appropriate worksheet 100.

This is accomplished, in part, through the use of electronic identifier codes 29, 31 which allow the precise location and contents of the prescription and non-prescription medications, pharmaceuticals, and nutraceuticals contained within a particular delivery module 33 to be known at all times, both prior to and during the dosage delivery process. This information is stored and monitored by the control center 101. A record of each dosing transaction, which includes an updated inventory of unused unit dose packages 27, is transmitted to the clinical facility immediately after each transaction occurs. The healthcare practitioner reviews the updated inventory listing which appears on his/her computer monitor (user interface 100). If an unscheduled dosage and/or schedule adjustment is deemed appropriate by the prescribing physician, the healthcare practitioner selects an alternate dosage or different medication from the list of prescribed therapies available to the patient and enters appropriate delivery criteria. The new dosage information is saved within the clinical software 32 database. The patient does not have to travel to a physician's office or to a pharmacy in order to obtain and fill a new prescription. There are no delays or interruptions in the continuity of treatment and compliance with the prescribed treatment regimen is addressed almost immediately.

In a similar fashion, the system of the present invention enables the healthcare practitioner to actively respond to an unexpected change in the health condition of a patient almost immediately. The invention is suited for situations where appropriate dosage amounts are evaluated on an ongoing basis, for example, through laboratory tests that change over time in accordance with the patient's needs. In these situations, the healthcare practitioner is able to remotely adjust the patient's dosage amount or deliver a different medication almost immediately, without the need for a new prescription. This is particularly important where narrow therapeutic index drugs are prescribed and over-medicating or under-medicating the patient can cause serious side effects and illness. The present system prevents the patient's condition from deteriorating since the patient is able to continue his/her course of treatment without potentially harmful interruptions.

Every few minutes, the clinical software 32 initializes a routine that monitors modifications to the database that houses the schedule and instructions entered by the healthcare practitioner. When the software 32 detects a dosage and/or schedule change, the information is conveyed to the URL of the control center 101 computer server using an encrypted Secure Socket Layer 36. As described previously, the information is formatted into an XML command instruction set that contains the Unit Internal Number (UIN) and other identifiers required for authentication by the control center 101 server. The control software 35 installed on the server authenticates and decodes instructions received from the clinical software 32. A reply signal is then sent to the clinical software 32, acknowledging receipt of such instructions. Utilizing the UIN, the control software 35 correlates the adjusted dosage delivery criteria to a particular delivery module 33. The control software 35 then references its database to determine the specific location, within the delivery module 33, of the unit dose package 27 or therapeutic product that is to be delivered to the patient based on the then current inventory of unit dose packages 27 stored within the module 33. The delivery module 33 is able to expel the packages 27 or therapeutic products non-sequentially, without being limited by a serial delivery restriction.

The control software 35 utilizes a look-up routine to retrieve the vertical location (z-coordinate) of the particular medication carrier 26 that contains the desired unit dose package 27, as well as the row and column positions of the stall 28 containing such dose (y- and x-coordinates, respectively). In addition, the look-up routine identifies specific dose ejection parameters based on the internal configuration of the medication carrier 26 and the type of medication contained therein. This is accomplished using the stored electronically coded identifiers 29, 31. The control software 35 simultaneously monitors the current time versus the scheduled drop time for the modified dosage. When the current time equals the scheduled drop time, the software 35 transmits a command signal to the delivery module 33 by means of radio frequency, or other suitable communications link 36. Included in the signal are instructions for the delivery module 33 to drop the modified dosage, based on the specified location coordinates.

When the command signal is received by the delivery module 33 to be activated, the module's controller decodes, verifies and loads the command signal into the controller execution queue by means of the logic program stored within the controller's memory. Immediately thereafter, the controller alerts the patient through visual, audible or other means, of the need to take the adjusted dosage. Once the patient responds to the alert generated by the delivery module 33, e.g., by articulating a prescribed verbal command or pressing the drop key 43 within the programmed time period, the dosage delivery sequence is initialized. Once the desired dosage has been delivered to the patient, confirmation and status information is sent to the control center 101 server. These results are immediately processed and conveyed to the clinical facility, enabling designated medical personnel to review the patient's dose delivery results in real time by way of the user interface 100. Hence, the feedback arrangement described herein permits the patient's medication regimen to be instantly adjusted and tailored to adapt to fluid medical conditions.

The healthcare practitioner can communicate with the patient at the time of dose delivery via telephone, email or by entering an appropriate command into his/her computer terminal. The command signal is processed by the control software 35 and thereafter transmitted to the patient's delivery module 33. Through this remote interface, which includes, for example, a keypad and/or speaker, the patient can be prompted to provide information or respond to questions.

While conventional pharmaceutical delivery systems provide a healthcare practitioner with data regarding a patient's health status, the present system allows a healthcare practitioner to actively respond to a change in a patient's health condition from a remote location. Each of the unit dose packages 27 contained within the delivery module 33 is separately encoded 31 and inventoried so as to be independently accessible and traceable. This allows the healthcare practitioner to deliver medication in non-consecutive order, on a dose by dose basis, and in a controlled and auditable fashion. In this manner, patient compliance with a prescribed regimen is precisely monitored. Moreover, dosage adjustments and other treatment decisions are made within parameters specified by a doctor in real time, simultaneously with the receipt of a communication regarding a change in a patient's health condition. This feature is particularly important given the overall increase in telehealth and telepharmacy based services.

As discussed above, the delivery module 33 of the exemplary embodiment can accommodate a plurality of medication carriers 26, each containing diverse therapeutic agents. For purposes of illustration, therefore, a typical carrier 26 loading operation is described below (FIGS. 7-10, 17 and 25*a*).

Loading of an empty or partially empty delivery module 33 is typically initiated by a patient, caregiver, or other authorized operator when a new supply of medication carriers 26 is received. The user simply depresses a load key 43 located on the front panel 41 of the housing, prompting the controller to transmit a load verification request to the control center 101 via radio frequency or other suitable transmission method 36. Once received by the control center 101, the load request signal is authenticated by the control software 35 and in most cases is accepted. The load verification request is denied in instances where a security password or other authorization is required to initiate the load operation, but is not entered by the operator.

In an alternative embodiment, the load operation is initialized by the control software 35. The control center 101 server transmits an encrypted load instruction, containing a randomly generated communications token, to the delivery module 33. Upon receipt thereof, the signal is decoded and verified for authenticity by the module's controller. If authentic, the controller sends a reply signal to the server, confirming receipt of the load instruction. Thereafter, the delivery module 33 generates an audible, visual or other alert in order to prompt the patient, or other operator, to depress the load key 43.

Once the operator activates the load key 43, the storage elevator 47 is immediately raised from its rest position in the lower section of the housing to a position operative for loading of a new medication carrier 26 into a storage bay 48. Movement of the storage elevator 47 to the appropriate level within the housing occurs by operation of the motor 80 and lead screw assembly 81, through controller actuation. The storage elevator 47 is raised to a height at which the storage bay 48 to be loaded generally abuts the horizontal guide rails 57, 58 that extend along the side panels 38, 39 of the housing. In this position, the lower surface of the transport carriage 49 is situated slightly above the guide rails 57, 58 so that upon exiting the storage bay 48, the carriage 49 automatically rests against the guide rails. As discussed above, the storage elevator 47 is automatically moved to a correct position through operation of the encoder.

When the storage elevator 47 is properly positioned, the actuator 60 lowers the latch apparatus 59 to its unobtrusive position below the guide rail 57 so that the loading pathway is clear. The transport carriage 49 is advanced forwardly from its home position 99 within the storage bay 48 to a point at which the carriage 49 extends into the loading area of the housing. As the carriage 49 enters the loading area, its movement is detected by a sensor which relays positional information to the controller. A control signal is sent to the swivel bracket mounted actuator 72, wherein the actuator 72 distends downward so as to achieve contact with the upper surface of the carriage 49. Simultaneous therewith, the swivel bracket 65 pivots downwardly, causing the drive wheels 70, 71 to be lowered onto the upper surface of the carriage 49. The drive wheels 70, 71, through operation of the motor 73 and pulley assembly 74, rotate outwardly so as to move the carriage 49 along the guide rails 57, 58 in a further frontward direction.

When the front edges of the transport carriage 49 come into contact with the front panel 41 of the housing so as to be flush therewith, i.e. the prime position, the controller temporarily disengages the motor 73 so that frontward movement of the carriage 49 ceases. The distended actuator 72 moves upward to its original, raised position, simultaneously causing the swivel bracket 65 and drive wheels 70, 71 to pivot upwardly so as to release contact with the carriage 49. In this position, the carriage 26 abuts the insertion/retrieval slot 45 configured in the front panel 41 of the housing. The transport carriage 49 is now in position to receive an incoming medication carrier 26. Because the delivery module 33 is capable of accessing and delivering the patient's dosages in random sequence, the medication carriers 26 need not be loaded into the delivery module 33 in any particular order. This overcomes a significant drawback associated with prior art devices in that medication must be loaded in the order in which it is to be delivered.

At this point, the operator is prompted through audible, visual or other means, to open the handle equipped loading door 44 in order to insert a new medication carrier 26 into the insertion/retrieval slot 45, preferably with the medications facing downward. The controller determines whether a medication carrier 26 has been placed in the slot 45 by monitoring the sensor. When the sensor detects that a medication carrier 26 has been fully inserted, i.e. that peripheral edges of the medication carrier 26 extend sufficiently into the loading area (e.g. three inches or other predetermined distance) so as to activate a limit switch, the controller signals the drive wheels 70, 71 to distend and rotate in a reverse, or inward, direction and correspondingly advance the medication carrier 26 through the insertion/retrieval slot 45, into the awaiting carriage 49.

When the sensor detects that the medication carrier 26 is fully entrenched in the carriage 49, the actuator 60 causes the latch apparatus 59 to resume its original, indexed position above the guide rail 57 so as to secure the carriage 49 in place on the guide rails 57, 58 for transport by the drive wheels 70, 71. As the medication carrier 26 and carriage 49 move rearward, toward the empty storage bay 48, an electronic scanner 98 located in proximity to the medication carrier 26 is actuated in response to a control signal. The scanner 98 reads the encoded identifier 29 label attached to the upwardly oriented surface of the medication carrier 26, which identifies the carrier's serial number. The scanner 98 also records the specific storage bay 48 in which the medication carrier 26 is to be stored. Immediately thereafter, the scanner 98 retrieved information is communicated to the computers servers housed at the control center 101.

Once the medication carrier 26 and transport carriage 49 approach the opening to the storage bay 48, the motor and pulley assembly 54 causes the spur gears 53 mounted about the opening of the storage bay 48 to rotate, effecting rearward movement of the carriage 49 into the home position 99. The motor 73 attached to the swivel bracket 65 is then disengaged so that the drive wheels 70, 71 stop rotating. When this occurs, the distended actuator 72, moves upward to its original, raised position, simultaneously causing the swivel bracket 65 to pivot upwardly so as to be locked into its initial position.

Almost immediately thereafter, the storage elevator 47 is raised or lowered to a different position, i.e. level, operative for loading a second medication carrier 26. At this point, the operator is prompted to insert another medication carrier 26 into the insertion/retrieval slot 45. Each new carrier 26 is loaded in similar fashion, with the carriage 49 being advanced to receive and transport an incoming carrier 26 to the storage elevator 47, until all the medication carriers 26 are present in the delivery module 33. The operator is then alerted through audible, visual or other means, that the loading operation is complete. The entire process occurs very rapidly, generally within three minutes.

As described above, an electronic scanner 98 such as a bar code reader, optical recognition reader or radio frequency identification tag reader scans the electronic identifier codes 29 imprinted on the exposed surface of each medication carrier 26 as the carrier advances toward the storage elevator 47, and images the specific location of the carrier 26 therein. This information is provided to the control center 101 computer servers for later retrieval. Once the loading operation is complete, each of the scanned medication carriers 26 is temporarily removed from its storage bay 48, in turn. The scanner 98 locates and reads the electronic identifier codes 31 imprinted on the seal of each unit dose package 27 within the carrier 26 and images the specific storage bay 47 in which the unit dose package 27 is stored. The controller then transmits the scanner retrieved information to the control center 101, where it is correlated with the encoded data previously entered into the control software 35 database. In this manner, the precise location and contents of each unit dose and unit-of-issue package 27 contained within a particular delivery module 33 are stored within the control software layer 35 such that each dose 27 can be accurately tracked from the time of manufacture to the time of delivery to a patient. This stored data enables a healthcare practitioner to remotely select and deliver an appropriate therapy to a patient, as described above.

Figure 25A:
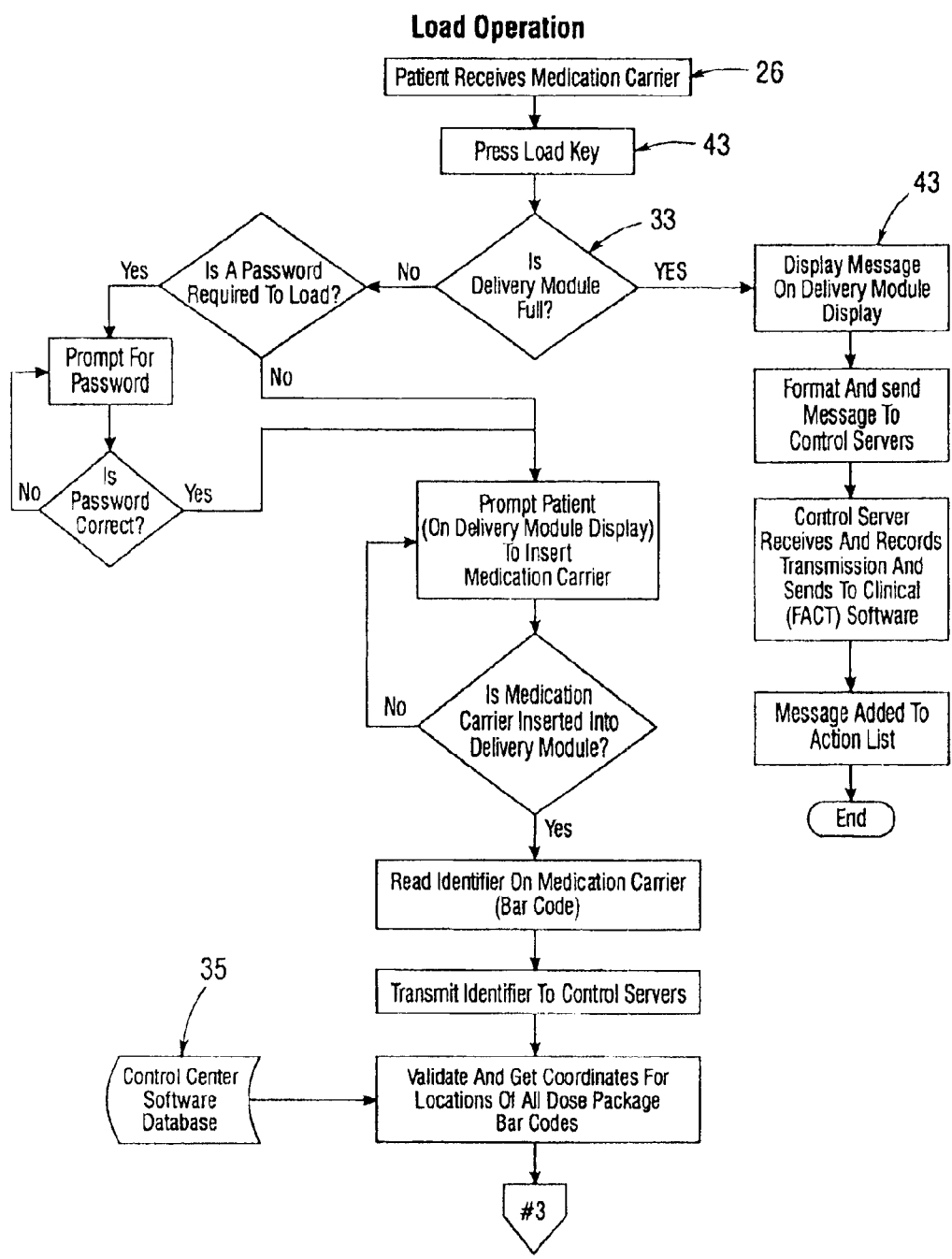
Figure 25B:
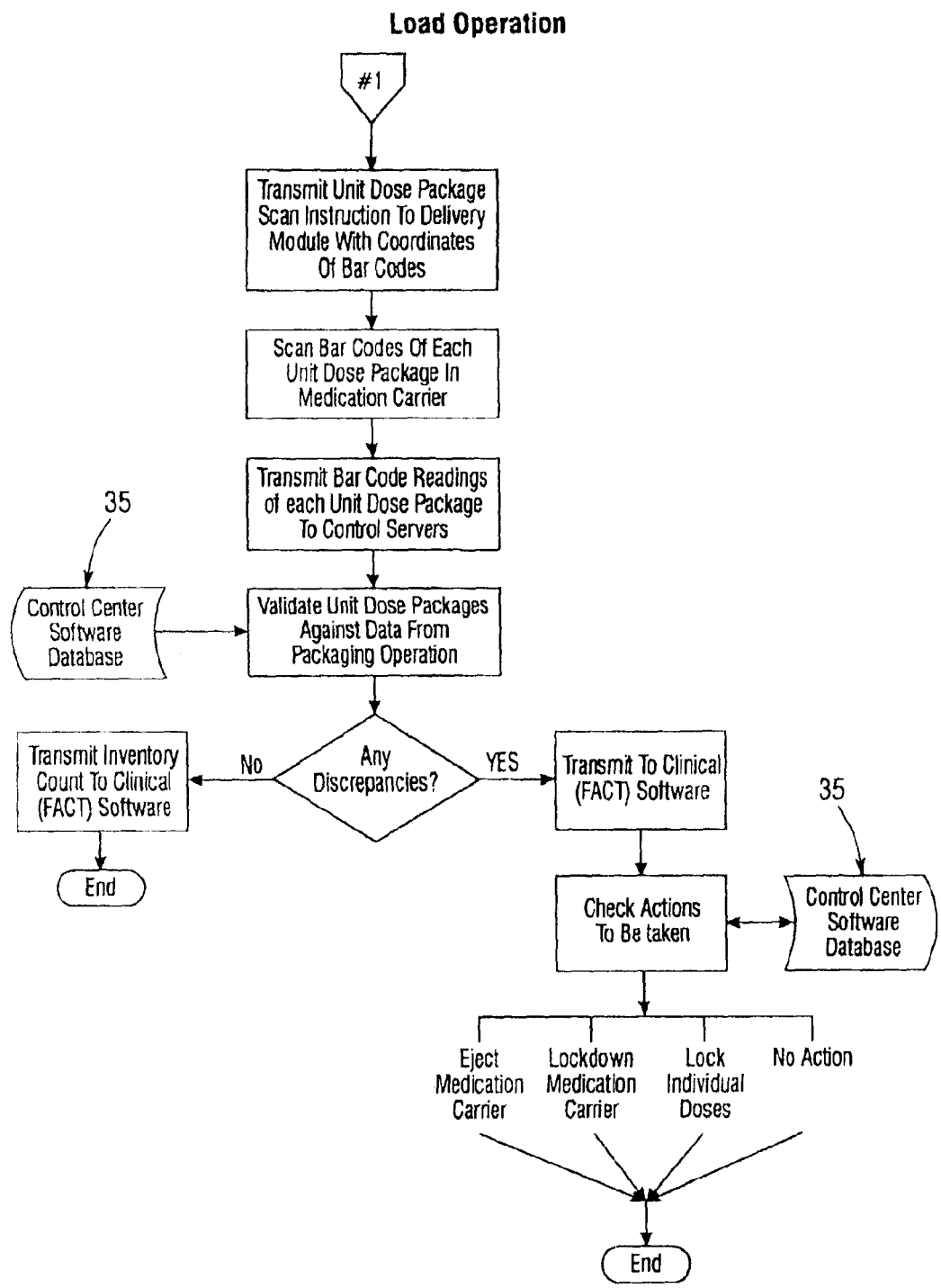
Figure 25C:
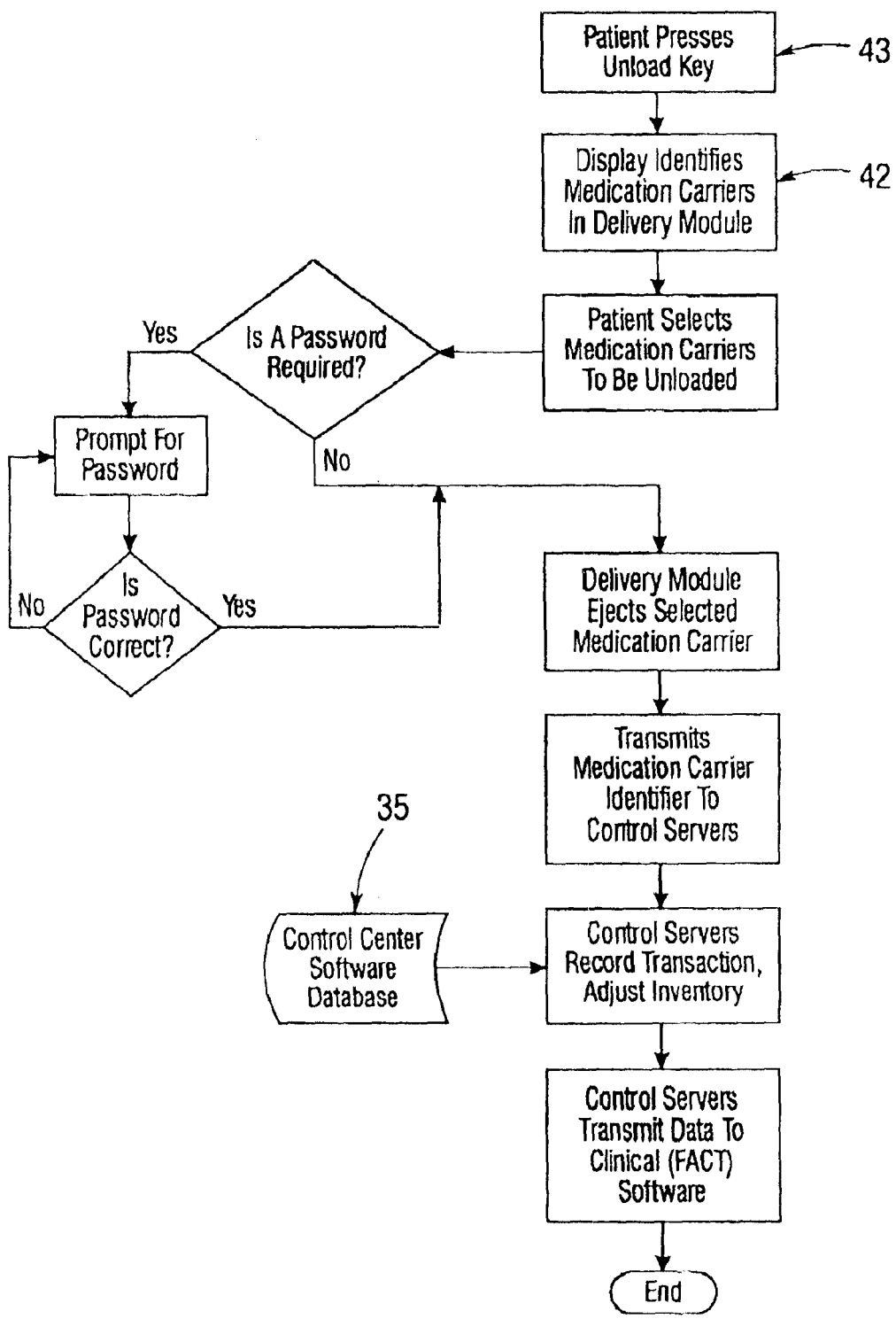

FIG. 25b illustrates a typical unloading operation. Medication carriers 26 are typically unloaded by a patient, caregiver, or other authorized operator when the patient's supply of medication is depleted. The operator simply presses the "unload" key 43 located on the front panel 41 of the housing, prompting the controller to transmit a verification request signal to the control center 101 server. Once received by the server, the signal is authenticated 25 by the control software 35 and thereafter authorized, once the control center 101 database verifies that a preselected number of stalls 28 of one or more medication carriers 26 is empty. Information necessary for verification of the request is stored in the server database, which maintains a continuously updated record of the location and status of each unit dose package 27 within the delivery module 33 through the use of electronically coded identifiers 29, 31. In this manner, the control center 101 is able to account for each unit dose package 27 at all times.

In an alternative embodiment, the unload operation originates from the control software layer 35. The control center 101 server transmits an encrypted 25 unload instruction to the delivery module 33 when the patient's medication supply falls below a predetermined level, as reflected by the server database. The signal is decoded and verified for authenticity by the delivery module 33 controller. If authentic, the controller sends a reply signal to the server, confirming receipt of the unload instruction. Thereafter, the delivery module 33 generates an audible, visual or other alert in order to prompt the patient, or other operator, to depress the unload key 43.

Once the operator activates the unload key 43, the storage elevator 47 is immediately raised from its rest position to a position operative for removal of a depleted medication carrier 26 from a storage bay 48. Thereafter, the transport carriage 49 and medication carrier 26 are ushered into the loading area of the housing in the manner described above. When the front edges of the carriage 49 come into contact with the front panel 41 of the housing so as to be flush therewith, i.e. the prime position, frontward movement of the carriage 49 ceases. The drive rollers 70, 71, however, continue to rotate outwardly, moving the depleted medication carrier 26 out of the carriage 49 and into the insertion/retrieval slot 45. A sensor is located to monitor movement of the outgoing medication carrier 26 through the insertion/retrieval slot 45.

Once the front edges of the medication carrier 26 have cleared the front panel 41 of the housing so as to protrude approximately three inches (or other distance suitable for manual retrieval of the carrier 26 by an operator), the controller briefly disengages the motor 73, preventing further rotation of the drive wheels 70, 71. The depleted medication carrier 26 is now in position to be removed by the operator. At this point, the operator is prompted, through audio, visual or other means, to open the handle equipped loading door 44 in order to retrieve the medication carrier 26 from the insertion/retrieval slot 45.

When the sensor detects that the depleted medication carrier 26 has been removed, the controller signals the motor 73 to rotate the drive wheels 70, 71 in a reverse direction, that is, inwardly, so as to move the transport carriage 49 in a rearward direction toward the empty storage bay 48. Once the carriage 49 reaches its home position 99, the motor 73 is disengaged so that the drive wheels 70, 71 stop rotating. When this occurs, the bracket actuator 72 moves upward to its original, raised position, simultaneously causing the swivel bracket 65 to pivot upwardly into its initial position. At such time, the latch apparatus 59 resumes its indexed orientation adjacent the guide rail 57.

The storage elevator 47 is then raised or lowered to unload the next empty medication carrier 26. Each storage bay 48 is vacated in similar fashion until all the depleted carriers 26 have been removed from the delivery module 33. It should be understood that unloading of the medication carriers 26 occurs in rapid succession, with the storage elevator 47 being correctly positioned for removal of a depleted carrier 26 from a corresponding storage bay 48 virtually simultaneously with the ejection of a carrier 26 through the insertion/retrieval slot 45. With the operator in position to receive each ejected carrier 26, the entire process can take as little as three minutes.

Once all the empty medication carriers 26 have been removed from the delivery module 33, the control center 101 servers transmit a load signal to the controller of the empty module 33. The operator is then notified, through audio, visual or other means, that the module 33 is ready for refilling. At such time, the operator simply depresses the load key 43 located on the front panel 41 of the housing, and thereafter, opens the loading door 44 in order to insert a new medication carrier 26 into the insertion/retrieval slot 45.

As described above, a remote medication management system is composed of clinical and communications software, a medication delivery unit, and medication packaging. Such a system provides a means for: a patient's prescribed medications to be stored in a delivery unit, for a medical provider to remotely schedule the patient's prescribed medications, for a medical provider to provide notification to the patient when the prescribed medications are due to be taken, to release the prescribed medications to a tray of the delivery unit accessible to the patient on the patient's command and to provide to the medical provider a history of the event. As such, the system is intended for use as an aid to healthcare providers in managing therapeutic regimens for patients in the home or clinic.

In addition to the functionality described above, various additional functionality may be beneficial, particularly where it addresses issues concerning the safe delivery of medications. For example, a significant concern is the inability of a patient to properly identify his/her medications. The medication delivery unit should identify the medication or the package containing the medication without relying upon the patient to accomplish this task. The medication delivery unit should identify the medications using the manufacturer's or pharmacist's label. If the device is unable to identify the medication, the device should not accept the medication and should provide notification that the medication is unidentifiable and cannot be used with the device. Furthermore, it should be assumed that a patient will rely on the medication delivery unit to properly deliver his/her medications. The electromechanical systems of the medication delivery unit should reliably discharge a medication at the prescribed time and in the prescribed dose and verify that the dose has been successfully delivered. In the alternative, the medication delivery unit should provide a notification that medications have not been released as prescribed. A complete history log of the delivery events should be maintained.

Further still, the ability of the medication delivery unit to deliver the proper medication is dependent on the medication delivery unit's ability to identify each medication and verify that the number of the medications contained within the medication delivery unit is consistent with the scheduled therapy. If there are insufficient medications contained within the medication delivery unit to deliver the medications prescribed at a particular dosing period, the device should provide a notification. Therefore, the device should be able to verify the specific quantity of each medication contained within it.

Further still, the medication delivery unit should not accept medication past its expiration date and should provide notification that the medication has expired and cannot be used with the device. Given these concerns, a medication delivery unit should at least be able: automatically eject packaged medication upon a failure to identify the package; confirm selection and delivery of the proper medication; provide notification in the event of a failure, improper medication, expired medication, etc.; verify a quantity of one or more medications; and provide notification upon failure of the medication delivery unit to verify medication quantity. Regardless of the source, risk can be mitigated by real-time anomaly reporting system. Errors (including conditional successes) on all parts of the system (including, in particular, the medication delivery unit), should be logged and reported.

A risk is presented if a power failure would prevent a patient from removing their medications from the medication delivery unit, or the control software is unable to communicate with the medication delivery unit to adjust the dosing schedule or monitor compliance. To this end, it would be advantageous to provide a battery backup that maintains the ability of the medication delivery unit to communicate and continue to operate for a period of time. In addition, there should be a method for the patient to easily remove the medications from the medication delivery unit in the event that a power failure causes the unit to not operate, such as a manual method of removal or the automatic ejection of all of the medication packages in the event that the battery power drops below a minimum operating level.

The inability of a patient to use the medication delivery unit presents a risk. To this end, it may be desirable to limit patient control of the medication delivery unit. The medication delivery unit and its control software should be designed so that none of the interactions between the medication delivery unit and the patient require that the patient enter any information used in the management, scheduling, or even identification of the medication.

Scheduling and delivery of medications presents numerous risks, for example when a medication dosing schedule is changed after the patient has already received their medications from the medication delivery unit. This may occur if the device has a feature to allow the patient to receive their medications in advance of the scheduled dosing delivery. Such a situation could result in rescheduling the delivery. Adequate software controls should be in place to prevent such an occurrence and should alert the patient's care provider that the patient has already received their medications and the dosing change will not take place until the next scheduled dosing period. Alternatively, such rescheduling may be necessary when a medication dosage is removed from the medication carrier and administered while the medication package is being transported from the pharmacy by a care provider or the patient and before the medication carrier is inserted into the medication delivery unit. A similar situation occurs if a power failure causes the patient to manually administer their medications without the use of the medication delivery unit. A potential risk occurs if the medication delivery unit tries to deliver a medication that is missing from the package. The device should be capable of identifying if medications are missing from a medication carrier. In yet another example, in the process of administering his/her medications, a potential risk occurs if the patient drops a pill on the floor, or loses the dose prior to taking it and the patient does not have an easy and convenient method of obtaining a replacement dose. The medication delivery unit should be capable of allowing the patient to remove the medication package from the medication delivery unit, manually administer a medication, and then reinsert the package into the unit.

Various other risks concern labeling of medications. For example, a risk is presented if the prescription label affixed by the pharmacist to the medication carrier is no longer visible to the patient after the medication carrier has been inserted into the medication delivery unit. Important information printed on such labels, including but not limited to drug name, form and dose, drug expiration date, a warning label (if needed), etc. may be vital to the treatment of the patient. This risk may be mitigated by having the medication delivery unit either display the essential prescription information to the patient at the time the medication delivery unit delivers medications, or the design of the medication delivery unit should be such that the information from the pharmacist's prescription label is in full visible view of the patient at all times. Should the label not be in full view of the patient, then the medication delivery unit should be programmed so that it will not deliver medication to the patient that has passed its expiration date.

A risk is presented if a medication comes directly into contact with the medication delivery unit or with other medications stored in the medication delivery unit. Cross-contamination between different medications, either through contact within the medication delivery unit or through residue dust remaining in the medication delivery unit creates potential risks of adverse reactions, especially if a medication is no longer delivered to the patient as a result of an allergic reaction to that medication. This risk can be mitigated either by keeping each dose of each medication contained within a package until the patient actually receives the medications thereby eliminating any direct contact between medications or between any medication and the medication delivery unit, or insuring that the medications do not come in contact with surfaces of the medication delivery unit that may retain the medication residue.

Embodiments of various aspects of the present invention, particularly those addressing the risks described above, are further illustrated and described below with reference to FIGS. 32-61. It will be recognized that many of the same operation structures and devices are already described above, which may be equally applied to the embodiments described below. For example, FIG. 2 described above illustrates a particular example of the use of a remote controller 101 and/or remote units 32 in conjunction with a medication delivery unit 33. That is, one or more medication delivery units 33 communicate with a remote controller, such as a control center 101, via a communication network 36. Note that a single remote controller will typically communicate with a plurality of medication delivery units 33. Additional details concerning an alternative embodiment of a medication delivery unit 33 are described below with further reference to FIGS. 32-40 and accompanying description. As noted above, the communication network 36 may include any suitable communication network such as a wireless/wired, public/private communication network of the various types known in the art, including combinations thereof or any other suitable communication system.

Additionally, one or more remote units, such as the software-equipped computer residing within one or more clinical facilities 32, may also communicate with the remote controller via the communication network 36. The remote units may include any suitable processing device capable of communicating via the network 36, such as a desktop/laptop computer or handheld or mobile wireless computing devices, all having a suitable user interface 100 as known to those having skill in the art. In one embodiment, healthcare providers use the remote units to initialize and/or modify patient dosing regimens, access data/information provided by the medication delivery units or access the medication delivery units. As used herein, a "healthcare provider" includes any authorized entity that provides medical care or services to a user of a given delivery unit, e.g., a physician, nurse, pharmacist, etc. In another embodiment of the present invention, non-healthcare providers may also be allowed restricted access via the remote units.

The remote controller 101 operates in conjunction with the medication delivery unit 33 to facilitate the proper delivery of medications. Generally, the remote controller 101 may be embodied as one or more suitable programmed application and database server computers, as know in the art. A user interface may also be provided as part of the remote controller 101, thereby allowing authorized personnel, such as providers of the services implemented by the medication delivery units 33, to access stored data/information provided by either the medication delivery units 33 or remote units 32. Although the remote controller 101 is illustrated as a separate device in FIG. 2, akin to an implementation in which the various server computers are independently owned, programmed, operated and maintained by a single entity, other implementations are possible. For example, the remote controller 101, rather than being independently operated, may instead be implemented in a hosted environment, such as through the use of an Internet or web hosting service within the communication network 36, as known in the art. Regardless where the implementing hardware is located, access to the server computers implementing the functionality of the remote controller 101 (as described above and below) may be through one or more suitable interfaces, e.g., through specialized interfaces 100 provided by the remote units 32. As described above, the remote unit 32 can maintain its own patient data that is also stored by the remote controller 101, as well as security policies and internal network access. In this vein, each remote unit 32 can also include a user interface for the entry and modification of patient information, dosing regimens, etc. particular to that remote unit 32. In another embodiment, all of this functions can be incorporated into the remote controller 101 that as a web service accessible via an appropriate web interface, as known in the art. Regardless of the specific interfaces used, different types of users are provided access to the functionality and stored data of the remote controller 101 based on passwords or authentication mechanisms that provide the appropriate level of access. For example, physicians should have full access to any data/information concerning their respective patients, but not other patients.

As noted, the functionality of the remote controller 101, rather than being centralized, may be implemented in a decentralized fashion as described above. That is, the remote units 32 may include suitably programmed processing devices that provide greater functionality than a user interface that accesses a web application system. For example, one or more physicians may each have a computer and suitable software and storage devices that allow the physician to create and maintain dosing regimens for patients and other patient-related information. While this information is likewise stored by the remote controller 101, ultimate control over such information is retained by the respective remote units 32. Additionally, the physician's computing device (remote unit) can, for example, access the requisite medication delivery units 33 to download the necessary dosing regimen and to receive communications directly from the medication delivery units 33. An advantage of such an implementation, as noted previously, is that confidential patient information (such as would be protected under the auspices of HIPAA) may be more directly controlled by healthcare providers through the use of suitable firewalls, etc. However, any suitable configuration may be used.

As described above, the remote controller 101 and/or remote units 32 may operate to directly control operation of the medication delivery unit 33 through the use of commands sent through the network 36, which commands are subsequently acknowledged back to the controlling entity upon receipt and/or execution by the medication delivery unit. In an alternative implementation, information and data is communicated to the medication delivery unit 33 by the remote controller 101 that allows the medication delivery unit 33 to operate in an essentially autonomous fashion. In this implementation, the medication delivery unit 33 is provided (in addition to any necessary software programs and/or software program upgrades as needed) with one or more dosing regimens by the remote controller 101. In this regard, the medication delivery units 33 are programmed to periodically contact the remote controller 101 to determine whether any data/information is available for download to the medication delivery unit. In a presently preferred embodiment, this is achieved using a wireless link, such as a General Packet Radio Service (GPRS) modem or similar device implementing a suitable encryption protocol such as SSL. An advantage of this implementation is that the medication delivery unit 33 can ignore any incoming communications via this link if it has not previously initiated communications with the controller 101. As described in greater detail below, the medication delivery unit 33 may also initiate unscheduled communications with the remote controller 101 in those instances in which the medication delivery unit has data/information to upload to the controller. During these unscheduled communications, the medication delivery unit can still request updates as would be the case during scheduled communications. Because the medication delivery unit in this implementation can operate according to the stored dosing regimen, the need for back and forth communications with the remote controller 101 is substantially reduced, thereby decreasing operating costs and improving responsiveness of the medication delivery unit 33.

As described above and below, the medication delivery units 33 operate to store medication carriers and deliver necessary medications. In particular, various mechanical and electrical components are provided to implement basic functions of any medication delivery unit. Thus, for example, suitable components are provided such that individual medication carriers can be provided at an input port of the medication delivery unit and automatically drawn in for subsequent storage. As part of that process, identifying indicia on each input medication carrier may be inspected to determine information regarding the input medication carrier and/or the medications stored therein. Additionally, each input (or previously stored) medication carrier may be inspected to ensure the proper condition of each unit dose package. Properly received input medication carriers are subsequently placed in suitable storage areas of the medication delivery unit such that the stored medication carriers can be subsequently retrieved as necessary for various dispensing operations. In that vein, other components are provided to effectuate the actual removal of individual unit dose packages and subsequent delivery of removed unit dose packages to a user (e.g., patient) of the medication delivery unit. The same mechanisms used to handle input medication carriers may likewise be employed to eject or unload medication carriers as needed.

Figure 32:
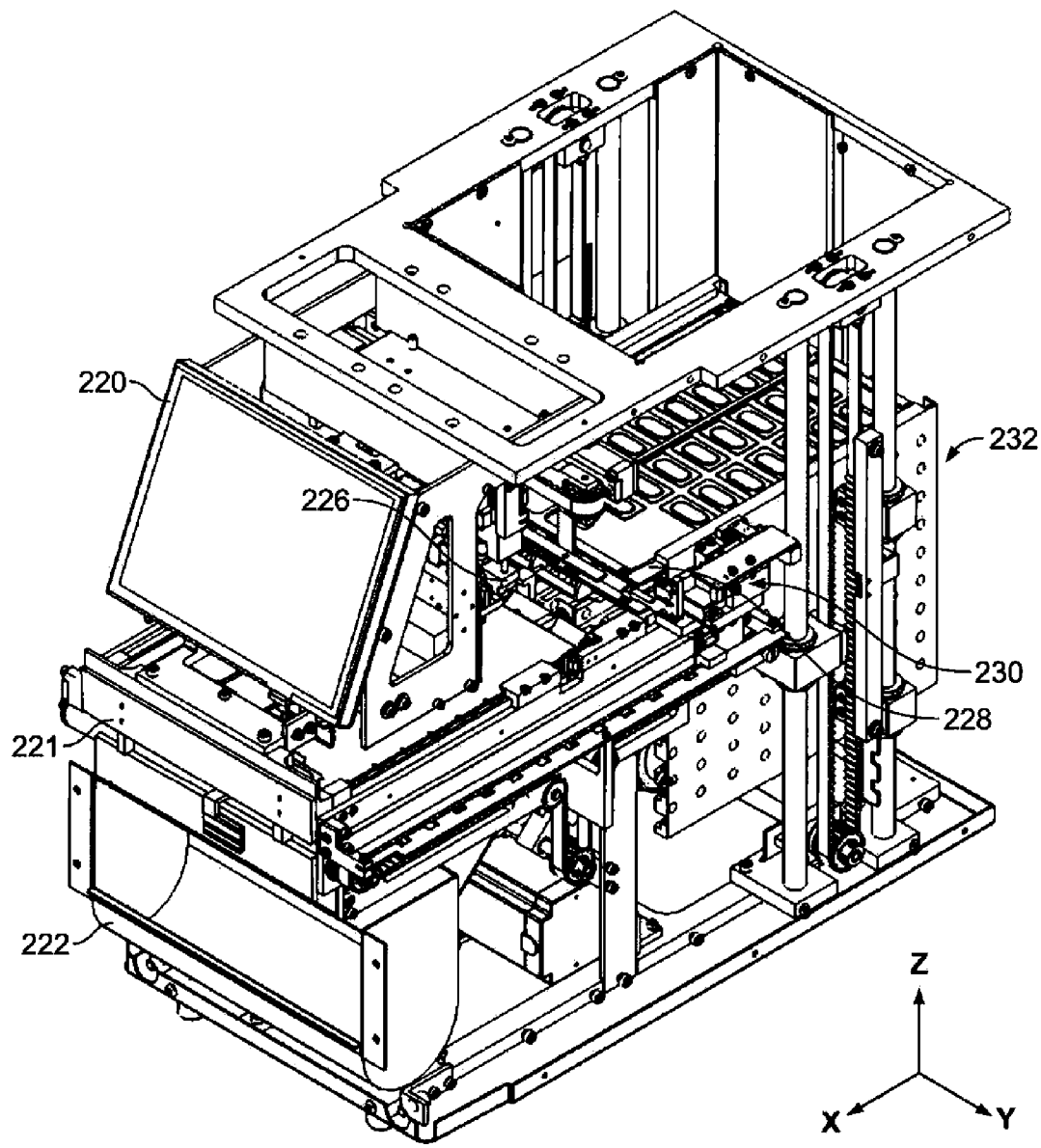
FIG. 32 is a perspective view of a partially assembly of an alternative embodiment of a medication delivery unit.

Referring now to FIG. 32, a perspective view of an alternative medication delivery unit, without its external housing, is shown. In general, the alternative medication delivery unit is similar in operation to the medication delivery unit described above relative to FIG. 3 et seq. In one embodiment, operation of the medication delivery unit 33 is controlled through the use of stored software programs executed by one or more suitable processing devices, such as microprocessors, microcontrollers, digital signal processors, programmable logic arrays, application specific integrated circuits, etc. or combinations thereof, i.e., "processors", as known in the art. Thus, using stored software control programs, the medication delivery unit 33 may accept user commands through the touch screen display 220, as noted above. In addition to the touch screen display 220, a user interface for the medication delivery unit 33 may include a speaker 219 (see FIG. 36) or similar device capable of emitting audible signals. Further input and output devices, such as (but not limited to) mouse and cursor input means, microphone, indicator lights, printer, or other display device may be equally incorporated into the user interface of the medication delivery unit 33 as known to those having ordinary skill in the art. As noted above, the medication delivery unit includes one or more external communication interfaces that allow it to communicate via the network 36 with the remote controller 101 and/or the remote units 32. In addition to the wireless connection described above, hardware and software supporting, for example, an Ethernet connection or other wired communication protocol may be employed. In a presently preferred embodiment, the communication interface(s) as well as the processing devices and software storage devices (in addition to any other control circuitry know to those of skill in the art) are implemented using one or more printed circuit boards (not shown in FIG. 33). Still other implementations known to those of skill in the art may be equally employed.

The medication delivery unit 33 accepts/ejects medication carriers 224 through an access door 221 and loads/unloads each medication carrier 224 into/from a corresponding carriage 228 along an x-axis, as shown. The carriages 228, in turn, may be removed from/replaced into an elevator 232 (capable of movement along a z-axis) as storage for the medications. Although a horizontal orientation of the carriages 228 is shown, it will be recognized that any suitable orientation may be used. In this embodiment, movement of both the medication carriers 224 and the carriages 228 is accomplished through the use of a tractor assembly 230, although other means may be equally employed. As noted above, using an ejection mechanism such as a plunger 226 that is capable of being moved along a y-axis, the delivery unit 33 causes individual unit dose packages (or, in another embodiment, individual unit doses) to be removed from one or more medication carriers 224 and deposited in a collection chute 222 accessible to a user of the delivery unit 33. More detailed explanation of the various components used along the x-, y- and z-axes is provided with further reference to FIGS. 33-40.

Referring now to FIG. 33-36, various components forming a part of an x-axis assembly are shown. It is noted that various supporting and frame structures have been hidden in FIG. 33 for sake of simplicity. The x-axis assembly includes two tractor support assemblies 240*a*, 240*b* each including a tractor assembly 230*a*, 230*b* that traverses a corresponding rail 242*a*, 242*b* along the x-axis under the power of a corresponding timing belt 244*a*, 244*b*. As each tractor assembly 230*a*, 230*b* moves along its corresponding rail 242*a*, 242*b*, the position of the tractor assembly 230 is monitored using an encoder bar 246*a*, 246*b* and an encoder bar sensor 248*a*, 248*b*. As shown, each encoder bar 246 includes a number of notches at specific locations along its length. Each encoder bar sensor 248, which preferably includes an integral light source and light sensor as known in the art, is capable of determining when it is positioned precisely above a given notch in a corresponding encoder bar 246. By keeping track of the number of notches that the encoder bar sensor 248 passes over (relative to a known position) as the tractor assembly 230 traverses the rail 242, a controller in communication with the encoder bar sensor 248 determines the location of the tractor assembly 230. Additionally, a pair of tractor home position sensors 249*a*, 249*b* are provided at a distal end of each of the tractor support assemblies 240*a*, 240*b*. Preferably embodied as a light source/sensor as noted above, the tractor home position sensors 249*a*, 249*b* determine when their corresponding tractor assemblies 230 are positioned at their home position, i.e., at the distal end of the rails 242.

Figure 34:
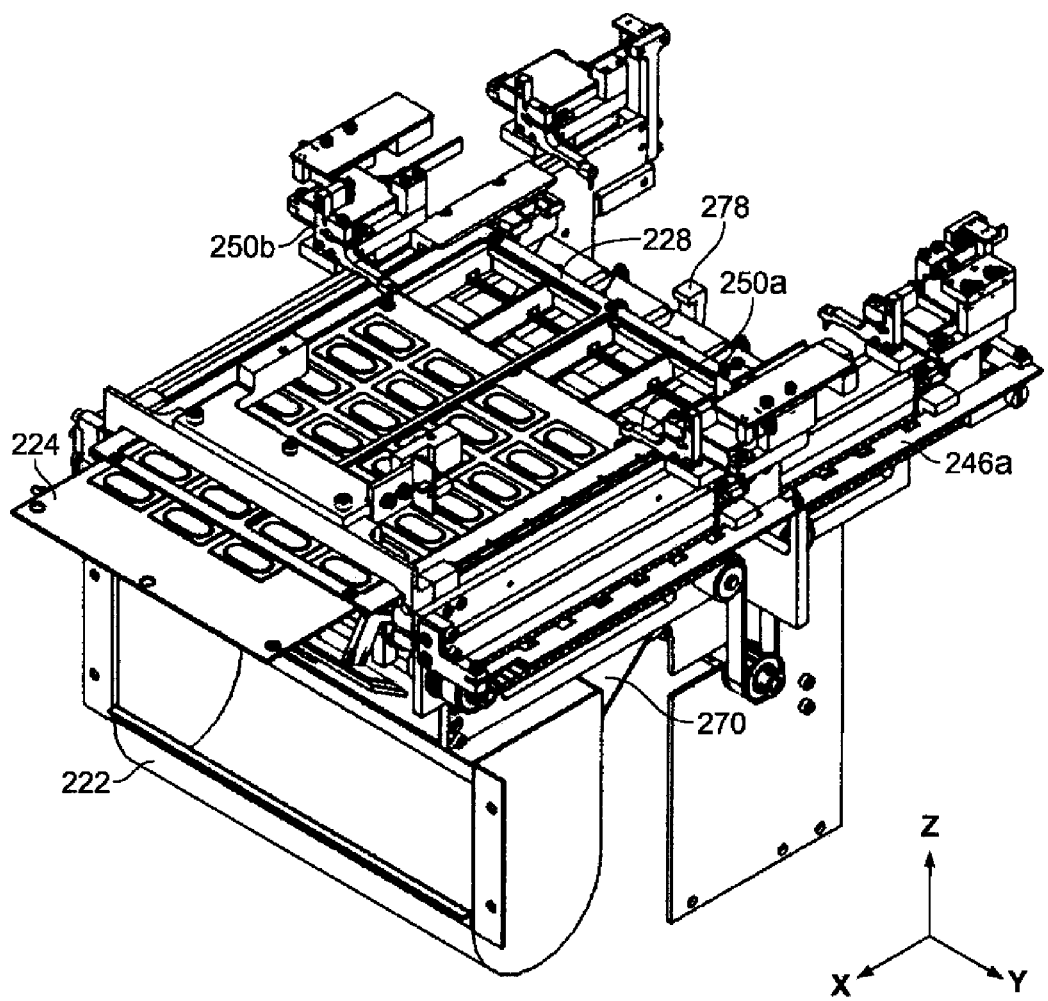
FIGS. 34 and 35 are front perspective views of the x-axis assembly of FIG. 33.
Figure 35:
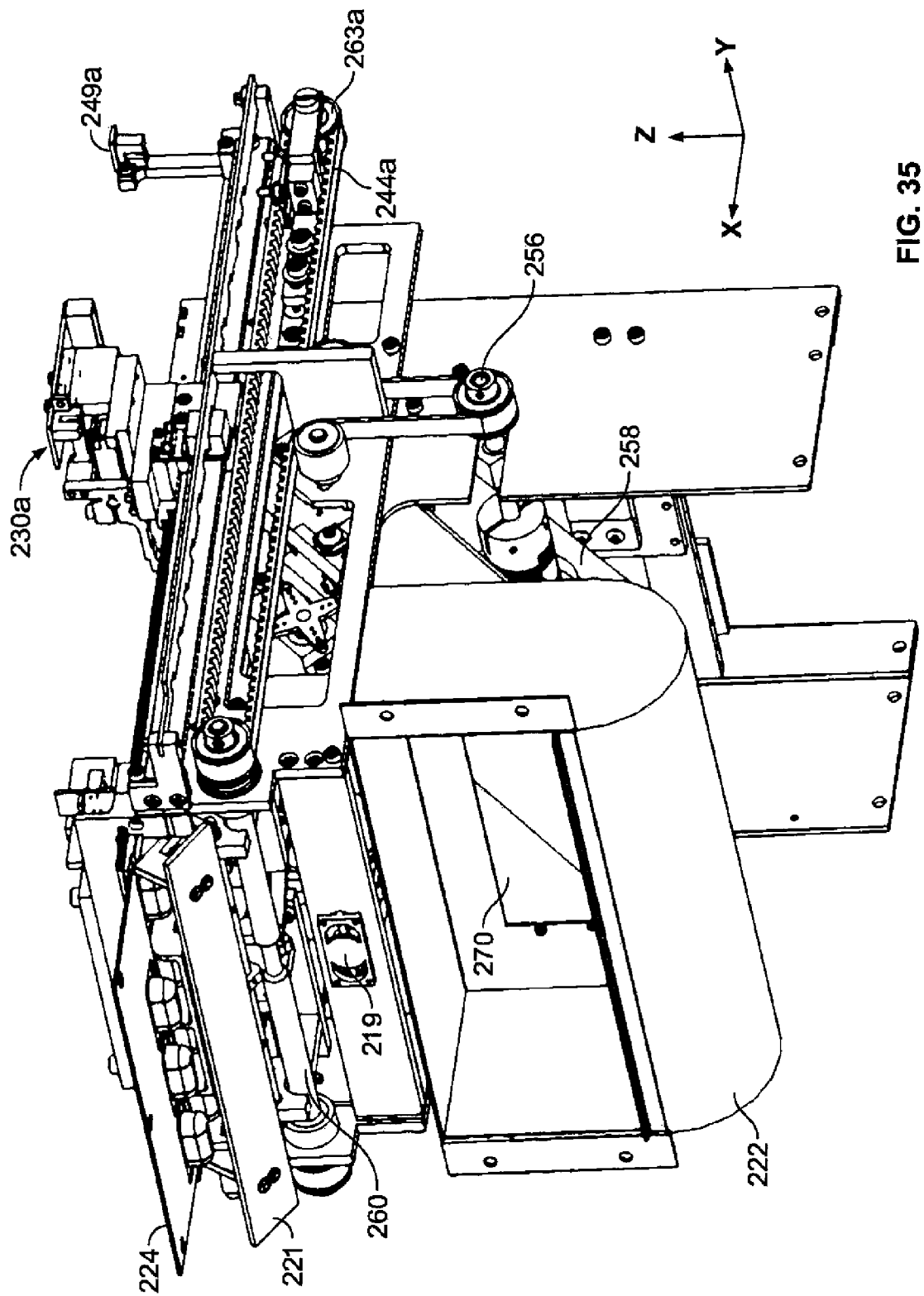
Figure 36:
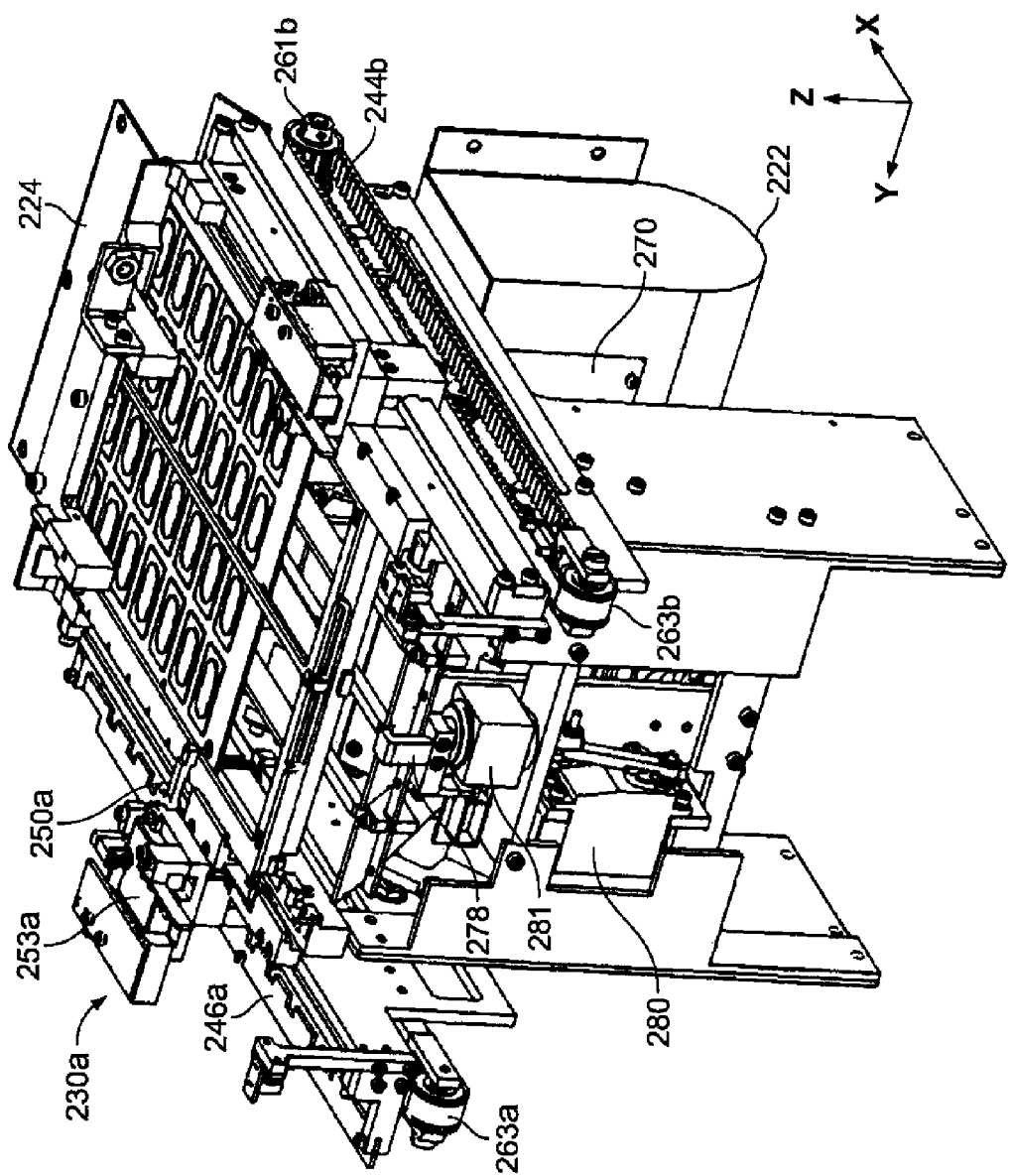
FIG. 36 is a rear perspective view of the x-axis assembly of FIG. 33.

Each tractor assembly 230*a*, 230*b* also includes a tractor arm 250*a*, 250*b* that, in turn, has a peg 252*a*, 252*b* disposed substantially perpendicularly relative to a longitudinal axis of its corresponding arm 250. Under control of a corresponding tractor arm servo motor 253*a*, 253*b*, each tractor arm 250 is freely rotatable through a limited arc within the y-z plane in which it resides. Because the tractor assembly 230 is free to move along the x-axis, the number of potential y-z planes for each tractor arm 250 to move in is virtually unlimited, although in practice it is limited to those y-z planes along the x-axis associated with the notches in the encoder bar 246. As best illustrated in FIGS. 34 and 36, the tractor arms 250 and pegs 252 are used to engage openings 368 (see FIG. 44) in a medication carrier 224 (for either loading or unloading purposes) and, through this engagement, move the medication carriers 224 into or out of a carriage 228 along the x-axis. Additionally, as best shown in FIG. 32, the tractor arms 250 and pegs 252 may also be operated to engage openings 350 (see FIG. 41) in a carriage 228 to move the carriage into and out of a corresponding slot in the elevator 232. Those having ordinary skill in the art will appreciate that mechanisms other than the arms 250 and pegs 252 could be used for these purposes. When moved out of the elevator 232, each carriage 228 is supported by a pair of carriage support rails 254a, 254b. In a presently preferred embodiment, each of the carriage support rails 254 is notched to minimize the points of contact between the carriage support rails 254 and each carriage 228, thereby minimizing friction.

Figure 37:
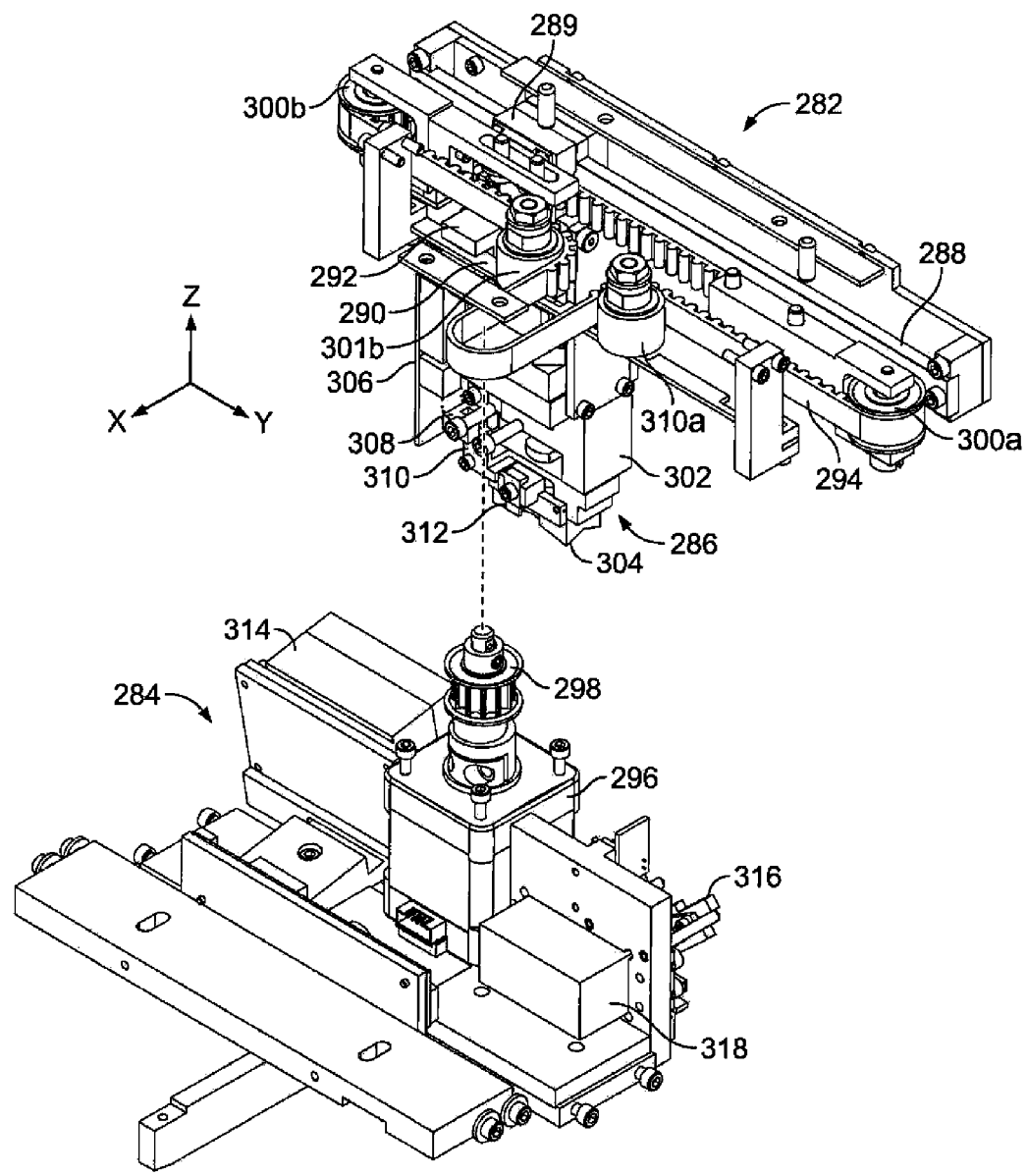
FIG. 37 is a partially exploded, perspective view of a y-axis assembly in accordance with the alternative embodiment of a medication delivery unit of FIG. 32.

Movement of the right timing belt 244a in the right tractor support assembly 240a is provided by a stepper motor drive pulley 256 mounted on the axle of a stepper motor 258. The stepper motor 258 turns the stepper motor drive pulley 256 thereby causing movement of the right timing belt 244a and corresponding right tractor assembly 230a. In this example, a single stepper motor 258 is provided. In order to translate the movement provided by the stepper motor 258 to the left timing belt 244b, a drive shaft 260 is coupled at its end to a right drive pulley 261a that is driven by the right timing belt 244a. A left drive pulley 261b, coupled to the other end of the drive shaft 260, in turn induces movement in the left timing belt 244b thereby moving the left tractor assembly 230b accordingly. Note that both the right and left timing belts 244a, 244b are further supported by corresponding right and left idler pulleys 263a, 263b (FIG. 37). Those having ordinary skill in the art will appreciate that the arrangement of a single stepper motor and multiple timing belts described above is but one of many techniques that may be employed for the purpose of moving the tractor assemblies as required. For example, each tractor assembly 230 may incorporate its own motive source, such as a suitably sized motor that directly engages the support (i.e., rails 242) for the tractor assembly 230.

Figure 33:
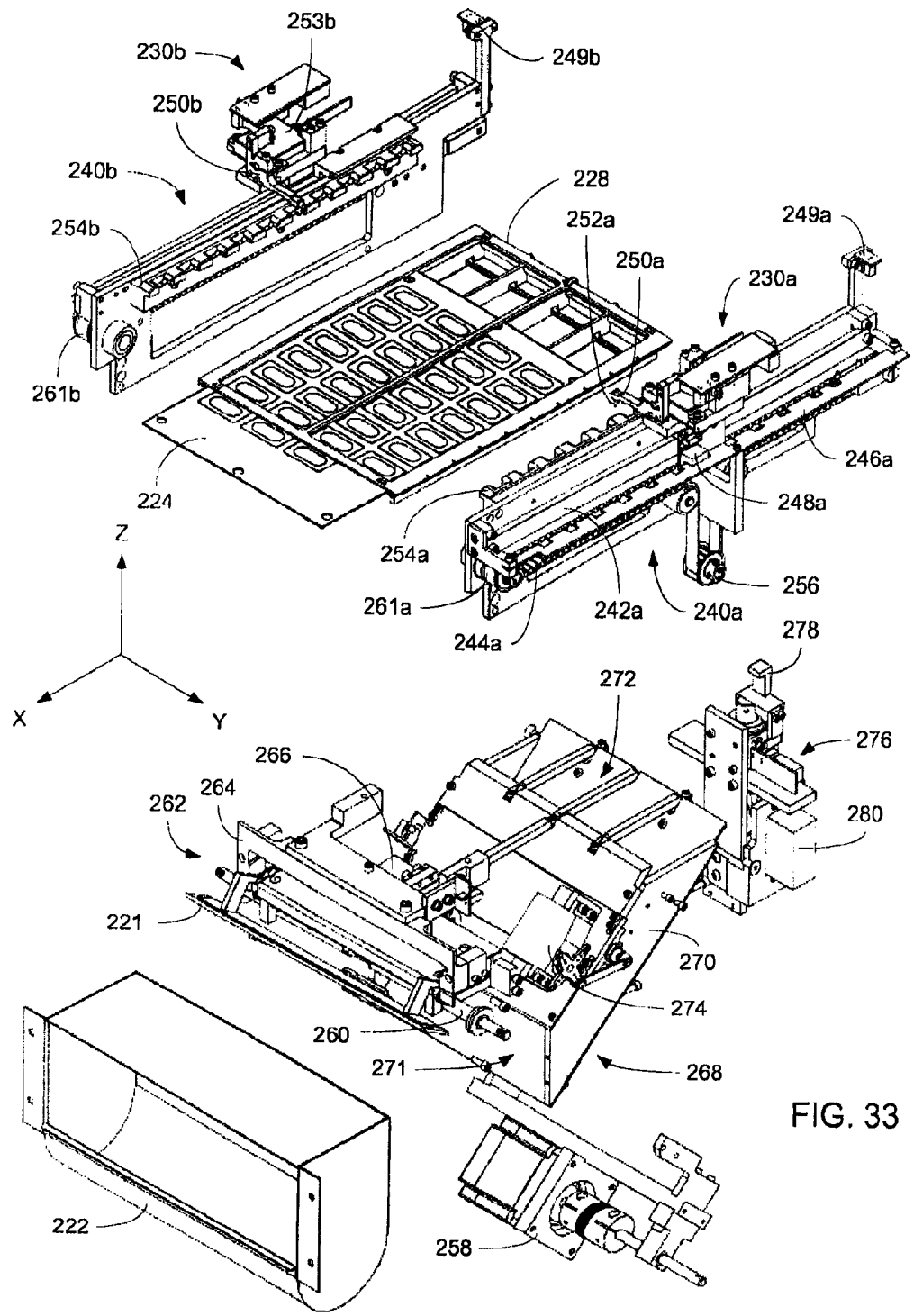
FIG. 33 is a partially exploded, perspective view of an x-axis assembly in accordance with the alternative embodiment of a medication delivery unit of FIG. 32.

Additional assemblies, particularly illustrated in FIG. 33, include an access door assembly 262, a delivery chute assembly 268 and a rear guard assembly 276. The access door assembly 262 includes the access door 221 as well as the necessary components for opening and closing the access door 221. Using a processor-controlled servo motor 266 coupled to the access door 221 via a suitable linking mechanism (not shown), the access door may be automatically opened and closed. An access frame 264, used in part to provide rotatable support of the access door 221, is preferably aligned with the tractor support assemblies 240 such that a carriage 228 that has been removed from the storage elevator 232 may be extended up to and through (by virtue of operation of the tractor assemblies 230) a suitably configured opening in the access frame 264. In this manner, a user inserting a medication carrier 224 into the medication delivery unit 33 may properly align the carrier 224 within the carriage 228. As also described with respect to FIG. 3 et seq., medication carriers are automatically drawn into the unit, read and stored in the elevator.

The delivery chute assembly 268 includes a diagonal delivery chute 270 that couples via a lower opening 271 to a rear opening in the collection chute 222. An upper opening 272 of the delivery chute 270 is positioned between the tractor support assemblies 240 and along the x-axis beneath an ejector assembly (not shown; see FIGS. 38-40) that removes individual unit dose packages from a medication carrier. Arranged in this manner, the ejected unit dose packages are gravity-fed into the upper opening 272 where they are collected behind a gate (not shown). Through operation of a processor-controlled gate servo motor 274 and corresponding linkage, the gate may be rotated to a substantially open position thereby allowing the ejected unit dose packages to be released into the collection chute 222, and thereafter rotated back into a substantially closed position for subsequent ejection operations.

A rear stop gate assembly 276 includes a rear stop gate 278 reciprocally movable within a supporting bushing 281 (FIG. 36) along the z-axis via a processor-controlled rear stop gate servo motor 280. Positioned along the x-axis behind the upper opening 272 of the delivery chute 270, the rear stop gate serves to prevent any carriages 228 from being inadvertently withdrawn from the elevator 232 during loading and unloading operations. Although the rear stop gate 278 is shown in a reciprocally moving implementation, those having ordinary skill in the art will appreciate that other implementations may be equally employed, e.g., a rear stop gate that is rotated into and out of position.

Referring now to FIG. 37, two sub-assemblies 282, 284 of a y-axis assembly are shown. A first y-axis subassembly 282 encompasses an ejector such as a punch subassembly 286. Corresponding drive structures are used to move the punch subassembly 286 along a fixed y-axis defined by a rail 288 to which the punch subassembly 286 is slidingly attached via a mounting block 289. To precisely determine location of the punch subassembly 286 along the rail 288, an encoder bar 290 is provided. As described above with respect to the encoder bars 260 used in conjunction with the tractor assemblies 230, the encoder bar 290 incorporates notches, at predetermined locations, that may be detected with relatively high precision by an encoder bar sensor 292, which may again include a light source and sensor. Movement of the punch subassembly 286 is induced by a timing belt 294 coupled to a suitable processor-controlled stepper motor 296 via a stepper motor drive pulley 298. As shown, idler pulleys 300 and cam followers 301 may be employed to properly position and tension the timing belt 294. The mounting block 289 is affixed to the timing belt 294. Once again, other arrangements known to those of skill in the art may be equally employed for inducing and controlling movement of the punch assembly 286. Furthermore, although the punch assembly 286 is illustrated as having movement solely along a y-axis, it will be further appreciated that this is not a steadfast requirement and that the punch assembly 286 could be provided with additional degrees of freedom, e.g., along an x-axis as well.

Figure 38:
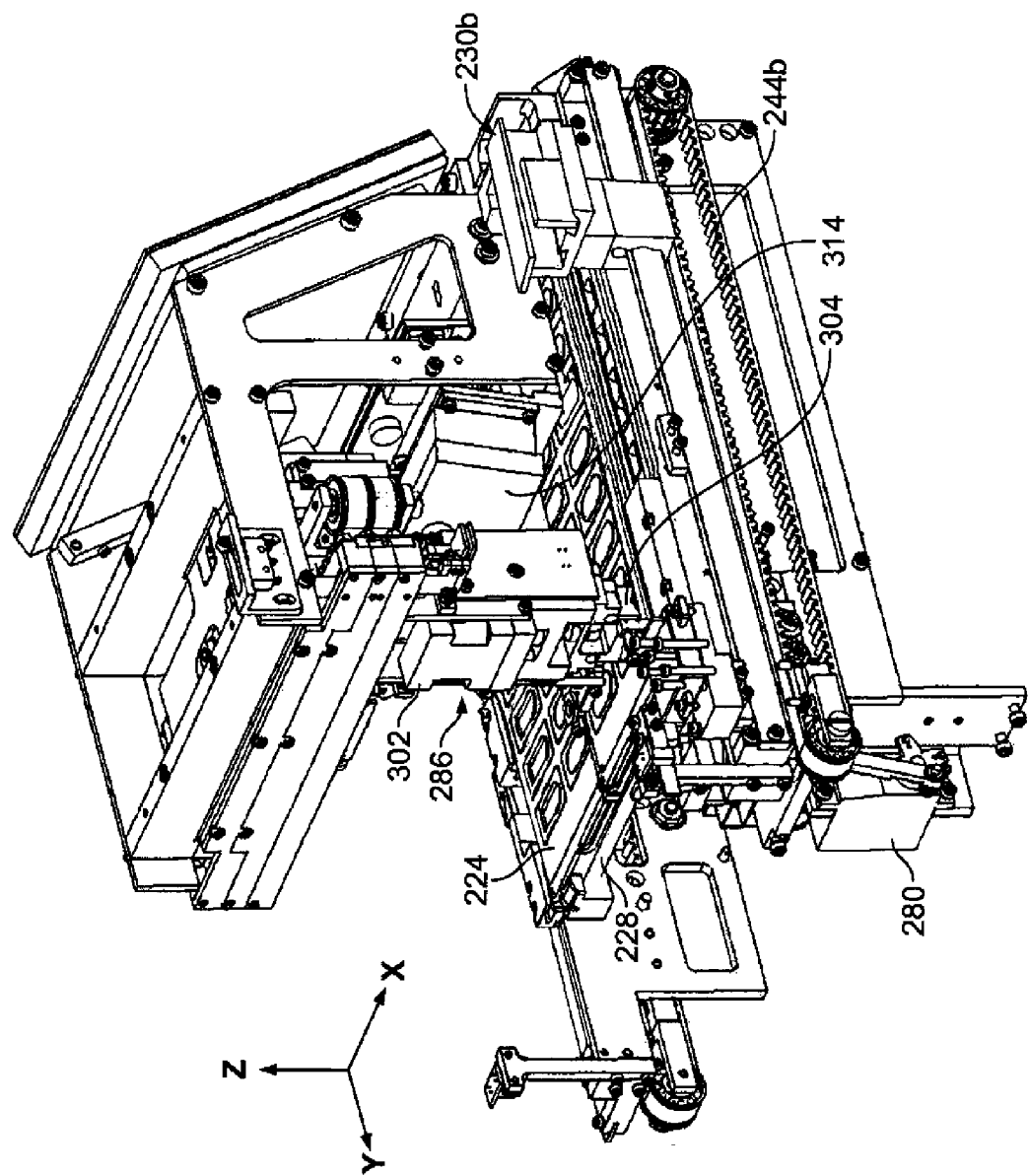
FIGS. 38 and 39 are rear perspective views of the y-axis assembly of FIG. 37.
Figure 39:
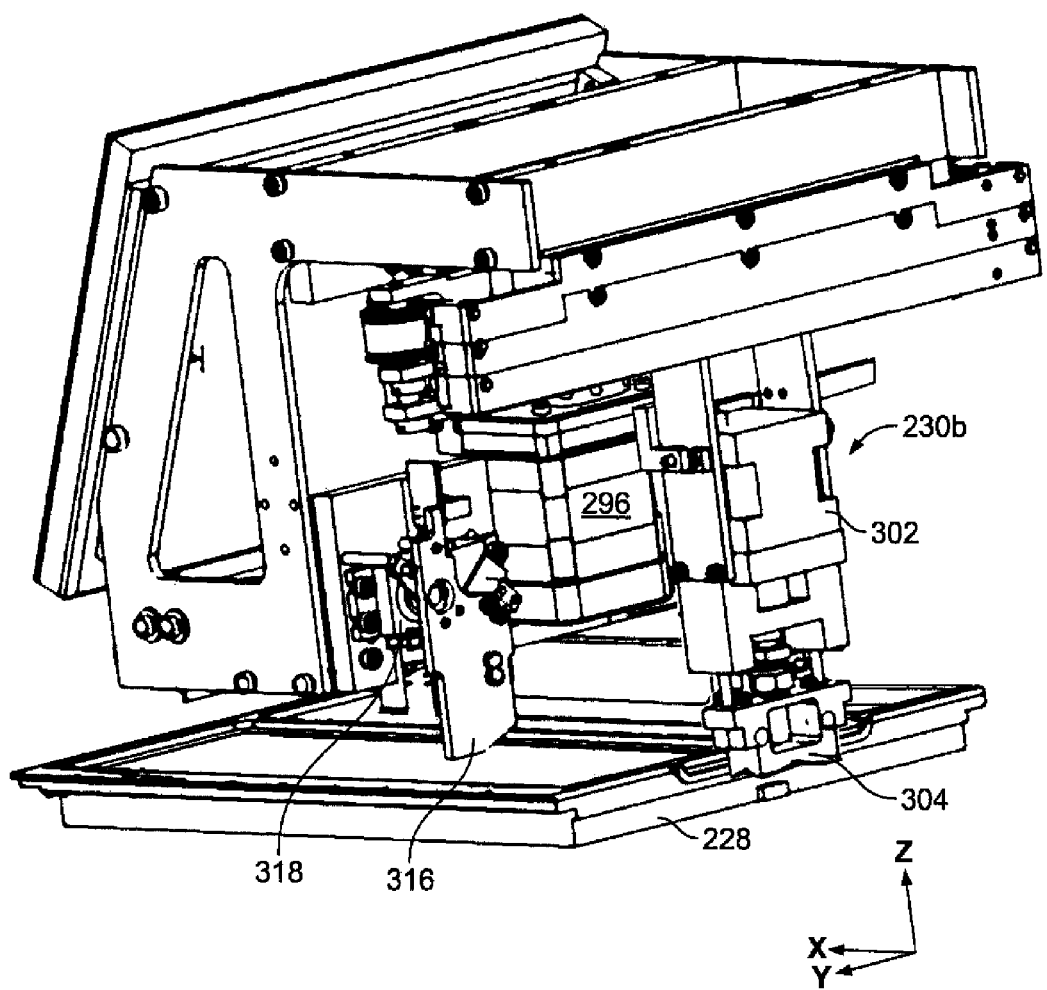
Figure 39A:
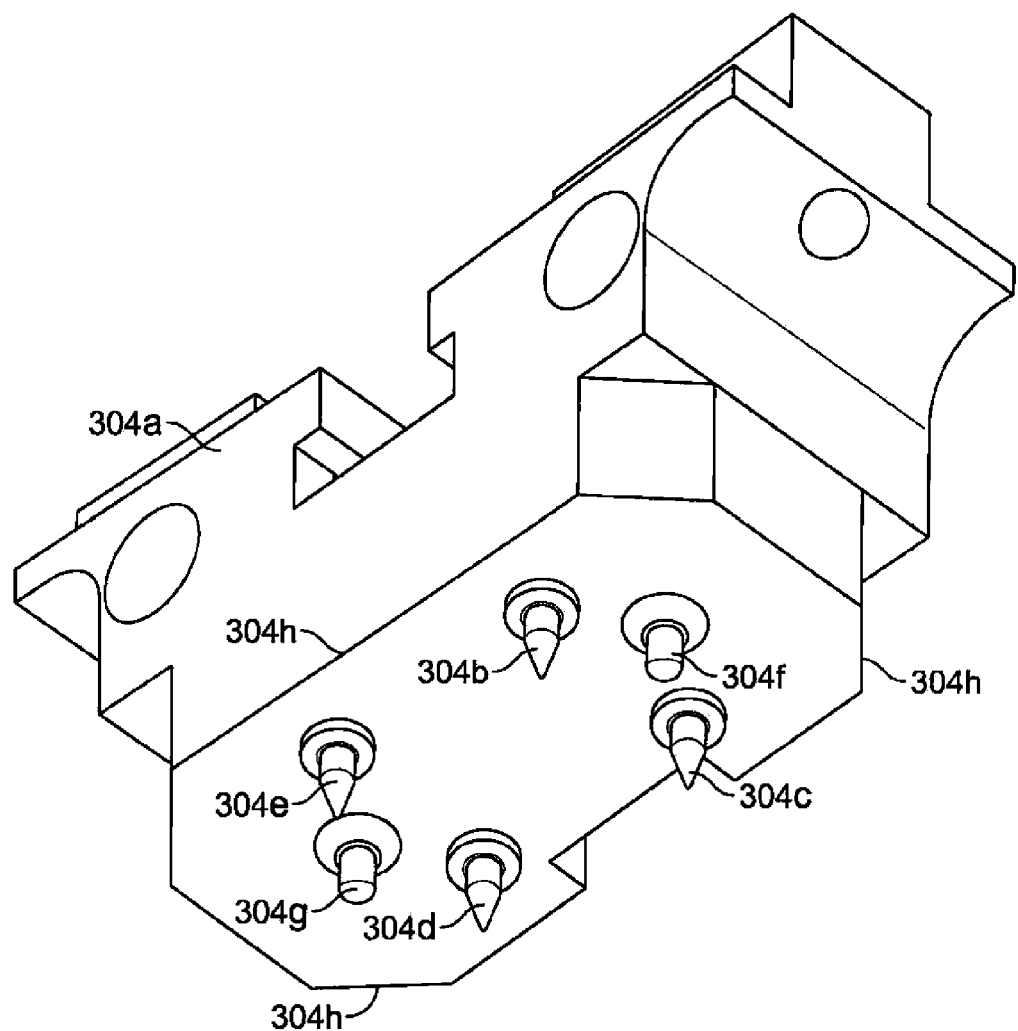
FIG. 39A is a bottom perspective view of an alternative punch tool for use with the y-axis assembly of FIG. 37.

The punch subassembly 286 includes a punch servo motor 302 that, under suitable control, reciprocally moves a punch tool 304 along the z-axis. Circuitry for operating the punch servo motor 302 as well as the encoder bar sensor 292 may be disposed on a suitable circuit board 306 as known to those having ordinary skill in the art. As described in greater detail below, the punch tool 304 is sized and configured to remove unit dose packages from a medication carrier 224. In the embodiment illustrated in FIGS. 37-39, a downward-facing surface of the punch 304 comprises four symmetrically arranged, pyramid-like structures having their most downwardly projecting points aligned at the corners of the punch 304 (see FIG. 37). In this embodiment, the four projecting points of the inverted pyramid-like structures are configured to engage the four corners of the perforations around each unit dose package (see FIG. 45) and break through the perforations around the entire periphery of a unit dose package as the punch 304 is advanced downward. An alternative embodiment of the punch 304 is illustrated in FIG. 39A. In this embodiment, the pyramid-like structures are replaced by a plurality of pins 304b-e and one or more spring-loaded plungers 304f-g disposed on a downward-facing surface of the punch 304a. Note that greater or lesser numbers of the pins 304b-e and plungers 304f-g illustrated may be employed as a matter of design choice and that any suitable shape or size of pins 304*b-e* may be used. For example, in the illustrated embodiment, the pins 340*b-e* terminate in a conically-shaped portion. As in the previously described embodiment, the outer edges 304*h* of the punch 304*a* are configured to match the perforation pattern found in individual unit dose packages. Preferably, the pins 304*b-e* are positioned within the outer edges 304*h* of the punch 304*a*. Thus, when the punch 304*a* is lowered to remove a unit dose package from a medication carrier, the plurality of pins 304*b-e* are designed, in one embodiment, to pierce the back label of the medication carrier within the periphery of the cavity comprising the unit dose, i.e., within the inner perforations 374 illustrated in FIG. 45. Alternatively, the pins 304*b-e* may be located within the region 375 between the outer perforations 372 and the inner perforations 374 illustrated in FIG. 45. This feature is useful in those (rare) instances in which a unit dose package does not completely break off from the frame of the medication carrier (resulting in a situation sometimes referred to as a "hanging chad"). To counter this possibility, the pins 304*b-e*, by piercing into the label, allow the plunger to temporarily secure the unit dose package as the punch 304*a* continues its downward movement until such time as the outer edges 304*h* of the punch 304*a* completely tear through the perforations defining the unit dose package. By securing the unit dose package in this manner, it is prevented from rotating as the punch breaks the perforations, a situation that causes the hanging chad problem. Substantially simultaneously, the resistance of the unit dose package to the movement of the punch 304*a* causes compression of the spring loaded plungers 304*f-g*. Once the perforations of the unit dose package have been completely broken, the resistance of the unit dose package is removed, thereby allowing the spring force of plunger 304*f-g* to remove the unit dose package from the pins 304*b-e*.

In yet another embodiment, the punch tool 304 may be configured to remove individual unit doses themselves (i.e., the medication only) from the unit dose packages in those instances in which cross-contamination of medications is not a concern.

A position sensor 308 is preferably mounted on the circuit board 306 to detect a position of a flange 310, mounted to the punch tool 304, along the z-axis. In this manner, the position sensor 308 can determine whether the punch tool 304 has been fully extended (e.g., when removing a unit dose package from a medication carrier) or retracted (e.g., when moving the punch subassembly 286 along the rail 288). Additionally, a finger 312 is mounted on a forward-facing surface of the punch tool 304. As described in further detail below with reference to FIGS. 39 and 41-43, the finger 312 is used in one embodiment to engage a corresponding structure of a carriage 228 to restrict movement of the carriage 228 and permit full insertion of a medication carrier 224 into the carriage. FIG. 38 illustrates alignment of the punch subassembly 286 relative to a carriage 228 loaded with a medication carrier 224. As shown, the carriage 228 has been moved into position beneath the punch assembly 286 such that one row of unit dose packages is directly beneath the y-axis of the punch assembly 286.

Figure 40:
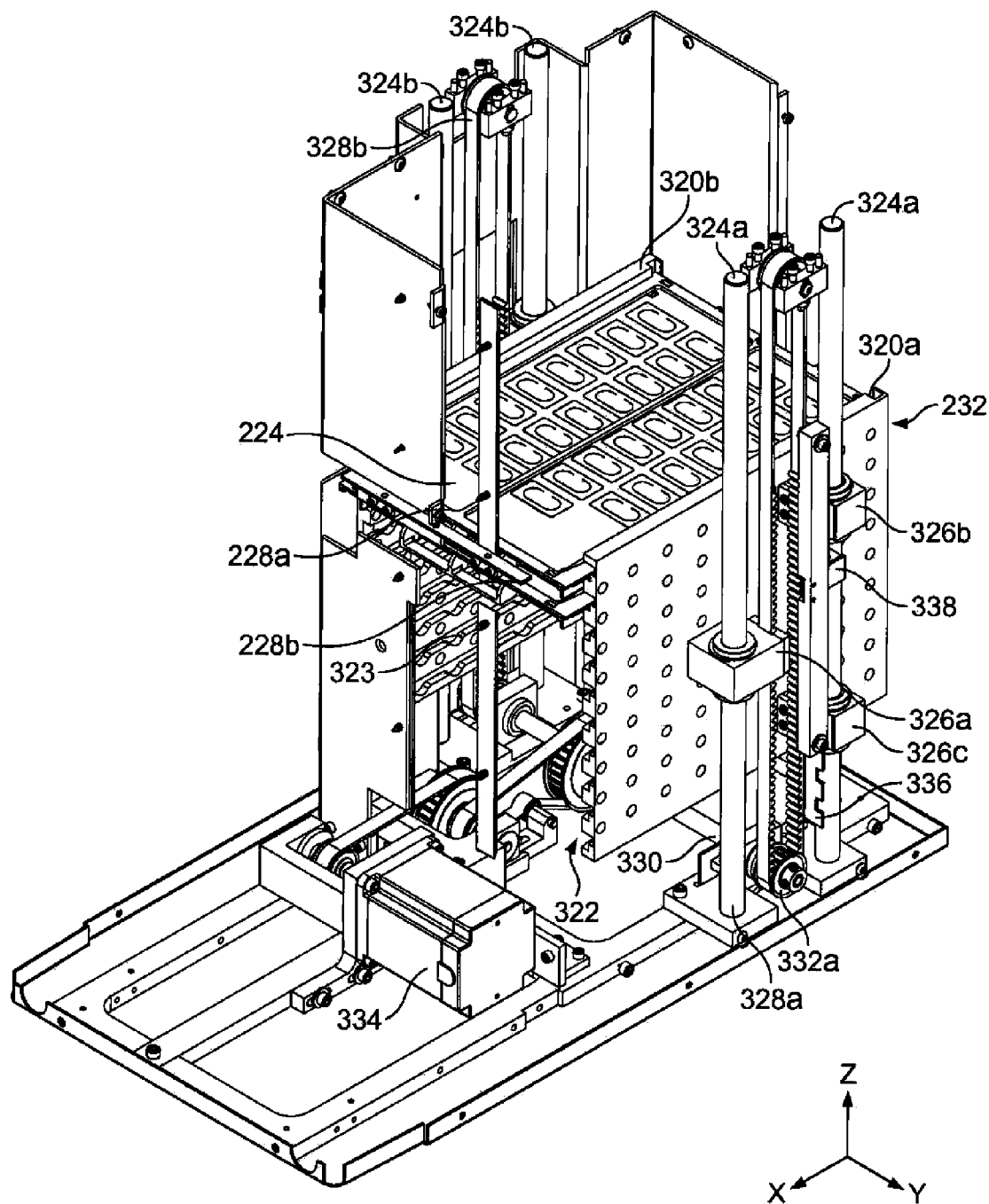
FIG. 40 is a partial cutaway, perspective view of a z-axis assembly in accordance with the alternative embodiment of a medication delivery unit of FIG. 32.

As noted above, and referring once again to FIG. 37, the second subassembly 284 includes the stepper motor 296 and stepper motor driver pulley 298. As shown, the second subassembly 284 also includes a barcode reader 314 arranged so that a scanner/input surface thereof is facing downward (toward the surface of a medication carrier). In the embodiment shown, the barcode reader 314 illustrated in FIGS. 38-40 is fixedly attached to its supporting frame and therefore only capable of reading bar codes that are positioned immediately below it, which may not constitute all of the possible barcodes presented on the surface of a medication carrier. However, it is understood that other arrangements may be employed. For example, multiple such fixed bar code readers may be employed such that, by virtue of their arrangement, all possible bar codes are read as the medication carrier is moved past the bar code readers along the x-axis. Alternatively, the bar code scanner may be mounted so as to be freely moveable along either or both of the x- and y-axes. For example, a bar code reader may be mounted on the punch subassembly 286 such that, through the combined x-axis freedom of movement of the medication carrier/carriage and the y-axis free of movement of the punch subassembly 286, virtually any location on the upward-facing surface of a medication carrier may be read using the bar code reader.

A loading stop gate 316 is also partially illustrated in FIG. 38 as forming part of the second subassembly 284. The loading stop gate 316, positioned according to a processor-controlled servo motor 318, is used to position a manually-input medication carrier at a predetermined location such that the tractor assemblies 230 may be automatically moved into position to engage the medication carrier and complete insertion of the medication carrier in a corresponding carriage. When the second subassembly 284 is mounted on top of the x-axis assembly described above, the loading stop gate 316 is positioned approximately mid-way along the longitudinal length of, and in between, the tractor support assemblies 240 as best shown in FIG. 32. In its retracted position (shown in FIG. 37), the loading stop gate 316 does not inhibit movement of medication carriers. However, when placed in its extended position (shown in FIG. 39), a portion of the loading stop gate 316 extends below a plane defined by an upper surface of the carriage 228 a sufficient distance so as to impede insertion of a medication carrier 224 (not shown in FIG. 39) beyond the loading stop gate 316. Because the location of the loading stop gate 316 is precisely known along the x-axis, an abutting engagement between a medication carrier and the loading stop gate 316 allows loading/unloading openings 368 (see FIGS. 44 and 45) to precisely positioned for subsequent engagement by the tractor arms 250 and pegs 252. FIG. 39 also illustrates alignment of the punch tool 304 such that the finger 312 (not visible in FIG. 39) attached thereto may engage the carrier 228 during loading and unloading, described in further detail below.

Referring now to FIG. 40, a z-axis assembly is illustrated. Generally, the z-axis assembly concerns those components of the delivery module 33 involved in the storage of the medication carriers 224 and corresponding carriages 228. As best illustrated in FIG. 32, the z-axis assembly is constructed such that carriages 228 stored within the elevator 232 may be directly unloaded into the x-axis assembly by operation of the tractor assemblies 230.

As shown, the elevator 232, in the illustrated embodiment, includes two parallel plates 320 each including a plurality of grooves 322 formed therein substantially along the entire length of each plate 320. In this embodiment, the plates 320 are not connected to each other (unlike the embodiment shown in FIGS. 3-6). As shown, each plate includes ten grooves, although a greater or less number may be employed as a matter of design choice. Corresponding pairs of grooves 322 from each plate together establish slots that may be used to store medication carriers 228, as shown. Note that, in one embodiment, each groove 322 includes notches 323 along its length to minimize contact between the grooves 322 and carriages 228, thereby minimize friction when loading or unloading the carriages 228 from the elevator 232. Further, as noted above, the slots need not be restricted to a substantially horizontal alignment and, instead, could be aligned in virtually any suitable vertical or diagonal alignment as a matter of design choice. Should such alternative alignments be employed, those of skill in the art will appreciate that the loading and unloading mechanisms, for example, would likely need to be similarly realigned accordingly.

Pairs of posts 324a, 324b slidably engage bearings 326 (only one set shown) upon which each plate 320 is mounted. A pair of timing belts 328a, 328b is provided, one for each plate 320, that are driven by a drive shaft 330 and corresponding drive pulleys 332 attached to either end of the drive shaft 330. In the embodiment shown, the drive shaft 330 is driven by an arrangement of belts and pulleys coupled to a processor-controlled stepper motor 334. It will be appreciated that other arrangements for driving a drive shaft may be equally employed for this purpose. Within each set of bearings 326, a first bearing 326a is coupled to a timing belt 328 such that rotation of the timing belt 328 induces movement in the corresponding plate 320. Similarly, an encoder bar 336 is affixed to the other bearings 326b, 326c such that movement of the encoder bar 336 along the z-axis tracks movement of the elevator 232. As in previous examples, the encoder bar 336 includes notches at predetermined position. An encoder bar sensor 338, similar in operation to those previously described and fixedly mounted to a portion of the housing (not shown), senses each of the notches in the encoder bar 336 with high precision such that location of the elevator along the z-axis may be determined.

Figure 41:
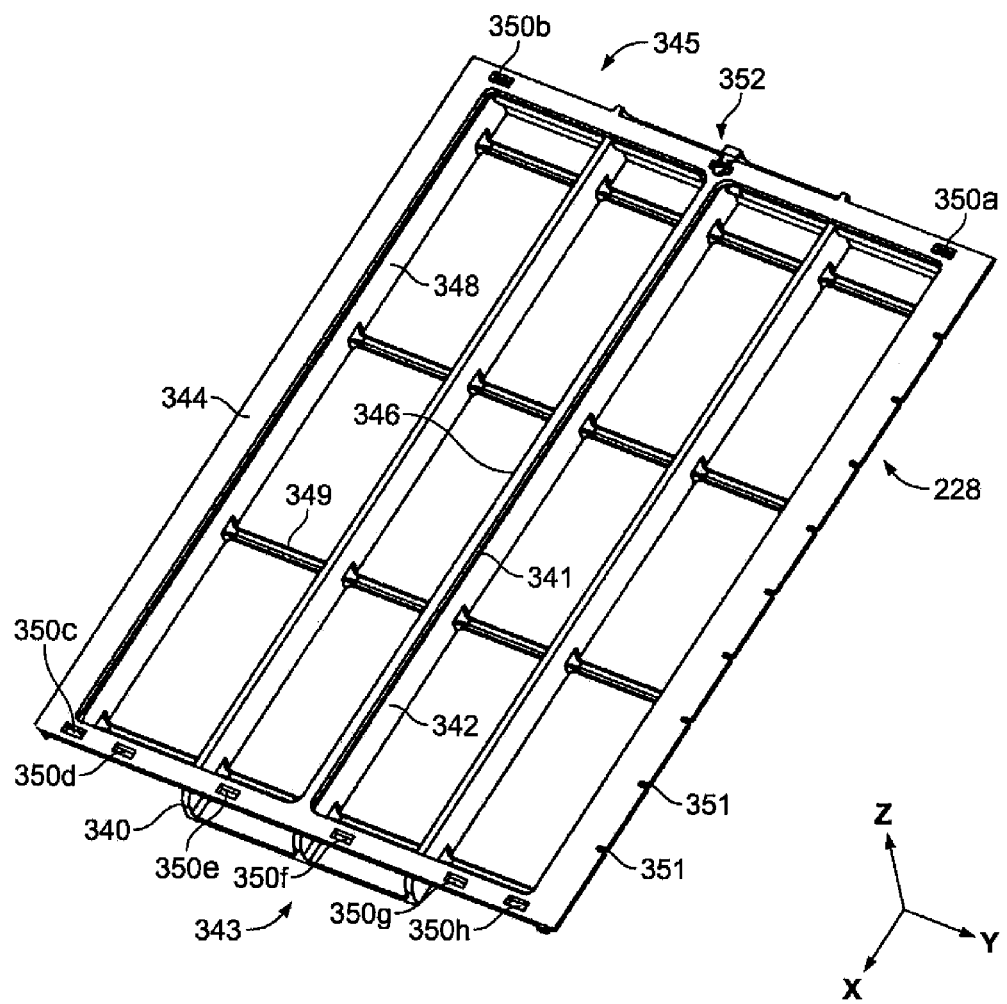
FIG. 41 is a perspective view of an exemplary carriage for use in a medication delivery unit.
Figure 42:
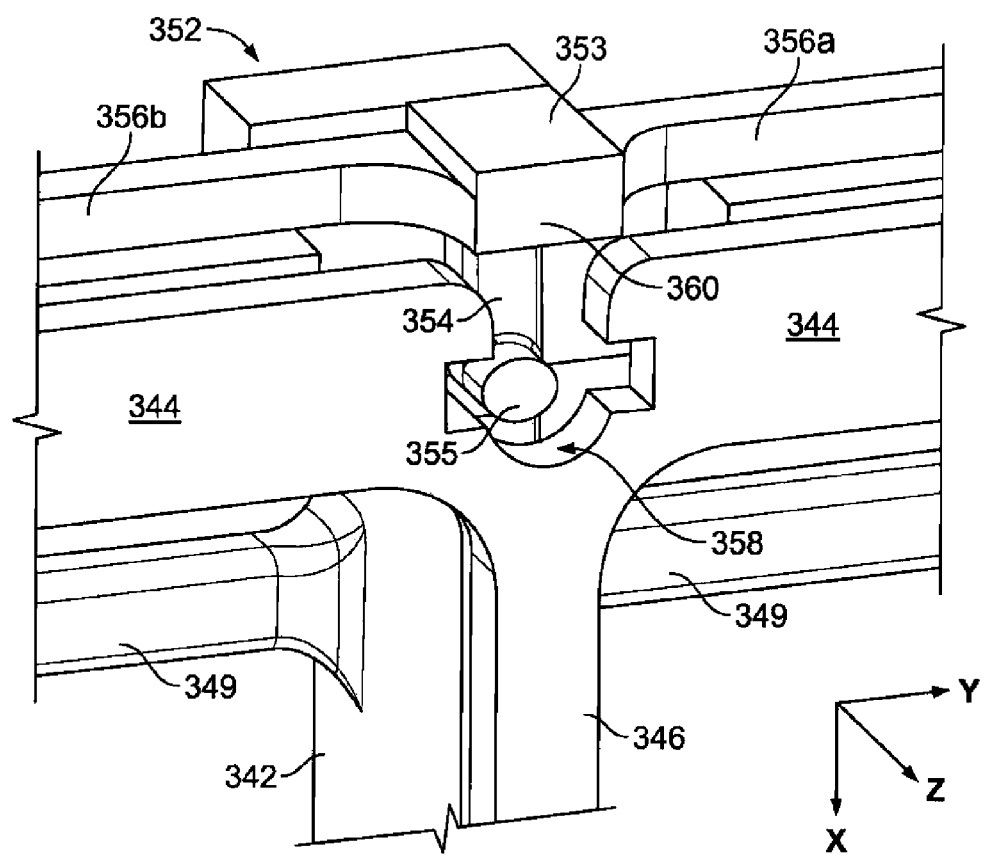
FIGS. 42 and 43 are magnified views from various perspectives illustrating in greater detail a holding mechanism of the exemplary carriage of FIG. 41.
Figure 43:
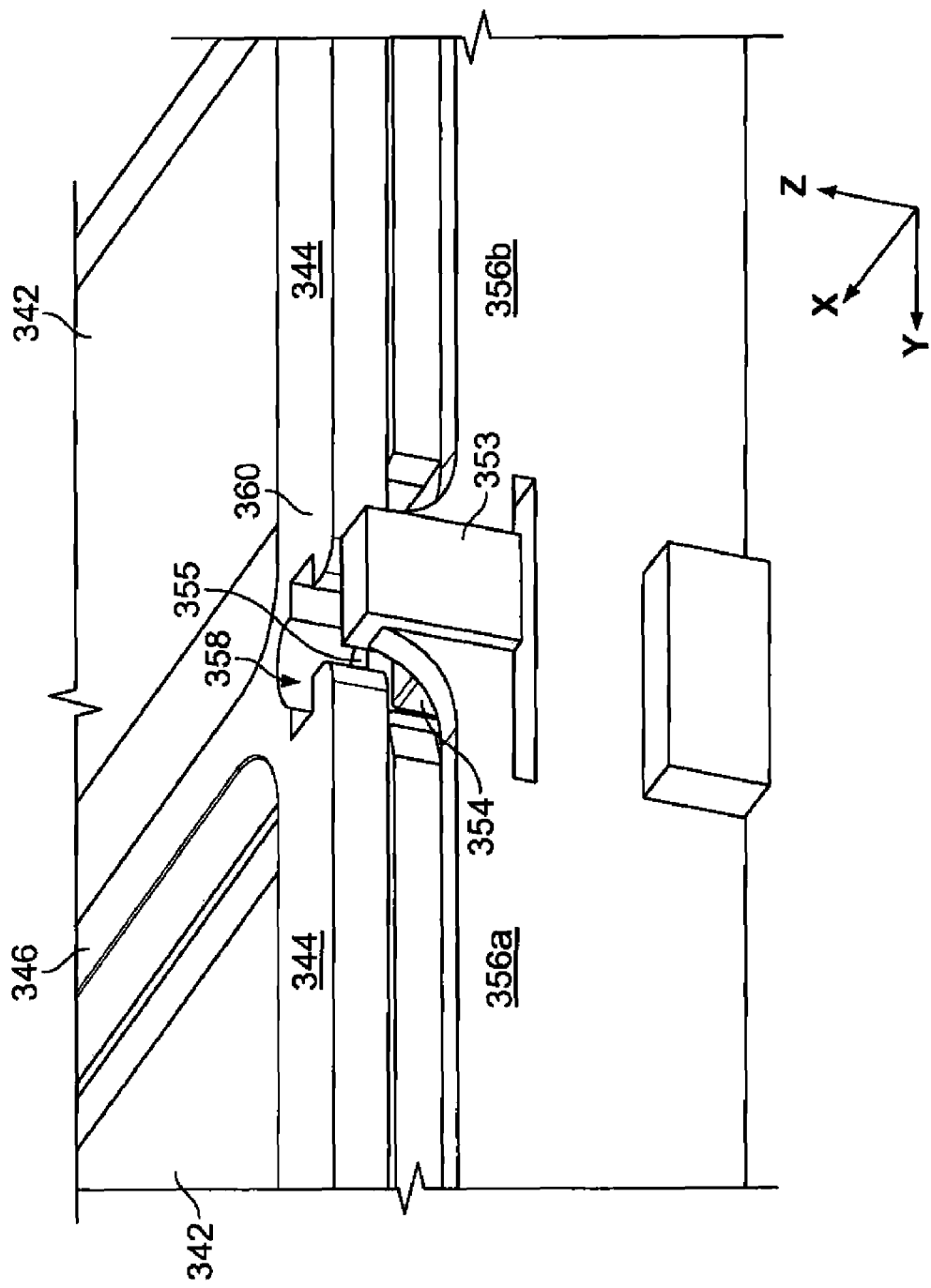

Referring now to FIGS. 41-43, various aspects of an exemplary embodiment of a carriage 228 are illustrated. As shown in FIG. 42, the carriage 228 includes a bottom section 340 having a plurality of bottom rails 342, a top section 344 having a plurality of top rails 346, and one or more side sections 348, connecting the top section 344 and the bottom section 340. Collectively, the bottom and top sections 340, 344 form a relatively narrow opening 341 therebetween of sufficient dimension to freely accept the thickness of an input medication carrier (inserted beginning at proximal end 343 of the carriage 228). The dimension of the opening 341 may be selected as a matter of design choice and depending on the thickness of those portions of the medication carrier that come into contact with the carriage 228.

Struts 349 between bottom rails 342 provide greater rigidity to the carriage 228 if desired. Note that similar struts may be applied to the top rails 346 as a matter of design choice. The rails, particularly the bottom rails 342, support input medication carriers and, in a preferred embodiment, enhance the rigidity of the medication carrier when unit dose packages are ejected from the medication carrier. Although substantially uniform spacing between the various rails 342, 346 is shown, this is not a requirement an such spacing may be variable as a matter of design choice. As further shown, the bottom and top rails 342, 346 extend in parallel to the longitudinal axis (the x-axis) of the carriage 228. In an alternate embodiment, the rails (on either the bottom or top sections 340, 344) may instead extend perpendicularly to the longitudinal axis, i.e., from one side section 348 to the other, or a combination of such parallel and perpendicular rails may be used and may include cutout portions to allow clearance of unit dose packages as the carrier is drawn into the unit. Further still, one or both sets of rails may be replaced by a sheet-like member in which in which openings are formed in a pattern such that the remaining material in the sheet-like member provides a similar supporting function (for a medication carrier) as the rails depicted in FIG. 41.

The carriage 228 may include one or more holes or notches 351 on at least one side member of the carriage 228. The holes 351 may be used to determine the location of carriage when the carriage is inserted into a storage unit such as the elevator 232 described above. For example, the elevator 232 may include a sensor, such as an optical interrupt sensor, and a light source, such as a light emitting diode, positioned opposite the sensor. When a hole 351 is coincident with the light source, the sensor senses the light source thereby allowing the location of the carriage 228 to be determined. Properly determining the location of the medication carrier 224 within the storage unit may be required in order to properly remove unit dose packages stored within the medication carrier, or to determine the degree that the carriage 228 is inserted into the elevator 232. Other methods of determining the location of a carriage 228 within a storage unit will be apparent to those of ordinary skill in the art based on this disclosure.

In one embodiment, the carriage 228 includes at least one holding mechanism 352 on an edge of the distal end 345 of the carriage 228. A single holding mechanism 352 is illustrated in FIG. 41. It is noted, however, that one or more such mechanism could be employed, which mechanisms could also be deployed at various other locations of the carriage 228. The holding mechanism 352 is used to hold a medication carrier 224 in place within the carriage 228 (via a corresponding holding feature in the medication carrier 224, i.e., an opening 366 therein) when the medication carrier 224 has been completely inserted into the carriage 228. The holding mechanism 352 engaged/disengaged or otherwise actuated to accept/release the medication carrier 224 during insertion/removal of the medication carrier 224 into/from the carriage 228, as described below.

A plurality of openings or holes 350 are also depicted in FIG. 41. Preferably, the openings 350 are positioned in either or both of the bottom and top section 340, 344 such that they may be engaged by a suitable mechanism to move the carriage 228 as necessary, e.g., the tractor assemblies 230 described above. The particular dimensions and locations of the holes 350 may vary as a matter of design choice and may be different between different types of carriages 228.

Referring now to FIGS. 42 and 43, further detail of the holding mechanism 352 is shown. In particular, the presently preferred holding mechanism 352 includes a body member 353 having a cantilevered arm 354 extending therefrom. The body member 353 is supported by a pair of flexible arms 356 coupled to the bottom section 340. The cantilevered arm 353 is exposed through an opening 358 in the top section 344 such that a hook portion 355 of the arm 354 faces into the opening 358. An upper surface 354 of the body member 353 is configured to receive a complementary surface of the finger 312 described above relative to FIG. 37. The finger 312, being coupled to the punch 304, is positioned to engage and push downward against the upper surface 360. In the manner the flexible arms 356 allow the body member 353, and hence the cantilevered arm 354 to be displaced a sufficient distance to allow an opening 366 in the medication carrier 224 to be positioned for locking engagement with the hook portion 355 or, in the case of unloading, to allow the opening 366 to be disengaged from the hook portion 355. Although a particular cantilevered arm and hook configuration has been illustrated in FIGS. 42 and 43, those having ordinary skill in the art will appreciate that other constructions may be equally employed for implementing the holding mechanism 352. For example a pinching, clamping or press fit arrangement may be used. In such an embodiment, on one or more of the bottom rails 342 and/or one or more of the top rails 346 may be used to create an interference fit between the carriage 228 and the medication carrier 224.

It should be noted that, in the embodiments shown, a separate carriage 228 is provided for each medication carrier 224 to be stored in the medication delivery unit. However, it is understood that, if the medication carriers 224 are of sufficient strength and stiffness, the carriages 228 could be eliminated altogether. Alternatively, a single structure similar to the carriages 228 described herein could be incorporated into, for example, the x-axis assembly described above. In such an embodiment, the carriage-like structure would only be necessary when used to support the medication carriers (via structures akin to the rails 342) during application of substantially perpendicular forces to the medications carriers, e.g., when ejecting a unit dose package.

Figure 44:
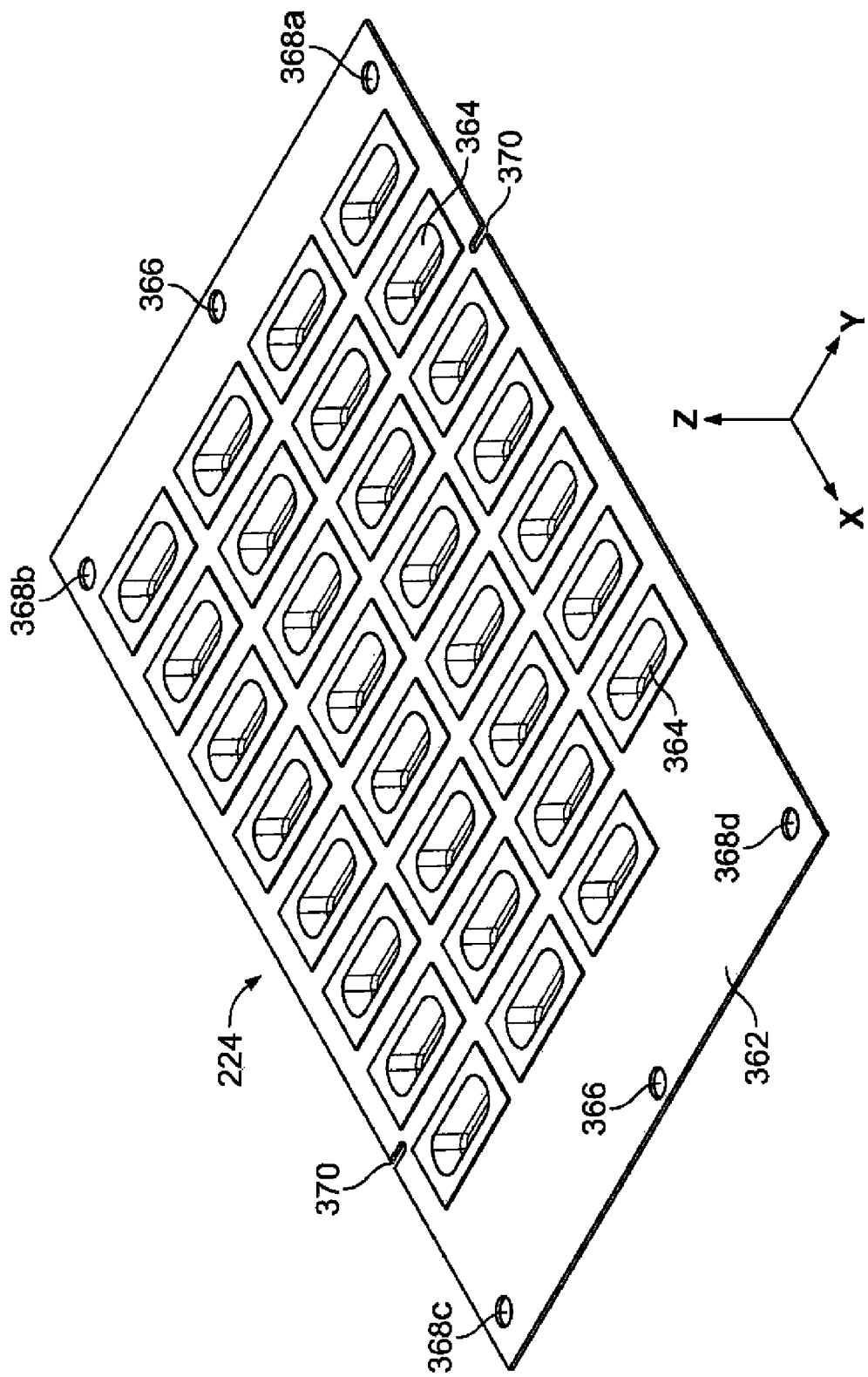
FIG. 44 is a perspective view of an exemplary medication carrier comprising a plurality of unit dose packages in two-dimensional arrangement for use in a medication delivery unit.
Figure 45:
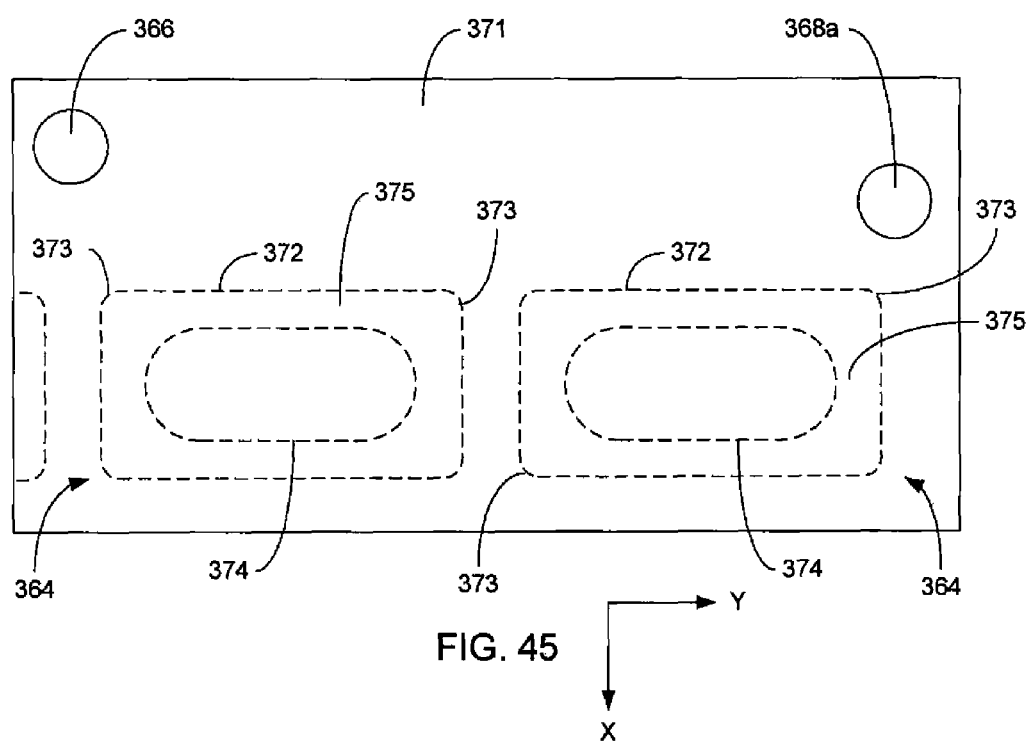
FIG. 45 is a top magnified view illustrating in greater detail various features of the exemplary medication carrier of FIG. 44.

Referring now to FIGS. 44 and 45, a medication carrier 224 in accordance with a presently preferred embodiment is illustrated. Generally, the construction of the medication carrier 224 is commensurate with that disclosed in pending U.S. patent application Ser. No. 11/366,295, the teachings of which are incorporated herein by this reference. That is, the medication carrier 224 may comprise three layers that are bonded together using appropriate adhesives: a first layer for support, a second layer bonded to the first layer and comprising a plurality of blisters or indentations formed therein that correspond to openings in the first layer for receiving the blisters, and a third layer bonded to the second layer providing a backing or label layer that encloses and seals each of the blisters. In a presently preferred embodiment, each medication carrier is approximately 6 inches (15.24 cm) wide by 9 inches (22.86 cm) long and approximately 0.070 inches (1.778 mm) thick and conform to an industry standard size. As shown, the medication carrier 224 includes a substantially planar body portion 362 including a plurality of unit dose packages 364 distributed in a two-dimensional arrangement over the area of the planar body portion 362. For the sake of clarity, a label sheet (illustrated, for example, in FIGS. 33, 34 and 36) is not shown. It is preferred to arrange the unit dose packages 364, which may include bubble-shaped blister packages as known in the art, in a uniform row and column configuration as shown in FIG. 44. However, this is not a requirement and variable spacing between unit dose packages 364 may be employed. Further, it is preferred that all unit dose packages 364 have the same shape and dimensions. Again, this is not a requirement and unit dose packages of varying sizes and shapes may be incorporated into a single medication carrier 228.

The planar body portion 362 may include a unitary element in which the unit dose packages 364 are formed. In this instance, the body portion 362 is preferably fabricated from a suitable material (such as plastic as known in the art) of sufficient thickness in order to provide sufficient rigidity of the body portion 362. In another embodiment, the body portion 362 is a lamination of a relatively thin layer of material (e.g., plastic) in which the individual unit dose packages are formed and a relatively more rigid (possibly thicker) layer of suitable material (e.g., cardboard) for added structural support. For example, in one presently preferred embodiment, thin layer in which the unit dose packages are formed is fabricated from a general purpose 0.012 inch (0.3 mm) PVC plastic. The bubble-shaped blisters in each individual unit dose package 364 are formed using a molding tool. Subsequently, each unit dose package 364 is punched/scored around its perimeter completely slicing through the plastic except in two (2) locations on each end (along the y-axis; four total) of the unit dose package 364. At these four locations a 1.5 mm perforation remains. In this preferred embodiment, the structural support layer comprises a cardboard layer of 18 point Solid Bleach Sulfate Board with a heat seal adhesive on one side and a clay coating on the other. This support layer is then punched to match the locations and pattern of the bubble-like blisters with an opening approximately 1.5 mm larger then the blister size cut into each of the plastic layer and the label layer in each of the x and y axes. The larger opening in the support layer is employed to ensure that the individual unit dose packages 364, when "punched" out of the carrier, can pass through the support layer as the perforations on the label and plastic break.

Regardless of the underlying construction of the body portion 362, each unit dose package, as noted above, is preferably defined by outer scoring marks or perforations 372 along the periphery thereof, as shown in FIG. 45. In the depiction of FIG. 45, a label layer 371 (which may include a single layer such as paper or foil or a combination thereof) is present. As known in the art, these outer perforations 372, which entirely penetrate the label layer 371 and at least a portion of the thickness of the underlying body portion 362, allow each unit dose package 364 to be removed relatively easily from the body portion 362 of the medication carrier 224. A feature of the outer perforations 372 is that the corners thereof 373 are rounded. By rounding these corners 373, the force required to dislodge the unit dose package 364 through breakage of the outer perforations 372 is reduced in comparison with sharper, i.e., square, corners. In a presently preferred embodiment, each unit dose package 364 also includes inner scoring marks or perforation 374, preferably in the label layer 371 and only through a portion of the label layer's thickness to preserve sterility, such that each individual unit dose of medication, e.g., a single pill, can be expelled from the unit dose package 364 independent of whether the unit dose package 264 has been previously removed from the medication carrier 224.

Although not shown in FIGS. 44 and 45, the label layer, in the presently preferred embodiment, is a 9 point Solid Bleach Sulfate Board with a heat seal adhesive on one side and a coating on the other side that prevents the ink (from an inkjet printer) from running when applied. Scoring/punching in the label layer exactly matches the plastic layer, i.e., the layer in which the unit dose packages are formed. During the application of the heat seal adhesive to the label, an area around the perimeter of where each unit dose package 364 is located is preferably masked so that no glue is applied thereupon. This prevents the adhesive from flowing into the punched/scored area around each blister (364) and forming a bond between the unit dose package 364 and the surround plastic. Also during the punching/scoring process, a score line that is only punched 90% of the way through the label material is preferably cut in the general area of, and aligns with, the bubble-like blister in the plastic. These scored area (previously described) may be in the form of a straight line, cross, or circular pattern and enables the pill to be removed from the sealed blister easier by making the label weaker in this area. Regardless, the label can be printed using a standard ink jet printer utilizing computer software and, at this time, the identifying indicia described herein may be printed onto the surface of the label.

In the presently preferred embodiment, a medication carrier is fabricated by placing first placing the support layer onto a fixture and aligned onto pins that fit into the slots 370 formed therein. Thereafter, the layer in which the bubble-like blisters are formed (i.e., the plastic layer described above) is placed onto the fixture such that the bubbles are facing down and fit into openings in the fixture. Then the desired medications are placed into the bubble-like blisters using any suitable technique. Thereafter, the label is placed onto plastic layer using the slots 370 for alignment. The entire fixture and assembly is placed into a heat seal press and compressed at 300° F. (149° C.) for approximately 5 seconds. The heat seal coating is thereby activated causing the three layers to laminate. Thereafter, the laminated assembly is removed from the fixture.

As noted above, one or more openings 366 may be provided in the medication carrier 224 for engagement with the holding mechanism 352 of the carriage 228. In a presently preferred embodiment, a single, centrally-aligned opening 366 is provided near the edge of each transverse side of the medication carrier 224. With this symmetrical arrangement, interlocking engagement of an opening 366 and the holding mechanism 352 is assured regardless of the front-to-back orientation of the medication carrier 224. Alternatively, an asymmetrical arrangement of such openings (or similar devices) may be employed if it is desirable to enforce specific alignments of the medication carriers 224. Furthermore, the opening(s) 366 may be positioned along the edges of either or both of the lateral sides of the medication carrier 224 to engage similarly positioned holding mechanisms deployed on the carriage 228. In a similar vein, openings 370 may be provided, for example, along the lateral edges of the medication carrier 228, for use in either determining a position or location of the card (as described above relative to the preferred embodiment of the carriage 228) or holding the medication carrier 224 in the carriage 228.

Additional openings 368 are provided in the body portion 362 to facilitate movement of the medication carrier 224 through the medication delivery unit 33. As described above, the openings 368 allow the tractor assemblies 230 (through the tractor arms 250 and pegs 252) to engage the medication carrier 224 and thereby impart a force to move the medication carrier 224. As shown, the openings 368 are preferably located near the corners of the medication carrier. However, this may be varied as a matter of design choice. For example, the openings 368 may be positioned closer to the middle, and away from the corners, of either the transverse or lateral sides. Alternatively, the openings 368 may be placed away from the edges of the medication carrier and, instead, placed within an interior region of the planar body portion 362. Further still, the number of openings 368 may be greater or lesser than the number shown, and they are not necessarily limited to the symmetrical placement shown.

As noted above, movement of the medication carrier 224 may be induced using means other than the tractor assemblies 230 described above. For example, one or more wheels may be positioned in contact with the medication carrier 224 on a top surface or a bottom surface thereof. The wheel may be rotated so that a force is applied, via friction, to the medication carrier 224 in the desired direction. Further still, a gripping arrangement may be employed to take hold of an edge of the medication carrier 224 to thereby induce movement in the medication carrier 224. Other arrangements for this purpose will be apparent to those of ordinary skill in the art based on the teachings of this disclosure.

Although not illustrated in FIG. 44 or 45, the various identifying indicia referred to above may be used to assist in locating or positioning a medication carrier 224. As stated above, the identifying indicia may include any mechanism at least capable of being detected or read through automated means including, without limitation, printed bar codes or dots, RFID tags, magnetic strips or imprints, indentations, bumps, holes or openings, etc. A corresponding detecting element may include, for example and without limitation, a bar code scanner, an optical sensor, a mechanical switch, and/or any other mechanism capable of detecting a particular type of indicia. For example, a bar code scanner may be used to scan for a particular bar code and/or bar code label corresponding to a predefined value, or a light sensor may sense when light shines through a hole in the medication carrier. Similarly, a mechanical switch may be in contact with a surface of the medication carrier 224 to detect when a hole or indentation corresponding to the desired location is present. Further still, an indentation or bump may cause the mechanical sensor to deviate at least a predefined distance form a nominal position of the planar body section 362 of the medication carrier 224.

Various operations enabled by the medication delivery system (FIG. 2) are further described below with reference to FIGS. 46-61. Various portions of the techniques illustrated in FIGS. 46-61 are described above. In general, the methods described hereinbelow are preferably implemented using stored, processor-executable instructions controlling operation of one more suitable processors, as described above, that, in turn, control the various hardware elements described herein, as well as inter-device communications between the various system elements (e.g., the remote controller 101 and medication delivery units 33) and intra-device communications (e.g., between the various position sensors and the servo and stepper motors with a medication delivery unit 33). Techniques for implementing such instructions are well known to those having ordinary skill in the art. Of course, other implementation techniques, such as programmable logic arrays, application specific integrated circuits or other suitable technologies may be equally employed for this purpose as a matter of design choice. Further still, it is noted that, although the techniques illustrated in FIGS. 46-61 (as well as the processing described above) are depicted as independent of one another, in actual operation, many of the depicted techniques could be combined as necessary. For example, a user of a medication delivery unit may request his/her medications without regard to a dosing regimen therefore, as describe relative to FIG. 61 below. To this end, the user may be provided with one or more medication carriers from which the user may manually dispense unit dose packages and/or unit doses. Thereafter, the user may re-insert the medications carrier(s) and have the inventory of the medication carrier(s) re-determined as described relative to FIG. 47 below. Those having skill in the art will appreciate that other such combinations of distinctly illustrated techniques may be equally employed through use of the illustrated embodiments.

Figure 46:
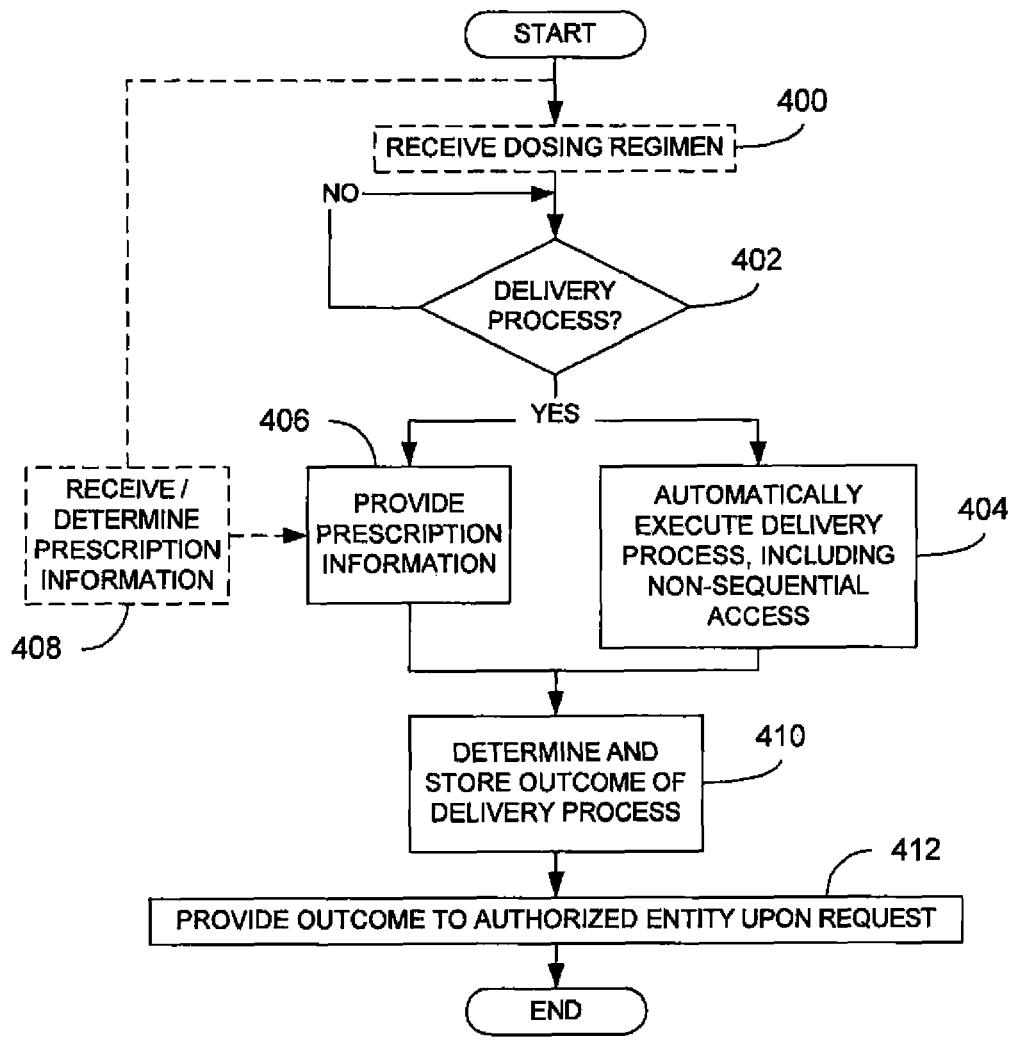
FIG. 46 is a flowchart illustrating exemplary processing concerning delivery of medications by a medication delivery unit.

Referring now to FIG. 46, processing begins at block 400 where a medication delivery unit optionally receives and stores (in suitable persistent memory) a dosing regimen. As used herein a dosing regimen includes data and information necessary for a medication delivery unit to properly deliver medications for a patient. In practice, a single medication delivery unit may operate based on a single dosing regimen or multiple dosing regimens. In the latter situation, the multiple dosing regimens may be combined into a single dosing regimen in which specific dosing events are differentiated according to the different patients. Dosing events are actions or to be taken or determinations to be made by the medication delivery unit concerning the dispensing of medication. For example, the deliver unit may determine that a specific time point has been reached indicating that the medication delivery unit should issue an audible or visible alarm indicating to a user of the medication delivery unit that one or more medications are available to be dispensed, and dispense the medications in response to a user input. In support of properly executing such dosing event, each dosing regimen may include identifications of specific medications to be dispensed, data concerning such medications (i.e., dosage strengths, quantities, images of each medication, etc.), dosing schedules for each medication, etc. In one example, dosing regimens (and other data/information) are provided to each medication delivery unit by the remote controller and/or remote unit. However, it may also be desirable for at least some portion of a dosing regimen to provided to the medication delivery unit via an interface included on the medication delivery unit, e.g., via a graphical user interface or a processor communication port.

Regardless of when or how a dosing regimen is received, processing continues at block 402 where it is determined whether a delivery process should occur. A delivery process is a specific dosing event in which one or more medications are to be dispensed by the medication delivery unit. Preferably, the determination that the delivery process should take place is done in accordance with a stored delivery regimen, however, this is not an absolute requirement. For example, it may be desirable that patients should always have access to their medications regardless of the stored dosing regimen. Thus, a patient (or other authorized user) can request an unscheduled dispensing of a stored medication (described in further detail below with regard to FIG. 61). Such unscheduled requests may be entered via a user interface on the medication delivery unit itself, or may be received by the medication delivery unit in command form from a remote device, such as a remote controller or remote unit. Techniques for determining when an action in accordance with a dosing regimen (or in response to an unscheduled request) should be taken are well known to those having ordinary skill in the art.

Thereafter, processing continues in parallel at blocks 404 and 406 to perform operations previously described above. In particular, at block 404, the delivery process is executed via a non-sequential (or sequential if desired) access of the required stored medications and subsequent ejection of the required unit dose package or unit dose packages from their corresponding medication carriers. Note that, when individual unit dose packages are ejected, contact between the medication delivery unit and the actual unit doses (e.g., the pills) is avoided, which is desirable to prevent contamination. To this end, the dosing regimen (or unscheduled request) may include information regarding the specific unit dose packages to be dispensed, or information sufficient to allow the medication delivery unit to determine which unit dose packages to eject (without precisely specifying individual unit dose packages) based on knowledge of its current inventory (as described below). In parallel, at block 406, prescription information concerning the at least one medication being delivered is provided to a user of the medication delivery unit. Such provision of prescription information may occur prior to, during or after the actual dispensing of the at least one medication. As used herein, such prescription information may comprise, but is not necessarily limited to, warning information for the particular medications being dispensed, the prescription dosage being dispensed, what the prescription schedule for this medication is (e.g., "three times daily"), an identification (either generic or brand name) of the medication being dispensed, one or more images of the medication being dispensed as well as any instructions for administering the medication. Preferably, the prescription information is provided to the user via a suitable user interface on the medication delivery unit, e.g., a graphical display, and/or via any other suitable device and format, e.g., via a printer in printed form or a speaker in audible form. In practice, as shown in block 408, the prescription information may be obtained using a variety of techniques. For example, the medication delivery unit either receives the prescription information from a remote device (such as a remote controller or remote unit), for example as an Extensible Markup Language (XML) file, or is provided with information (again, from a remote device such as a remote controller or remote unit) that allows the medication delivery unit to request/access the prescription information, e.g., an address of an appropriate server where the necessary prescription information is stored. Either process may occur as many times as needed. For example, the prescription information may be obtained once for all medications currently stored by the medication delivery unit, or every time a delivery process is to be performed, or on some other basis as a matter of design choice.

Processing continues at block 410, where an outcome of the delivery process is determined and stored. In general, there are two possible outcomes of a delivery process, either the at least one medication was properly dispensed or it was not. In the former, the medication delivery unit is able to determine that the necessary unit dose packages were successfully ejected from the medication carrier(s) (using techniques such as those described in greater detail below relative to FIGS. 50-55). In the case of a successful ejection of the necessary medications, it may be further desirable to obtain an affirmative indication that the dispensed medications were removed from the medication delivery unit, i.e., retrieved from a delivery chute thereof, and/or to obtain an indication from a user (e.g., the patient) that the medications were in fact administered to the patient. For the former, appropriately configured sensors, e.g., a camera and image recognition software, may be deployed to determine whether the dispensed medications were removed from the medication delivery unit. For the latter, the user may be prompted (via an appropriate user interface mechanism) to confirm administration of the medication(s). Such additional information may be included as part of the indication of a successful outcome.

Regarding the latter possibility of improperly dispensed medications, a number of causes may be identified, e.g., a unit dose package was not properly ejected from its medication carrier (see FIGS. 50-55), a malfunction occurred with the medication delivery unit during the delivery action or any other identifiable cause. Regardless of the particular outcome of the delivery process, the outcome is preferably stored for logging, tracking and/or auditing purposes. For example, the medication delivery unit may persistently store the outcome (in any suitable format) within its own internal storage device. In this embodiment, the stored outcome data/information may be subsequently uploaded to a remote device or devices and thereafter deleted or allowed to persist in the medication delivery unit's internal storage. Alternatively, the outcome may be provided directly to a remote controller or remote unit (other than temporary storage in volatile or non-persistent storage internal to the medication delivery unit) for subsequent storage thereat. In one example, delivery outcomes are persistently stored in the medication delivery unit for a given period of time (e.g., three days). Additionally, as the medication delivery units periodically communicates with a remote controller or remote unit (e.g., every half hour), any new delivery outcomes stored by the medication delivery unit are uploaded to the remote controller or remote unit for long term storage. Regardless of the manner in which such storage is achieved, sufficient information allowing the delivery outcome to be associated with a particular medication delivery unit and/or a particular patient is also stored and may be stored on a secure web server or other device for later access.

Finally, at block 412, one more delivery outcomes (regardless of where they are stored) may be provided to an authorized entity of the medication delivery system. For example, a healthcare provider, accessing stored data maintained by either a remote controller or a specific medication delivery unit, may gain access to specific delivery outcomes as desired. Alternatively, such delivery outcomes may be "pushed" to authorized entities. For example, a given patient's healthcare providers (e.g., physicians) and caregiver (e.g., hospice or nursing home provider, children, etc.) may request to be notified (through any convenient or desirable communication medium) upon the occurrence of any delivery outcome for a the patient or for specific types of delivery outcomes, i.e., only when a delivery outcome indicates an improper delivery.

Figure 47:
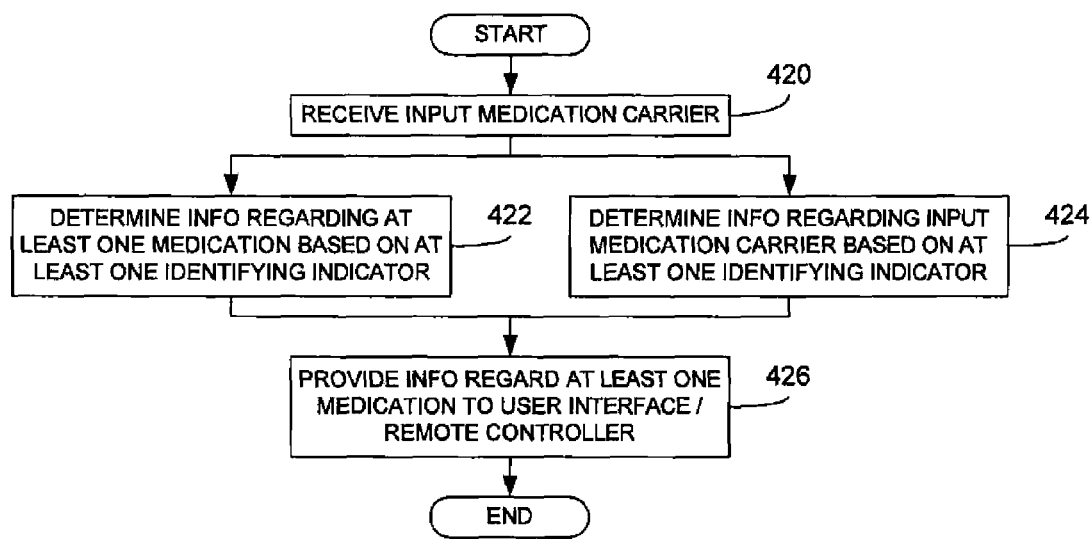
FIG. 47-49 are flowcharts illustrating various exemplary embodiments of handling of input medication carriers.

FIG. 47 illustrates a method whereby a medication delivery unit may obtain information regarding medications and/or medication carriers provided to and/or stored therein, as describe in part above. Thus, beginning at block 420, the medication delivery unit receives an input medication carrier, preferably medication carriers in the various forms described above, i.e., substantially planar carriers having individual unit dose packages arranged in two-dimensions and including one more identifying indicators provided thereon. This may include automatically pulling in the medication carrier using the structures described above. As noted above, such identifying indicators (or identifying indicia) may be embodied in virtually any form that is at least perceivable by the medication delivery unit including, but not limited to, one- and two-dimensional barcodes, magnetic strips and inks, RFID tags or even printed text. In this latter example, an imaging device and suitable optical character recognition (OCR) software may be employed such that the medication delivery unit is able to "read" the text. Combinations of such forms are also possible, i.e., barcodes and printed text.

Regardless of the form or forms employed for the at least one identifying indicator, processing continues at either or both of blocks 422 and 424. At block 422, the medication delivery unit determines information regarding at least one medication based on at least one identifying indicator on the input medication carrier. In one embodiment of the present invention, this process is performed for each medication in each unit dose package found in the medication carrier, although this is not a requirement. There are a variety of techniques whereby the medication delivery unit may determined the information regarding the at least one medication. For example, where the at least one identifying indicator used directly includes the desired information, the medication delivery unit can directly "read" the at least one identifying indicator to ascertain the information. For example, as noted above, where the at least one identifying indicator includes text, the medication delivery unit can employ OCR software to directly read the information regarding the medication(s). Alternatively, the information may be encoded directly into the identifying indicator(s) such that the medication delivery unit is able to decode the information directly without reference elsewhere. Further still, the medication delivery unit may read the identifying indicator(s) to provide decoded data, e.g., converting a bar code into a string of digitally represented data that is not directly representative of the desired information. Thereafter, the medication delivery unit can provide the decoded data to a remote controller or remote unit that is capable of "translating" the decoded data into the desired information by, for example, using the decoded data as the basis for a table lookup. Those having ordinary skill in the art will appreciate that further techniques in this regard may be equally employed. It should be noted that the information regarding the at least one medication may comprise, by way of example and not limitation: a name of the medication (e.g., generic or brand name); a dosage strength, manufacturer lot number, expiration date, national drug code number for all unit dose packages in the medication carrier or for individual unit dose packages; or a unique unit dose package serial number.

Alternatively, or in addition to the processing of block 422, processing at block 424 may occur where the medication delivery unit determines information regarding the at least one input medication carrier itself (as opposed, or in addition to, the medications stored therein) based on the at least one identifying indicator. Using substantially the same techniques described above with regard to block 422, the information regarding the input medication carrier may be ascertained by the medication delivery unit alone or in combination with a remote controller or remote unit. In a presently preferred embodiment, such information may include (but is not limited to) a number of unit dose packages included in the input medication carrier and a layout definition of the input medication carrier. Regarding layout definitions, each medication carrier may conform to a predefined layout definition of a plurality of layout definitions. For example, one layout definition may include thirty-one unit dose packages of a certain size arranged into seven rows having four columns, and an eighth row having only three of the four columns, whereas another layout may include ten larger unit dose packages arranged in five rows and two columns. Regardless, the layout definition can be used by the medication delivery unit (having prior knowledge of the possible layout definitions and the specifics of each as provided, for example, by a remote controller or remote unit) to establish exactly where it should go to find specific unit dose packages.

Regardless whether either or both of blocks 422 or 424 are carried out, processing continues at block 426 where the information regarding the at least one medication (or the input medication carrier) is provided to either a user interface of the medication delivery unit or, if necessary, to a remote controller or remote unit such as a remote controller. For example, in the event that the medication delivery unit determines the information, it may provide it to either the user interface (e.g., cause it to be displayed or otherwise presented to a user of the medication delivery unit) or the remote controller or remote unit. Alternatively, where the medication delivery unit enlists the assistance of a remote controller or remote unit to ascertain the information, provision of the information to the user interface includes the remote controller or remote unit first providing the information back to the medication delivery unit. It will be recognized that the various operations described above with respect to medication delivery unit may be carried out by any suitable component depending on the desired design.

Figure 48:
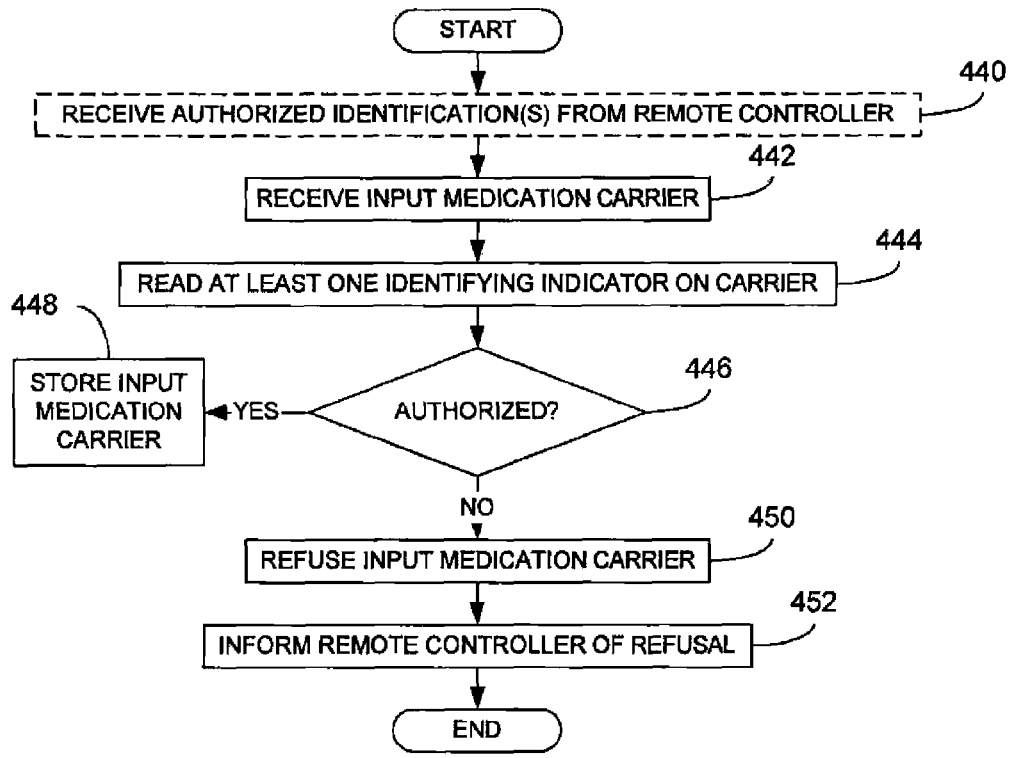

Referring now to FIG. 48, handling of input medication carriers by a medication delivery unit is further described below (and as described, in part, above). At block 440, a medication delivery unit may optionally receive authorized medication carrier information from, for example, a remote controller. As used herein, authorized medication carrier information includes any suitable information concerning specific medication carriers that a given medication delivery unit is allowed to accept. Thus, the authorized medication carrier information may include identification of specific medication carriers (e.g., by unique medication carrier serial number). Alternatively, the authorized medication carrier information may include identification of specific names, types or families of medication that the medication delivery unit is allowed to receive and store. Those having ordinary skill in the art will appreciate that other restrictions may be similarly provided in this manner.

Regardless, at block 442, the medication delivery unit receives an input medication carrier. Based on at least one identifying indicator found on the input medication carrier, the medication delivery unit can determine whether the input medication carrier is authorized to be accepted and stored by the medication delivery unit, as shown at blocks 444 and 446. That is, the medication delivery unit may read or otherwise decode one or more identifying indicia from the medication carrier and, based on the resulting information regarding the input medication carrier, determine if the input medication carrier is authorized. This may be done directly by the medication delivery unit as in the case where the medication delivery unit receives authorized medication carrier information, as described above per block 440, and compares the information regarding the input medication carrier with the authorized medication carrier information. Alternatively, the medication delivery unit may provide the information regarding the input medication carrier to a remote controller (or remote unit) that, in turn, can perform the necessary comparison. Regardless of how the authorization determination is performed, if the input medication carrier is authorized for the medication delivery unit, processing continues at block 448 where the medication delivery unit stores the medication carrier using the techniques described above.

However, if the input medication carrier is not authorized for the medication delivery unit, processing continues at block 450 where the medication delivery unit refuses to store the input medication carrier. In a presently preferred embodiment, this refusal is carried out automatically by the medication delivery unit causing it to impede further insertion or otherwise eject the input medication carrier (in essentially the same manner that the medication delivery unit is controlled to eject the carrier when unloading it from the elevator). Thereafter, at block 452, the medication delivery unit may provide an indication to a remote controller or remote unit of the refusal to store the input medication carrier. Such indication may also include any available identifying information concerning the input medication carrier (e.g., serial numbers, etc.) as well as other pertinent information such as time of day, etc. In a manner akin to that described above relative to block 410 (FIG. 45), the medication delivery unit may store such information locally for later retrieval. Note that the processing illustrated and described relative to FIG. 48 may be repeated as often as necessary when receiving multiple input medication carriers.

Figure 49:
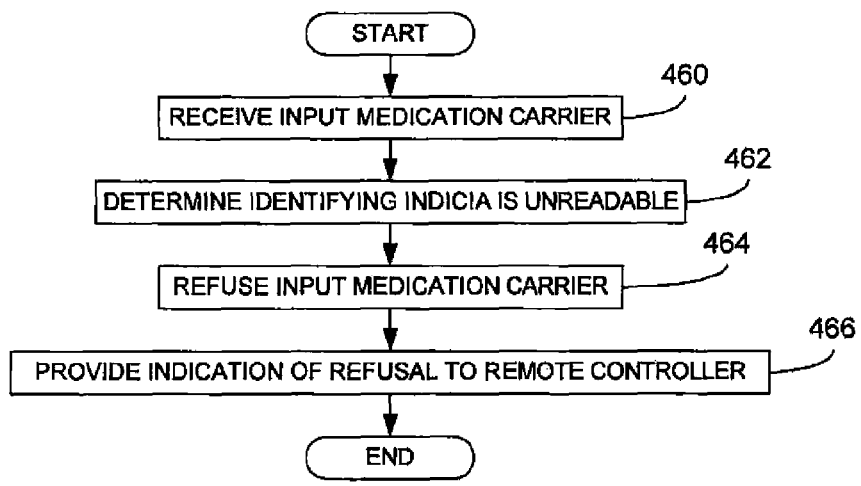

As a corollary to the processing described above relative to FIG. 48, further processing is described with reference to FIG. 49. In particular, at block 460, an input medication carrier is received by a medication delivery unit as before. Thereafter, at block 462, the medication delivery unit determines that one or more identifying indicators are unreadable. Reasons for concluding that an identifying indicator is unreadable are well known to those having ordinary skill in the art including, but not limited to, the absence, concealment, misalignment, destruction, incompatibility or other defect of a given identifying indicator. Regardless why the one or more identifying indicia are unreadable, processing then continues at block 464 where, as described above, the medication delivery unit refuses the input medication carrier and, at block 466, notifies a remote controller or remote unit and/or stores data/information memorializing the refusal.

One desirable feature for the medication delivery unit, as noted above, is the ability to determine the condition of individual unit dose packages and/or unit doses, particularly during dispensing operations and loading/unloading operations. To this end, various techniques for determining such conditions are further described and illustrated with reference to FIGS. 50-55. As used herein, a condition of a unit dose package can refer to whether or not the unit dose package is present or not present within its medication carrier, or may refer to other intermediate states, e.g., partially dislodged. Further still, a condition may encompass other states not necessarily related to presence, but rather integrity of the unit dose, e.g., whether the unit dose package is partially ruptured or otherwise damaged.

Figure 50:
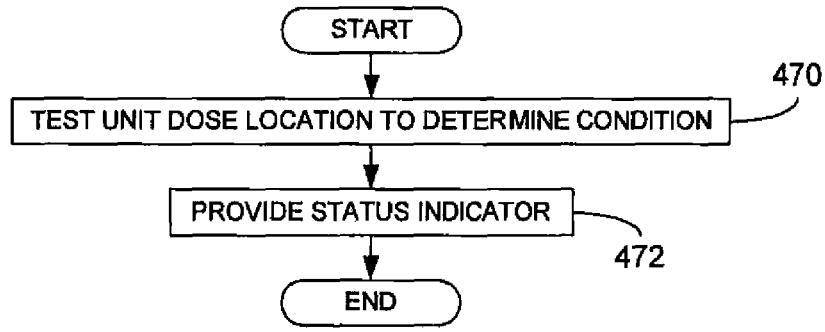
FIGS. 50-52 are flowcharts describing various exemplary embodiment concerning condition testing of unit dose packages in medication carriers.

FIG. 50 illustrates basic processing in this regard. Beginning at block 470, a medication delivery unit tests a unit dose location within in medication carrier to determine a condition of the unit dose location. A unit dose location describes a particular location within an medication carrier of a given unit dose package (and its corresponding unit dose of medication). This testing is preferably accomplished using a condition tester implementing any of a number of techniques describe in further detail below. Thereafter, at block 472, the deliver unit, via a suitable notification component, provides a status indication corresponding to the tested unit dose location based on the determined condition. In a presently preferred embodiment, the status indication informs the medication delivery unit and/or a remote controller or remote unit of an outcome of a dosing or other event concerning the particular unit dose location. In a presently preferred embodiment, the specific implementation of the notification component depends on the entity being notified. For example, where the intended recipient is a user of the medication delivery unit, the notification component may include a display, speaker or other user-perceptible device. Alternatively, where the notification is destined for a device, such as a remote controller or remote unit, the notification component may include suitable software instructions configured to generate a message including the status indication and a communication interface capable of providing the message to the remote controller or remote unit. Specific instances incorporating the processing of FIG. 50 are further described below with reference to FIGS. 51 and 52.

Figure 51:
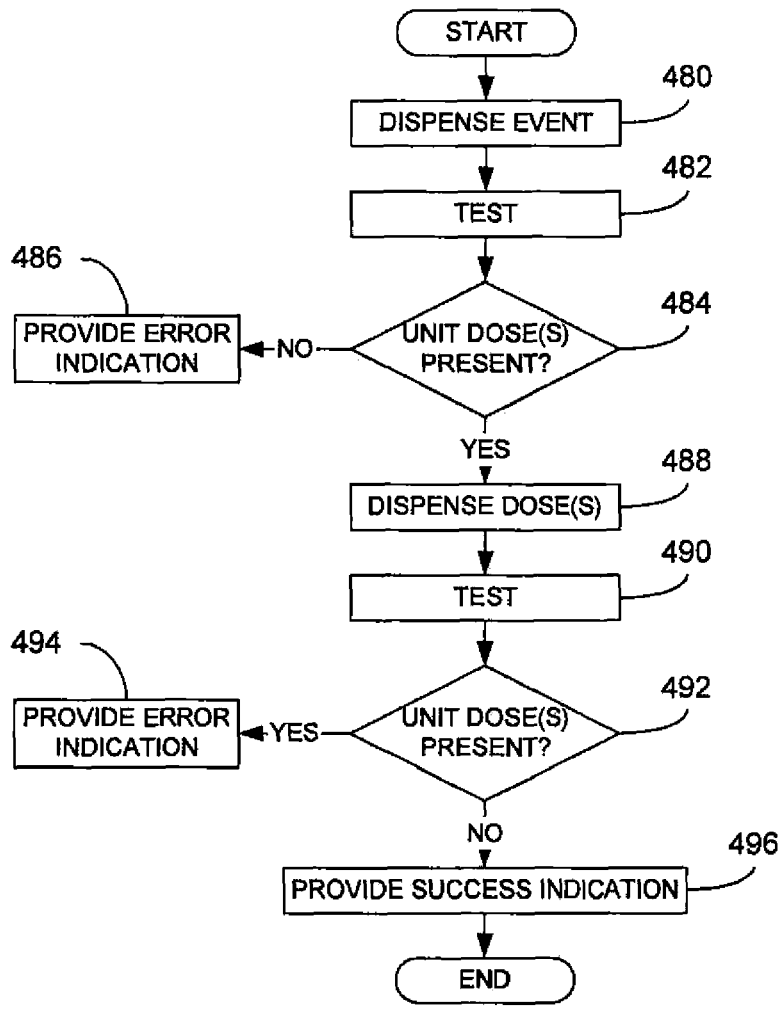

Referring now to FIG. 51, condition testing in the context of a dispensing event is further described. Thus, at block 480, it is determined that a dispense (or dosing) event should occur (once again, as determined by a dosing schedule or in response to an unscheduled dosing request). In a presently preferred embodiment, such a determination causes a condition test to be performed on the one or more unit dose locations (which may arise within multiple medication carriers), as illustrated by block 482, prior to dispensing the unit dose package(s). In this instance, the testing performed at block 482 is to determine whether the desired unit dose package(s) is(are) present in the corresponding medication carrier(s). If, at block 484, it is determined (based on the returned present/not present condition) that any of the desired unit dose package(s) is(are) not present, processing continues at block 486, where a suitable error indication is provided. Once again, such error indication may be stored by the medication delivery unit and/or provided to a remote controller or remote unit. Note that the threshold for concluding that an error exists, or for determining a relative importance of the error, may depend on the nature of particular medications being dispensed. For example, absence of any unit dose package in situations where critical medications are being delivered may give rise to an error of a most urgent level. On the other hand, absence of a unit dose package concerning a non-critical medication (e.g., a vitamin or nutraceuticals) may not give rise to any error indication or, if so, an error indication of relatively low priority. Those having ordinary skill in the art will appreciate the further error alerting schemes may be implemented as a matter of design choice.

If the desired unit dose package(s) is(are) present, processing continues at block 488 where the desired unit dose package(s) is(are) dispensed as described above. Thereafter, at block 490, further testing at the unit dose location(s) of the desired unit dose package(s) is performed to once again ascertain a present/not present indication. If at block 492, it is determined that one more of the desired unit dose package(s) is(are) still present, processing continues at block 494 where another error indication may be provided. Note that, in a presently preferred embodiment, a present condition will be determined in those situations where a unit dose package is only partially, but not entirely, dislodged from its medication carrier. For example, if all of the perforations surrounding a given unit dose are not completely broken during the dispensing process (block 488; resulting in a so-called "hanging chad" state), this should be detected as a present condition. However, if the desired unit dose package(s) is(are) no longer present, processing continues at block 496 where an indication or indications that the desired unit dose package(s) has (have) been successfully dispensed is provided.

Figure 52:
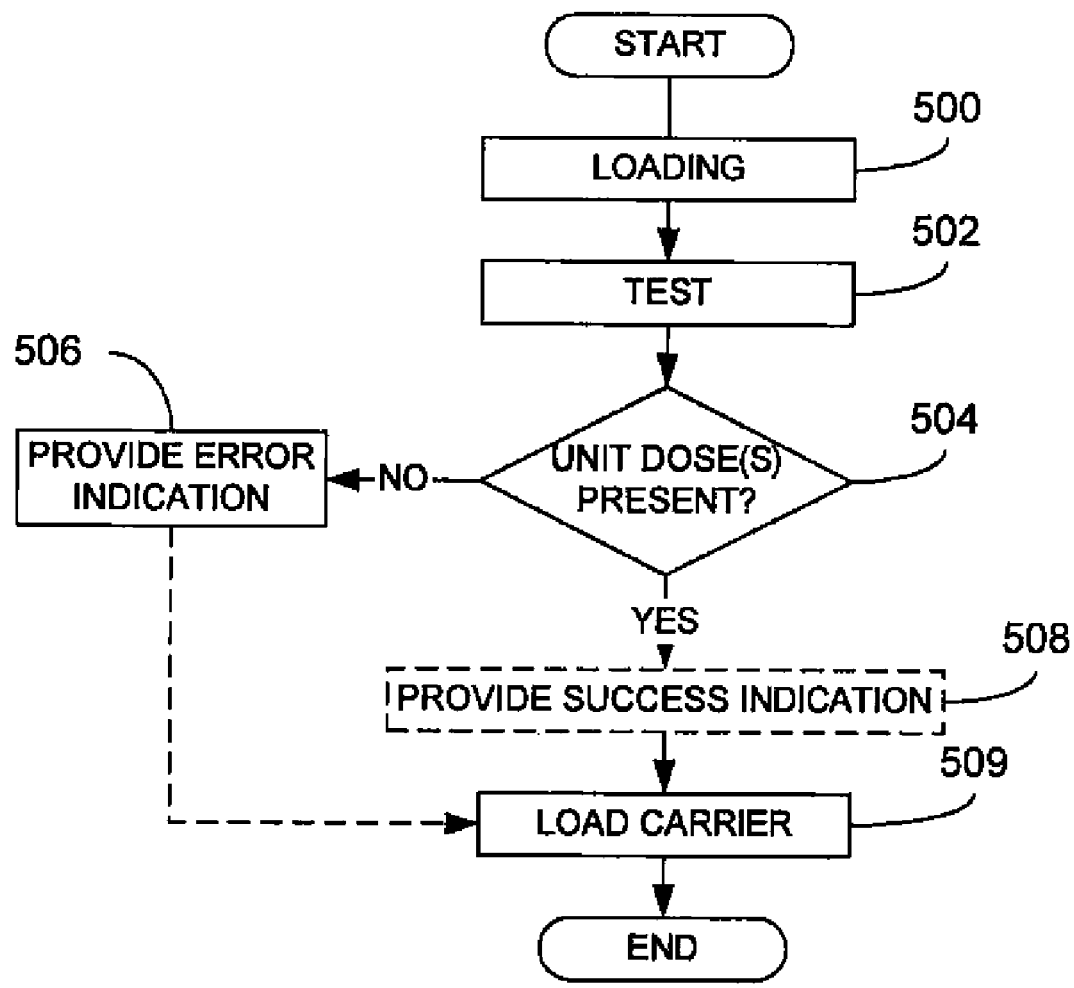

An alternative testing scenario, particularly directed to loading of medication carriers, is describe with further reference to FIG. 52. Thus, beginning at block 500, it is determined, by the medication delivery unit, that a medication carrier loading operation (or, optionally, an unloading operation) is being, or is about to be, performed. Thereafter, at block 502, testing of one or more unit dose locations is performed prior to the loading (or unloading) operation. In one embodiment of the present invention, such testing may be performed at the entrance of the storage area used to store the medication carriers. In the loading scenario, if the determination at block 504 reveals that one or more unit dose packages are not present, processing continues at block 506 where an error indication is provided, as described above. In this situation, it is possible that the input medication carrier is still loaded (block 509) into the storage area of the medication delivery unit. For example, this may occur in those instances where the medications contained in the input medication carrier are optional or non-critical medications. On the other hand, if all of the unit dose packages are determined to be present, processing continues at block 508 where a success indication may be optionally provided. Thereafter, the medication carrier is loaded into the medication delivery unit at block 509. In the case of unloading a medication carrier substantially similar process may be executed. However, in this case, those conditions that constitute an error condition may depend on the expected conditions of the various unit dose packages in the medication carrier being unloaded. For example, if the medication delivery unit (or remote controller controlling operation of the medication delivery unit) expects a medication carrier to be completely depleted of unit dose carriers but, prior to unloading, determines that one or more unit dose carriers are still present, an error indication may be warranted. Conversely, where a medication carrier thought to still contain certain unit dose packages is in fact missing such unit dose packages, an error indication may again be warranted.

As noted above, various techniques may be used to carry out the condition testing. A number of these techniques are further described with reference to FIGS. 53-55. In one embodiment, illustrated in FIG. 53, a condition tester including a test signal source 512 and a test signal sensor 516, arranged in either a pass-through configuration or a reflective configuration, may be employed. In this embodiment, the test signal source 512 provides a test signal 514. By way of non-limiting example, the test signal 514 may include virtually any kind of detectable signal such as an electromagnetic wave (e.g., infrared, visible or ultraviolet light, radio frequency waves, etc.), a physical wave such as a sound wave, or an electrical signal. Sources for providing such signals are well known in the art. Regardless, the test signal 514 is directed to the medication carrier under consideration, specifically, to the one or more unit dose locations under consideration. In this regard, it is noted that the test signal 514 may be relatively specific (i.e., focused) in its configuration, as in the case of a substantially collimated beam of light directed to a single unit dose location, or more broadly directed to a number of unit dose locations, as in the case of more diffuse light.

One or more test signal sensors 516, as known in the art, are selected to match the nature of the test signal 514 employed. Equally significant, the configuration and/or placement of the test signal sensor 516 relative to the test signal source 512 varies according to whether a pass-through or reflective configuration is employed. In the pass-through configuration, the test signal sensor 516 is position relative to the test signal source 512 and the medication carrier 510 so as to sense that portion 518, if any, of the test signal 514 that passes through the medication carrier 510. In this configuration, a "present" condition of a unit dose package is indicated when at least a portion of the test signal 518 is not sensed (or sensed at a relatively attenuated level, depending on the nature of the test signal 514 being used) by the sensor 516, and a "not present" condition is indicated when a portion of the test signal 518 is sensed (or sensed at a relatively unattenuated level, again depending on the nature of the test signal 514) by the sensor 516. In the reflective configuration, the test signal sensor 516a is position relative to the test signal source 512 and the medication carrier 510 so as to sense that portion 518a, if any, of the test signal 514 that reflects off of the medication carrier 510. In this configuration, a "present" condition of a unit dose package is indicated when a portion of the test signal 518a is sensed (or sensed at a relatively unattenuated level) by the sensor 516a, and a "not present" condition is indicated when at least a portion of the test signal 518a is not sensed (or sensed at a relatively attenuated level) by the sensor 516a.

Figure 53:
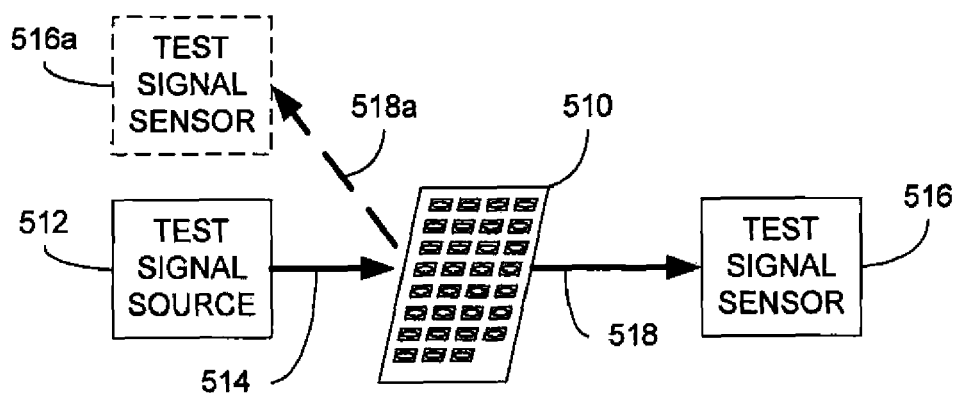
FIGS. 53-55 are schematic illustrations of various exemplary unit dose package condition testing techniques in support of the embodiments described with reference to FIGS. 50-52.

A potential advantage of the embodiment illustrated in FIG. 53 is that, for example, where the plastic in which the unit dose package is formed (i.e., the bubble or blister) is transparent to the test signal 514 (e.g., clear plastic and visible light), the testing described may function in a dual sense. That is, not only can this arrangement detect the presence/absence of a unit dose package, but it may also be used to detect the presence/absence of the unit dose itself. For example, where the unit dose package is present, but the foil backing of the unit dose has been ruptured, thereby allowing the unit dose to be released, this technique may nevertheless still indicate absence of the unit dose to the extent that the test signal 514 may pass through (or not be reflected by) the bubble and the opening formed by the ruptured foil.

Figure 54:
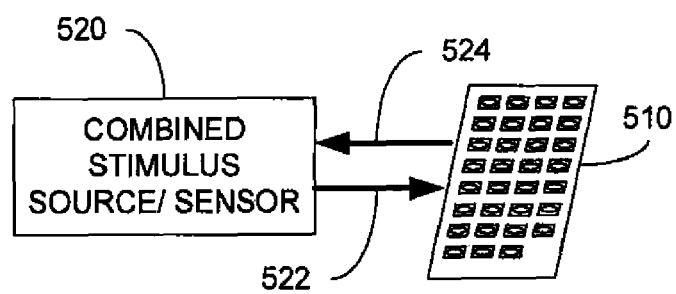

Referring now to FIG. 54, a condition tester including a single combined stimulus source and sensor 520 is provided. That is the combined device 520 serves to provide both a stimulus or test signal 522 and sense (or not sense, as the case may be) a returned stimulus or signal 524 when testing for condition at the unit dose location.

For example, in one embodiment, the device 520 may include a mechanically actuated device such as a deflectable, spring-loaded probe coupled to a suitable electrical switch. In this embodiment, the probe may be brought into contact with the medication carrier 510 at the unit dose location. If a unit dose is present, the spring force of the probe will be overcome causing the probe to deflect, thereby closing (or opening, as the case may be) the electrical switch and providing a signal that a unit dose package (or a substantially intact unit dose package) is present. Conversely, if no unit dose package is present, or if it has been weakened by prior damage, the probe will not deflect (or not to a sufficient degree) thereby leaving the electrical switch in an open (or closed, by design choice) state, resulting in a signal indicating the unit dose package is present (or damaged in some fashion).

In another embodiment, the device 520 may include an RFID tag reader. As known in the art, such readers emit a first signal 522 that causes a compatible RFID tag to respond with a second signal 524. In this manner, the RFID reader, as used herein, can be brought into proximity to the unit dose location. In this embodiment, each unit dose package is equipped with a uniquely corresponding RFID tag. Thus, if the reader detects a returned signal at a given unit dose location, an indication may be provided that the unit dose package is both present and undamaged (at least not to a degree to damage the corresponding RFID tag). Conversely, if the reader fails to detects a returned signal at a given unit dose location, an indication may be provided that the unit dose package is not present and/or has been damaged to a degree sufficient to render the corresponding RFID tag inoperable.

In yet another embodiment, the device 520 includes an electrical signal 522 output and a return signal 524 input. In this case, the electrical signal 522 may be as simple as a direct current (DC) voltage or a more complex time-varying waveform. In this embodiment, each unit dose package includes a conductive path, such as conductive ink or a very thin conductive trace as know in the art, that retains its electrical continuity so long as the unit dose package is present and relatively undamaged. When the electrical signal output is brought into electrical contact with the expected location of the conductive path at the unit dose location, presence of a substantially intact unit dose package will be detected when a return signal 524 is detected, i.e., the circuit established by the electrical signal output, conductive path and return signal input is complete. Conversely, absence of and/or damage to the unit dose package will be detected when the return signal 524 is not detected, i.e., the circuit established by the electrical signal output, conductive path and return signal input is not complete.

Figure 55:
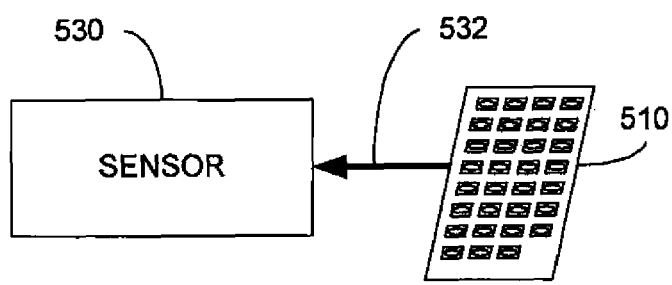

Another testing embodiment is illustrated in FIG. 55 where the condition tester includes only a sensor 530. In this embodiment, the sensor 530 is configured to sense some inherent parameter or presumed characteristic 532 of the unit dose location. For example, the sensor 530 may include a magnetic sensor configured to detect a magnetic field 532 field that is emanated by a unit dose package when present in the medication carrier. In this embodiment, each unit dose package is provide with magnetic material such as a magnetic strip or ink as known to those of skill in the art. Thus, when the magnetic sensor 530 is brought into sufficient proximity to the unit dose location, presence of the unit dose package is indicated if the magnetic field is sensed, and presence is not indicated if the magnetic field is not sensed. In yet another embodiment, the sensor 530 may include an image sensor and corresponding image analysis processing capability, i.e., software. In this embodiment, the image sensor 530, such as a suitable still image or video camera, may capture one or more images of the unit dose location (assuming the presence of sufficient ambient light). Using known image analysis techniques (particularly software-based techniques), the captured image or images may be analyzed to determine if a unit dose package is depicted in the captured image(s). If the unit dose package is depicted in the image(s), presence is indicated, otherwise presence is not indicated. Similarly, rather than analyzing the captured image for the unit dose package, the analysis may be performed to ascertain whether the unit dose itself is depicted in the image (as in the case, for example, where the plastic bubble of the unit dose package is sufficiently transparent to allow a suitable image to be captured).

Figure 56:
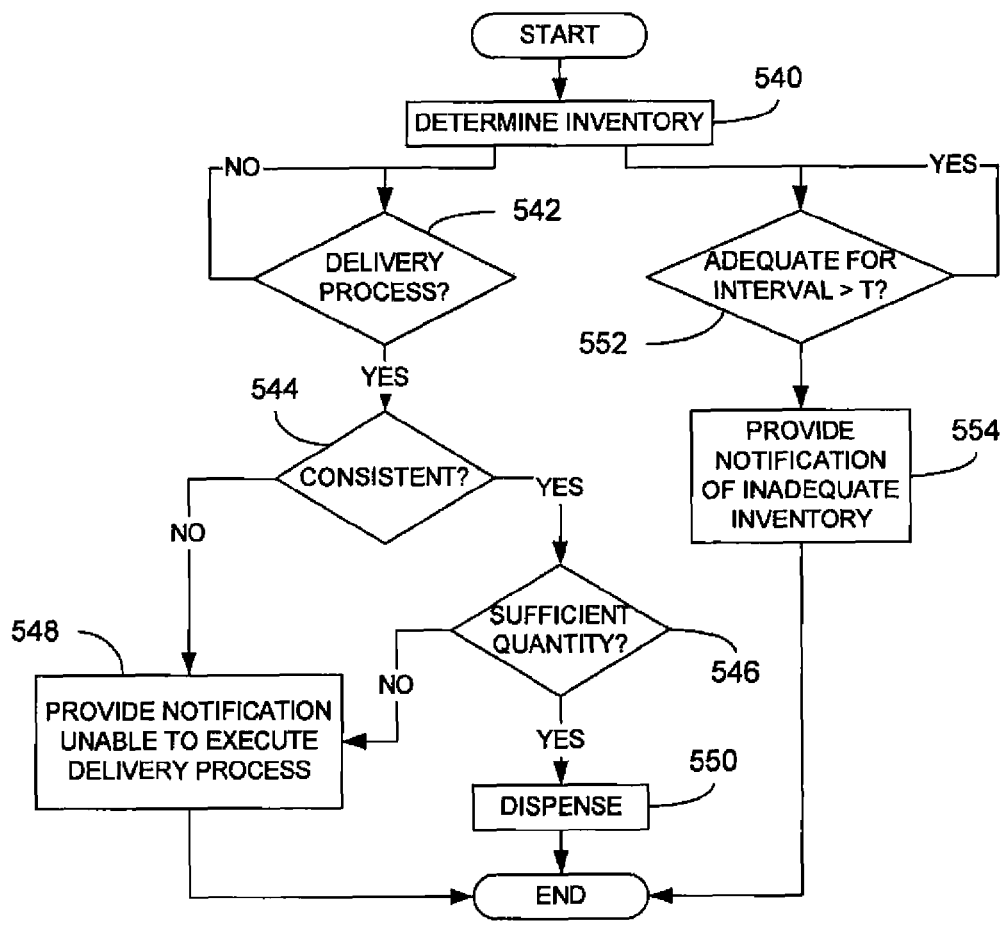
FIG. 56 is a flowchart illustrating various exemplary embodiments of handling of stored medication carriers.

Referring now to FIG. 56, various techniques concerning handling of stored medications are shown. Beginning at block 540, a medication delivery unit or a remote controller may determine an inventory of medications stored in the medication delivery unit. In a presently preferred embodiment, this is done based on the identifying indicia provided on the stored medication carriers as described above. For example, using the techniques described above, inventory of a given medication delivery unit is updated every time a medication carrier is loaded and stored in the medication delivery unit. Thereafter, the occurrence of dosing events causes further updates to the inventory. Further still, unloading of medication carriers or restrictions placed on certain medications found within the medication carriers (described below with regard to FIG. 59) may cause further updates to the inventory. In this manner, the inventory determination becomes a continuous process. In an alternative embodiment, inventory may be performed as a single event in which each currently stored medication carrier is inspected, as described above, to determine what unit dose packages (and their corresponding medications) are present.

Regardless of the manner in which inventory is determined, processing may continue along either of two paths shown. Along a first path, beginning at block 542, it is determined whether a delivery process for a given medication needs to occur according to a dosing regimen or unscheduled request, as described previously. If so, processing continues at block 544 to first determine whether at least one stored medication in the medication delivery unit (as indicated by the inventory) is consistent with the dosing regimen or unscheduled request. As used herein, consistency between medication indicated by the dosing regimen/unscheduled request with the stored medications is judged by identities and configurations of the medications. That is, the requested and stored medications are not consistent if none of the stored medications has the same identity as the requested medication. Alternatively, assuming the necessary medication is currently stored, it must occur in the necessary dosage strength. Assuming these conditions to be satisfied, processing continues at block 546 where it is determined if sufficient quantities of the (consistent) medication are stored to satisfy the delivery process/unscheduled request. If so, processing continues at block 550 where the identified stored medications are dispensed in accordance with the dosing regimen or unscheduled request. If the stored medications are either inconsistent with or do not exist in sufficient quantities (even if consistent), processing concludes at block 548 where an indication is provided that the medication delivery unit has been unable to execute the delivery process. As in previously described embodiments, the notification of block 548 may be provided to a user interface of the medication delivery unit or to a remote controller or remote unit. Further still, the notification may include various data elements regarding the reasons why the medication delivery unit was unable to execute the dosing regimen or unscheduled request.

Along the other path depicted in FIG. 56, processing begins at block 552 where it is determined, based on the inventory, whether at least one medication stored in the medication delivery unit exists in sufficient quantity to fulfill a dosing regimen beyond expiration of time interval, T. For example, each time a dose of a given medication is dispensed (either by virtue of a dosing regimen or unscheduled request) and the corresponding inventory updated, it may be determined whether the remaining inventory for that medication is sufficient to fulfill the remaining dosing events for that medication scheduled to occur (per the dosing regimen only) over the next, say, three days. If adequate inventory to cover the time interval (assuming no unscheduled requests) is currently stored, no further action is necessary. However, when the existing inventory is not sufficient to cover the time interval, processing continues at block 554 where notification of the inadequate inventory is provided. As in previously described embodiments, the notification of block 554 may be provided to a user interface of the medication delivery unit or to a remote controller or remote unit. By notifying a user of the delivery device or a healthcare provider (e.g., a pharmacist) of the impending shortfall, it is possible for the user or healthcare provider to remedy the situation through automatic or requested replenishment of the necessary medication.

Figure 57:
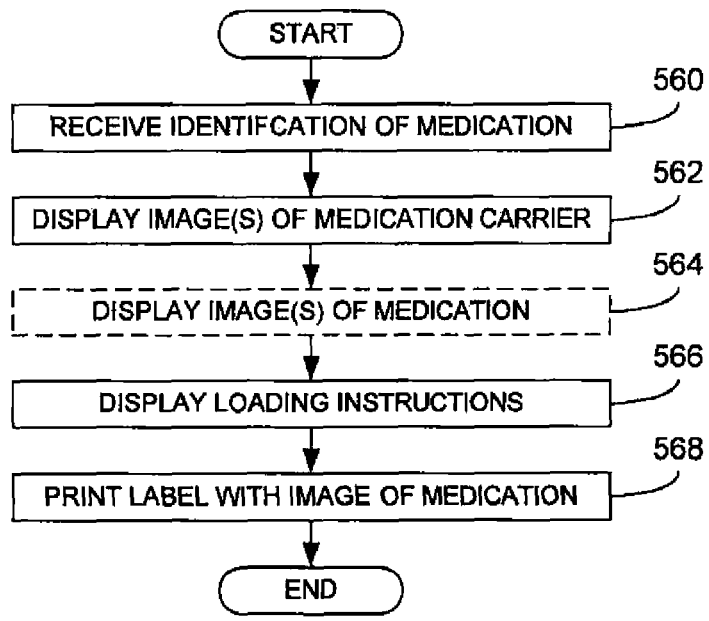
FIG. 57 is a flowchart illustrating an exemplary embodiment for providing packaging instructions for medication.

Referring now to FIG. 57, a process for providing packaging instructions for a given medication is further described. The process of FIG. 57 assumes that an entity (e.g., a pharmacist) performing the packaging of medication has a processing device, preferably including a graphical user interface, capable of executing instructions in accordance with the illustrated process. Further, a medium capable of being read by the processing device may include the executable instructions used to implement the illustrated process.

Thus, beginning at block 560, an identification of the medication (or medications) to be packaged is provided to the processing device. For example, suitable identification may be provided through the graphical user interface using known mechanisms such as a mouse and cursor arrangement, selectable lists and/or menus, search fields, etc. or combinations thereof as know in the art. In response, at block 562, the processing device displays one or more images of a medication carrier to be used to package the identified medications. For example, a graphic depiction of the necessary medication carrier, such as those described above, may be provided on the graphical user interface. Optionally, at block 564, one or more images of the identified medication may also be provided via the graphical user interface. In a presently preferred embodiment, more than one image is provided illustrating the identified medication(s) from various viewpoints, i.e., front and back.

At block 566, loading instructions for placing the at least one medication into to the depicted medication carrier are simultaneously displayed via the graphical user interface. For example, the loading instructions may include text indicating where individual doses of the at least one medication should be placed within the medication carrier. In presently preferred embodiment, graphical indicia, such as images of each unit dose of medication, may be overlayed onto the image of the medication carrier so as to very closely replicate the appearance of a correctly loaded medication carrier. In this manner, loading errors may be reduced. Finally, at block 568, a label or set of labels may be printed by the processing device, which label includes one or more images of the identified medication (in addition to any identifying indicia, as described above). In this manner, still further confirmation may be obtained that the medication carrier has been correctly loaded. Furthermore, the medication images provided on the label may be used by patients to confirm the identity of medications provided to them.

Figure 58:
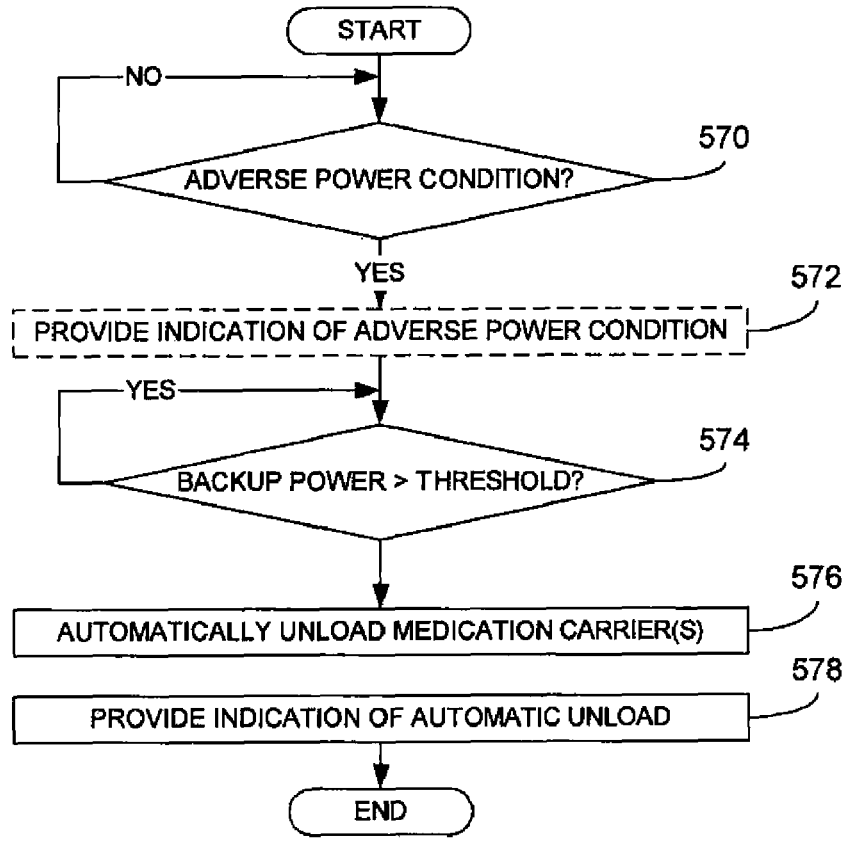
FIG. 58 is a flowchart illustrating an exemplary embodiment for handling adverse power conditions at a medication delivery unit.

Referring now to FIG. 58, processing of adverse power situations is further described. Beginning at block 570, it is determined whether an adverse power condition exists in a medication delivery unit. Techniques for determining whether an adverse power condition exists are well know to those of ordinary skill in the art. As used herein, an adverse power condition includes any state of a medication delivery unit where the available power supply is such that the medication delivery unit's continued ability to automatically deliver medications is in doubt. Thus, for example, a failure of the power grid, resulting in the total loss of external power to the medication delivery unit would constitute an adverse power condition, as would an accidental disconnect of the medication delivery unit from its external power source. Generally, when an adverse power condition occurs, it may be necessary to automatically unload at least some, if not all, of the stored medications carriers so as to ensure that each patient has continued access to his/her medications.

If an adverse power condition is detected, processing continues at block 572 where an indication of the adverse power condition is provided. As in other embodiments described above, the indication provided may be to a user interface of the medication delivery unit (such as through the use of a visible and/or audible alarm) and/or to a remote controller or remote unit.

Thereafter, at block 574, it is determined—in furtherance of an embodiment in which each medication delivery unit includes a battery backup to continue supplying power during adverse power conditions—whether remaining backup power for the medication delivery unit has fallen below a given threshold. A threshold is chosen to satisfy two criteria. First, the threshold must be low enough so as to outlast relatively small interrupts in external power, such as so-called "brown outs". Second, the threshold must be chosen so as to ensure that a sufficient amount of power will be left to automatically unload some or all of the stored medication carriers and to provide last communications with a remote controller or remote unit as described below.

If the remaining backup power falls below the threshold, some or all of the stored medication carriers are automatically unloaded at block 576. In one embodiment, multiple such thresholds may be employed such that medication carriers of varying priority are unloaded in sequence. For example, when a first, highest threshold is crossed, one or more of the most important medication carriers are unloaded. Thereafter, additional medication carriers will not be unloaded until additional, lower thresholds are crossed, thereby effectuating a staged unloading of medications in accordance with the remaining backup power. As medication carriers are unloaded and/or after the last medication carrier is unloaded, indications of such automatic unloading operations are provided to a remote controller as indicated by block 578.

Figure 59:
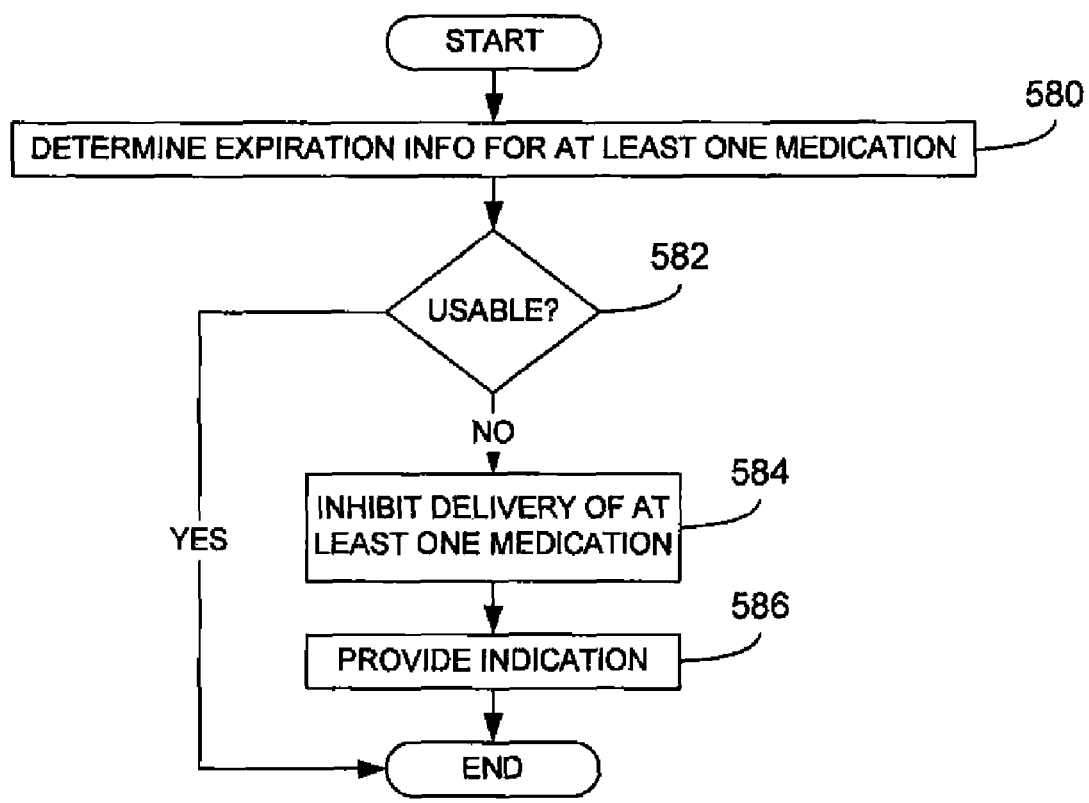
FIG. 59 is a flowchart illustrating an exemplary embodiment for handling of expired medications in a medication delivery unit.

Referring now to FIG. 59, processing for the handling of expired medications is further described. At block 580, expiration information for at least one medication stored in a medication delivery unit is determined. As in prior embodiments, the determination of the expiration information may be determined by either the medication delivery unit in question or by a remote controller. In the former, the expiration information is ascertained by the medication delivery unit through inspection, as described above, of the one or more identifying indicators provide on each medication carrier. As noted above, such identifying indicators may include expiration information for the medications stored in the corresponding medication carriers. Alternatively, the expiration information may be provided by the remote controller (or other remote unit). In one embodiment, the expiration information is represented as an absolute date when the usable life of the corresponding medication expires. However, this is not requirement and other representations of the expiration information may be equally employed.

Thereafter, processing continues at block 582 where it is determined whether the at least one medication is still usable based on the expiration information. For example, a current date, as determined by a real-time clock provided in the medication delivery unit and/or remote controller or remote unit, may be periodically compared with the expiration information. If the comparison is favorable, i.e., the current date is still prior to an expiration date indicated by the expiration information, processing is complete (at least until the next check of the expiration information). On the other hand, if the comparison is unfavorable, i.e., if the current date is not still prior to the expiration date, processing continues at block 584 where future delivery of the expired medication(s) is inhibited. Any of a number of techniques may be employed when inhibiting delivery of a medication. For example, each unit dose of the expired medication may be dispensed within a compartment of the medication delivery unit, i.e., quarantined, so as to prevent access to the medication. Alternatively, the expired medications may be dispensed or otherwise expelled by the medication delivery unit in response to receiving a specific authorization or command to dispense such expired medications. Such command may be received from a user of the medication delivery unit directly through its user interface, for example, through the entry of a special code. Alternatively, the required command may be provided from a remote controller. Further still, the expired medication may be flagged in the medication delivery unit's internal storage devices as being expired such that future attempts to dispense the medication will be refused. Regardless of the particular technique employed to inhibit dispensing, processing thereafter continues at block 586 where a suitable indication that the at least one medication is not longer usable is provided. Once again, such indication may be provided to a user via the medication delivery unit's user interface, and/or the indication may be provided to a remote controller or remote unit for long term storage and use to generate suitable alerts.

Figure 60:
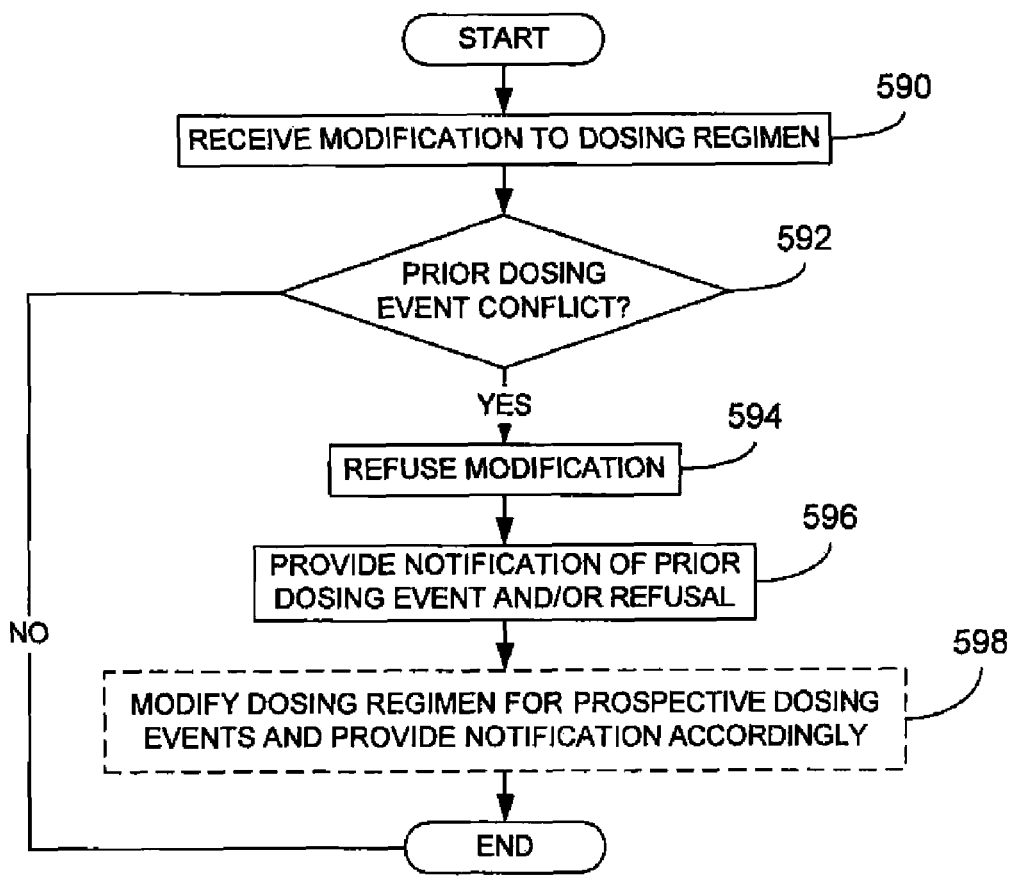
FIG. 60 is a flowchart illustrating an exemplary embodiment for handling modifications to dosing regimen for a medication delivery unit.

Referring now to FIG. 60, processing for handling modifications to a dosing regimen stored in a medication delivery unit is described. Beginning at block 590, a modification to an existing dosing regimen is received. In a presently preferred embodiment, such modifications are entered via use of a remote unit 32 or remote controller 101, as described above. The remote controller or remote unit may store the dosing regimen using storage devices under its control or otherwise accessible to the remote controller or remote unit. Alternatively, as in the instance of a hosted remote controller environment, as described above, the modifications may be entered via a web interface or similar mechanism implemented by the remote controller or remote unit. Because dosing regimens are specifically tailored to individual patients, and patients are uniquely associated with specific medication delivery units, any modifications to a given dosing regimen, e.g., changes to the frequency, dose strength, etc., must first take into account any dosing events that have recently occurred at the specific medication delivery unit before being implemented.

Thus, at block 592, it is determined, by the remote controller or remote unit, whether the received modification to the dosing regimen conflicts with a prior dosing event. For example, a modification to a dosing regimen may concern a particular delivery time set forth in the current, unmodified dosing regimen. However, due to differences in time representations (for example, due to different time zones) between the remote controller or remote unit and the specific medication delivery unit, it may be that the affected delivery time has already passed. Alternatively, as described above and below, the modification may concern a specific dosage delivery. However, because of unscheduled dispensing requests or due to other causes (e.g., a power outage, etc.), the specific dosage delivery may have already occurred or been canceled. Regardless of the cause, if such a conflict is detected by the remote controller or remote unit, processing continues at block 594 where the remote controller or remote unit refuse the received modification, i.e., it refuses to modify the specific dosing regimen due to the conflict. Thereafter, at block 596, the remote controller or remote unit provides one or more notifications concerning the prior dosing event giving rise to the conflict as well as the refusal to modify the dosing regimen. These notifications may, in a presently preferred embodiment, be provided in the form of an alarm, alert, message or other communication mechanism that may be provided through a graphical user interface implemented by, or otherwise accessible to, the remote controller or remote unit. Finally, block 598 provides for the optional modification of the dosing regimen for prospective dosing events, i.e., for those dosing events where it can be demonstrated that no conflict currently exists. Additionally, a notification of the prospective modification may be provided by the remote controller or remote unit as described above.

Figure 61:
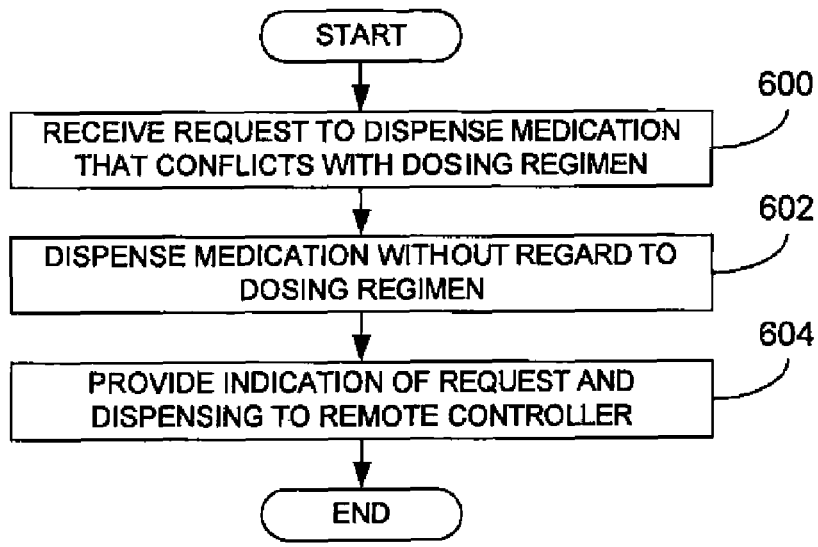
FIG. 61 is a flowchart illustrating an exemplary embodiment for handling of unscheduled dispensing requests received by a medication delivery unit.

Referring now to FIG. 61, processing for handling unscheduled dispensing requests is further described. In particular, beginning at block 600, a medication delivery unit receives a request to dispense at least one medication, which request conflicts with a previously stored dosing regimen. The request may be received by the medication delivery unit, for example, via its user interface or from a remote controller or remote unit. For example, such a conflict may arise where the requested medication is being dispensed too soon relative to a previously dosing event for the same medications. Other such conflicts will be readily apparent to those having skill in the art. As noted above, a desirable policy is to provide a patient with complete and total control over their medications, notwithstanding the dosing regimens or other possible restrictions that have been established on his/her behalf. As such, processing continues at block 602 where the requested medication(s) is(are) dispensed notwithstanding the conflict with the dosing regimen, presuming of course that the requested medications are available from the stored medication carriers. However, as in previous embodiments, an indication of the unscheduled request and subsequent dispensing of medications is provided at block 604, preferably to a remote controller or remote unit for logging and, possibly, alert generation.

Various operations performed by the medication delivery unit 33 may require user authentication prior to execution. For example, one or more of loading a medication carrier 26 into a delivery module 33, unloading a medication carrier 26 from a delivery module 33, receiving a unit dose and/or unit dose package 27 from the delivery module 33 and viewing an inventory of medications in a delivery module 33 may require entry of particular user information. For example, the requisite user information may include, without limitation, one or more of a password, a voice command, an identification card (e.g., a magnetic stripe card, a bar coded card, and/or a card including an RFID tag or similar device), and a biometric scan (e.g., fingerprint, voice sample, retinal scan, etc.). In this manner, more secure operations are provided by the medication delivery unit 33 and useful data for generating an audit trail (i.e., that positive instructions to perform a given action were received from an identified entity prior to performing the action) may be obtained.

In an embodiment, a patient's complete regimen for medications, i.e., inclusive of all prescriptions potentially issued by one or more healthcare providers, may be assembled by the delivery module 33. For example, medications prescribed by one or more physicians and the resulting prescriptions filled by one or more pharmacists may be stored within the same delivery module 33. The delivery module 33 may determine the dosing regimen (including the delivery schedule for each of the medications) based on one or more electronic identifier codes 29, 31, or receive the dosing regimen from a remote controller, such as the control center 35. The delivery module may then store the dosing regimen information for a particular patient. Medications for more than one patient may be stored in a single delivery module 33 and, correspondingly, different dosing regimens for each such patient may also be stored in a single delivery module. To better facilitate patient usage, a different alert may be provided by the medication delivery unit 33 for each patient, e.g., distinctly different audible alerts for each patient. Alternatively or additionally, the display device 42 may be used to display information identifying a particular patient.

The delivery module 33 may include a printer, i.e., included within the housing of the delivery module 33 and/or in communication with the delivery module 33 via a communications interface, such as through a wireless interface, a Universal Serial Bus (USB) port, and/or a printer port. The printer may be used to print out a prescription regimen for a patient, a medication description list, and/or the like.

In addition to the operations described above, various other refinements of the various embodiments of the present invention are possible, as described below.

For example, in one embodiment, a remote computer system accessible by, for example, a pharmacist may be used to query a delivery module 33 during a prescription filling process to determine an amount of unused medication of the same type and/or previously issued by the pharmacist located in the delivery module 33. If unused medication remains, the pharmacist may reassign the unused medication to the new prescription to reduce the cost to the patient. Alternately, the pharmacist may send a medication discard signal to the delivery module 33 to dispense the unused medication to prevent an oversupply from being made available to the patient. The discarded medication may be dispensed into, for example, a secure area accessible only by authorized personnel.

In an embodiment, the delivery module 33 may receive a recall notification, for example, from a remote source via a communications interface, such as a wireless interface or a communications network. The recall notification may be received, for example and without limitation, for medication that has been determined to be unsafe and/or when medication within a delivery module 33 expires. The recall notification may include medication identification information, such as a medication carrier identifier, lot number information, and the like, for the product being recalled. The delivery module 33 may determine whether it contains any remaining medication that has been recalled, is undesired and/or has expired.

In an embodiment, the delivery module 33 may perform an inventory based on the received information and dispense the recalled medication from a medication carrier 26 to a separate area inside the delivery module 33. The separate area may only be securely accessible by authorized personnel via a touch pad code and/or key. In this manner, the recalled medication may not be available to a patient. The delivery module 33 may record the number and/or types of recalled doses and report this information to the remote source initiating the recall and/or any other remote source once the recalled medication has been secured and/or inventoried. In an embodiment, the delivery module 33 may determine whether it contains unused medication that has been recalled. If so, the quantity and/or the next time that the medication is to be dispensed may be reported to the remote server. The remote server may then direct the delivery module 33 to discard the recalled medication.

In an alternate embodiment, the delivery module 33 may locate and record the existence of the recalled medication in one or more medication carriers 26 to prevent dispensing of medications from those locations. The recalled medication may only be dispensed in response to a command from an authorized user. If the command is entered locally, the delivery module 33 may dispense one or more medication carriers 26 containing the recalled medication through the insertion/retrieval slot 45. Alternately, the delivery module 33 may dispense the recalled medication into the receiving area 46. The recalled medication may also be dispensed into a secured location accessible only by an authorized user.

The delivery module 33 may transmit a recall notification to a patient and/or caregiver. Additionally and/or alternately, the delivery module 33 may notify a manufacturer that the delivery module 33 has located a recalled medication.

Similar operations may be performed if medication has been identified as having expired. The delivery module 33 may perform an expiration detection algorithm on medication carriers 26 loaded therein. In an embodiment, expiry date information on the medication carriers 26 and/or a unit dose package 27 may be detected when they are first inserted or thereafter. The information may then be stored. The information may be compared with a time of day, time stamp or other suitable time information to determine whether the delivery module 33 contains expired medication. The delivery module 33 may dispense expired medication to a separate chamber inside the unit, record where the medication is located in the one or more medication carriers 26 and not dispense such medication, and/or eject the expired medication out the insertion/retrieval slot 45 and/or the receiving area 46 upon receipt of, for example, an authorization code. The delivery module 33 may transmit a signal to a remote server and/or notify the patient and/or caregiver.

In an alternate embodiment, a remote server may notify the delivery module 33 that the module contains expired medication. In response to a medication expiration notification, the delivery module 33 may then perform the one or more of the above listed and/or other actions. In addition, the delivery module 33 can notify a physician, pharmacist, patient and/or backend server and confirm that the module has taken an action and/or placed the recalled medication and/or expired medication in a secure area.

A remote server may, for example, compile recall information from a plurality of patients using a plurality of delivery modules 33 and may thus be a valuable medication recall and patient safety system. The remote server may notify manufacturers and/or government agencies directly via, for example, computer-based communication systems to directly indicate the number of doses that have been identified, securely stored and/or dispensed to an authorized individual for product safety and public safety concerns.

Various alternative embodiments of a medication carrier in accordance with the present invention, particularly that described above relative to FIGS. 44 and 45, are further described with reference to FIGS. 62-70. Note that, for ease of illustration, not all dimensions illustrated in FIGS. 62-70 are drawn to scale. As before, the alternative embodiment may comprise a multi-layered structure similar to the layers depicted in FIGS. 44 and 45. Although, in a presently preferred embodiment, the alternative embodiment comprises three distinct layers (a support layer 606, a blister layer 614 and a backing layer 636, described below) used to fabricate a medication carrier or blister pack, those having skill in the art will appreciate that one or more of the layers may be left out or incorporated into any of the other layers. For example, the support layer 606 may be incorporated into either the blister layer 614 or backing layer 636 by increasing a relative thickness of at least a portion of either or both of the latter two layers.

Figure 62:
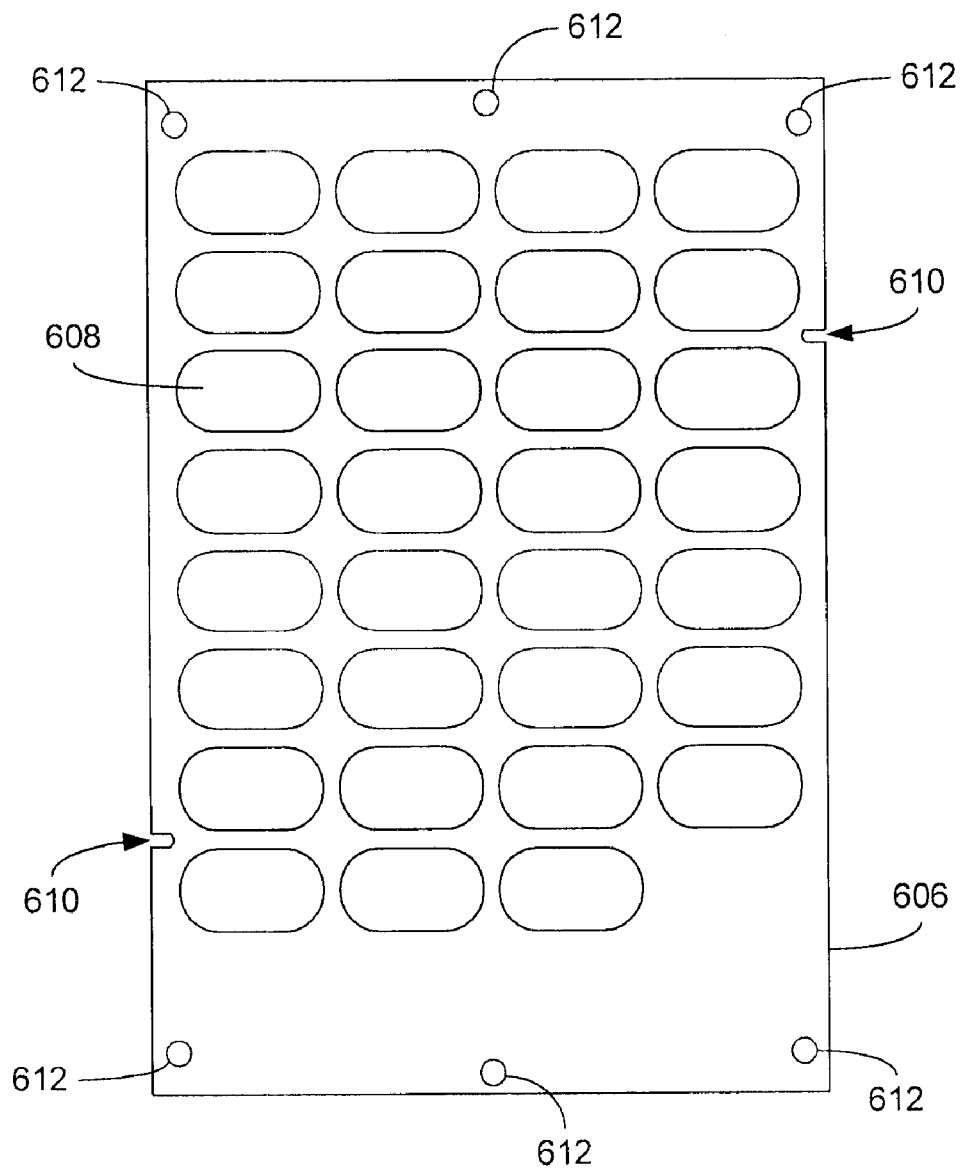
FIG. 62 depicts a front view of a support layer in accordance with an alternative embodiment of a medication carrier or blister pack.

Referring now to FIG. 62, a support layer 606 is shown. Generally, the support layer 606 is fabricated from a suitable material such as paper, cardboard, plastic or the like of a suitable thickness. As before, the support layer 606 (as well as the other layers 614, 636) are preferably about 9 inches (22.86 cm) by 6 inches (15.24 cm). In a presently preferred embodiment, the support layer is fabricated from a solid bleach sulfate (SBS) paperboard having a thickness of approximately 0.018 inches (0.457 mm). Additionally, the support layer 606 may have a suitable adhesive, such as a pressure-sensitive or heat-sensitive adhesive, applied to one side thereof (i.e., that side coming into contact with the blister layer 614). The support layer 606 comprises at least one opening 608 and, in the presently preferred embodiment, comprises a plurality of such openings and, in a presently preferred embodiment, a number of openings equivalent to the number of days (i.e., 30 or 31) in a single month. Preferably, each opening 608 is about 0.718 inches (18.24 mm) by 1.28 inches (32.51 mm). Although the two-dimensional arrangement of the openings 608 as illustrated in FIG. 62 is preferred, those having ordinary skill in the art will appreciate that a variety of arrangements may be equally employed. As described in greater detail below, each of the openings 608 is configured to receive a corresponding blister from a blister layer 614.

The support layer 606 includes a plurality of guide holes 610 positioned along the lateral edges of the medication carrier. As before, the guide holes 368 may be used to align the medication carrier when disposed within a suitable automatic medication dispensing device, such as an MDU described above. In the illustrated embodiment, additional guide holes 612 are provided along the transverse edges of the medication carrier, which guide holes 612 may be used for aligning the support layer 606 with the other layers during fabrication of a medication carrier, moving the a medication carrier into position and/or securing the medication carrier in position within a suitable medication dispensing device. Note that the dimensions of the various guide holes 612, along with their specific location, may vary as a matter of design choice.

Figure 63A:
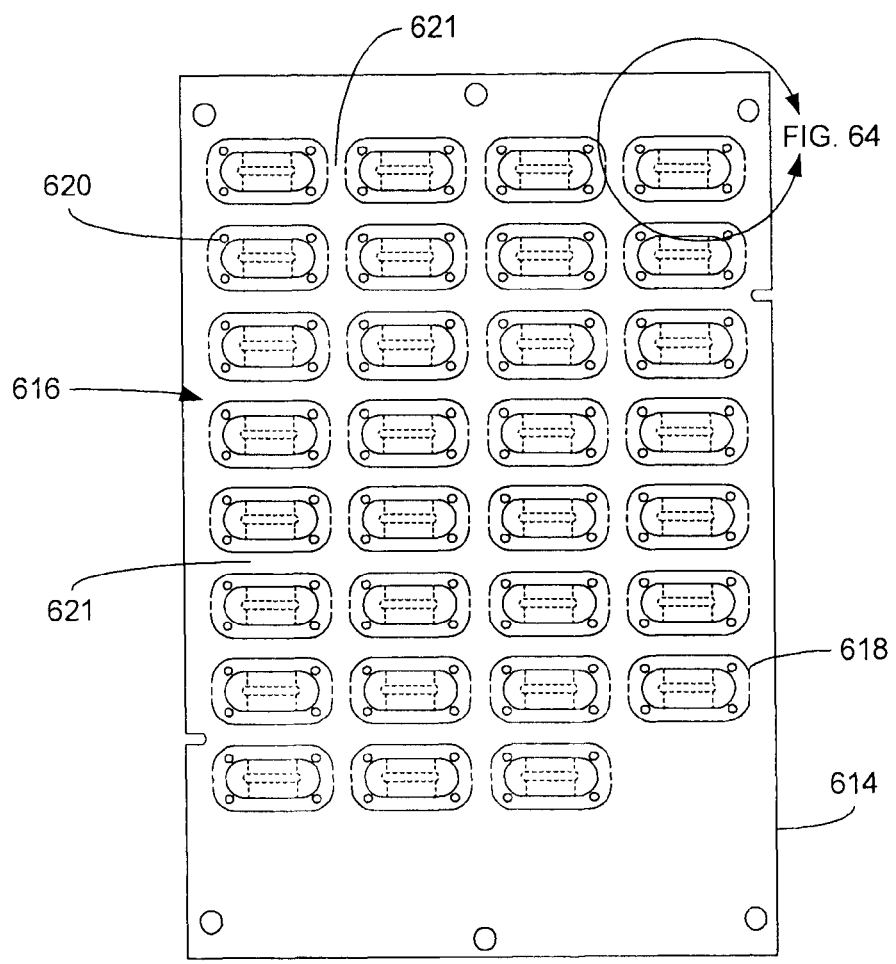
FIG. 63A depicts a front view of a blister layer in accordance with the alternative embodiment of a medication carrier or blister pack.
Figure 63B:
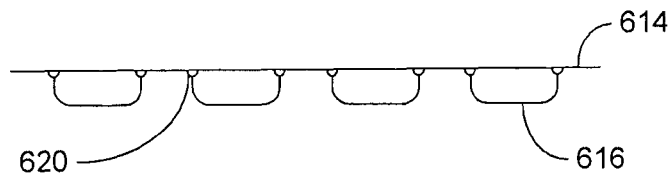
FIG. 63B depicts a side view of the blister layer of FIG. 63A.
Figure 64:
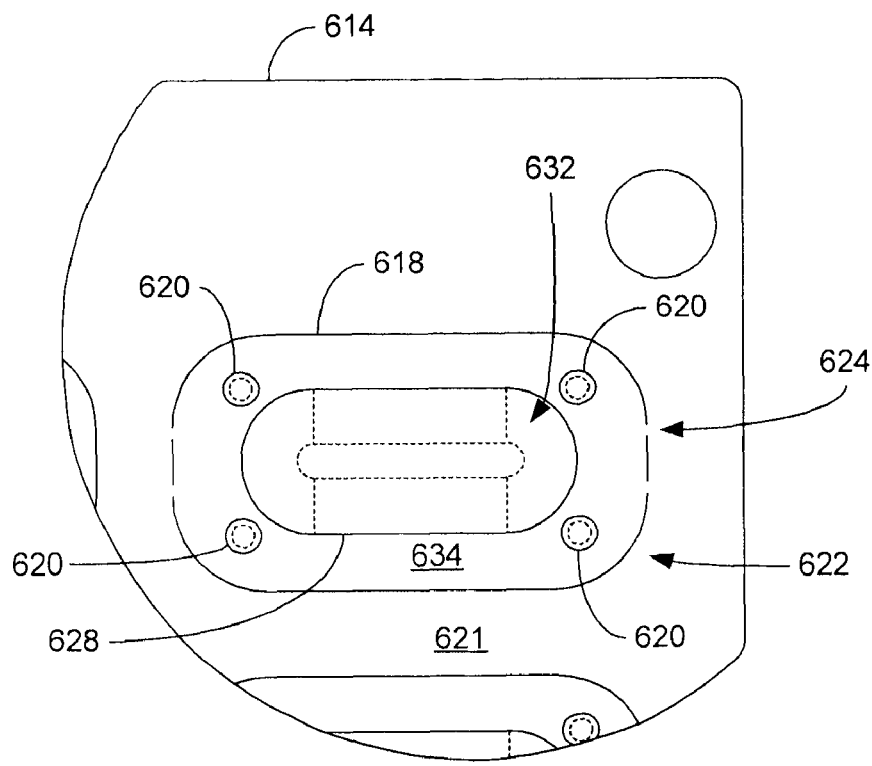
FIG. 64 depicts a front, magnified view of a blister within a blister layer in accordance with the alternative embodiment of a medication carrier or blister pack.
Figure 65:
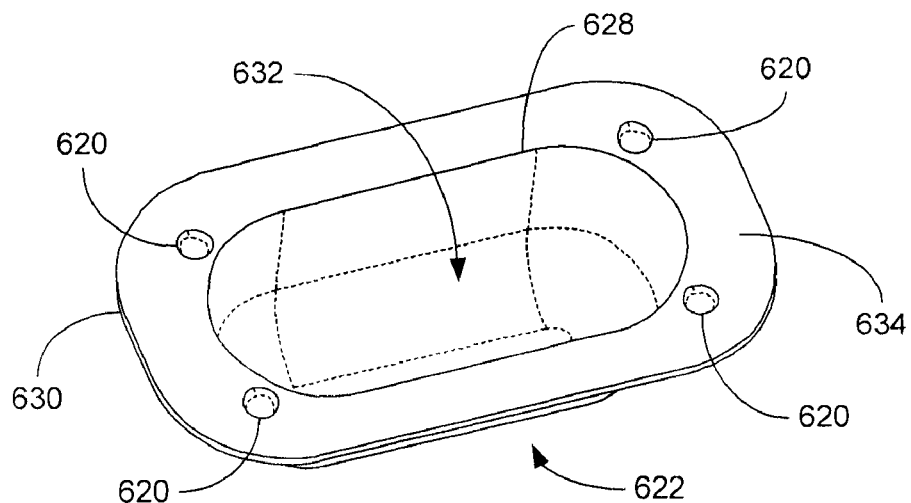
FIG. 65 depicts a perspective, magnified view of a blister removed from a blister layer according to the alternative embodiment of a medication carrier or blister pack.

Referring now to FIGS. 63A and 63B, a blister layer 614 in accordance with the alternative embodiment is illustrated. In particular, the blister layer 614 is of dimensions equivalent to the support layer 606 (i.e., about 9 inches by 6 inches) and having guide holes that align with the guide holes of the support layer 606. The blister layer 614 is preferably made of a suitable plastic material, such as polyvinyl chloride (PVC) having a thickness of approximately 0.015 inches (0.381 mm). The blister layer 614 comprises at least one blister 616 formed therein, such as a number of blisters 616 matching the number of openings 608 in the support layer 606. As best illustrated in FIGS. 64 and 65, each blister 616 comprises a cavity or indentation 632 formed within the blister layer 614, as well as a flange region 634 between an opening perimeter 628 of the cavity 632 and a first perforation 618 surrounding the blister 616. Each cavity 632 is configured to receive a unit dose of a medicament and, in presently preferred embodiment, is approximately 0.386 inches (9.8 mm) by 0.866 inches (22 mm) and having a depth of approximately 0.375 inches (9.53 mm). Similarly, the flange region 634 preferably varies from about 0.176 inches (4.47 mm) along the lateral sides of the cavity 632 to about 0.145 inches (3.68 mm) along the transverse sides of the cavity 632. The first perforation 618 allows its corresponding blister 616 to be readily removed from the blister layer 614. In a presently preferred embodiment, the dimensions of each blister as defined by its first perforation is about 0.657 inches (16.69 mm) by 1.219 inches (30.96 mm). Note that, in the illustrated embodiment, each blister 616 comprises its own corresponding first perforation 618 surrounding the blister 616. However, it is understood that groups of blisters 616 could be arranged with a first perforation 618 surrounding the group such that the group of blisters can be removed together.

Within the flange region 634 of each blister 616, one or more dimples 620 are provided. As described in further detail below, the dimples are provided to ensure removal of unit dose packages by an automated medication delivery device, such as an MDU. As shown, and in a presently preferred embodiment, four dimples are provided in proximity to the corners of the opening perimeter 628 of the cavity 632, although any other number of dimples, or positioning within the flange 634, may be employed as a matter of design choice. Each dimple is preferably formed to a shallower depth relative to the cavity 632, for example, at a preferred depth of about 0.065 inches (1.65 mm). In addition to the blisters 616, the blister layer 614 further comprises ribbing areas 621 surrounding each of the blisters 616. As described below with reference to FIG. 64, the ribbing 621 provides support to the individual unit dose packages (each comprising a blister 616 and a corresponding flange 634) when they are removed from the medication carrier. Although the width of the ribbing 621 between unit dose packages may vary as a matter of design choice, in a presently preferred embodiment, the ribbing is approximately 0.2 inches (5.08 mm) in width between any two unit dose packages.

Referring now to FIG. 64, a magnified view of a single unit dose package 622 (without the corresponding portion of the backing layer 636) is further illustrated. In particular, in the presently preferred embodiment, each of the first perforations 618 defining the unit dose package 622 are interrupted by one or more web members 624 attaching the unit dose packaging to the surrounding ribbing 621. Because each of the first perforations 618 penetrate entirely through the thickness of the blister layer 614, the web member 624 is provided to maintain the unit dose package 622 within the medication carrier until such time as it is forcibly removed, either manually or through the use of an automated medication dispensing system. Although a matter of design choice depending in part upon the material used to fabricate the blister layer 614 as well as the desired force required to remove unit dose package 622 from the blister layer 614, in a presently preferred embodiment, each web member 624 is approximately 0.02 inches (0.51 mm) in width. The blister or cavity 632 is defined by an opening perimeter 628 and is preferably configured to provide sufficient volume to accept a unit dose of a medicament. As best illustrated in FIG. 65, when the unit dose package 622 is removed from the medication carrier, each unit dose package 622 is defined by a boundary 630 corresponding to edges created by the first perforations 618.

Figure 66:
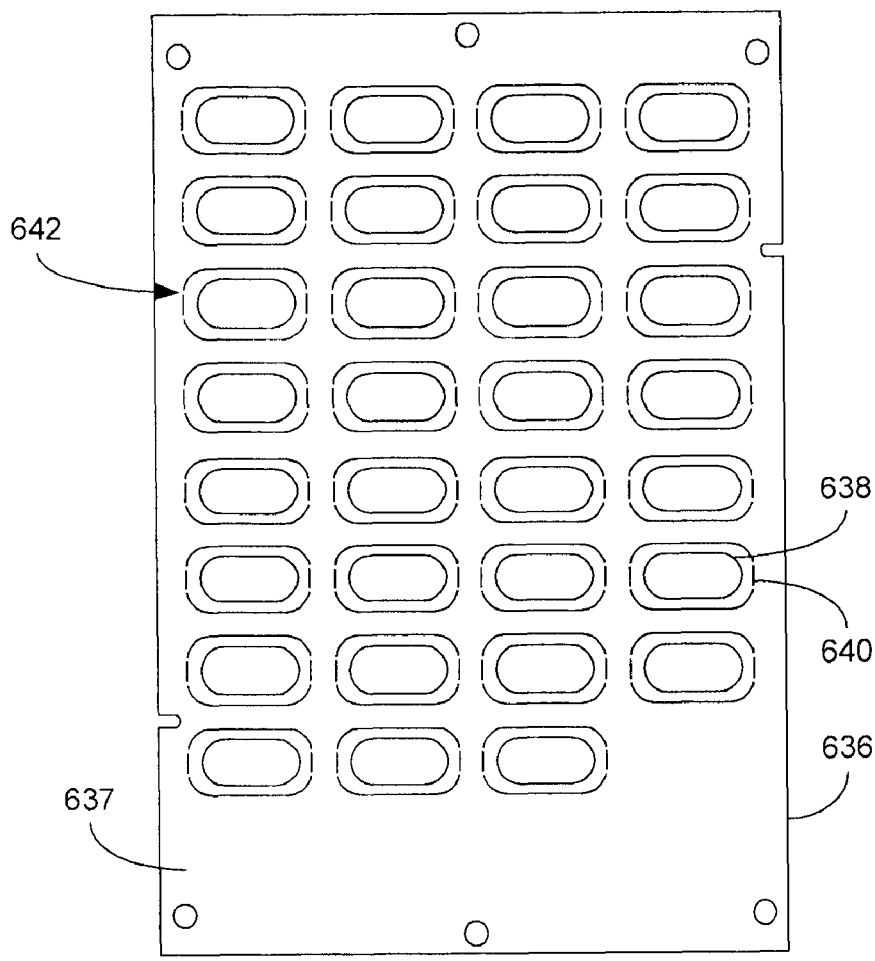
FIG. 66 depicts a front view of a backing layer in accordance with the alternative embodiment of a medication carrier or blister pack.
Figure 68:
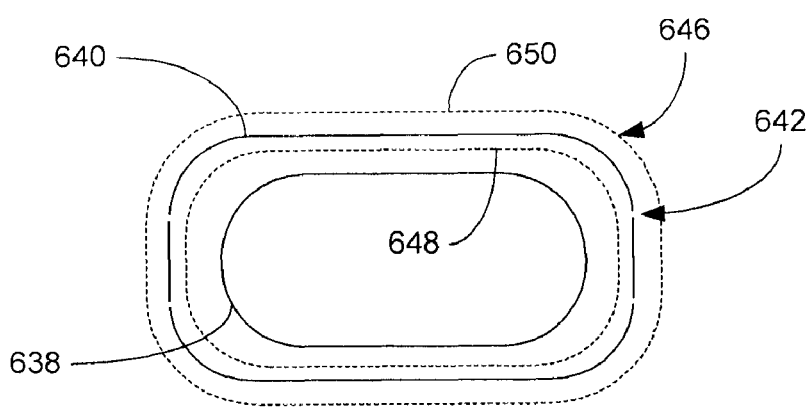
FIG. 68 depicts a front, magnified view of a portion of the backing layer in accordance with the alternative embodiment of a medication carrier or blister pack.
Figure 67:
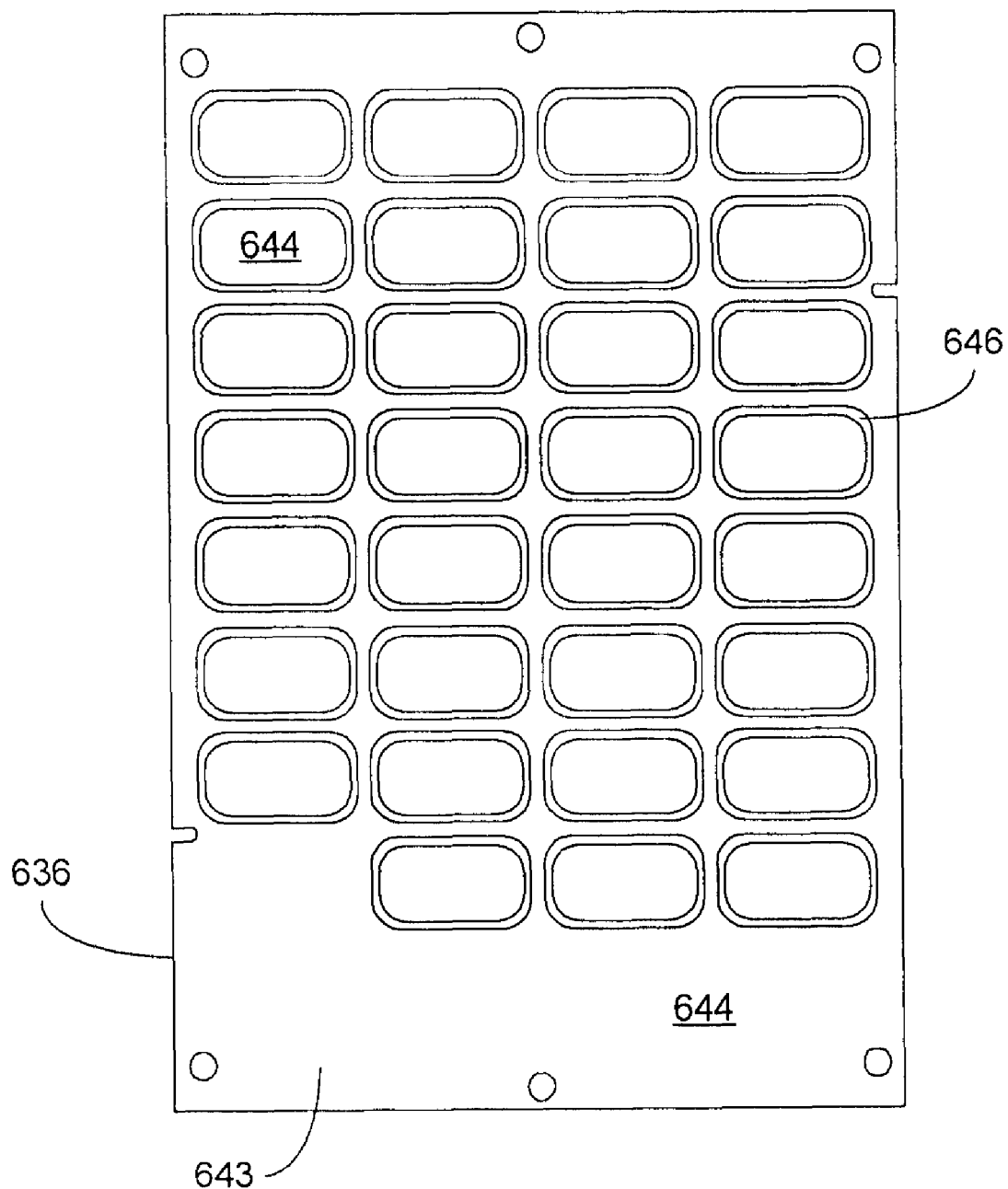
FIG. 67 depicts a back view of the backing layer of FIG. 66.

Referring now to FIGS. 66-68, a backing layer 636 is illustrated. The backing layer 636 may be made from a suitable paper, cardboard, plastic material or even a lamination of materials such as paper and foil. In a presently preferred embodiment, the backing layer 636 is manufactured from SBS paperboard or #65 paper. As in the prior embodiment described above relative to FIGS. 44 and 45, at least a first side 637 of the backing layer 636 may comprise the same information printed thereon, e.g., one or more identifiable indicia such as barcodes, textual information, graphics, etc. Conversely, on a second side 643 of the backing layer 636, an adhesive 644, such as a pressure-sensitive or heat-sensitive adhesive as known in the art, is applied across the entirety of the surface with the exception of adhesive free regions 646 described in greater detail below.

Referring once again to FIG. 66, the backing layer 636 further comprises at least one partial-thickness cut 638 that, when the backing layer 636 is attached to the blister layer 614, substantially aligns with a corresponding one of the at least one blister 616 formed in the blister layer 614. More particularly, in a presently preferred embodiment, each of the partial-thickness cuts 638 is the substantially the same shape as and aligned with the opening perimeter 628 of the corresponding blister 614. As used herein, "substantial" similarity of alignment or shape of the partial-thickness cut 638 may be determined by the relative ease with which a unit dose may be removed from the blister in which it is held. That is, the alignment or shape of the partial-thickness cut 638 should be such that removal of the unit dose is facilitated as compared to a total absence of the partial-thickness cut 638. Thus, a partial-thickness cut 638 entirely within the projected region of the opening perimeter 628 is substantially, even if not identically, aligned and shaped. Likewise, a partial-thickness cut 638 residing outside the projection of the opening perimeter 628 may also be substantially aligned and shaped provided that the partial-thickness cut 638 still facilitates removal of the units dose. Each of the at least one partial-thickness cuts 638 penetrates into, but not through the entirety of, the thickness of the backing layer 636. For example, in a presently preferred embodiment, each of the partial-thickness cuts 638 penetrates approximately 95% into the thickness of the backing layer, although other penetration percentages could be employed. However, because each partial-thickness cut 638 does not penetrate the entirety of the thickness of the backing layer 636, the seal of the corresponding unit dose package is not violated, thereby maintaining sterility required for use with various medications. Note that, in a presently preferred embodiment, each of the partial-thickness cuts 638 is made in the first side 637 of the backing layer 636, although it is understood that such cuts 638 could instead be made in the second side 643 of the backing layer 636 as a matter of design choice.

As further illustrated in FIGS. 66 and 68, the backing layer 636 further comprises at least one second perforation 640 that, in a presently preferred embodiment, substantially aligns with the one or more first perforation 618 when the backing layer 636 is adhered to the blister layer 614. However, it is understood that the at least one second perforation 640 is not a requirement. As in the case of the first perforation 618, the second perforation 640 is preferably interrupted by one or more web members 642 (of substantially the same dimensions and locations as the web members 624 interrupting the first perforations 618), thereby further enhancing attachment of each unit dose package to the medication carrier. Likewise, "substantial" alignment of the at least one second perforation 640 with the at least one first perforation 618 may be defined by alignment not exceeding a threshold distance from the at least one first perforation 618, e.g., approximately 0.0156 inches (0.4 mm).

Referring now to FIGS. 67 and 68, one or more adhesive-free regions 646 are illustrated. In particular, each adhesive-free region 646 is configured to substantially align with the second perforations 640 within the backing layer 636 in such a manner that substantially no adhesive is applied in contact with the second perforations 640. For example, as shown in FIG. 68, each adhesive-free region 646 (formed on the second side 643 of the backing layer 636) includes or otherwise straddles a corresponding one of the second perforations 640. Thus, an inner adhesive boundary 648 is within the second perforation 640, whereas an outer adhesive boundary 650 is outside the second perforation 640. For example, in a presently preferred embodiment, the inner adhesive boundary 648 is no closer than approximately 0.009 inches (0.229 mm) to an inner edge of the second perforation 640, whereas the outer adhesive boundary 650 is no closer than approximately 0.063 inches (1.6 mm) to an outer edge of the second perforation 640. The adhesive-free region 646 is provided in order to prevent the adhesive from causing the unit dose package to stick to or otherwise fail to be ejected from the medication carrier during ejection by an automated medication dispensing system.

Figure 69:
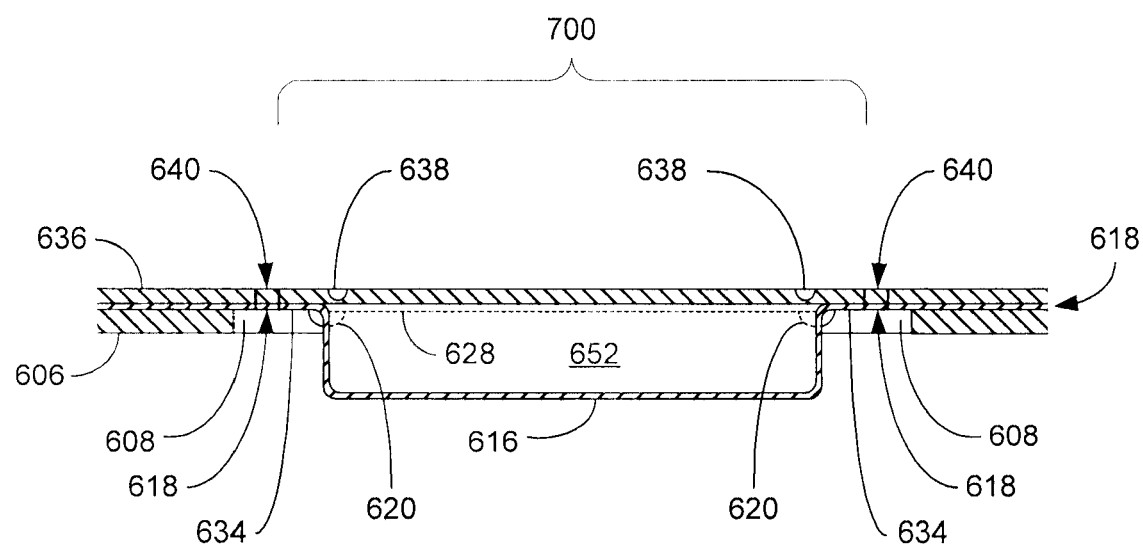
FIG. 69 depicts a cross-sectional, magnified view of a unit dose package while still retained in a medication carrier according to the alternative embodiment of a medication carrier or blister pack.
Figure 70:
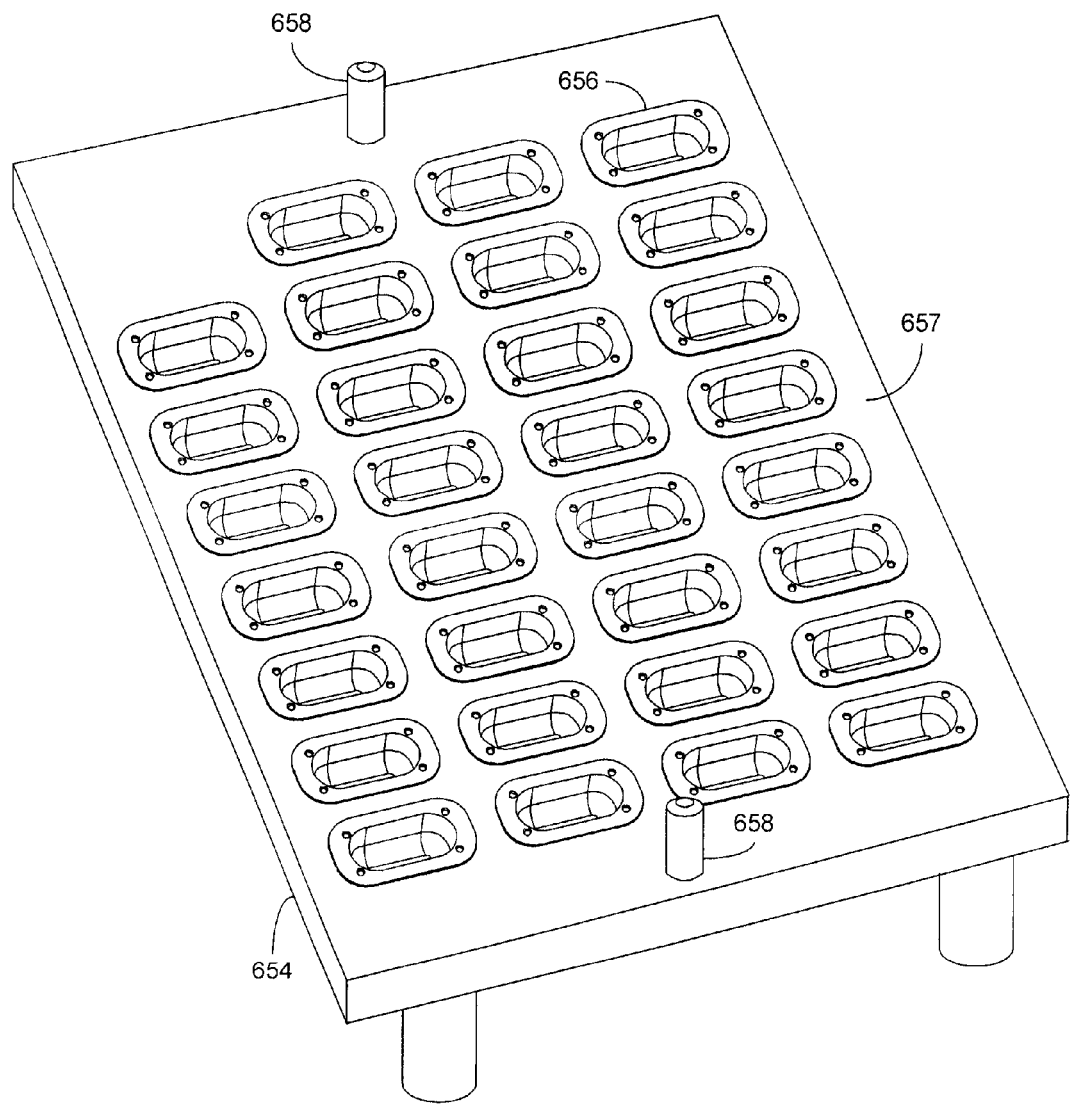
FIG. 70 depicts a perspective view of a loading tray that may be used in conjunction with a medication carrier or blister pack in accordance with the alternative embodiment.

When all of the layers 606, 614, 636 are assembled as described previously, a plurality of unit dose packages are formed. This is further illustrated in FIG. 69, which depicts a magnified, cross-sectional view of a single unit dose package 622 (along its longitudinal axis) within a medication carrier comprising the three layers described above, i.e., the support layer 606, the blister layer 614, and the backing layer 636. As shown, the blister layer 614 is sandwiched between the support layer 606 and the backing layer 636 by virtue of the adhesive material applied to both the support layer 606 and backing layer 636, as described above. The blister 616 resides within the opening 608 of the support layer 606, which opening 608 is of sufficient dimensions to encompass not only the blister 616, but the flange 634 encompassing the dimples 620. As described above, the flange 634, as well as the unit dose package 622, are delimited by the first perforation 618 and the second perforation 640 illustrated by the heavy black lines traversing both the blister layer 614 and the backing layer 636. In contrast, the partial-thickness cut 638 is illustrated as penetrating a substantial portion, but not the entirety, of the thickness of the backing layer 636. FIG. 69 additionally illustrates the manner in which the partial-thickness cut 638 is substantially aligned with the opening perimeter 628 of the blister 616. Additionally, the resulting enclosure 652 formed by the blister 616 and backing layer 636 is effectively sealed from the outside environment by virtue of the overlap of that portion of the backing layer 636 adhered to the flange 634 formed at the upper periphery of the blister 616. Although not illustrated in FIG. 69, the enclosure 652 is of sufficient dimensions to hold a unit dose of a medicament.

Referring once again to FIG. 39A, it is noted that the punch 304a may be positioned over a particular unit dose package 622 and caused to impact a medication carrier in a direction that is substantially perpendicular to the substantially flat, upper surface (i.e., the printed surface) of the medication carrier. As shown, the plurality of pins 304b-e preferably match both the number and alignment of the dimples 608. Additionally, any suitable shape or size of pins 304b-e may be used provided that they are each capable of fitting within or otherwise engaging a corresponding one of the dimples 620 when brought into contact with the unit dose package 622. Outer edges 304h of the punch 304a are preferably configured to substantially match the first (and/or second) perforation defining the unit dose package 622.

When the punch 304a is brought into contact with a unit dose package 622 of a medication carrier, the pins 304b-e are designed, in one embodiment, to pierce that portion of the backing layer 636 overlying the blister 616 and flange 634 to engage corresponding ones of the dimples 620. To counter the "hanging chad" problem described above, the pins 304b-e, by engaging the dimples 620, allow the punch 304a to secure and tear the unit dose package 622 away from the medication carrier. Substantially simultaneously, the resistance of the unit dose package to the movement of the punch 304a, prior to dislocation of the unit dose package from the medication carrier, causes compression of the spring loaded plungers 304f-g. Once the web members of the unit dose package have been completely broken, the resistance of the unit dose package is removed, thereby allowing the spring force of plungers 304f-g to remove the unit dose package from the pins 304b-e.

In an alternative embodiment that takes advantage of the partial-thickness cuts 638 provided as part of each unit dose package, when provided, an automatically controlled punch tool configured to engage and apply force to the blister 616 of a unit dose package (rather than the label-side surface of a unit dose package) is supplied. In this embodiment, the first perforation 618 and second perforation 640 are either not provided or configured to provide a greater amount of resistance to removal of the unit dose package than would be required to deform the blister 616 and rupture the partial-thickness cut 638. That is, the punch tool can apply sufficient force to deform the blister 616 and force the enclosed unit dose into the backing layer with enough force to cause the unit dose to rupture the partial-thickness cut, all before the unit dose package itself is ejected. In this embodiment, it is understood that the automatic delivery device used to eject the unit dose must be configured to accept the medication carrier in an orientation that allows the punch tool to be brought into contact with the blister, e.g., blister-side up. In this manner, those features designed to facilitate removal of a unit dose from a unit dose package may be exploited by an automatic delivery device.

As described previously, the medication carrier described relative to FIGS. 62-69 may be advantageously used to deliver medications to patients, particularly in conjunction with an automated delivery device as described above. Thus, when a medicament is to be administered or delivered, the desired dose may be determined from, for example, the identifying label on the medication carrier. Force may be applied (e.g., through use of a punch tool, as described above) to a particular unit dose package in order to dislodge the unit dose package from the medication carrier. This process of dislodging a unit dose package may also be performed manually. Thereafter, the unit dose of medication in the unit dose package may then be removed from the unit dose package by applying force of the blister, causing the partial thickness cut formed in the backing layer to rupture. The removed medication may then be administered.

It is noted that the process of assembling a medication carrier or blister pack described above relative to FIGS. 44 and 45 is equally applicable to the medication carrier or blister pack described above relative to FIGS. 62-69. That is, the support layer 606 is placed on a loading tray and the blister layer 614 is placed over the support layer 606 in the loading tray. Thereafter, unit doses of a medication are placed in the blisters of the blister layer 614. In parallel, suitable printing/markings may be applied to the backing layer 636 (the third layer), which is subsequently placed over the blister layer 614 that has previously been loaded with the desired medication. Thereafter, application of a suitable force and/or heat bonds the three layers together to form the medication carrier. An exemplary loading tray 654 for use in conjunction with fabrication of the medication carrier or blister card of the alternative embodiment is further illustrated in FIG. 70. As shown, the tray 654 comprises a number of receptacles 656 configured to receive all of the blisters 616 (and corresponding dimples 620) of the blister layer 614. Note that, preferably, an upper surface of each receptacle 656 is raised above an upper surface 657 of the tray 654 to account for the thickness of the support layer 606. Additionally, alignment posts 658 are provided to engage the corresponding guide holes formed in each of the layers 606, 614, 636 to ensure proper alignment of the various features of each of the layers, as described above. Note that the alignment posts 658 may be placed along the transverse sides of the tray 654, as shown, along the lateral side or both as a matter of design choice.

The present invention is a fully integrated, real-time, non-sequential, medication management and compliance system that ensures accurate delivery of both custom packaged and commercially available sealed unit dose and unit-of-issue medications to patients. Importantly, the invention fosters patient compliance with a prescribed treatment regimen by, for example, protecting the patient from adverse drug reactions and ensuring that the patient remains within recommended therapeutic levels.

Furthermore, because the delivery of medication occurs on a unit dosage basis, the patient avoids purchasing an unnecessary number of doses and only purchases the number of units required for the prescribed regimen. This is a tremendous advantage over existing systems, in which prescriptions are normally filled in standard thirty day or sixty day allotments. The present invention reduces the incidence of medication waste by supplying only necessary doses to the patient rather than an aggregate number of doses, which are ultimately discarded. A further advantage to the patient is that each unit dose package remains completely sealed until the point of administration to avoid the medication contamination and degradation problems which plague remote medication delivery systems known in the art.

In the event of a change in the health condition of the patient or other situation requiring a dosage adjustment, other medications and doses having higher or lower strengths are immediately available to the patient, eliminating the need to travel to a physician's office and/or to a pharmacy to obtain the requisite medication. This feature is particularly important with respect to mobility impaired patients. In addition, patient expenses are reduced since the new dosage is already on hand and need not be purchased.

Healthcare practitioners such as physicians and pharmacists also benefit from the present invention. The system enables a provider to treat a greater number of patients with better control of high risk patients, including patients with cognitive, visual, and/or auditory impairments who require more frequent monitoring. The invention allows the healthcare practitioner to rectify a patient's failure to take a scheduled dosage in minutes. In addition, the invention reduces the number of non-reimbursable medical services, which include, for example, telephone calls to and from the patient. Also, the invention eliminates the need to write a new prescription every time a dosage needs to be adjusted. The healthcare practitioner makes proper dose adjustments in a prompt and timely fashion, all duly recorded, without any disruption to the patient's course of treatment. This is a significant advantage over existing systems, which allow a remotely based healthcare practitioner to communicate a change in medication or dosage amount to a patient but do not enable the practitioner to remotely change a prescribed dosage in real time.

As previously mentioned, with existing dispensing systems, there is no accurate way to inventory pharmaceuticals and/or to audit patient compliance or consumption of the products. This is due, in part, to the fact that the pharmaceuticals are dispensed in a lot, whereby not every pill or dose is separately identifiable and traceable. In the present invention, medication delivery is accomplished on a unit dosage basis wherein each dose is inventoried with its own electronically coded identifier, allowing a healthcare practitioner to accurately monitor patient compliance with a prescribed treatment regimen. The system enables the healthcare practitioner to remotely manage and deliver individual unit dose packages of prescription and non-prescription medications, medical supplies, diagnostic materials, pharmaceuticals and nutraceuticals to a patient, non-consecutively, without being limited by a sequential delivery restriction. Such unit doses may include, for example, solid orally consumed doses, liquid orally consumed doses, and injection devices containing doses that are administered directly into the body, wherein the doses may include a single compound or several compounds.

Managed care providers and other third party payors realize significant advantages from the integrated, non-sequential, remote medication management and compliance system described herein. The invention provides a platform for the control and electronic billing of healthcare products distributed to one or more remote locations on consignment. In this regard, consignment medications may be immediately billed upon dispensing, significantly reducing inventory costs associated with medications that are billed and reimbursed at the time of consumption and providing pharmaceutical companies with a competitive advantage.

Notably, the invention reduces the incidence of medication waste by eliminating the need for a patient to discard remaining doses or obtain a new prescription in the event of a dosage adjustment. This increases the likelihood that a patient will receive a required treatment, reducing the incidence of emergency room visits and hospital admissions occasioned by non-adherence to a prescribed drug regimen. In addition, visits to healthcare providers such as physicians and pharmacists are reduced, significantly decreasing provider related costs.

While the invention has been particularly shown and described with reference to preferred embodiments thereof, it will be understood by those skilled in the art that various alterations in form and detail may be made therein without departing from the spirit and scope of the invention. In particular, while the invention illustrated by the Figures shows a specific size and shape of the delivery module, these parameters can vary considerably and are not limited by the preferred embodiments described herein and depicted in the Figures.

Additionally, while this application generally addresses use of the secure data communication process to deploy communications to and from a delivery module based in a patient's home while protecting patient privacy, the use of such process is by no means limited to this application. The data communication process described herein can be adapted for use in a variety of applications where secure data transmission is desirable (e.g. in conjunction with a patient monitoring system).

While the particular preferred embodiments of the present invention have been shown and described, it will be obvious to those skilled in the art that changes and modifications may be made without departing from the teachings of the invention. It is therefore contemplated that the present invention cover any and all modifications, variations or equivalents that fall within the scope of the basic underlying principles disclosed above and claimed herein.

What is claimed is:

1. A medication carrier comprising:
   a blister layer comprising a plurality of blisters arranged in a two-dimensional array, a ribbing between each of the plurality of blisters and a plurality of first perforations corresponding to the plurality of blisters, each one of the plurality of first perforations defining a boundary between the ribbing and an individually-ejectable, unit dose package comprising a corresponding blister of the plurality of blisters; and
   a backing layer, coupled to a first side of the blister layer such that the plurality of blisters and the backing layer form a plurality of enclosures each for holding at least one unit dose of a medicament, the backing layer further comprising a plurality of partial-thickness cuts through a thickness of the backing layer corresponding to and substantially aligned with the plurality of blisters.

2. The medication carrier of claim 1, each one of the plurality of blisters further comprising at least one dimple disposed within the boundary.

3. The medication carrier of claim 1, each one of the plurality of blisters further comprising at least one first web member interrupting a corresponding one of the plurality of first perforations and attaching the blister to the ribbing.

4. The medication carrier of claim 3, the backing layer further comprising a plurality of second perforations substantially aligned with the plurality of first perforations.

5. The medication carrier of claim 4, the backing layer further comprising, for each one of the plurality of second perforations, at least one second web member interrupting the second perforation.

6. The medication carrier of claim 4, the backing layer further comprising an adhesive applied to a second side of the backing layer facing the blister layer, except that a plurality of adhesive-free regions is provided corresponding to the plurality of second perforations.

7. The medication carrier of claim 1, each of the plurality of partial-thickness cuts substantially aligned with an opening perimeter of a corresponding one of the plurality of blisters.

8. The medication carrier of claim 1, further comprising:
   a support layer, coupled to a second side of the blister layer, comprising a plurality of openings, each of the plurality of openings configured to receive a corresponding one of the plurality of blisters.

9. A medication carrier comprising:
   a blister layer comprising a plurality of blisters formed therein, each of the plurality of blisters for holding a unit dose of a medicament, the blister layer further comprising a ribbing between each of the plurality of blisters and a plurality of first perforations corresponding to the plurality of blisters, each one of the plurality of first perforations defining a boundary between the ribbing and an individually-ejectable, unit dose package comprising a corresponding blister of the plurality of blisters; and
   a backing layer, coupled to the blister layer, comprising a plurality of second perforations substantially aligned with the plurality of first perforations and further comprising an adhesive applied to a side of the backing layer facing the blister layer, except that a plurality of adhesive-free regions is provided corresponding to the plurality of second perforations.

10. The medication carrier of claim 9, wherein each one of the plurality of adhesive-free regions includes a corresponding one of the plurality of second perforations.

11. The medication carrier of claim 9, the backing layer further comprising, for each one of the plurality of second perforations, at least one web member interrupting the second perforation.

12. The medication carrier of claim 9, the backing layer further comprising a plurality of partial-thickness cuts through a thickness of the backing layer corresponding to and substantially aligned with the plurality of blisters.

13. The medication carrier of claim 12, each one of the plurality of partial-thickness cuts substantially aligned with an opening perimeter of a corresponding one of the plurality of blisters.

14. The medication carrier of claim 9, each one of the plurality of blisters further comprising at least one dimple disposed within the boundary.

15. The medication carrier of claim 9, further comprising:
   a support layer, coupled to a second side of the blister layer, comprising a plurality of openings, each one of the plurality of openings configured to receive a corresponding one of the plurality of blisters.

16. The medication carrier of claim 9, the blister layer further comprising the plurality of blisters arranged in a two-dimensional array.

17. A medication carrier comprising:
- a blister layer comprising a plurality of blisters formed therein, the blister layer further comprising a ribbing between each of the plurality of blisters and a plurality of first perforations corresponding thereto, each one of the plurality of first perforations defining a boundary between the ribbing and an individually-ejectable, unit dose package comprising a corresponding blister of the plurality of blisters, each blister of the plurality of blisters further comprising at least one dimple disposed within the boundary; and
- a backing layer, coupled to a first side of the blister layer such that the plurality of blisters and the backing layer form a plurality of enclosures each for holding at least one unit dose of a medicament.

18. The medication carrier of claim 17, each blister of the plurality of blisters further comprising a plurality of dimples disposed within the boundary.

19. The medication carrier of claim 18, each blister of the plurality of blisters further comprising four dimples disposed within the boundary.

20. The medication carrier of claim 17, the at least one dimple disposed outside an opening perimeter of the blister.

21. The medication carrier of claim 17, the at least one dimple aligned to receive at least one pin of a punch used to eject each unit dose package.

22. The medication carrier of claim 17, the backing layer further comprising a plurality of partial-thickness cuts through a thickness of the backing layer corresponding to and substantially aligned with the plurality of blisters.

23. The medication carrier of claim 17, the backing layer comprising a plurality of second perforations substantially aligned with the plurality of first perforations, the backing layer further comprising an adhesive applied to a side of the backing layer facing the blister layer, except that a plurality of adhesive-free regions is provided corresponding to the plurality of second perforations.

\* \* \* \* \*